United States Patent
Inoue et al.

(10) Patent No.: US 11,319,347 B2
(45) Date of Patent: May 3, 2022

(54) PEPTIDE COMPOUND AND METHOD FOR PRODUCING SAME, COMPOSITION FOR SCREENING USE, AND METHOD FOR SELECTING PEPTIDE COMPOUND

(71) Applicant: FUJIFILM Corporation, Tokyo (JP)

(72) Inventors: Masaaki Inoue, Ashigarakami-gun (JP); Takashi Tamura, Ashigarakami-gun (JP); Yuji Yoshimitsu, Ashigarakami-gun (JP); Takahiro Hohsaka, Nomi (JP); Takayoshi Watanabe, Nomi (JP)

(73) Assignee: FUJIFILM Corporation, Tokyo (JP)

( * ) Notice: Subject to any disclaimer, the term of this patent is extended or adjusted under 35 U.S.C. 154(b) by 113 days.

(21) Appl. No.: 16/577,517

(22) Filed: Sep. 20, 2019

(65) Prior Publication Data

US 2020/0040039 A1 Feb. 6, 2020

Related U.S. Application Data

(63) Continuation of application No. PCT/JP2018/011143, filed on Mar. 20, 2018.

(30) Foreign Application Priority Data

Mar. 21, 2017 (JP) .............................. JP2017-053954

(51) Int. Cl.
  *C07K 7/64* (2006.01)
(52) U.S. Cl.
  CPC ...................... *C07K 7/64* (2013.01)
(58) Field of Classification Search
  None
  See application file for complete search history.

(56) References Cited

U.S. PATENT DOCUMENTS

| | | |
|---|---|---|
| 2002/0182687 A1 | 12/2002 | Kurz et al. |
| 2011/0213124 A1 | 9/2011 | Gryshuk et al. |
| 2011/0224411 A1 | 9/2011 | Hohsaka |
| 2013/0178394 A1 | 7/2013 | Suga et al. |
| 2015/0056137 A1 | 2/2015 | Rao et al. |

FOREIGN PATENT DOCUMENTS

| | | |
|---|---|---|
| JP | 2010-284172 A | 12/2010 |
| JP | 2012-058092 A | 3/2012 |
| JP | 4917044 B2 | 4/2012 |
| WO | 00/032823 A1 | 6/2000 |
| WO | 2006/004841 A1 | 1/2006 |
| WO | 2009/096541 A1 | 8/2009 |
| WO | 2010/033617 A2 | 3/2010 |
| WO | 2012/075048 A2 | 6/2012 |
| WO | 2012/083078 A2 | 6/2012 |
| WO | 2016/144665 A1 | 9/2016 |

OTHER PUBLICATIONS

Office Action dated Aug. 13, 2020 in Canadian Application No. 3,057,419.
Extended European Search Report dated Nov. 16, 2020 in European Application No. 18771827.5.
Office Action dated Feb. 17, 2021, from the Intellectual Property Office of Singapore in Singapore application No. 11201908817W.
Hayashi G. et al., "Ribosomal Synthesis of Nonslandard Cyclic Peptides and its Application to Drug Discovery", The Journal of Japanese Biochemical Society, 2010, vol. 82, No. 6, pp. 505-514.
Roberts R.W. et al., "RNA-peptide fusions for the in vitro selection of peptides and proteins", Proc. Natl. Acad. Sci. USA, Nov. 1997, vol. 94, No. 12, pp. 12297-12302.
Nemoto N. et al., "In vitro virus: bonding of mRNA bearing puromycin at the 3'-terminal end to the C-terminal end of its encoded protein on the ribosome in vitro", FEBS Letters, 1997, vol. 414, pp. 405-408.
Yamaguchi J. et al., "cDNA display: a novel screening method for functional disulfide-rich peptides by solid-phase synthesis and stabilization of mRNA-protein fusions", Nucleic Acids Research, 2009; vol. 37, No. 16, e108, pp. 1-13.
Mattheakis L.C. et al., "An in vitro polysome display system for identifying ligands from very large peptide libraries", Proc. Natl. Acad. Sci. USA, Sep. 1994, vol. 91, pp. 9022-9026.
Reiersen H. et al., "Covalent antibody display—an in vitro antibody-DNA library selection system", Nucleic Acids Research, 2005, vol. 33, e10, pp. 1-9.
Odegrip R. et al., "CIS display: In vitro selection of peptides from libraries of protein-DNA complexes", Proc. Natl. Acad. Sci. USA, 2004, vol. 101, No. 9, pp. 2806-2810.
Tawfik D. S. et al., "Man-made cell-like compartments for molecular evolution", Nature Biotechnology, Jul. 1998, vol. 16, 652-656.

(Continued)

*Primary Examiner* — Christina Bradley
(74) *Attorney, Agent, or Firm* — Sughrue Mion, PLLC

(57) ABSTRACT

An object of the present invention is to provide a novel cyclic peptide compound excellent in cell membrane permeability, a method for producing the same, a composition for screening use, and a method for selecting a cyclic peptide compound that binds to a target substance. According to the present invention, a peptide compound represented by Formula (1) or a salt thereof is provided. In the formula, the symbols have the meanings as defined in the specification of the present application.

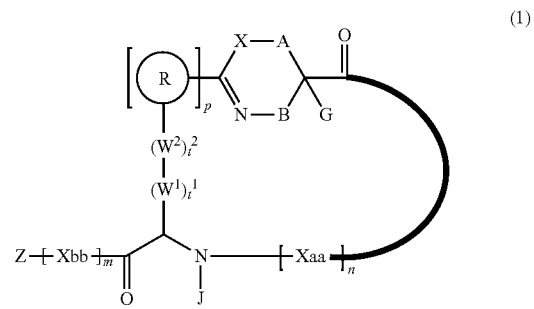

(1)

18 Claims, No Drawings

Specification includes a Sequence Listing.

(56) References Cited

OTHER PUBLICATIONS

Chen H.Z. et al., "Prokaryotic coupled transcription-translation", Methods In Enzymology, 1983; vol. 101, pp. 674-690 (23 pages total).
Gasior E. et al., "The preparation and characterization of a cell-free system from *Saccharomyces cerevisiae* that translates natural messenger ribonucleic acid", The Journal of Biological Chemistry, May 25, 1979, vol. 254, No. 10, pp. 3965-3969 (6 pages total).
Erickson A.H. et al., "Cell-free translation of messenger RNA in a wheat germ system", Methods In Enzymology, 1983, vol. 96, pp. 38-50 (21 pages total).
Jackson R.J. et al., "Preparation and use of nuclease-treated rabbit reticulocyte lysates for the translation of eukaryotic messenger RNA", Methods In Enzymology, 1983, vol. 96, pp. 50-74.
Barton D.J. et al., "Assays for poliovirus polymerase, $3D^{Pol}$, and authentic RNA replication in HeLa S10 extracts", Methods In Enzymology, 1996, vol. 275, pp. 35-57 (28 pages total).
Swerdel M.R. et al., "Cell-free translation in lysates from *Spodoptera frugiperda* (Lepidoptera: Noctuidae) cells", Comp. Biochem. Physiol., 1989, vol. 93B, No. 4, pp. 803-806.
Shimizu Y. et al., "Cell-free translation reconstituted with purified components", Nature Biotechnology, vol. 19, 2001, pp. 751-755.
Shimizu Y. et al., "PURE technology", Methods Molecular Biology, 2010, vol. 607, pp. 11-21.
Anderson J.C. et al., "Adaptation of an orthogonal archaeal leucyl-tRNA and synthetase pair for four-base, amber, and opal suppression", Biochemistry, 2003, vol. 42, pp. 9598-9608.
Murakami H. et al., "Using a solid-phase ribozyme aminoacylation system to reprogram the genetic code", Chemistry and Biology, Nov. 2003, vol. 10, pp. 1077-1084.
Kiga D. et al., "An engineered *Escherichia coli* tyrosyl-tRNA synthetase for site-specific incorporation of an unnatural amino acid into proteins in eukaryotic translation and its application in a wheat germ cell-free system", Proc Natl Acad Sci USA, 2002, vol. 99, No. 15, pp. 9715-9720.
Chin J. W. et al., "An expanded eukaryotic genetic code", Science, 2003, vol. 301, pp. 964-967.
Hartman M.C. et al., "Enzymatic aminoacylation of tRNA with unnatural amino acids", Proc Natl Acad Sci USA, 2006, vol. 103, No. 12, pp. 4356-4361.
Subtelny A.O. et al., "Ribosomal synthesis of N-methyl peptides", J. Am. Chem. Soc., 2008, vol. 130, pp. 6131-6136.
Heckler T.G. et al., "T4 RNA ligase mediated preparation of novel "chemically misacylated" $tRNA^{Phe}_s$", Biochemistry, 1984, vol. 23, pp. 1468-1473.
Murakami H. et al., "Aminoacyl-tRNA synthesis by a resin-immobilized ribozyme", J. Am. Chem. Soc., 2002, vol. 124, pp. 6834-6835.
Hashimoto N.et al., "Simple and quick chemical aminoacylation of tRNA in cationic micellar solution under ultrasonic agitation", Chem. Commun., 2005, vol. 34, pp. 4321-4323.
Ninomiya K. et al., "In situ chemical aminoacylation with amino acid thioesters linked to a peptide nucleic acid", J. Am. Chem. Soc., 2004, vol. 126, pp. 15984-15989.
Josephson K. et al., "Ribosomal synthesis of unnatural peptides", J. Am. Chem. Soc., 2005, vol. 127, p. 11727-11735.
Kwon I., el al., "Breaking the degeneracy of the genetic code", J. Am. Chem. Soc., 2003, 125, pp. 7512-7513.
Meinnel T. et al., "Methionine as translation start signal: A review of the enzymes of the pathway in *Escherichia coli*", Biochimie, 1993, vol. 75, pp. 1061-1075.
Goto Y. et al., "Translation initiation with initiator tRNA charged with exotic peptides", J. Am. Chem. Soc., 2009, vol. 131, No. 14, pp. 5040-5041.
International Search Report dated Jun. 19, 2018 from the International Searching Authority in counterpart International Application No. PCT/JP2018/011143.
International Preliminary Report on Patentability dated Aug. 7, 2019 from the International Bureau in counterpart International Application No. PCT/JP2018/011143.
Written Opinion dated Jun. 19, 2018 from the International Bureau in counterpart International Application No. PCT/JP2018/011143.
Hohsaka T. et al., "Incorporation of Nonnatural Amino Acids into Streptavidin through In Vitro Frame-Shift Suppression", J. Am. Chem. Soc. vol. 118, 1996, pp. 9778-9779.
Clausen D.J. et al., "Modular synthesis and biological activity of pyridyl-based analogs of the potent Class I Histone Deacetylase Inhibitor Largazole", Bioorganic & Medicinal Chemistry, vol. 23, Mar. 31, 2015, pp. 5061-5074.
Just-Baringo X. et al. "Dissecting the Structure of Thiopeptides: Assessment of Thiazoline and Tail Moieties of Baringolin and Antibacterial Activity Optimization", Journal of Medicinal Chemistry, vol. 57,Apr. 16, 2014, pp. 4185-4195.
Clausen, D.J. et al., "Modular Synthesis and Biological Activity of Pyridyl-based Analogs of the Potent Class I Histone Deacetylase Inhibitor Largazole", Bioorg Med Chem., Aug. 1, 2015, vol. 23, No. 15, pp. 5061-5074 (total 36 pages).
Just-Baringo, X. et al., "Dissecting the structure of thiopeptides: assessment of thiazoline and tail moieties of baringolin and antibacterial activity optimization.", J Med Chem., May 22, 2014, vol. 57, No. 10, pp. 4185-4195, Abstract (total 2 pages).
Office Action dated Feb. 12, 2020 from the Intellectual Property India in Indian Application No. 201947039670.
Rouf et al., "Bioactive thiazole and benzothiazole derivatives", European Journal of Medicinal Chemistry, vol. 97, pp. 911-927, XP029171114, 2015 (17 pages total).
Partial Supplementary European Search Report dated Aug. 14, 2020, from the European Patent Office in EP Application No. 18771827.5.
Office Action dated Mar. 25, 2020, from Australian Patent Office in AU Application No. 2018238892.
Office Action dated Mar. 13, 2020, from the Russian Patent Office in Russian Application No. 2019129607.
Office Action dated Nov. 4, 2020, from the Japanese Patent Office in Application No. 2019-507701.
Hearing Notice dated Jul. 2, 2021 issued by the Indian Patent Office in the corresponding Indian patent application No. 201947039670.

PEPTIDE COMPOUND AND METHOD FOR PRODUCING SAME, COMPOSITION FOR SCREENING USE, AND METHOD FOR SELECTING PEPTIDE COMPOUND

CROSS-REFERENCE TO RELATED APPLICATIONS

This application is a Continuation of PCT International Application No. PCT/JP2018/011143 filed on Mar. 20, 2018, which claims priority under 35 U.S.C § 119(a) to Japanese Patent Application No. 2017-053954 filed on Mar. 21, 2017. Each of the above application(s) is hereby expressly incorporated by reference, in its entirety, into the present application.

BACKGROUND OF THE INVENTION

1. Field of the Invention

The present invention relates to a peptide compound, a method for producing the same, and a composition for screening use. The present invention further relates to a method for selecting a peptide compound that binds to a target substance.

2. Description of the Related Art

Peptides containing a cyclic structure or an unnatural amino acid are attracting attention as new drug discovery seeds because those peptides exhibit excellent membrane permeability, target-binding ability, and in vivo stability. For example, JP2012-058092A and literature [Translational synthesis of special cyclic peptides and development for drug discovery, Biochemistry Vol. 82, No. 6, pp 505 to 514, 2010] disclose a method for producing a cyclic peptide compound including a thioether cyclization method or a triazole cyclization method, and a drug search method using the cyclic peptide compound.

The drug search method is based on determining a peptide structure by forming a complex in which a translated peptide and a gene from which the peptide is derived are linked and decoding the gene of the peptide complex bound to a target substance. As a method of forming the complex, WO2000/032823A discloses a method for producing a deoxyribonucleic acid (DNA)-peptide complex including a step of cross-linking a peptide acceptor with a ribonucleic acid (RNA) molecule; a step of translating the RNA to produce a peptide product; and a step of reverse-transcribing the RNA to produce the DNA/peptide complex. In addition, JP2010-284172A discloses a method for producing an RNA-peptide complex including a step of providing an RNA molecule; and a step of chemically linking a peptide acceptor to a 3' end of the RNA molecule to form a covalent bond therebetween.

On the other hand, several methods are known as methods for synthesizing a cyclic compound. For example, US2015/0056137A discloses a method of forming a thiazoline ring, which involves reduction of a disulfide and hydrolysis of an amide bond.

SUMMARY OF THE INVENTION

An object of the present invention is to provide a novel peptide compound exhibiting excellent cell membrane permeability, a method for producing the same, and a composition for screening use. Another object of the present invention is to provide a method for selecting a peptide compound that binds to a target substance.

As a result of extensive studies to achieve the foregoing objects, the present inventors have found that a compound represented by General Formula (1) described in the present specification or a salt thereof has excellent cell membrane permeability. Further, the present inventors have found that the compound represented by General Formula (1) or a salt thereof is a compound useful as a cyclic peptide library. In addition, the present inventors have found that a cyclic peptide can be produced by reacting an amino acid having a cyano group with an amino acid represented by General Formula (2) (an amino acid having a reactive group such as cysteine) in a cell-free translation system. Further, the present inventors found that a method for producing a cyclic peptide by the reaction of an amino acid having a cyano group with an amino acid represented by General Formula (2) is useful for constructing a cyclic peptide library. The present invention has been completed based on these findings.

That is, according to the present invention, the following inventions are provided.

<1> A peptide compound represented by Formula (1) or a salt thereof:

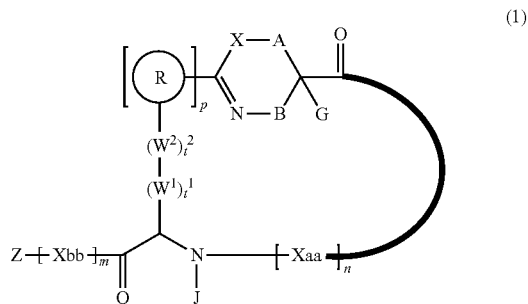

(1)

in the formula,

X represents S, NH, or O;

A represents a single bond, a linear alkylene group having 1 or 2 carbon atoms which may have a substituent, or a divalent group represented by *—CR$^0$=C(B)— together with the carbon atom to which B is bonded, in which R$^0$ represents a hydrogen atom or a substituent, and * represents a position that is bonded to X;

B represents a single bond or a linear alkylene group having 1 or 2 carbon atoms which may have a substituent, provided that A and B are not simultaneously a single bond;

Z represents a hydroxyl group or an amino group;

p pieces of R's may be the same as or different from one another and each represent a heteroarylene group which may have a substituent or an arylene group having 6 to 10 carbon atoms which may have a substituent;

G represents a hydrogen atom or an alkyl group having 1 to 6 carbon atoms which may have a substituent in a case where the carbon to which G is bonded together with A does not form a divalent group represented by *—CR$^0$=C(B)—;

$t^1$ pieces of W$^1$'s may be the same as or different from one another and each represent a single bond, —CH$_2$(C$_6$H$_5$NH)—, —CH$_2$(C$_6$H$_5$O)—, an amino acid residue which may have a substituent, a heteroarylene group which may have a substituent, an arylene group having 6 to 20 carbon atoms which may have a substituent, or an alkylene group having 1 to 6 carbon atoms which may have a substituent;

$t^2$ pieces of $W^2$'s may be the same as or different from one another and each represent a single bond, —CO—, —COO—, —NHCO—, —NHCONH—, —CONHCO—, —(CH$_2$CH$_2$O)—, —(CH$_2$CH$_2$CH$_2$O)—, an amino acid residue which may have a substituent, a heteroarylene group which may have a substituent, an arylene group having 6 to 20 carbon atoms which may have a substituent, or an alkylene group having 1 to 6 carbon atoms which may have a substituent;

J represents a hydrogen atom or an alkyl group having 1 to 6 carbon atoms which may have a substituent;

n pieces of Xaa's each independently represent any amino acid residue or any amino acid analog residue;

m pieces of Xbb's each independently represent any amino acid residue or any amino acid analog residue;

p represents an integer of 0 to 4;

$t^1$ represents an integer of 0 to 6;

$t^2$ represents an integer of 0 to 6;

m represents an integer of 0 to 20; and n represents an integer of 1 to 20.

<2> The peptide compound or the salt thereof according to <1>, in which the peptide compound represented by Formula (1) is a peptide compound represented by Formula (1A):

(1A)

in the formula, $A^1$ represents a linear alkylene group having 1 or 2 carbon atoms which may have a substituent, or a divalent group represented by *—CH=C(N)— together with the carbon atom to which N is bonded, in which * represents a position that is bonded to S;

$p^1$ pieces of $R^1$'s may be the same as or different from one another and each represent a heteroarylene group which may have a substituent or an arylene group having 6 to 10 carbon atoms which may have a substituent;

$t^{11}$ pieces of $W^{11}$'s may be the same as or different from one another and each represent a single bond, —CH$_2$(C$_6$H$_5$NH)—, —CH$_2$(C$_6$H$_5$O)—, an amino acid residue which may have a substituent, a heteroarylene group which may have a substituent, an arylene group having 6 to 20 carbon atoms which may have a substituent, or an alkylene group having 1 to 6 carbon atoms which may have a substituent;

$t^{21}$ pieces of $W^{21}$'s may be the same as or different from one another and each represent a single bond, —CO—, —COO—, —NHCO—, —NHCONH—, —CONHCO—, —(CH$_2$CH$_2$O)—, —(CH$_2$CH$_2$CH$_2$O)—, an amino acid residue which may have a substituent, a heteroarylene group which may have a substituent, an arylene group having 6 to 20 carbon atoms which may have a substituent, or an alkylene group having 1 to 6 carbon atoms which may have a substituent;

$G^1$ represents a hydrogen atom or an alkyl group having 1 to 6 carbon atoms which may have a substituent in a case where the carbon to which $G^1$ is bonded together with $A^1$ does not form a divalent group represented by *—CH=C(N)—;

$J^1$ represents a hydrogen atom or an alkyl group having 1 to 6 carbon atoms which may have a substituent;

$p^1$ represents an integer of 0 to 4;

$t^{11}$ represents an integer of 0 to 6;

$t^{21}$ represents an integer of 0 to 6; and

Z, Xaa, Xbb, m, and n have the same meaning as the definition in <1>.

<3> The peptide compound or the salt thereof according to <1>, in which the peptide compound represented by Formula (1) is a peptide compound represented by Formula (1B):

(1B)

in the formula, $A^2$ represents a linear alkylene group having 1 or 2 carbon atoms which may have a substituent, or a divalent group represented by *—CH=C(N)— together with the carbon atom to which N is bonded, in which * represents a position that is bonded to S;

$G^2$ represents a hydrogen atom or an alkyl group having 1 to 6 carbon atoms which may have a substituent in a case where the carbon to which $G^2$ is bonded together with $A^2$ does not form a divalent group represented by *—CH=C(N)—;

$p^2$ pieces of $R^2$'s may be the same as or different from one another and each represent a heteroarylene group which may have a substituent or an arylene group having 6 to 10 carbon atoms which may have a substituent;

$J^2$ represents a hydrogen atom or an alkyl group having 1 to 6 carbon atoms which may have a substituent;

$p^2$ represents an integer of 0 to 4;

$q^2$ represents an integer of 0 to 6, provide that $p^2$ and $q^2$ are not simultaneously 0; and Z, Xaa, Xbb, m, and n have the same meaning as the definition in <1>.

<4> The peptide compound or the salt thereof according to any one of <1> to <3>, in which the R, $R^1$, or $R^2$ is at least one structure selected from a benzothiazolylene group which may have a substituent, a benzooxazolylene group which may have a substituent, a benzoimidazolylene group which may have a substituent, a benzothiophenylene group which may have a substituent, a benzofuranylene group which may have a substituent, an isobenzofuranylene group which may have a substituent, an indolylene group which may have a substituent, a quinolylene group which may have a substituent, an isoquinolylene group which may have a substituent, a quinazolylene group which may have a substituent, a cinnolylene group which may have a substituent, an indazolylene group which may have a substituent, a benzothiadiazolylene group which may have a substituent, a pyridinylene group which may have a substituent, a pyridazinylene group which may have a substituent, a pyrimidinylene group which may have a substituent, a pyrazinylene group which may have a substituent, a thiazolylene group which may have a substituent, an imidazolylene group which may have a substituent, an oxazolylene group which may have a substituent, an oxadiazolylene group which may have a substituent, a thiadiazolylene group which may have a substituent, a pyrazolylene group which may have a substituent, an isoxazolylene group which may have a substituent, a triazolylene group which may have a substituent, an imidazothiazolylene group which may have a substituent, an imidazopyridinylene group which may have a substituent, an imidazopyridazinylene group which may have a substituent, an imidazopyrimidinylene group which may have a substituent, an imidazopyrazinylene group which may have a substituent, a pyrazolopyrimidinylene group which may have a substituent, a pyrrolopyridinylene group which may have a substituent, a thiophenylene group which may have a substituent, a furanylene group which may have a substituent, a pyrrolene group which may have a substituent, a phenylene group which may have a substituent, and a naphthylene group which may have a substituent.

<5> The peptide compound or the salt thereof according to any one of <1> to <4>, in which R, $R^1$, or $R^2$ is at least one structure selected from a benzothiophenylene group which may have a substituent, an indolylene group which may have a substituent, a quinolylene group which may have a substituent, an indazolylene group which may have a substituent, a pyrrolopyridinylene group which may have a substituent, an imidazopyrazinylene group which may have a substituent, a pyridinylene group which may have a substituent, a pyridazinylene group which may have a substituent, a pyrazinylene group which may have a substituent, a thiazolylene group which may have a substituent, an oxazolylene group which may have a substituent, a triazolylene group which may have a substituent, a thiophenylene group which may have a substituent, and a phenylene group which may have a substituent.

<6> The peptide compound or the salt thereof according to any one of <1> to <5>, in which the total number of amino acid residues and amino acid analog residues constituting a cyclic portion of the peptide compound is 3 to 20.

<7> The peptide compound or the salt thereof according to any one of <1> to <6>, in which the total number of amino acid residues and amino acid analog residues constituting the peptide compound is 3 to 20.

<8> A composition for screening use, comprising:
the peptide compound or the salt thereof according to any one of <1> to <7>.

<9> A method for selecting a peptide compound or a salt thereof that binds to a target substance, comprising:
bringing a target substance into contact with a peptide library containing the peptide compound or the salt thereof according to any one of <1> to <7> to select a peptide compound or a salt thereof that binds to the target substance.

<10> A method for producing a peptide compound or a salt thereof, comprising;
a step of producing a peptide chain having an amino acid residue or amino acid analog residue having a cyano group in the side chain in the peptide chain or at the C-terminus and having a structure of Formula (2) at the N-terminus; and
a step of reacting the cyano group with the structure of Formula (2) to form a cyclic portion having a bond represented by Formula (3):

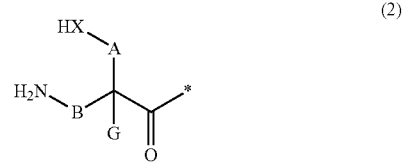

in the formula,
X represents S, NH, or O;
A represents a single bond or a linear alkylene group having 1 or 2 carbon atoms which may have a substituent;
B represents a single bond or a linear alkylene group having 1 or 2 carbon atoms which may have a substituent;
G represents a hydrogen atom or an alkyl group having 1 to 6 carbon atoms which may have a substituent;
* represents a bonding site to a peptide chain; and
A and B are not simultaneously a single bond;

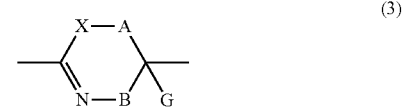

in the formula,
X, A, G, and B have the same meaning as the definition in Formula (2).

<11> A method for selecting a peptide compound that binds to a target substance, comprising:
a step of producing a peptide compound having a cyclic portion by the method according to <10>; and
a step of bringing a target substance into contact with a peptide library containing the peptide compound or the salt thereof to select a peptide compound or a salt thereof that binds to the target substance.

<12> The selection method according to <11>, comprising the following steps:
(i) a step of preparing a nucleic acid library, carrying out translation by a cell-free translation system containing an elongating tRNA acylated with an unnatural amino acid, and preparing a library containing a peptide compound in which the unnatural amino acid is randomly incorporated into a peptide sequence;
(ii) a step of bringing the peptide library into contact with a target substance; and
(iii) a step of selecting a peptide compound that binds to the target substance,
in the step (i), each peptide compound constituting the library is translated from the nucleic acid sequence encoding each peptide compound constituting the library, and the nucleic acid sequence and the peptide as the translation product thereof are linked to construct an in vitro display library, and
the step (iii) includes determining a nucleic acid sequence encoding a peptide compound that binds to a target substance, determining a peptide sequence from the nucleic acid sequence, and selecting a peptide compound.

<13> The method according to any one of <10> to <12>, in which the amino acid residue and/or the amino acid analog residue having the cyano group in the side chain is a structure represented by Formula (4):

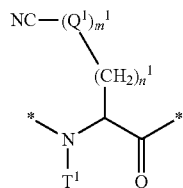

(4)

in the formula, $m^1$ pieces of $Q^1$'s may be the same as or different from one another and represent at least one of a heteroarylene group which may have a substituent, an arylene group having 6 to 10 carbon atoms which may have a substituent, or an alkylene group having 1 to 6 carbon atoms which may have a substituent;

$T^1$ represents a hydrogen atom or an alkyl group having 1 to 6 carbon atoms which may have a substituent;

$n^1$ represents an integer of 0 to 6, and $m^1$ represents an integer of 1 to 4; and

* represents a binding position to the amino acid residue and/or amino acid analog residue constituting the peptide chain.

<14> The method according to any one of <10> to <12>, in which the amino acid residue and/or the amino acid analog residue having the cyano group in the side chain is a structure represented by Formula (5):

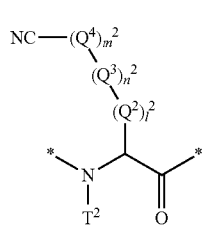

(5)

in the formula, $l^2$ pieces of $Q^2$'s may be the same as or different from one another and each represent a single bond, $-CH_2(C_6H_5NH)-$, $-CH_2(C_6H_5O)-$, an amino acid residue which may have a substituent, a heteroarylene group which may have a substituent, an arylene group having 6 to 20 carbon atoms which may have a substituent, or an alkylene group having 1 to 6 carbon atoms which may have a substituent;

$n^2$ pieces of $Q^3$'s may be the same as or different from one another and each represent a single bond, $-CO-$, $-COO-$, $-NHCO-$, $-NHCONH-$, $-CONHCO-$, $-(CH_2CH_2O)-$, $-(CH_2CH_2CH_2O)-$, an amino acid residue which may have a substituent, a heteroarylene group which may have a substituent, an arylene group having 6 to 20 carbon atoms which may have a substituent, or an alkylene group having 1 to 6 carbon atoms which may have a substituent;

$m^2$ pieces of $Q^4$'s may be the same as or different from one another and represent at least one of a heteroarylene group which may have a substituent, an arylene group having 6 to 10 carbon atoms which may have a substituent, or an alkylene group having 1 to 6 carbon atoms which may have a substituent;

$T^2$ represents a hydrogen atom or an alkyl group having 1 to 6 carbon atoms which may have a substituent;

$l^2$ represents an integer of 0 to 6;

$n^2$ represents an integer of 0 to 6;

$m^2$ represents an integer of 1 to 4; and

* represents a binding position with the amino acid residue and/or amino acid analog residue constituting the peptide chain.

<15> The method according to <13> or <14>, in which the $Q^1$ or $Q^4$ is at least one structure selected from a benzothiazolylene group which may have a substituent, a benzooxazolylene group which may have a substituent, a benzoimidazolylene group which may have a substituent, a benzothiophenylene group which may have a substituent, a benzofuranylene group which may have a substituent, an isobenzofuranylene group which may have a substituent, an indolylene group which may have a substituent, a quinolylene group which may have a substituent, an isoquinolylene group which may have a substituent, a quinazolylene group which may have a substituent, a cinnolylene group which may have a substituent, an indazolylene group which may have a substituent, a benzothiadiazolylene group which may have a substituent, a pyridinylene group which may have a substituent, a pyridazinylene group which may have a substituent, a pyrimidinylene group which may have a substituent, a pyrazinylene group which may have a substituent, a thiazolylene group which may have a substituent, an imidazolylene group which may have a substituent, an oxazolylene group which may have a substituent, an oxadiazolylene group which may have a substituent, a thiadiazolylene group which may have a substituent, a pyrazolylene group which may have a substituent, an isoxazolylene group which may have a substituent, a triazolylene group which may have a substituent, an imidazothiazolylene group which may have a substituent, an imidazopyridinylene group which may have a substituent, an imidazopyridazinylene group which may have a substituent, an imidazopyrimidinylene group which may have a substituent, an imidazopyrazinylene group which may have a substituent, a pyrazolopyrimidinylene group which may have a substituent, a pyrrolopyridinylene group which may have a substituent, a thiophenylene group which may have a substituent, a furanylene group which may have a substituent, a pyrrolene group which may have a substituent, a phenylene group which may have a substituent, and a naphthylene group which may have a substituent.

<16> The method according to any one of <13> to <15>, in which the $Q^1$ or $Q^4$ is at least one structure selected from a benzothiophenylene group which may have a substituent, an indolylene group which may have a substituent, a quinolylene group which may have a substituent, an indazolylene group which may have a substituent, a pyrrolopyridinylene group which may have a substituent, an imidazopyrazinylene group which may have a substituent, a pyridinylene group which may have a substituent, a pyridazinylene group which may have a substituent, a pyrazinylene group which may have a substituent, a thiazolylene group which may have a substituent, an oxazolylene group which may have a substituent, a triazolylene group which may have a substituent, a thiophenylene group which may have a substituent, and a phenylene group which may have a substituent.

<17> The method according to any one of <10> to <16>, in which Formula (2) is a structure represented by Formula (2A):

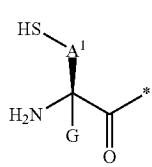

(2A)

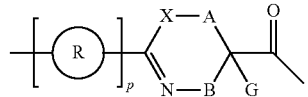

(6)

in the formula,

A¹ represents a linear alkylene group having 1 or 2 carbon atoms which may have a substituent; and G represents a hydrogen atom or an alkyl group having 1 to 6 carbon atoms which may have a substituent.

<18> The method according to any one of <10> to <17>, in which Formula (2) is at least one structure selected from the following formulae.

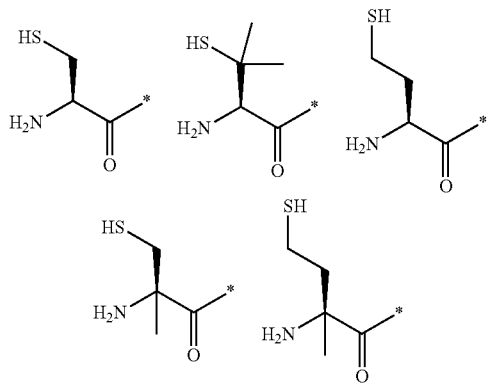

<19> The method according to any one of <10> to <18>, in which a reaction solvent in the step of reacting the cyano group with the structure of Formula (2) to form a bond represented by Formula (3) is water.

<20> The method according to any one of <10> to <19>, in which a pH of a reaction solution in the step of reacting the cyano group with the structure of Formula (2) to form the bond represented by Formula (3) is 6.0 to 8.5.

<21> The method according to any one of <10> to <20>, in which the total number of amino acid residues and amino acid analog residues constituting the cyclic portion of the peptide compound having a cyclic portion is 3 to 20.

<22> The method according to any one of <10> to <21>, in which the total number of amino acid residues and amino acid analog residues constituting the peptide compound having a cyclic portion is 3 to 20.

<23> The method according to any one of <10> to <22>, in which the amino acid residues or amino acid analog residues having a heteroarylene group having a cyano group, an arylene group having a cyano group, or an alkylene group having a cyano group in the side chain are incorporated into the peptide chain using codons that become empty codons by excluding natural amino acids from codons assigned in the translation of natural amino acids, stop codons, or four-base codons.

<24> A composition for screening use, comprising a peptide compound having a cyclic portion or a salt thereof, in which the cyclic portion has a structure represented by Formula (6):

in the formula,

X represents S, NH, or O;

A represents a single bond, a linear alkylene group having 1 or 2 carbon atoms which may have a substituent, or a divalent group represented by *—CR⁰=C(B)— together with the carbon atom to which B is bonded, in which R⁰ represents a hydrogen atom or a substituent and * represents a position that is bonded to X;

B represents a single bond or a linear alkylene group having 1 or 2 carbon atoms which may have a substituent, provided that A and B are not simultaneously a single bond;

p pieces of R's may be the same as or different from one another and each represent a heteroarylene group which may have a substituent or an arylene group having 6 to 10 carbon atoms which may have a substituent;

G represents a hydrogen atom or an alkyl group having 1 to 6 carbon atoms which may have a substituent in a case where the carbon to which G is bonded together with A does not form a divalent group represented by *—CR⁰=C(B)—; and p represents an integer of 0 to 4.

The peptide compound of the present invention exhibits excellent cell membrane permeability. According to the method for producing a peptide compound of the present invention, a cyclic peptide compound having excellent cell membrane permeability can be produced. The peptide compound and composition for screening use of the present invention are useful in a method for selecting a cyclic peptide compound that binds to a target substance.

DESCRIPTION OF THE PREFERRED EMBODIMENTS

Hereinafter, the present invention will be described in detail.

In the present invention, % is % by mass unless otherwise specified.

In the present invention, each term has the following meaning, unless otherwise specified.

In the present invention, "to" is used in the meaning including the numerical values described before and after "to" as the lower limit value and the upper limit value, respectively.

The halogen atom refers to a fluorine atom, a chlorine atom, a bromine atom, or an iodine atom.

The $C_{1-6}$ alkyl refers to a linear or branched $C_{1-6}$ alkyl group such as a methyl group, an ethyl group, a propyl group, an isopropyl group, an n-butyl group, a sec-butyl group, an isobutyl group, a tert-butyl group, a pentyl group, an isopentyl group, a 2-methylbutyl group, a 2-pentyl group, a 3-pentyl group, or a hexyl group.

The $C_{3-8}$ cycloalkyl group refers to a $C_{3-8}$ cycloalkyl group such as a cyclopropyl group, a cyclobutyl group, a cyclopentyl group, a cyclohexyl group, or a cycloheptyl group.

The $C_{1-6}$ alkoxy $C_{1-6}$ alkyl group refers to a $C_{1-6}$ alkyloxy $C_{1-6}$ alkyl group such as a methoxymethyl group or a 1-ethoxyethyl group.

The $C_{6-20}$ aryl $C_{1-6}$ alkyl group refers to a $C_{6-20}$ aryl $C_{1-6}$ alkyl group (aralkyl group in which the alkyl moiety is $C_{1-6}$ alkyl) such as a benzyl group, a diphenylmethyl group, a trityl group, a phenethyl group, a 2-phenylpropyl group, a 3-phenylpropyl group, or a naphthylmethyl group.

The $C_{1-6}$ alkoxy group refers to a linear, cyclic, or branched $C_{1-6}$ alkyloxy group such as a methoxy group, an ethoxy group, a propoxy group, an isopropoxy group, a cyclopropoxy group, a butoxy group, an isobutoxy group, a sec-butoxy group, a tert-butoxy group, a cyclobutoxy, a pentyloxy group, or a hexyloxy group.

The $C_{6-20}$ aryloxy group refers to a $C_{6-20}$ aryloxy group such as a phenoxy group or a naphthyloxy group.

The $C_{1-6}$ alkylthio group refers to a linear or branched $C_{1-6}$ alkylthio group such as a methylthio group, an ethylthio group, a propylthio group, an isopropylthio group, a butylthio, a sec-butylthio group, an isobutylthio group, a tert-butylthio group, a pentylthio group, an isopentylthio group, a 2-methylbutylthio group, a 2-pentylthio group, a 3-pentylthio group, or a hexylthio group.

The $C_{6-20}$ arylthio group refers to a $C_{6-20}$ arylthio group such as a phenylthio group or a 2-naphthylthio group.

The $C_{1-6}$ alkylamino group refers to a linear or branched $C_{1-6}$ alkylamino group such as a methylamino group, an ethylamino group, a propylamino group, an isopropylamino group, a butylamino group, a sec-butylamino group, a tert-butylamino group, a pentylamino group, or a hexylamino group.

The $C_{6-20}$ arylamino group refers to a $C_{6-20}$ arylamino group such as a phenylamino group, a p-tolylamino group, or a 2-naphthylamino group.

The $C_{2-6}$ alkenyl group refers to a linear or branched $C_{2-6}$ alkenyl group such as a vinyl group, an allyl group, propenyl, an isopropenyl group, a butenyl group, an isobutenyl group, a 1,3-butadienyl group, a pentenyl group, or a hexenyl group.

The $C_{3-8}$ cycloalkenyl group refers to a $C_{3-8}$ cycloalkenyl group such as a cyclopropenyl group, a cyclobutenyl group, a cyclopentenyl group, or a cyclohexenyl group.

The $C_{2-6}$ alkynyl group refers to a linear or branched $C_{2-6}$ alkynyl group such as an ethynyl group, a propynyl group, a butynyl group, a pentynyl group, or a hexynyl group.

The $C_{1-6}$ alkylcarbonyl group refers to a $C_{1-6}$ alkylcarbonyl group such as an acetyl group, a propionyl group, a butyryl group, an isobutyryl group, or a pivaloyl group.

The $C_{1-30}$ alkylcarbonyl group refers to a $C_{1-30}$ alkylcarbonyl group such as an acetyl group, a propionyl group, a butyryl group, an isobutyryl group, a pivaloyl group, or a palmitoyl group.

The $C_{6-20}$ arylcarbonyl group refers to an arylcarbonyl group having 6 to 20 carbon atoms such as a benzoyl group.

The heterocyclic carbonyl group refers to a heterocyclic carbonyl group such as a nicotinoyl group, a thenoyl group, a pyrrolidinocarbonyl group, or a furoyl group.

The $C_{1-6}$ alkylsulfonyl group refers to a $C_{1-6}$ alkylsulfonyl group such as a methylsulfonyl group, an ethylsulfonyl group, or a propylsulfonyl group.

The $C_{6-20}$ arylsulfonyl group refers to a $C_{6-20}$ arylsulfonyl group such as a benzenesulfonyl group, a p-toluenesulfonyl group, or a naphthalenesulfonyl group.

The $C_{1-6}$ alkylsulfinyl group refers to a $C_{1-6}$ alkylsulfinyl group such as a methylsulfinyl group, an ethylsulfinyl group, or a propylsulfinyl group.

The $C_{6-20}$ arylsulfinyl group refers to a $C_{6-20}$ arylsulfinyl group such as a benzenesulfinyl group, a p-toluenesulfinyl group, or a naphthalenesulfinyl group.

The $C_{6-20}$ aryl group refers to an aryl group having 6 to 20 carbon atoms such as a phenyl group or a naphthyl group.

The monocyclic nitrogen-containing heterocyclic group refers to a monocyclic nitrogen-containing heterocyclic group containing heteroatoms forming a ring such as an aziridinyl group, an azetidinyl group, a pyrrolidinyl group, a pyrrolinyl group, a pyrrolyl group, a piperidyl group, a tetrahydropyridyl group, a dihydropyridyl group, a pyridyl group, a homopiperidinyl group, an octahydroazocinyl group, an imidazolidinyl group, an imidazolinyl group, an imidazolyl group, a pyrazolidinyl group, a pyrazolinyl group, a pyrazolyl group, a piperazinyl group, a diazepanyl group, a pyrazinyl group, a pyridazinyl group, a pyrimidinyl group, a homopiperazinyl group, a triazolyl group, or a tetrazolyl group and also containing a monocyclic nitrogen-containing heteroaryl.

The monocyclic oxygen-containing heterocyclic group refers to a monocyclic oxygen-containing heterocyclic group containing only an oxygen atom as a heteroatom forming a ring such as an oxetanyl group, a tetrahydrofuranyl group, a furanyl group, a tetrahydropyranyl group, a pyranyl group, a 1,3-dioxanyl group, or a 1,4-dioxanyl group.

The monocyclic sulfur-containing heterocyclic group refers to thienyl, tetrahydrothiopyranyl, 1,1-dioxidotetrahydrothiopyranyl, or the like.

The monocyclic nitrogen/oxygen-containing heterocyclic group refers to a monocyclic nitrogen/oxygen-containing heterocyclic group containing only a nitrogen atom and an oxygen atom as heteroatoms forming a ring such as an oxazolyl group, an isoxazolyl group, an oxadiazolyl group, a morpholinyl group, or an oxazepanyl group.

The monocyclic nitrogen/sulfur-containing heterocyclic group refers to a monocyclic nitrogen/sulfur-containing heterocyclic group containing only a nitrogen atom and a sulfur atom as heteroatoms forming a ring such as a thiazolyl group, an isothiazolyl group, a thiadiazolyl group, a thiomorpholinyl group, a 1-oxidothiomorpholinyl group, or a 1,1-dioxidothiomorpholinyl group.

The monocyclic heterocyclic group refers to a monocyclic nitrogen-containing heterocyclic group, a monocyclic oxygen-containing heterocyclic group, a monocyclic sulfur-containing heterocyclic group, a monocyclic nitrogen/oxygen-containing heterocyclic group, or a monocyclic nitrogen/sulfur-containing heterocyclic group.

The bicyclic nitrogen-containing heterocyclic group refers to a bicyclic nitrogen-containing heterocyclic group containing only a nitrogen atom as a heteroatom forming a ring such as an indolinyl group, an indolyl group, an isoindolinyl group, an isoindolyl group, a benzimidazolyl group, an indazolyl group, a benzotriazolyl group, a pyrazolopyridinyl group, a quinolyl group, a tetrahydroquinolinyl group, a tetrahydroisoquinolinyl, an isoquinolinyl group, a quinolidinyl group, a cinnolinyl group, a phthalazinyl group, a quinazolinyl group, a dihydroquinoxalinyl group, a quinoxalinyl group, a naphthyridinyl group, a purinyl group, a pteridinyl group, or a quinuclidinyl group.

The bicyclic oxygen-containing heterocyclic group refers to a bicyclic oxygen-containing heterocyclic group containing only an oxygen atom as a heteroatom forming a ring such as a 2,3-dihydrobenzofuranyl group, a benzofuranyl group, an isobenzofuranyl group, a chromanyl group, a chromenyl group, an isochromanyl group, a 1,3-benzodioxolyl group, a 1,3-benzodioxanyl group, or a 1,4-benzodioxanyl group.

The bicyclic sulfur-containing heterocyclic group refers to a bicyclic sulfur-containing heterocyclic group containing only a sulfur atom as a heteroatom forming a ring such as a 2,3-dihydrobenzothienyl group or a benzothienyl group.

The bicyclic nitrogen/oxygen-containing heterocyclic group refers to a bicyclic nitrogen/oxygen-containing heterocyclic group containing only a nitrogen atom and an oxygen atom as heteroatoms forming a ring such as a benzoxazolyl group, a benzoisoxazolyl group, a benzooxadiazolyl group, a benzomorpholinyl group, a dihydropyranopyridyl group, a dioxolopyridyl group, a furopyridinyl group, a dihydrodioxynopyridyl group, or a dihydropyridooxazinyl group.

The bicyclic nitrogen/sulfur-containing heterocyclic group refers to a bicyclic nitrogen/sulfur-containing heterocyclic group containing a nitrogen atom and a sulfur atom as heteroatoms forming a ring such as a benzothiazolyl group, a benzoisothiazolyl group, or a benzothiadiazolyl group.

The bicyclic heterocyclic group refers to a bicyclic nitrogen-containing heterocyclic group, a bicyclic oxygen-containing heterocyclic group, a bicyclic sulfur-containing heterocyclic group, a bicyclic nitrogen/oxy gen-containing group, or a bicyclic nitrogen/sulfur-containing heterocyclic group.

The spiro heterocyclic group refers to a spiro heterocyclic group containing one or more nitrogen atoms, oxygen atoms, or sulfur atoms as heteroatoms forming a ring such as a 2,6-diazaspiro[3.3]heptyl group, a 2,7-diazaspiro[3.5]nonyl group, a 2-oxa-6-azaspiro[3.3]heptyl group, a 1,4-dioxaspiro[4.5]decyl group, a 1-oxa-8-azaspiro[4.5]decyl group, or a 1-thia-8-azaspiro[4.5]decyl group.

The bridged heterocyclic group refers to a bridged heterocyclic group which contains one or more nitrogen atoms as heteroatoms forming a ring such as a 3-oxa-8-azabicyclo[3.2.1]octyl group, a 8-oxa-3-azabicyclo[3.2.1]octyl group, or a quinuclidinyl group and may further contain one or more oxygen atoms or sulfur atoms.

The heterocyclic group refers to a monocyclic heterocyclic group, a bicyclic heterocyclic group, a spiro heterocyclic group, or a bridged heterocyclic group.

The alkylene group having 1 to 6 carbons refers to a linear or cyclic $C_{1-6}$ alkylene group, such as a methylene group, an ethylene group, a propylene group, an isopropylene group, an n-butylene group, an n-pentylene group, an n-hexylene group, or a cyclohexylene group.

The arylene group having 6 to 10 carbon atoms refers to an arylene group having 6 to 20 carbon atoms, such as a phenylene group or a naphthylene group.

Here, the number of carbon atoms in the alkylene group having 1 to 6 carbon atoms and the arylene group having 6 to 10 carbon atoms does not include the number of carbon atoms in the substituent. The heteroarylene group refers to a divalent heterocyclic group.

The peptide compound is a general term for compounds formed by an amide bond or ester bond of amino acids or amino acid analogs. In addition, a peptide compound having a cyclic portion (also referred to as a cyclic peptide compound) is a generic term for compounds in which peptide compounds are cyclized through covalent bonds in the same molecule. Compounds obtained by further chemically modifying the above-mentioned compounds are also included in the peptide compound according to the embodiment of the present invention. The peptide compound according to the embodiment of the present invention may have a linear portion.

The amino acid and amino acid analog that constitute the peptide compound may be referred to as amino acid residues and amino acid analog residues, respectively. The amino acid residue and the amino acid analog residue refer to a monovalent or divalent group derived from the amino acid and amino acid analog residue.

The amino acids in the present invention are α, β, and γ-amino acids, and are not limited to natural amino acids (natural amino acids refer to 20 types of amino acids contained in proteins. Specifically, natural amino acids refer to Gly, Ala, Ser, Thr, Val, Leu, lie, Phe, Tyr, Trp, His, Glu, Asp, Gin, Asn, Cys, Met, Lys, Arg, and Pro) and may be unnatural amino acids. Unnatural amino acids refer to amino acids other than the above-mentioned natural amino acids. Natural amino acids present in nature other than the 20 amino acids contained in proteins are unnatural amino acids. In a case of an α-amino acid, it may be either an L-amino acid or a D-amino acid or may be an α,α-dialkyl amino acid. The amino acid side chain may be substituted by a group selected from, for example, a $C_{1-6}$ alkyl group which may have a substituent, a $C_{3-8}$ cycloalkyl group which may have a substituent, a $C_{2-6}$ alkenyl group which may have a substituent, a $C_{2-6}$ alkynyl group which may have a substituent, a $C_{6-20}$ aryl group which may have a substituent, a heterocyclic group which may have a substituent, and a $C_{6-20}$ aryl $C_{1-6}$ alkyl group which may have a substituent, in addition to by a hydrogen atom.

The amino acid analogs are preferably α-hydroxycarboxylic acid and α-mercaptocarboxylic acid. The side chains of α-hydroxycarboxylic acid and α-mercaptocarboxylic acid may have various substituents other than hydrogen atoms as in amino acids (may have free substituents). The steric structures of α-hydroxycarboxylic acid and α-mercaptocarboxylic acid may correspond to either L-form or D-form of amino acid, and the side chains of α-hydroxycarboxylic acid and α-mercaptocarboxylic acid may be substituted by a group selected from, for example, a $C_{1-6}$ alkyl group which may have a substituent, a $C_{3-8}$ cycloalkyl group which may have a substituent, a $C_{2-6}$ alkenyl group which may have a substituent, a $C_{2-6}$ alkynyl group which may have a substituent, a $C_{6-20}$ aryl group which may have a substituent, a heterocyclic group which may have a substituent, and a $C_{6-20}$ aryl $C_{1-6}$ alkyl group which may have a substituent. The number of substituents is not limited to one, and the side chains of α-hydroxycarboxylic acid and α-mercaptocarboxylic acid may have two or more substituents. For example, the side chains of α-hydroxycarboxylic acid and α-mercaptocarboxylic acid may have an S atom and may further have a functional group such as an amino group or a halogen atom.

<Peptide Compound According to Embodiment of Present Invention or Salt Thereof>

The peptide compound according to the embodiment of the present invention or the salt thereof is a peptide compound represented by Formula (1) or a salt thereof. The peptide compound according to the embodiment of the present invention or the salt thereof is excellent in cell membrane permeability, and preferably also in metabolic stability.

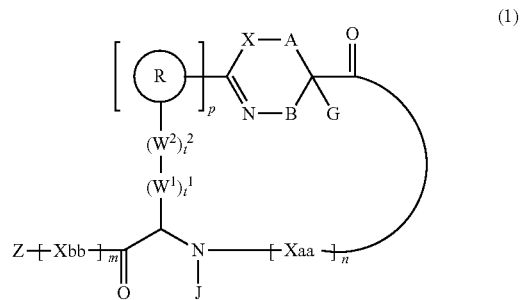

(1)

X represents S, NH, or O. X preferably represents S.

A represents a single bond, a linear alkylene group having 1 or 2 carbon atoms which may have a substituent, or a divalent group represented by *—CR$^O$=C(B)— together with the carbon atom to which B is bonded, in which R$^O$ represents a hydrogen atom or a substituent, and * represents a position that is bonded to X.

A preferably represents a linear alkylene group having 1 or 2 carbon atoms which may have a substituent, or a divalent group represented by *—CR$^O$=C(B)— together with the carbon atom to which B is bonded, in which R$^O$ represents a hydrogen atom or a substituent.

A more preferably represents a linear alkylene group having 1 or 2 carbon atoms which may have a substituent.

A still more preferably represents an ethylene group, or a methylene group which may have a substituent.

A particularly preferably represents a methylene group.

R$^O$ preferably represents a hydrogen atom.

B represents a single bond or a linear alkylene group having 1 or 2 carbon atoms which may have a substituent, provided that A and B are not simultaneously a single bond. B preferably represents a single bond.

In the definitions of A and B, examples of the substituent in the "linear alkylene group having 1 or 2 carbon atoms which may have a substituent" include a $C_{1-6}$ alkyl group, a $C_{3-8}$ cycloalkyl group, a $C_{2-6}$ alkenyl group, a $C_{2-6}$ alkynyl group, a $C_{6-20}$ aryl group, a heterocyclic group, and a $C_{6-20}$ aryl $C_{1-6}$ alkyl group.

Examples of the substituent in the definition of R$^O$ include a $C_{1-6}$ alkyl group, a $C_{3-8}$ cycloalkyl group, a $C_{2-6}$ alkenyl group, a $C_{2-6}$ alkynyl group, a $C_{6-20}$ aryl group, a heterocyclic group, and a $C_{6-20}$ aryl $C_{1-6}$ alkyl group.

G represents a hydrogen atom or an alkyl group having 1 to 6 carbon atoms which may have a substituent in a case where the carbon to which G is bonded together with A does not form a divalent group represented by *—CR$^O$=C(B)—.

G is preferably a methyl group, an ethyl group, or a hydrogen atom, and more preferably a hydrogen atom.

Z represents a hydroxyl group or an amino group. Z preferably represents an amino group.

R represents a heteroarylene group which may have a substituent or an arylene group having 6 to 10 carbon atoms which may have a substituent.

The arylene group having 6 to 10 carbon atoms which may have a substituent that is R is preferably a phenylene group which may have a substituent or a naphthylene group which may have a substituent, and more preferably a phenylene group which may have a substituent.

A preferred example of R may be at least one structure selected from a benzothiazolylene group which may have a substituent, a benzooxazolylene group which may have a substituent, a benzoimidazolylene group which may have a substituent, a benzothiophenylene group which may have a substituent, a benzofuranylene group which may have a substituent, an isobenzofuranylene group which may have a substituent, an indolylene group which may have a substituent, a quinolylene group which may have a substituent, an isoquinolylene group which may have a substituent, a quinazolylene group which may have a substituent, a cinnolylene group which may have a substituent, an indazolylene group which may have a substituent, a benzothiadiazolylene group which may have a substituent, a pyridinylene group which may have a substituent, a pyridazinylene group which may have a substituent, a pyrimidinylene group which may have a substituent, a pyrazinylene group which may have a substituent, a thiazolylene group which may have a substituent, an imidazolylene group which may have a substituent, an oxazolylene group which may have a substituent, an oxadiazolylene group which may have a substituent, a thiadiazolylene group which may have a substituent, a pyrazolylene group which may have a substituent, an isoxazolylene group which may have a substituent, a triazolylene group which may have a substituent, an imidazothiazolylene group which may have a substituent, an imidazopyridinylene group which may have a substituent, an imidazopyridazinylene group which may have a substituent, an imidazopyrimidinylene group which may have a substituent, an imidazopyrazinylene group which may have a substituent, a pyrazolopyrimidinylene group which may have a substituent, a pyrrolopyridinylene group which may have a substituent, a thiophenylene group which may have a substituent, a furanylene group which may have a substituent, a pyrrolene group which may have a substituent, a phenylene group which may have a substituent, and a naphthylene group which may have a substituent.

More preferred example of R may be at least one structure selected from a benzothiophenylene group which may have a substituent, an indolylene group which may have a substituent, a quinolylene group which may have a substituent, an indazolylene group which may have a substituent, a pyrrolopyridinylene group which may have a substituent, an imidazopyrazinylene group which may have a substituent, a pyridinylene group which may have a substituent, a pyridazinylene group which may have a substituent, a pyrazinylene group which may have a substituent, a thiazolylene group which may have a substituent, an oxazolylene group which may have a substituent, a triazolylene group which may have a substituent, a thiophenylene group which may have a substituent, and a phenylene group which may have a substituent.

W$^1$'s may be the same as or different from one another and each represent a single bond, —CH$_2$(C$_6$H$_5$NH)—, —CH$_2$(C$_6$H$_5$O)—, an amino acid residue which may have a substituent, a heteroarylene group which may have a substituent, an arylene group having 6 to 20 carbon atoms which may have a substituent, or an alkylene group having 1 to 6 carbon atoms which may have a substituent. Preferably, W$^1$'s each represent a single bond, CH$_2$(C$_6$H$_5$NH)—, or —CH$_2$(C$_6$H$_5$O)—.

W$^2$'s may be the same as or different from one another and each represent a single bond, —CO—, —COO—, —NHCO—, —NHCONH—, —CONHCO—, —(CH$_2$CH$_2$O)—, —(CH$_2$CH$_2$CH$_2$O)—, an amino acid residue which may have a substituent, a heteroarylene group which may have a substituent, an arylene group having 6 to 20 carbon atoms which may have a substituent, or an alkylene group having 1 to 6 carbon atoms which may have a substituent. Preferably, W$^2$'s each represent a single bond, —NHCO—, —(CH$_2$CH$_2$O)—, an amino acid residue which may have a substituent, or a heteroarylene group which may have a substituent.

As the substituent in the definitions of R, W$^1$, and W$^2$, and the substituent in the structure exemplified as the preferred example of R and the more preferred example of R, the substituents described in Substituent group A$_1$ can be mentioned.

Substituent group A$_1$:
a halogen atom,
a cyano group,
a nitro group,
a formyl group,
a carboxyl group,
a sulfo group, a hydroxyl group,
an amino group,
a mercapto group,
a $C_{1-6}$ alkyl group which may have one or more substituents selected from Substituent group $A_2$,
a $C_{3-8}$ cycloalkyl group which may have one or more substituents selected from Substituent group $A_2$,
a $C_{1-6}$ alkoxy $C_{1-6}$ alkyl group which may have one or more substituents selected from Substituent group $A_2$,
a $C_{6-20}$ aryl $C_{1-6}$ alkyl group which may have one or more substituents selected from Substituent group $A_2$,
a $C_{1-6}$ alkoxy group which may have one or more substituents selected from Substituent group $A_2$,
a $C_{6-20}$ aryloxy group which may have one or more substituents selected from Substituent group $A_2$,
a $C_{1-6}$ alkylamino group which may have one or more substituents selected from Substituent group $A_2$,
a $C_{6-20}$ arylamino group which may have one or more substituents selected from Substituent group $A_2$,
a $C_{1-6}$ alkylthio group which may have one or more substituents selected from Substituent group $A_2$,
a $C_{6-20}$ arylthio group which may have one or more substituents selected from Substituent group $A_2$,
a $C_{2-6}$ alkenyl group which may have one or more substituents selected from Substituent group $A_2$,
a $C_{3-8}$ cycloalkenyl group which may have one or more substituents selected from Substituent group $A_2$,
a $C_{2-6}$ alkynyl group which may have one or more substituents selected from Substituent group $A_2$,
a $C_{6-20}$ aryl group which may have one or more substituents selected from Substituent group $A_2$, a heterocyclic group which may have one or more substituents selected from Substituent group A2,
a $C_{1-30}$ alkylcarbonyl group which may have one or more substituents selected from Substituent group A2,
a $C_{6-20}$ arylcarbonyl group which may have one or more substituents selected from Substituent group A2,
a $C_{1-6}$ alkylsulfonyl group which may have one or more substituents selected from Substituent group A2,
a $C_{6-20}$ arylsulfonyl group which may have one or more substituents selected from Substituent group A2,
a $C_{1-6}$ alkylsulfinyl group which may have one or more substituents selected from Substituent group A2, and
a $C_{6-20}$ arylsulfinyl group which may have one or more substituents selected from Substituent group $A_2$.

Substituent group $A_2$.
a halogen atom,
a hydroxyl group,
a cyano group,
a $C_{1-6}$ alkyl group which may have one or more substituents selected from Substituent group $A_3$,
a $C_{3-8}$ cycloalkyl group which may have one or more substituents selected from Substituent group $A_3$,
a $C_{1-6}$ alkoxy group which may have one or more substituents selected from Substituent group $A_3$,
a $C_{1-6}$ alkoxy $C_{1-6}$ alkyl group which may have one or more substituents selected from Substituent group $A_3$,
a $C_{1-6}$ alkylcarbonyl group which may have one or more substituents selected from Substituent group $A_3$,
a $C_{1-6}$ alkylsulfonyl group which may have one or more substituents selected from Substituent group $A_3$,
a heterocyclic group which may have one or more substituents selected from Substituent group $A_3$,
$NR^{12}R^{13}$ ($R^{12}$ and $R^{13}$ each independently represent a hydrogen atom or a $C_{1-6}$ alkyl group), and
a heterocyclic carbonyl group which may have one or more substituents selected from Substituent group $A_3$.

Substituent group $A_3$:
a halogen atom,
a hydroxyl group,
a cyano group,
a $C_{1-6}$ alkyl group, and
a $C_{1-6}$ alkoxy group.

J represents a hydrogen atom or an alkyl group having 1 to 6 carbon atoms which may have a substituent, and is preferably a methyl group or a hydrogen atom and more preferably a hydrogen atom.

n pieces of Xaa's each independently represent any amino acid residue or any amino acid analog residue.

m pieces of Xbb's each independently represent any amino acid residue or any amino acid analog residue.

p represents an integer of 0 to 4, preferably 0 to 2, and more preferably 0 to 1.

$t^1$ represents an integer of 0 to 6 and preferably an integer of 0 to 2.

$t^2$ represents an integer of 0 to 6 and preferably an integer of 0 to 2.

m represents an integer of 0 to 20. m preferably represents an integer of 0 to 10 and more preferably 0 to 5.

n represents an integer of 1 to 20. n preferably represents an integer of 1 to 18 and more preferably 3 to 13.

The total number of amino acid residues and amino acid analog residues constituting the cyclic portion of the peptide compound is preferably 3 to 20 and more preferably 5 to 15.

The total number of amino acid residues and amino acid analog residues constituting the peptide compound is preferably 3 to 20 and more preferably 5 to 20.

Preferably, the peptide compound represented by Formula (1) is a peptide compound represented by Formula (1A).

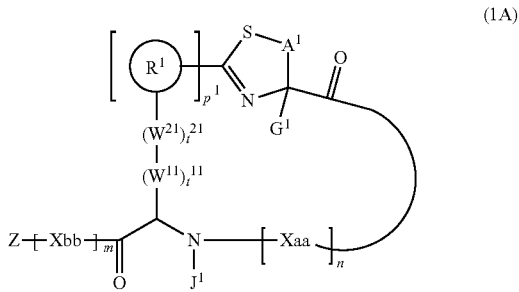

(1A)

$A^1$ represents a linear alkylene group having 1 or 2 carbon atoms which may have a substituent, or a divalent group represented by *—CH=C(N)— together with the carbon atom to which N is bonded, in which * represents a position that is bonded to S.

$A^1$ preferably represents a linear alkylene group having 1 or 2 carbon atoms which may have a substituent.

$A^1$ more preferably represents an ethylene group, or a methylene group which may have a substituent.

$A^1$ still more preferably represents a methylene group.

The substituents in the definition of $A^1$ are the same as described above for the definition of A in Formula (1).

$G^1$ represents a hydrogen atom or an alkyl group having 1 to 6 carbon atoms which may have a substituent in a case where the carbon to which $G^1$ is bonded together with $A^1$ does not form a divalent group represented by *—CH=C(N)—. $G^1$ preferably represents an ethyl group, a methyl group, or a hydrogen atom, and more preferably a hydrogen atom.

$R^1$ represents a heteroarylene group which may have a substituent or an arylene group having 6 to 10 carbon atoms which may have a substituent.

$R^1$ preferably represents a heteroarylene group which may have a substituent or a phenylene group which may have a substituent.

Preferred examples of $R^1$ and more preferred examples of $R^1$ are the same as the preferred examples of R and the more preferred examples of R.

The substituents in the definition of $R^1$ are the same as described above for the definition of R in Formula (1).

$W^{11}$ represents a single bond, $-CH_2(C_6H_5NH)-$, $-CH_2(C_6H_5O)-$, an amino acid residue which may have a substituent, a heteroarylene group which may have a substituent, an arylene group having 6 to 20 carbon atoms which may have a substituent, or an alkylene group having 1 to 6 carbon atoms which may have a substituent. Preferably, $W^{11}$ represents a single bond, $-CH_2(C_6H_5NH)-$, or $-CH_2(C_6H_5O)-$.

$W^{21}$ represents a single bond, $-CO-$, $-COO-$, $-NHCO-$, $-NHCONH-$, $-CONHCO-$, $-(CH_2CH_2O)-$, $-(CH_2CH_2CH_2O)-$, an amino acid residue which may have a substituent, a heteroarylene group which may have a substituent, an arylene group having 6 to 20 carbon atoms which may have a substituent, or an alkylene having 1 to 6 carbon atoms which may have a substituent. Preferably, $W^{21}$ represents a single bond, $-NHCO-$, $-(CH_2CH_2O)-$, an amino acid residue which may have a substituent, or a heteroarylene group which may have a substituent.

$J^1$ represents a hydrogen atom or an alkyl group having 1 to 6 carbon atoms which may have a substituent, and is preferably a methyl group or a hydrogen atom.

$p^1$ represents an integer of 0 to 4, and preferably 0 or 1.

$t^{11}$ represents an integer of 0 to 6, and preferably an integer of 0 to 2.

$t^{21}$ represents an integer of 0 to 6, and preferably an integer of 0 to 2.

Z, Xaa, Xbb, m, and n have the same meanings as the definition in (1).

Preferably, the peptide compound represented by Formula (1) is a peptide compound represented by Formula (IB).

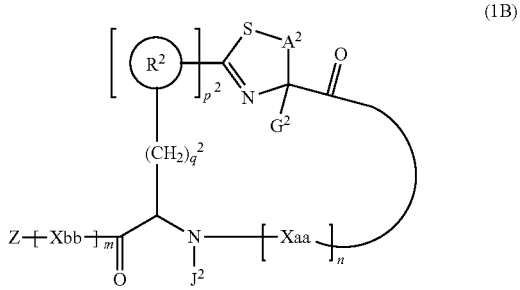

(IB)

$A^2$ represents a linear alkylene group having 1 or 2 carbon atoms which may have a substituent, or a divalent group represented by $*-CH=C(N)-$ together with the carbon atom to which N is bonded, in which * represents a position that is bonded to S.

$A^2$ preferably represents a linear alkylene group having 1 or 2 carbon atoms which may have a substituent.

$A^2$ more preferably represents an ethylene group, or a methylene group which may have a substituent.

$A^2$ still more preferably represents a methylene group.

The substituents in the definition of $A^2$ are the same as described above for the definition of A in Formula (1).

$G^2$ represents a hydrogen atom or an alkyl group having 1 to 6 carbon atoms which may have a substituent in a case where the carbon to which $G^2$ is bonded together with $A^2$ does not form a divalent group represented by $*-CH=C(N)-$. $G^2$ preferably represents an ethyl group, a methyl group, or a hydrogen atom.

$R^2$ represents a heteroarylene group which may have a substituent or an arylene group having 6 to 10 carbon atoms which may have a substituent.

$R^2$ preferably represents a heteroarylene group which may have a substituent or a phenylene group which may have a substituent.

Preferred examples of $R^2$ and more preferred examples of $R^2$ are the same as the preferred examples of R and the more preferred examples of R.

The substituents in the definition of $R^2$ are the same as described above for the definition of R in Formula (1).

$J^2$ represents a hydrogen atom or an alkyl group having 1 to 6 carbon atoms which may have a substituent, and is preferably a methyl group or a hydrogen atom.

$p^2$ represents an integer of 0 to 4, preferably an integer of 0 to 2, and more preferably 0 or 1.

$q^2$ represents an integer of 0 to 6, preferably an integer of 0 to 4, more preferably an integer of 0 to 2, and particularly preferably 0 or 1.

However, $p^2$ and $q^2$ are not simultaneously 0.

Z, Xaa, Xbb, m, and n have the same meanings as the definition in Formula (1).

Examples of the peptide compound or the salt thereof include salts in basic groups such as amino groups, acidic groups such as carboxyl groups, and hydroxyl groups, which are commonly known in the art.

In addition, in a case of simply referring to a peptide compound in the present specification, the peptide compound also includes a salt thereof.

Examples of salts in basic groups include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Examples of salts in acid groups include, for example, salts with alkali metals such as sodium and potassium; salts with Group II metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

In a case where isomers (for example, an optical isomer and a geometric isomer) are present in a peptide compound or a salt thereof, the present invention includes the isomers and also solvates, hydrates, and crystals of various forms.

Composition for Screening Use>

According to the present invention, there is provided a composition for screening use including the above-described peptide compound according to the embodiment of the present invention or a salt thereof.

According to the present invention, there is further provided a composition for screening use including a peptide compound having a cyclic portion or a salt thereof, in which the cyclic portion has a structure represented by Formula (6).

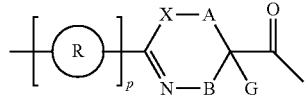
(6)

In the formula,

X represents S, NH, or O;

A represents a single bond, a linear alkylene group having 1 or 2 carbon atoms which may have a substituent, or a divalent group represented by *—CR⁰=C(B)— together with the carbon atom to which B is bonded, in which $R^0$ represents a hydrogen atom or a substituent, and * represents a position that is bonded to X;

B represents a single bond or a linear alkylene group having 1 or 2 carbon atoms which may have a substituent, provided that A and B are not simultaneously a single bond;

p pieces of R's may be the same as or different from one another and each represent a heteroarylene group which may have a substituent or an arylene group having 6 to 10 carbon atoms which may have a substituent;

G represents a hydrogen atom or an alkyl group having 1 to 6 carbon atoms which may have a substituent in a case where the carbon to which G is bonded together with A does not form a divalent group represented by *—CR⁰=C(B)—; and p represents an integer of 0 to 4;

The meanings and preferred ranges of the symbols in Formula (6) are the same as those described above for Formula (1).

The target substance for screening and the screening thereof will be described later in the present specification.

<Method for Producing Peptide Compound>

The method for producing the peptide compound according to the embodiment of the present invention is not particularly limited, and the peptide compound according to the embodiment of the present invention may be produced by a method using a cell-free translation system or may be produced by chemical synthesis of a peptide.

For example, a peptide compound having a cyclic portion can be produced from an acyclic peptide compound containing natural amino acids and unnatural amino acids, in such a manner that a peptide chain (chain-like peptide) having an amino acid residue or amino acid analog residue having a cyano group in the side chain in the peptide chain or at the C-terminus and having the structure of Formula (2) at the N-terminus is produced, and the cyano group is reacted with the structure of Formula (2) to form a cyclic portion having a bond represented by Formula (3).

The peptide compound according to the embodiment of the present invention can also be produced by chemical synthesis. The synthesis of the peptide compound may be solid phase synthesis or liquid phase synthesis, but preferably is solid phase synthesis. Solid phase synthesis of peptide compounds is known to those skilled in the art and examples thereof include a fluorenyl-methoxy-carbonyl group (Fmoc group) synthesis method in which an Fmoc group is used for protection of an amino group, and a tert-butyloxycarbonyl group (Boc group) synthesis method in which a Boc group is used for protection of an amino group. Chemical synthesis of peptide compounds can generally be carried out by an automatic peptide synthesizer.

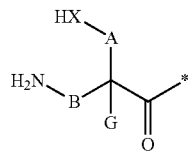
(2)

In Formula (2), X represents S, NH, or O. X preferably represents S.

A represents a single bond or a linear alkylene group having 1 or 2 carbon atoms which may have a substituent.

A preferably represents a linear alkylene group having 1 or 2 carbon atoms which may have a substituent.

A more preferably represents an ethylene group, or a methylene group which may have a substituent.

A still more preferably represents a methylene group.

B represents a single bond or a linear alkylene group having 1 or 2 carbon atoms which may have a substituent. However, A and B are not simultaneously a single bond.

B preferably represents a single bond.

G represents a hydrogen atom or an alkyl group having 1 to 6 carbon atoms which may have a substituent.

G preferably represents a hydrogen atom.

* represents a binding site to the peptide chain.

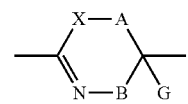
(3)

In the formula (3), X, A, G, and B are as defined in Formula (2).

In the definitions of A and B, examples of the substituent in the "linear alkylene group having 1 or 2 carbon atoms which may have a substituent" include a $C_{1-6}$ alkyl group, a $C_{3-8}$ cycloalkyl group, a $C_{2-6}$ alkenyl group, a $C_{2-6}$ alkynyl group, a $C_{6-20}$ aryl group, a heterocyclic group, and a $C_{6-20}$ aryl $C_{1-6}$ alkyl group.

The amino acid residue or amino acid analog residue having a cyano group in the side chain is preferably a structure represented by Formula (4).

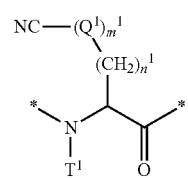
(4)

In Formula (4), $m^1$ pieces of $Q^1$'s may be the same as or different from one another and each represent at least one of a heteroarylene group which may have a substituent, an arylene group having 6 to 10 carbon atoms which may have a substituent, or an alkylene group having 1 to 6 carbon atoms which may have a substituent.

$Q^1$ preferably represents a heteroarylene group which may have a substituent or an arylene group having 6 to 20 carbon atoms which may have a substituent.

$Q^1$ more preferably represents a heteroarylene group which may have a substituent or a phenylene group which may have a substituent.

T¹ represents a hydrogen atom or an alkyl group having 1 to 6 carbon atoms which may have a substituent, and is preferably a methyl group or a hydrogen atom.

n¹ represents an integer of 0 to 6, preferably an integer of 0 to 3, more preferably 1 or 2, and still more preferably 1.

m¹ represents an integer of 1 to 4; preferably 1 or 2, and more preferably 1.

* represents a binding position with the amino acid residue and/or amino acid analog residue constituting the peptide chain.

The amino acid residue or amino acid analog residue having a cyano group in the side chain is preferably a structure represented by Formula (5).

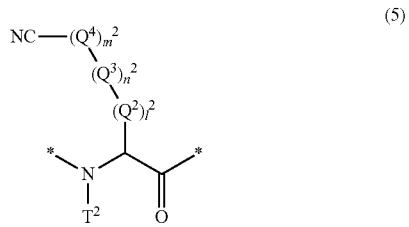

In Formula (5), $Q^2$ represents a single bond, —CH₂ (C₆H₅NH)—, —CH₂(C₆H₅O)—, an amino acid residue which may have a substituent, a heteroarylene group which may have a substituent, an arylene group having 6 to 20 carbon atoms which may have a substituent, or an alkylene group having 1 to 6 carbon atoms which may have a substituent. $Q^2$ preferably represents a single bond, —CH₂ (C₆H₅NH)—, —CH₂(C₆H₅O)—, an amino acid residue which may have a substituent, or a heteroarylene group which may have a substituent.

$Q^3$ represents a single bond, —CO—, —COO—, —NHCO—, —NHCONH—, —CONHCO—, —(CH₂CH₂O)—, —(CH₂CH₂CH₂O)—, an amino acid residue which may have a substituent, a heteroarylene group which may have a substituent, an arylene group having 6 to 20 carbon atoms which may have a substituent, or an alkylene having 1 to 6 carbon atoms which may have a substituent. $Q^3$ preferably represents a single bond, —NHCO—, —(CH₂CH₂O)—, an amino acid residue which may have a substituent, or a heteroarylene group which may have a substituent.

$Q^4$ represents at least one of a heteroarylene group which may have a substituent, an arylene group having 6 to 10 carbon atoms which may have a substituent, or an alkylene group having 1 to 6 carbon atoms which may have a substituent. $Q^4$ preferably represents a heteroarylene group which may have a substituent or an arylene group having 6 to 10 carbon atoms which may have a substituent.

T² represents a hydrogen atom or an alkyl group having 1 to 6 carbon atoms which may have a substituent, and is preferably a methyl group or a hydrogen atom.

$l^2$ represents an integer of 0 to 6 and preferably an integer of 0 to 2;

$n^2$ represents an integer of 0 to 6 and preferably an integer of 0 to 2.

$m^2$ represents an integer of 1 to 4, and preferably 1 or 2.

* represents a binding position with the amino acid residue and/or amino acid analog residue constituting the peptide chain.

A preferred example of $Q^1$ and $Q^4$ may be at least one structure selected from a benzothiazolylene group which may have a substituent, a benzooxazolylene group which may have a substituent, a benzoimidazolylene group which may have a substituent, a benzothiophenylene group which may have a substituent, a benzofuranylene group which may have a substituent, an isobenzofuranylene group which may have a substituent, an indolylene group which may have a substituent, a quinolylene group which may have a substituent, an isoquinolylene group which may have a substituent, a quinazolylene group which may have a substituent, a cinnolylene group which may have a substituent, an indazolylene group which may have a substituent, a benzothiadiazolylene group which may have a substituent, a pyridinylene group which may have a substituent, a pyridazinylene group which may have a substituent, a pyrimidinylene group which may have a substituent, a pyrazinylene group which may have a substituent, a thiazolylene group which may have a substituent, an imidazolylene group which may have a substituent, an oxazolylene group which may have a substituent, an oxadiazolylene group which may have a substituent, a thiadiazolylene group which may have a substituent, a pyrazolylene group which may have a substituent, an isoxazolylene group which may have a substituent, a triazolylene group which may have a substituent, an imidazothiazolylene group which may have a substituent, an imidazopyridinylene group which may have a substituent, an imidazopyridazinylene group which may have a substituent, an imidazopyrimidinylene group which may have a substituent, an imidazopyrazinylene group which may have a substituent, a pyrazolopyrimidinylene group which may have a substituent, a pyrrolopyridinylene group which may have a substituent, a thiophenylene group which may have a substituent, a furanylene group which may have a substituent, a pyrrolene group which may have a substituent, a phenylene group which may have a substituent, and a naphthylene group which may have a substituent.

A more preferred example of $Q^1$ and $Q^4$ may be at least one structure selected from a benzothiophenylene group which may have a substituent, an indolylene group which may have a substituent, a quinolylene group which may have a substituent, an indazolylene group which may have a substituent, a pyrrolopyridinylene group which may have a substituent, an imidazopyrazinylene group which may have a substituent, a pyridinylene group which may have a substituent, a pyridazinylene group which may have a substituent, a pyrazinylene group which may have a substituent, a thiazolylene group which may have a substituent, an oxazolylene group which may have a substituent, a triazolylene group which may have a substituent, a thiophenylene group which may have a substituent, and a phenylene group which may have a substituent.

The structure represented by Formula (2) is preferably a structure represented by Formula (2A).

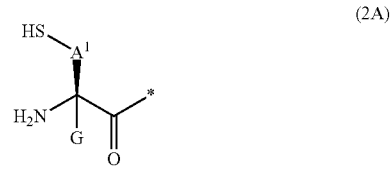

In Formula (2A), $A^1$ represents a linear alkylene group having 1 or 2 carbon atoms which may have a substituent. $A^1$ preferably represents an ethylene group, or a methylene group which may have a substituent. $A^1$ more preferably represents a methylene group.

G represents a hydrogen atom or an alkyl group having 1 to 6 carbon atoms which may have a substituent. G preferably represents an ethyl group, a methyl group, or a hydrogen atom.

Formula (2) is more preferably at least one structure selected from the following formulae.

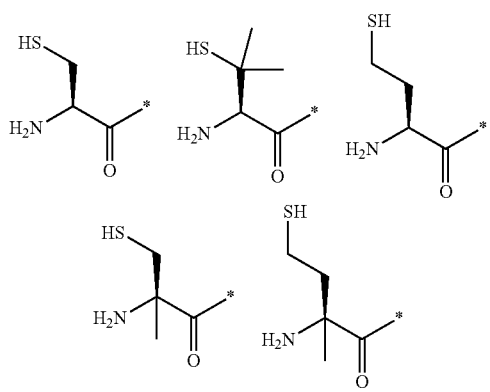

Preferably, a reaction solvent in the step of reacting the cyano group with the structure of Formula (2) to form a bond represented by Formula (3) is water or an organic solvent. In a case where synthesis by a cell-free translation system is used as a method for producing acyclic peptides and cyclic peptides, water is preferable as the reaction solvent.

Water may be pure distilled water, an aqueous solution of a buffer and a salt (such as NaCl), or the distilled water or the aqueous solution further containing an organic solvent and/or a surfactant. In a case of synthesis by a cell-free translation system, it is preferable to use water as the reaction solvent in this manner. Examples of the buffer include suitable buffers having buffer capacity, such as HEPES (2-[4-(2-hydroxyethyl)-1-piperazinyl]ethanesulfonic acid) buffer and phosphate buffer. The organic solvent is preferably an organic solvent that can be mixed with water or a buffer, and examples thereof include methanol, dimethyl sulfoxide, and polyethylene glycol. Examples of the surfactant include Triton X (trade name), Brij (trade name), and Tween (trade name).

The preferable range of the organic solvent content is 20% or less, the more preferable range is 15% or less, and the still preferable range is 10% or less. In a case where the organic solvent is contained, the organic solvent content is greater than 0%.

In a case where chemical synthesis is used as a method for producing acyclic peptides and cyclic peptides, an organic solvent is preferable as the reaction solvent. Examples of the organic solvent include dimethylacetamide, N-methyl-2-pyrrolidone, N,N-dimethylformamide, methanol, ethanol, isopropanol, tetrahydrofuran, dioxane, and acetonitrile. In this case, the organic solvent may be used in admixture with water. In a case of using an organic solvent in admixture with water, the content of the organic solvent is preferably 20% or more, more preferably 20% or more and 70% or less, and still more preferably 30% or more and 60% or less.

Preferably, the pH in the step of reacting the cyano group with the structure of Formula (2) to form a bond represented by Formula (3) is 6.0 to 8.5. The cyclic peptide can be obtained in good yield by adjusting the pH within the above range.

The step of producing a peptide chain having an amino acid residue and/or amino acid analog residue having a cyano group in the side chain in the peptide chain or at the C-terminus and having the structure of Formula (2) at the N-terminus is preferably a step of synthesizing an unprotected acyclic peptide. By synthesizing an unprotected acyclic peptide, the purification of the target cyclic peptide can be simplified in the subsequent step (the step of synthesizing a cyclic peptide). In addition, in a case of using the synthesized peptide as a peptide library, it can be evaluated as it is without post-synthesis deprotection step. The amino acid residue and/or amino acid analog residue having a cyano group in the side chain is preferably an amino acid residue and/or amino acid analog residue having a heteroarylene group having a cyano group, an arylene group having a cyano group, or an alkylene group having a cyano group in the side chain.

The step of reacting the cyano group with the structure of Formula (2) to form a bond represented by Formula (3) is preferably a step carried out without a catalyst. It is preferable from the viewpoint of simplicity that the above step can be carried out without a catalyst.

The total number of amino acid residues and amino acid analog residues constituting the cyclic portion of the peptide compound having a cyclic portion is preferably 3 to 20 and more preferably 5 to 15, from the viewpoint of achieving both binding ability to the target (pharmacological activity) and membrane permeability.

Preferably, the total number of amino acid residues and amino acid analog residues constituting the peptide compound having a cyclic portion is 3 to 20 and more preferably 5 to 20.

In a case where a peptide is synthesized in a cell-free translation system, the amino acid residue or amino acid analog residue having a cyano group in the side chain can be incorporated using stop codons, four-base codons, or codons that become empty codons by excluding natural amino acids from codons assigned in the translation of natural amino acids. Preferably, the amino acid residue or amino acid analog residue having a cyano group in the side chain is incorporated using stop codons and four-base codons.

<Method for Selecting Peptide Compound>

According to the present invention, provided is a method for selecting a peptide compound that binds to a target substance, including bringing a target substance into contact with a peptide library containing the peptide compound according to the embodiment of the present invention or the salt thereof, and selecting a peptide compound or a salt thereof that binds to the target substance.

Further, according to the present invention, provided is a method for selecting a peptide compound that binds to a target substance, including a step of producing a peptide compound further having a cyclic portion by the above-mentioned method of the present invention; and a step of bringing a target substance into contact with a peptide library containing the peptide compound or the salt thereof to select a peptide compound or a salt thereof that binds to the target substance.

The peptide library is an assembly composed of many types of peptides. The selection is an act of selecting a peptide comprising the desired function from the assembly and may be referred to as screening.

The peptide library may be one containing an acyclic peptide compound composed of natural amino acids or one containing a cyclic peptide compound composed of natural amino acids with respect to the peptide compound according to the embodiment of the present invention.

With respect to the peptide compound according to the embodiment of the present invention, one containing an acyclic peptide compound composed of natural amino acids or a cyclic peptide compound composed of natural amino acids is preferred.

The method for selecting a peptide compound that binds to a target substance according to the present invention preferably includes the following steps.

(i) a step of preparing a nucleic acid library, carrying out translation by a cell-free translation system containing an elongating tRNA acylated with an unnatural amino acid, and preparing a library containing a peptide in which the unnatural amino acid is randomly incorporated into a peptide sequence;

(ii) a step of bringing the peptide library into contact with a target substance; and (iii) a step of selecting a peptide compound that binds to the target substance.

The step (i) may be carried out in such a manner that each peptide constituting the library is translated from the nucleic acid sequence encoding the peptide, and the nucleic acid sequence and the peptide as the translation product thereof are linked to construct an in vitro display library.

In the nucleic acid sequence, the region encoding a peptide may include a random sequence consisting of a plurality of repeating different triplets; at least a part of the triplets in the random sequence is a sequence corresponding to a codon specifying an unnatural amino acid; and an unnatural amino acid may be incorporated into the peptide sequence by the pairing of the anticodon of the elongating tRNA acylated with the unnatural amino acid and the codon specifying the unnatural amino acid.

The step (iii) may include determining a nucleic acid sequence encoding a peptide that binds to a target substance, determining a peptide sequence from the nucleic acid sequence, and selecting a peptide compound.

The "nucleic acid" in the present invention can also include deoxyribonucleic acid (DNA), ribonucleic acid (RNA), or a nucleotide derivative having artificial bases. The nucleic acid can also include peptide nucleic acid (PNA). The nucleic acid in the present invention can be any of these nucleic acids or a hybrid thereof as long as the resulting nucleic acid retains genetic information of interest. That is, a DNA-RNA hybrid nucleotide or a chimeric nucleic acid in which different nucleic acids, such as DNA and RNA, are linked together to make a single strand is also included in the nucleic acid in the present invention.

In the present invention, a nucleic acid library (such as a display library) containing these nucleic acids as a template can be suitably used.

In in vitro display, a peptide synthesized using a cell-free translation system (also referred to as an in vitro translation system) is displayed in association with genetic information. As this method, ribosome display, mRNA display, DNA display, or the like is known. Each display method has a mechanism of linking the genetic information recorded in mRNA or DNA to a peptide encoded by the genetic information and thereby assigning them as a [genetic information]-[translation product] complex. In ribosome display, an mRNA-ribosome-peptide complex is formed. In mRNA display, an mRNA-peptide complex is formed. In DNA display, a DNA-peptide complex is formed. Any in vitro display library can be used in the present invention.

It is possible to enrich target-bound peptides by bringing the library into contact with desired immobilized targets and washing away the molecules that do not bind to the targets (panning method). The gene information associated with the peptide selected through such a process can be analyzed to determine the sequence of the protein bound to the target.

For example, a method using the nonspecific conjugation of an antibiotic puromycin, which is an analog of aminoacyl-tRNA, to a protein during its ribosomal mRNA translation elongation has been reported as mRNA display (Proc Natl Acad Sci USA. 1997; 94: 12297-302. RNA-peptide fusions for the in vitro selection of peptides and proteins. Roberts R W, Szostak J W.) or in vitro virus (FEBS Lett. 1997; 414: 405-8. In vitro virus: bonding of mRNA bearing puromycin at the 3'-terminal end to the C-terminal end of its encoded protein on the ribosome in vitro. Nemoto N, Miyamoto-Sato E, Husimi Y, Yanagawa H.).

Spacers such as puromycin are conjugated to the 3'-terminal of an mRNA library obtained by transcription from a DNA library containing a promoter such as T7 promoter. The mRNAs are translated into proteins in a cell-free translation system so that the puromycin is mistakenly incorporated in place of an amino acid into each protein by the ribosome to link the mRNA to the protein encoded thereby, resulting in a library in which mRNAs are associated with their products. This process, which does not involve the transformation of E. coli or the like, achieves high efficiency and can construct a large-scale display library ($10^9$ to $10^{14}$ types of members). cDNA is synthesized from the mRNA serving as a tag involving gene information in the molecule enriched and selected by panning, and then amplified by PCR. The PCR amplification products can be sequenced to determine the sequence of the protein linked to the mRNA. Sites encoding variable amino acid residues in the DNA library used as a template for the library can be obtained by synthesis using a mixture of bases. A string of mixes (N) of 4 bases A, T, G, and C is synthesized as a multiple of 3, or N for the first and second letters in each codon and a 2-base mix (W, M, K, S, and the like) for the third letter are synthesized. In another method, the third base may be set to one type in a case where 16 or less types of amino acids are incorporated. Also, codon units corresponding to 3 letters for each codon are prepared, and a mixture of these codon units at a certain ratio can be used in the synthesis to freely adjust the frequency of appearance of each amino acid residue.

In addition to the mRNA display, cDNA display which is a library composed of peptide-encoding cDNAs linked to peptide-puromycin complexes (Nucleic Acids Res. 2009; 37 (16): e108. cDNA display: a novel screening method for functional disulfide-rich peptides by solid-phase synthesis and stabilization of mRNA-protein fusions. Yamaguchi J, Naimuddin M, Biyani M, Sasaki T, Machida M, Kubo T, Funatsu T, Husimi Y, Nemoto N.); ribosome display which uses the relative stability of ribosome-translation product complexes during mRNA translation (Proc Natl Acad Sci USA. 1994; 91: 9022-6. An in vitro polysome display system for identifying ligands from very large peptide libraries. Mattheakis L C, Bhatt R R, Dower W J.); covalent display which uses the formation of a covalent bond between bacteriophage endonuclease P2A and DNA (Nucleic Acids Res. 2005; 33: e10 Covalent antibody display—an in vitro antibody-DNA library selection system. Reiersen H, Lobersli I, Loset G A, Hvattum E, Simonsen B, Stacy J E, McGregor D, Fitzgerald K, Welschof M, Brekke O H, Marvik O J.); and CIS display which uses the binding of a microbial plasmid replication initiator protein RepA to a replication origin ori (Proc Natl Acad Sci USA. 2004; 101: 2806-10. CIS display: In vitro selection of peptides from libraries of protein-DNA complexes. Odegrip R, Coomber D, Eldridge B, Hederer R, Kuhlman P A, Ullman C, FitzGerald K, McGregor D.) are known as display libraries using the cell-free translation system. In addition, in vitro compartmentalization (Nat Biotechnol. 1998; 16: 652-6. Man-made cell-like compartments for molecular evolution. Tawfik D S, Griffiths A D.) is known in which a transcription-translation system is encapsulated in a water-in-oil emulsion or liposome per DNA molecule constituting a DNA library and subjected to a translation reaction. The method described above can be carried out by appropriately using any of these methods known in the art.

In the present invention, these nucleic acid libraries can be translated using a cell-free translation system described below. In a case of using the cell-free translation system, a spacer-encoding sequence is preferably included downstream of the target nucleic acid. Examples of the spacer sequence include, but are not limited to, sequences containing glycine or serine. In addition, a linker formed by RNA, DNA, hexaethylene glycol (spc18) polymers (for example, five polymers), or the like is preferably included between a compound, such as puromycin or derivative thereof, which is incorporated into a peptide during ribosomal translation, and the nucleic acid library.

Cell-Free Translation System

A protein production system such as a cell-free translation system is preferably used in the method for producing a peptide compound according to the embodiment of the present invention. The cell-free translation system refers to a combination of ribosome extracted from cells as well as a protein factor group involved in translation, tRNAs, amino acids, energy sources (such as adenosine triphosphates (ATPs), and a regeneration system thereof and can translate mRNAs into proteins. The cell-free translation system of the present invention can additionally contain an initiation factor, an elongation factor, a dissociation factor, aminoacyl-tRNA synthetase (ARS), methionyl-tRNA transformylase, and the like. These factors can be obtained by purification from extracts of various cells. Examples of the cells for use in the purification of the factors can include prokaryotic cells and eukaryotic cells. Examples of the prokaryotic cells can include *E. coli* cells, extreme thermophile cells and *Bacillus subtilis* cells. As eukaryotic cells, those made from yeast cells, wheat germs, rabbit reticulocytes, plant cells, insect cells, or animal cells are known.

The cell-free translation system can be obtained by disrupting material cells and adding tRNAs, amino acids, ATPs, and the like to an extract prepared by centrifugation, dialysis, or the like. The material used can be, for example, *E. coli* (Methods Enzymol. 1983; 101: 674-90. Prokaryotic coupled transcription-translation. Chen H Z, Zubay G), yeast (J. Biol. Chem. 1979 254: 3965-3969. The preparation and characterization of a cell-free system from *Saccharomyces cerevisiae* that translates natural messenger ribonucleic acid. E Gasior, F Herrera, I Sadnik, C S McLaughlin, and K Moldave), wheat germs (Methods Enzymol. 1983; 96: 38-50. Cell-free translation of messenger RNA in a wheat germ system. Erickson A H, Blobel G), rabbit reticulocytes (Methods Enzymol. 1983; 96: 50-74. Preparation and use of nuclease-treated rabbit reticulocyte lysates for the translation of eukaryotic messenger RNA. Jackson R J, Hunt T.), Hela cells (Methods Enzymol. 1996; 275: 35-57. Assays for poliovirus polymerase, 3D(Pol), and authentic RNA replication in HeLa S10 extracts. Barton D J, Morasco B J, Flanegan J B.), or insect cells (Comp Biochem Physiol B. 1989; 93: 803-6. Cell-free translation in lysates from *Spodoptera frugiperda* (Lepidoptera: Noctuidae) cells. Swerdel M R, Fallon A M.). The translation can be coupled to transcription from DNA by the addition of RNA polymerase such as T7 RNA polymerase. Meanwhile, PUREfrex (registered trademark) is a reconstituted cell-free translation system containing extracted and purified protein factors necessary for translation in *E. coli*, energy regeneration enzymes, and ribosomes mixed with tRNAs, amino acids, ATPs, guanosine triphosphates (GTPs), and the like. Since PUREfrex has a low content of impurities and, furthermore, is a reconstituted system, a system free from protein factors and amino acids to be excluded can be easily constructed ((i) Nat Biotechnol. 2001; 19: 751-5. Cell-free translation reconstituted with purified components. Shimizu Y, Inoue A, Tomari Y, Suzuki T, Yokogawa T, Nishikawa K, Ueda T.; and (ii) Methods Mol Biol. 2010; 607: 11-21. PURE technology. Shimizu Y, Ueda T.). In the present invention, the method described above can be carried out by appropriately using these methods known in the art.

Various factors, such as ribosome and tRNAs, contained in the cell-free translation system can be purified from *E. coli* cells or yeast cells by a method well known to those skilled in the art. Naturally occurring tRNAs or aminoacyl-tRNA synthetase may be used, or artificial tRNAs or artificial aminoacyl-tRNA synthetase recognizing unnatural amino acids may be used. Use of the artificial tRNAs or artificial aminoacyl-tRNA synthetase can achieve synthesis of a peptide in which unnatural amino acids are incorporated in a site-specific manner.

The translational incorporation of unnatural amino acids into peptides requires aminoacylation of tRNA that has orthogonality and is efficiently incorporated into a ribosome ((i) Biochemistry. 2003; 42: 9598-608. Adaptation of an orthogonal archaeal leucyl-tRNA and synthetase pair for four-base, amber, and opal suppression. Anderson J C, Schultz P G; (ii) Chem Biol. 2003; 10:1077-84. Using a solid-phase ribozyme aminoacylation system to reprogram the genetic code. Murakami H, Kourouklis D, Suga H.; and (iii) JP4917044B). The following five methods can be used as a method for aminoacylating tRNA.

(1) Intracellular tRNA aminoacylation is provided with aminoacyl-tRNA synthetase for each amino acid that binds to tRNA. One method is based on the fact that a predetermined aminoacyl-tRNA synthetase accepts an unnatural amino acid such as N-Me His. That is, in this method, a mutant aminoacyl-tRNA synthetase that accepts an unnatural amino acid is prepared and used ((i) Proc Natl Acad Sci USA. 2002; 99: 9715-20. An engineered *Escherichia coli* tyrosyl-tRNA synthetase for site-specific incorporation of an unnatural amino acid into proteins in eukaryotic translation and its application in a wheat germ cell-free system. Kiga D, Sakamoto K, Kodama K, Kigawa T, Matsuda T, Yabuki T, Shirouzu M, Harada Y, Nakayama H, Takio K, Hasegawa Y, Endo Y, Hirao I, Yokoyama S.; (ii) Science. 2003; 301: 964-7. An expanded eukaryotic genetic code. Chin J W, Cropp T A, Anderson J C, Mukherji M, Zhang Z, Schultz P G. Chin, J W.; and (iii) Proc Natl Acad Sci USA. 2006; 103: 4356-61. Enzymatic aminoacylation of tRNA with unnatural amino acids. Hartman M C, Josephson K, Szostak J W.).

(2) A method of aminoacylating tRNAs and then chemically modifying amino acids in vitro can also be used (J Am Chem Soc. 2008; 130: 6131-6. Ribosomal synthesis of N-methyl peptides. Subtelny A O, Hartman M C, Szostak J W.).

(3) A tRNA lacking CA at the 3'-terminal CCA sequence can be ligated to aminoacylated pdCpA (a dinucleotide composed of deoxycytidine and adenosine) prepared separately by RNA ligase to obtain an aminoacyl-tRNA (Biochemistry. 1984; 23: 1468-73. T4 RNA ligase mediated preparation of novel "chemically misacylated" tRNAPheS. Heckler T Cc Chang L H, Zama Y, Naka T, Chorghade M S, Hecht S M.).

(4) The aminoacylation may be carried out by a ribozyme, called flexizyme, which enables binding of active esters of various unnatural amino acids to tRNAs (J Am Chem Soc. 2002; 124: 6834-5. Aminoacyl-tRNA synthesis by a resin-immobilized ribozyme. Murakami H, Bonzagni N J, Suga H.). Also, a method of ultrasonically mixing tRNAs and amino acid active esters in cationic micelle may be used (Chem Commun (Camb). 2005; (34): 4321-3. Simple and quick chemical aminoacylation of tRNA in cationic micellar solution under ultrasonic agitation. Hashimoto N, Ninomiya K, Endo T, Sisido M.).

J Am Chem Soc. 1996, 118, 9778.). That is, as an amino acid residue or amino acid analog residue having in its side chain a heteroarylene group having a cyano group, an arylene group having a cyano group, or an alkylene group having a cyano group, any of codons that become empty codons by excluding natural amino acids from codons assigned in the translation of the natural amino acids, stop codons, or four-base codons may be used.

In the naturally occurring translation, each one of the 20 types of proteinogenic amino acids and translation termination (stop) is assigned to each of the 64 types of codons according to the universal genetic code table shown below.

TABLE 1

|  |  | Second base | | | |
|---|---|---|---|---|---|
|  |  | U | C | A | G |
| First base | U | UUU, UUC Phenylalanine<br>UUA, UUG Leucine | UCU, UCC, UCA, UCG Serine | UAU, UAC Tyrosine<br>UAA, UAG Stop | UGU, UGC Cysteine<br>UGA Stop<br>UGG Tryptophan |
|  | C | CUU, CUC, CUA, CUG Leucine | CCU, CCC, CCA, CCG Proline | CAU, CAC Histidine<br>CAA, CAG Glutamine | CGU, CGC, CGA, CGG Arginine |
|  | A | AUU, AUC, AUA Isoleucine<br>AUG Methionine | ACU, ACC, ACA, ACG Threonine | AAU, AAC Asparagine<br>AAA, AAG Lysine | AGU, AGC Serine<br>AGA, AGG Arginine |
|  | G | GUU, GUC, GUA, GUG Valine | GCU, GCC, GCA, GCG Alanine | GAU, GAC Asparaginic acid<br>GAA, GAG Glutamic acid | GGU, GGC, GGA, GGG Glycine |

(5) The aminoacylation can be achieved by adding, to a tRNA, an amino acid active ester linked to a PNA complementary to a 3'-terminal region of the tRNA (J Am Chem Soc. 2004; 126: 15984-9. In situ chemical aminoacylation with amino acid thioesters linked to a peptide nucleic acid. Ninomiya K, Minohata T, Nishimura M, Sisido M.).

Although many methods using stop codons as codons for unnatural amino acid incorporation have been reported, a synthesis system from which natural amino acids and ARS are excluded can be constructed by using the PUREfrex (registered trademark). Therefore, unnatural amino acids can be incorporated in place of the excluded natural amino acids for codons encoding the amino acids, that is, unnatural amino acids can be incorporated using codons that become empty codons by excluding natural amino acids from codons assigned in the translation of the natural amino acids (J Am Chem Soc. 2005; 127: 11727-35. Ribosomal synthesis of unnatural peptides. Josephson K, Hartman M C, Szostak J W.). Furthermore, unnatural amino acids can be added without the exclusion of natural amino acids by breaking codon degeneracy and codon expansion by four-base codons (Kwon I, et al., Breaking the degeneracy of the genetic code. J Am Chem Soc. 2003, 125, 7512-3.; and T, Hohsaka et al.

In the present invention, in addition to the codons used in the peptide chain elongation reaction, an initiation codon can also be rewritten. The initiation codon is a codon that indicates the start of translation, and it encodes an initiation amino acid constituting the N-terminus of the peptide on the mRNA. The initiation of mRNA translation requires a specific tRNA, called the initiator tRNA. To initiate translation, the aminoacylated initiator tRNA binds to a small subunit of the ribosome together with an initiation factor (IF), and the small subunit of the ribosome binds to the initiation codon on the mRNA. The initiator tRNA has an anticodon corresponding to the initiation codon and recognizes the initiation codon. In the universal coding table, AUG which is the codon for methionine is generally used as the initiation codon, so the initiator tRNA has an anticodon corresponding to methionine and the initiator tRNA necessarily carries methionine (formyl methionine in a prokaryotic cell).

Use of initiation read-through (skipping of an initiation codon) eliminates the need of preparing plural types of aminoacyl translation initiator tRNAs for the method for synthesizing peptide compounds or peptide compound libraries having diverse termini by the N-terminal incorporation of the amino acid, amino acid analog, or N-terminal carboxylic acid analog other than methionine. The initiation read-through means a phenomenon in which a translated product is generated from an amino acid encoded by the 2nd or later codon in a cell-free translation system containing no translation initiation methionyl tRNA or at the initiation of translation from a translation initiator tRNA with an unnatural amino acid having low translation efficiency, though protein or peptide translation is generally initiated from methionine as the initial amino acid by the translation encoded by an AUG codon.

The method using the initiation read-through can involve allowing any natural amino acid other than methionine to be encoded by the 2nd codon following the initiation codon on a peptide-encoding mRNA sequence, and carrying out translation in a translation system containing neither methionine nor translation initiation methionine-tRNA to obtain a peptide or peptide library having any natural amino acid other than methionine at the N-terminus. According to another report, a method is known, which involves removing the N-terminal methionine of a peptide by the action of enzymes, for example, peptide deformylase and methionine aminopeptidase (Meinnel, T., et al., Biochimie (1993) 75, 1061-1075, Methionine as translation start signal: A review of the enzymes of the pathway in *Escherichia coli*).

Alternative amino acids could also translated as the N-terminus by using an aminoacylated tRNA of desired amino acid instead of that of methionine. The N-terminal incorporation of an unnatural amino acid is known to have higher amino acid tolerance than that during elongation and utilize an amino acid or amino acid analog largely structurally different from a natural amino acid (J Am Chem Soc. 2009 Apr. 15; 131(14): 5040-1. Translation initiation with initiator tRNA charged with exotic peptides. Goto Y, Suga H.).

(Cyclization of Peptide)

In the present invention, a peptide can be cyclized using an intramolecular specific reaction of the translationally synthesized acyclic peptide.

The cyclisation of the peptide is carried out by the following steps (i) and (ii).

(i) a step of synthesizing, by translational synthesis, an acyclic peptide compound having, in the molecule thereof, a pair of functional groups, that is, a functional group 1 and a functional group 2, capable of undergoing a bond formation reaction; and (ii) a step of cyclizing the acyclic peptide compound through the bond formation reaction between the functional group 1 and the functional group 2.

The term "a pair of functional groups capable of undergoing a bond formation reaction" means a pair of functional groups capable of undergoing a bond formation reaction therebetween, that is, between the functional group 1 and the functional group 2 and as a result of the reaction, converting the acyclic peptide compound into a cyclic peptide compound.

In the present invention, a combination of a cyano group and the structure of Formula (2) is used as the above-mentioned pair of functional groups.

That is, in the present invention, the cyclic peptide compound can be produced in such a manner that a peptide chain having an amino acid residue or amino acid analog residue having a cyano group in the side chain in the peptide chain or at the C-terminus and having the structure of Formula (2) at the N-terminus is produced, whereby the cyano group is reacted with the structure of Formula (2) to form the bond represented by Formula (3) described herein.

Since a ring is formed by the bond formation between the above-mentioned pair of functional groups present in the acyclic peptide compound, the elements (typically, amino acids) constituting the acyclic peptide compound need to be one unit, and such a pair of functional groups needs to be present on the units of different constituent element constituents. Such a constituent element is referred to as an amino acid compound, and a unit of the constituent element is referred to as an amino acid compound unit. That is, an acyclic peptide compound is a compound having a pair of functional groups on a different amino acid compound unit. In the acyclic peptide compound, preferably 1 to 18 amino acid compound units, more preferably 1 to 15 amino acid compound units, and still more preferably 3 to 13 amino acid compound units are present between the amino acid compound unit having one functional group and the amino acid compound unit having the other functional group.

Examples of amino acids having the functional group 2 include cysteine, serine, and threonine as natural amino acids. As unnatural amino acids, it is also possible to use unnatural amino acids having an —SH group (for example, penicillamine, homocysteine, and mercaptonorvaline), unnatural amino acids having an —NH$_2$ group (for example, α,β-diaminopropionic acid and α,γ-diaminobutyric acid), or unnatural amino acids having an OH group (for example, homoserine).

The amino acid having the functional group 2 is preferably cysteine, α-methyl cysteine, penicillamine, or homocysteine. The amino acid having a functional group 2 is incorporated in a peptide chain elongation reaction in a reconstituted translation system including at least this amino acid and the corresponding tRNA.

The cyclic peptide compound is synthesized by cyclizing the acyclic peptide compound synthesized as described above. The conditions for the bond formation reaction of functional group 1 and functional group 2 are set according to the type of functional group.

Cyclization of the acyclic peptide compound can be carried out by isolating the acyclic peptide compound and then exposing the isolated acyclic peptide compound to appropriate reaction conditions. Alternatively, cyclization of the acyclic peptide compound can be carried out by adjusting the cell-free translation system to appropriate reaction conditions without isolating the acyclic peptide compound. In addition, depending on the type of a pair of functional groups, cyclization may be carried out under cell-free translation system conditions for synthesizing an acyclic peptide compound. In this case, the cyclic peptide compound can be obtained without any special adjustment of reaction conditions.

Preferred reaction conditions for the cyclization of an acyclic peptide compound are as described hereinbefore.

(Template Nucleic Acid Encoding Peptide)

In the present invention, a library of peptides having a random amino acid sequence may be synthesized by carrying out translational synthesis from a template nucleic acid (mRNA or DNA corresponding thereto) having a random sequence in a region encoding a peptide in a cell-free translation system. Furthermore, by combining a translation system with an in vitro display technology, screening can be carried out in the state where the peptides constituting the library are associated with the nucleic acid sequences encoding the peptides. In this case, peptide aptamers will be selected from a display library in which genetic information is presented (displayed) as a peptide that is its translation product. As a result, each random peptide molecule in the library is attached with a tag that can be amplified and read by a molecular biological technique.

In the present invention, the sequence of RNA or DNA which is the template corresponding to the amino acid sequence of the peptide may be designed to encode a random library of peptides. Specifically, the region encoding the peptide in the base sequence includes a random sequence consisting of a plurality of repeating different triplets, and at least a part of the triplets in the random sequence will be a sequence corresponding to a codon specifying an unnatural amino acid.

In addition, in the region encoding the peptide, at least a part of the four-base (quartet) codons in the random sequence may be a sequence corresponding to a codon specifying an unnatural amino acid.

In the present invention, the RNA or DNA sequence may be designed to encode a cyclic peptide. Specifically, the region encoding the peptide in the base sequence includes, in order, the base sequences corresponding to the following (a) to (c) along the 5'→3' direction of the mRNA sequence:
  (a) a codon specifying an amino acid having a functional group 1;
  (b) a random sequence consisting of a plurality of repeating different triplets; and
  (c) a codon specifying an amino acid having a functional group 2.

The random mRNA sequence is designed such that unnatural amino acids appear with a certain probability in the translational product, random amino acid sequence. That is, in a case where at least a part of the triplets in the random sequence of (b) is a codon specifying an unnatural amino acid, the unnatural amino acid is incorporated into a part of the amino acid sequence of the random peptide which is a translation product. Incorporation of the unnatural amino acid is achieved by pairing an anticodon of tRNA for elongation reaction linked with an unnatural amino acid and a codon specifying an unnatural amino acid in the peptide chain elongation reaction on the ribosome. Furthermore, the bond formation reaction between the functional group 1 and the functional group 2 which is a pair of functional groups capable of undergoing a bond formation reaction cyclizes the peptide which is a translation product. As mentioned above, the tRNA used for incorporation of an unnatural amino acid is preferably an artificial tRNA prepared by an in vitro transcription reaction.

In the present invention, a DNA or RNA molecule corresponding to a base sequence serving as a translation template is added to a cell-free translation system comprised of components optimized according to the intended use. Similar to a protein expression system making use of living cells, the nucleic acid sequence may include a region encoding a desired amino acid sequence and in addition, a base sequence advantageous for translation, depending on a translation system to be employed. For example, in a system using a ribosome derived from *E. coli*, the efficiency of a translation reaction increases in a case where the sequence contains, upstream of the initiation codon, a Shine-Dalgarno (SD) sequence, an epsilon sequence, or the like.

An initiation codon is placed at the N-terminus of the region encoding the peptide. The initiation codon is usually a triplet sequence AUG At the C-terminal side of the sequence, a sequence for linking a nucleic acid molecule to a peptide which is a translation product thereof is included for in vitro display. For example, in a case of using an mRNA display method using a puromycin linker, an mRNA-peptide complex library is formed by adding, to a translation system, an mRNA library linked preliminarily with a puromycin linker. The linker is usually inserted between the 3' end side of the mRNA and puromycin in order to efficiently incorporate puromycin into the A site of a ribosome. Puromycin functions as a substrate (aminoacyl-tRNA analog) of a transpeptidation reaction on the ribosome and it links between mRNA and the peptide by binding to the C-terminus of the elongation peptide. The mRNA display method is a technology of integrating a genotype and a phenotype with each other by linking an mRNA and a peptide through an appropriate linker in an in vitro translation system. Insofar as such an object is achieved, puromycin may be replaced by a linker containing another substance having a similar function, which is within a range of the recognition of those skilled in the art.

The random sequence is composed of a repeat of a codon consisting of a triplet of any sequence an unnatural amino acid such as an amino acid having a cyano group in the side chain. In addition, four-base (quartet) codons may be included in the random sequence, and unnatural amino acids such as amino acids having a cyano group in the side chain may be designated as the four-base codons.

The triplets that make up the random sequence are represented by the $N^1N^2N^3$ codon to illustrate possible sequences. $N^1$ and $N^2$ can each independently be any one of A, U, C, or G In addition, $N^3$ can also be any one of A, U, C, or G Alternatively, $N^3$ can be any one selected from any three of the four bases of A, U, C, and G Alternatively, $N^3$ can be any one selected from any two of the four bases of A, U, C, and G Alternatively, $N^3$ can be defined as one of A, U, C, or G.

For example, the triplet on the mRNA sequence constituting the random sequence may be an NNU codon or NNK codon in which N is a ribonucleotide of any of A, U, C, or G, and K is a ribonucleotide of either C or G (In Vitro Selection)

In the present invention, the peptide library constructed in the cell-free translation system is compatible with in vitro display technology including mRNA display, so that it is possible to create peptide molecules that bind to a target from a high-diversity peptide library having $10^9$ or more peptides.

The in vitro display technology is used as a tool of evolutionary molecular engineering. In this evolutionary molecular engineering, with a view to creating proteins or peptides having a desired function or property, genes having this possibility are prepared on a large scale and a clone having a desired phenotype is selected therefrom. Basically, first, a DNA population (DNA library) is produced. Then, an RNA population (RNA library) is produced as an in vitro transcript, followed by production of a peptide population (peptide library) as an in vitro translation product. From this peptide library, peptides having a desired function or property are selected by using some screening system. For example, in a case where it is desired to obtain a peptide molecule that binds to a specific protein, the peptide population can be poured onto a column on which a target protein is immobilized, and a mixture of peptide molecules bound to the column can be recovered. At this time, each peptide molecule is attached with a nucleic acid molecule, which is a template of the peptide molecule, as if a tag, by in vitro display technology. In a case of mRNA display library, each peptide molecule is attached with mRNA. Therefore, the population of peptide-mRNA complexes thus recovered is converted back into DNA by using a reverse transcriptase, followed by amplification using a polymerase chain reaction (PCR) to obtain a biased library containing many clones having a desired phenotype. Then, the same selection experiment is carried out again. Alternatively, it is also possible to carry out reverse transcription before selection in order to change the nucleic acid portion to a double strand (DNA/RNA hybrid) and thereby avoid possible recovery of an RNA aptamer. By repeating this operation, clones having a desired phenotype are enriched in the population with the passage of the generation.

In a case where a peptide aptamer is identified, a gene of the peptide aptamer that binds to a target substance can be cloned by repeating a step of mixing an in vitro display library and the target substance; selecting an assigning molecule (active species) displaying the peptide that has bound to the target substance; and preparing a nucleic acid library by using PCR from the nucleic acid portion of the assigning molecule thus selected.

Examples of the target substance generally include proteins, nucleic acids, lipids including complex lipids, sugars including sugar chains, and other biomolecules, and further include metals and pigments.

The target substance is preferably an in vivo molecule for the treatment of a disease, in particular, a molecule that does not have a space which can be occupied by a conventional low molecular weight compound having a molecular weight of less than 500 or an intracellular protein that cannot be accessed by a high molecular weight compound such as an antibody, a nucleic acid, an intracellular region of a membrane protein, a transmembrane domain of a membrane protein, or the like.

Examples of target substances include G protein-coupled receptors (GPCRs), nuclear receptors, protein kinases, proteases, esterases, ion channels, metabolic enzymes, unstructured proteins, RNAs, DNAs, fatty acids, phospholipids, and sterols.

Specific examples of target substances include transcription factors such as c-Myc, STAT, AP1, CREB, and SREBP; G protein-coupled receptors (GPCRs) such as GPR143, GRM1, ADORA1, muscarinic acetylcholine receptor, cannabinoid receptor, GLP-1 receptor, and PTH receptor; cytokines such as TNF, TNFR, IL-6, and IL-6R, and receptors thereof; ionotropic receptors such as P2X receptor and nicotinic acetylcholine receptor; tyrosine kinase type receptors such as EGFR and PDGFR; cytoplasmic proteins such as p53, XIAP, Mcl-1, Bcl-2, MDM2, MLL, BRD4, USP7, and YAP; microRNAs such as miR-21 and miR206; and DNAs such as cfDNA and mitochondrial DNA.

In addition, a metal such as gold, silver, copper, platinum, or palladium or a metal salt thereof may be the target substance, or a pigment such as titanium oxide, barium sulfate, carbon black, silica, iron oxide, azo coloring agent, phthalocyanine, or anthraquinone may be the target substance.

In order to select the active species, it is necessary to bring a [genetic information]-[peptide] complex into contact with the target substance and separate and recover a complex that displays the peptide bound to the target substance from a number of other complexes not bound to the target substance by an appropriate method. Many techniques are known as such a recovery method.

For example, it is convenient to subject the target substance to a modification that can be recovered by binding to a solid phase. For example, the target substance may be biotin-modified and recovered using specific binding to an immobilized biotin-binding protein. Examples of such specific binding that can be used herein include, but are not limited to, a combination of maltose-binding protein/maltose, a combination of polyhistidine peptide/metal ion (nickel, cobalt, or the like), a combination of glutathione-S-transferase/glutathione, and a combination of antibody/antigen (epitope) combinations, in addition to a combination of biotin-binding protein (avidin, streptoavidin, or the like)/biotin.

The present invention includes creating a peptide that binds to a target substance by repeating in vitro selection having the following steps: bringing a peptide library into contact with a target substance, selecting an active species displaying the peptide that has bound to the target substance, amplifying the nucleic acid sequence of the thus-selected active species, and selecting the active species from the library of peptides synthesized again in a cell-free translation system with the amplified nucleic acid sequence as a template.

Creation of a peptide compound that binds to a target substance includes recovering an active species displaying the peptides that have bound to the target substance, analyzing the nucleic acid sequence of the recovered active species, determining a peptide sequence from the nucleic acid sequence, selecting appropriate peptides based on the resulting peptide sequence, and obtaining an amino acid sequence and a nucleic acid sequence of the peptides that bind to the target substance. Moreover, based on the sequence information thus obtained, peptides can be synthesized, purified, and isolated by using any method. By evaluating binding of the resulting peptides to the target protein and confirming inhibitory activity of the resulting peptides against the target protein, peptides with high activity can be obtained.

EXAMPLES

The present invention will be described with reference to the following Examples, but the present invention is not limited thereto.

Unless otherwise stated, purification by column chromatography was carried out using an automatic purification apparatus ISOLERA (available from Biotage AB) or a medium pressure liquid chromatograph YFLC W-prep 2XY (available from Yamazen Corporation).

Unless otherwise specified, a SNAP KP-Sil Cartridge (available from Biotage AB), or a high flash column W001, W002, W003, W004, or W005 (available from Yamazen Corporation) was used as the carrier for silica gel column chromatography.

SNAP KP-NH Cartridge (available from Biotage AB) was used as NH silica.

The mixing ratio in the eluent is a volume ratio.

For example, "chloroform/methanol=90/10→50/50" means that the eluent of "chloroform/methanol=90/10" is changed to the eluent of "chloroform/methanol=50/50".

Mass spectra (MS) were measured using an ionization method which simultaneously carries out ACQUITY SQD LC/MS System (available from Waters Corporation, Ionization: ElectroSpray Ionization (ESI)) or LCMS-2010 EV (available from Shimadzu Corporation, Ionization: ESI and Atmospheric Pressure Chemical Ionization (APCI)).

Unless otherwise stated, MS in the table means MS (ESI m/z): (M+H).

The microwave reactor used was Initiator™ (available from Biotage AB). The flow hydrogenation reactor used was H-Cube (available from ThalesNano, Inc.).

Nuclear magnetic resonance (NMR) spectra were measured using Bruker AV300 (available from Bruker Corporation) with tetramethylsilane as internal standard, in which all $\delta$ values are shown in ppm.

The retention time (RT) was measured using SQD (available from Waters Corporation) and is shown in minutes (min).

Column: Waters BEHC 18 1.7 μm, 2.1×30 mm
Solvent: liquid A: 0.1% formic acid-water
liquid B: 0.1% formic acid-acetonitrile
Gradient cycle: 0.00 min (liquid A/liquid B=95/5), 2.00 min (liquid A/liquid B=5/95), 3.00 min (liquid A/liquid B=5/95)
Flow rate: 0.5 mL/min
Column temperature: room temperature
Detection wavelength: 254 nm Matrix-assisted laser desorption ionization-time of flight mass spectrum (MALDI-TOF MS) used was UltrafleXtreme MALDI-TOF/TOF MS (manufactured by Bruker Daltonics, Inc.). The matrix used was α-cyano-4-hydroxycinnamic acid.

Synthesis of 4-bromo-2-cyanothiazole

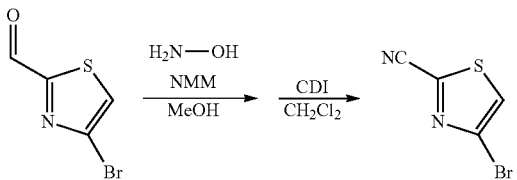

430 μL of N-methylmorpholine (NMM) and hydroxylamine hydrochloride (200 mg) were added to a methanol (MeOH) solution (5 mL) of 4-bromo-1,3-thiazole-2-carbaldehyde (500 mg), which was then stirred at room temperature for 12 hours. After the solvent was distilled off under reduced pressure, distilled water and ethyl acetate were added and an extraction operation was carried out. The organic layer was washed with distilled water and saturated saline and dried over magnesium sulfate. 10 mL of dichloromethane and 430 mg of 1,1'-carbonyldiimidazole (CDI) were added to the resulting residue, which was then stirred at room temperature for 2 hours. The solvent was distilled off, and the residue was purified by column chromatography (silica gel, ethyl acetate/hexane=0/100→10/90) to give 450 mg of the title compound as a yellow solid.

MS(ESI m/z): 190.9 (M+H)
RT(min): 1.06

Synthesis of 4-bromo-2-cyanofuran

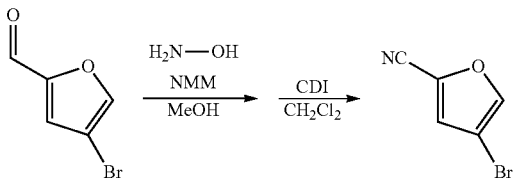

The procedure was carried out in the same manner as the synthesis of 4-bromo-2-cyanothiazole.

MS(ESI m/z): 172.0 (M+H)
RT(min): 1.18

Synthesis of 3-bromo-4-nitrobenzonitrile

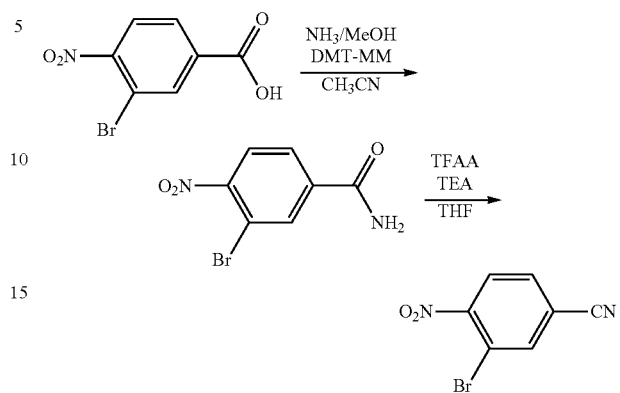

(1) Synthesis of 3-bromo-4-nitrobenzamide 4-(4,6-dimethoxy-1,3,5-triazin-2-yl)-4-methylmorpholinium chloride (DMT-MM) (3.95 g) and a methanol solution of ammonia (7 mol/L, 8 mL) were added to an acetonitrile solution (20 mL) of 3-bromo-4-nitrobenzoic acid (2.35 g), which was then stirred at room temperature for 3.5 hours. A saturated aqueous sodium hydrogen carbonate solution was added to the reaction solution, followed by extraction with ethyl acetate. The organic layer was washed with distilled water, a saturated aqueous sodium hydrogen carbonate solution and saturated saline, and dried over magnesium sulfate. The solvent was distilled off under reduced pressure to give 2.26 g of the title compound as a pale yellow solid.

MS(ESI m/z): 246.9 (M+H)
RT(min): 0.96

(2) Synthesis of 3-bromo-4-nitrobenzonitrile 10 mL of tetrahydrofuran (THF) and 4 mL of triethylamine (TEA) were added to 2.0 g of 3-bromo-4-nitrobenzamide. Under an ice bath, 1.8 mL of trifluoroacetic anhydride (TFAA) was added dropwise thereto, followed by stirring for 2 hours. After the solvent was distilled off, distilled water and ethyl acetate were added to the resulting residue, followed by extraction with ethyl acetate. The organic layer was washed with a saturated aqueous sodium hydrogen carbonate solution and saturated saline and dried over magnesium sulfate. The solvent was distilled off under reduced pressure, and the residue was purified by column chromatography (silica gel, ethyl acetate/hexane=0/100→15/85) to give 1.45 g of the title compound as a pale yellow solid.

MS(ESI m/z): 228.1 (M+H)
RT(min): 1.31

Synthesis of 6-bromobenzo[b]thiophene-2-carbonitrile

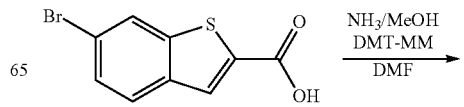

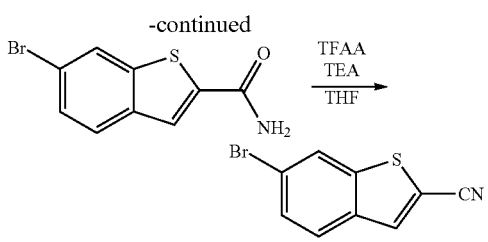

Starting from 6-bromobenzo[b]thiophene-2-carboxylic acid, the procedure was carried out in the same manner as the synthesis of 3-bromo-4-nitrobenzonitrile.

$^1$H-NMR (CDCl$_3$) δ: 8.03 (1H, s), 7.86 (1H, s), 7.75 (1H, d, J=8.6 Hz), 7.59 (1H, dd, J=8.6, 2.0 Hz).
MS(ESI m/z): 239.0 (M+H)
RT(min): 1.69

Synthesis of 6-bromobenzofuran-2-carbonitrile

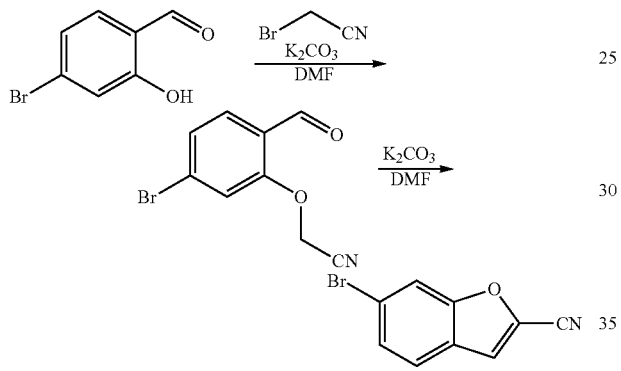

(1) Synthesis of 2-(5-bromo-2-formylphenoxy)acetonitrile

N,N-dimethylformamide (DMF) (5 mL), potassium carbonate (1.2 g), and bromoacetonitrile (460 μL) were added to 4-bromo-2-hydroxybenzaldehyde (1.1 g), which was then stirred at room temperature for 15 hours. Distilled water and ethyl acetate were added to the reaction solution, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=0/100→10/90→30/70) to give 1.1 g of the title compound as a pale yellow oil.
MS(ESI m/z): 241.0 (M+H)
RT(min): 1.25

(2) Synthesis of 6-bromobenzofuran-2-carbonitrile

DMF (10 mL) and potassium carbonate (0.95 g) were added to 2-(5-bromo-2-formylphenoxy)acetonitrile (1.1 g), which was then stirred at 100° C. for 1 hour. Distilled water and ethyl acetate were added to the reaction solution, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=0/100→10/90) to give 1.1 g of the title compound as a pale yellow solid.

$^1$H-NMR (CDCl$_3$) δ: 7.76 (1H, s), 7.59-7.47 (2H, m), 7.44 (1H, s).
MS(ESI m/z): 223.0 (M+H)
RT(min): 1.64

Synthesis of 4-bromo-1-(tetrahydro-2H-pyran-2-yl)-1H-pyrazole-3-carbonitrile

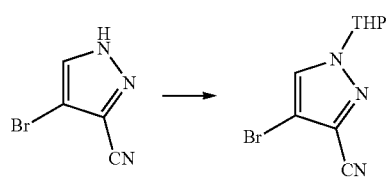

3,4-dihydropyran (0.98 mL) and trifluoroacetic acid (47 μL) were added to a solution of 4-bromo-1H-pyrazole-3-carbonitrile (1.06 g) in THF (14 mL), which was then stirred at 60° C. for 18 hours. The solvent was distilled off under reduced pressure, and the resulting residue was dissolved in dichloromethane. The organic layer was washed with a saturated aqueous sodium hydrogen carbonate solution and dried over magnesium sulfate. The solvent was distilled off under reduced pressure, and the residue was purified by column chromatography (silica gel, ethyl acetate/hexane=0/100→13/87→25/75) to give 1.30 g of the title compound as a white solid.
MS(ESI m/z): 256.8 (M+H)
RT(min): 1.44

Synthesis of tert-butyl (R)-2-((tert-butoxycarbonyl)amino)-3-iodopropanoate

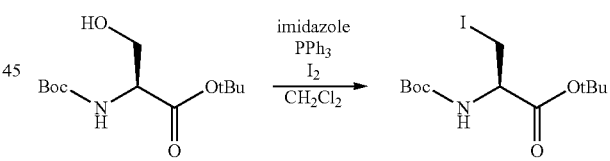

Iodine (7.29 g) was added to a dichloromethane solution (50 mL) of triphenylphosphine (PPh$_3$) (7.35 g) and imidazole (1.96 g) under an ice bath, and then the temperature of the solution was raised to room temperature, followed by stirring for 1 hour. Then, a dichloromethane solution (10 mL) of tert-butyl (tert-butoxycarbonyl)-L-serinate (Boc-Ser-OtBu) (5.0 g) was added dropwise thereto under an ice bath. Boc represents a tert-butoxycarbonyl group, and tBu represents t-butyl. After completion of the dropwise addition, the temperature of the solution was raised to room temperature, followed by stirring for 16 hours. The insolubles were filtered off, the solvent was distilled off under reduced pressure, and the residue was purified by column chromatography (silica gel, ethyl acetate/hexane=0/100→5/95) to give 5.35 g of the title compound as a pale yellow solid.
MS(ESI m/z): 372.1 (M+H)
RT(min): 1.83

Synthesis of tert-butyl (S)-2-((tert-butoxycarbonyl)amino)-3-(2-cyanoquinolin-6-yl)propanoate

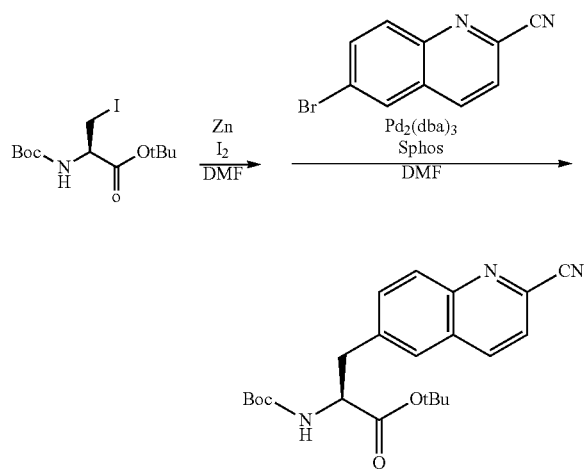

DMF (2 mL) and iodine (25 mg) were added to zinc powder (116 mg), which was then stirred for 5 minutes under a nitrogen atmosphere. Thereafter, tert-butyl (R)-2-((tert-butoxycarbonyl)amino)-3-iodopropanoate (226 mg) and iodine (25 mg) were added thereto, followed by further stirring at room temperature under a nitrogen atmosphere for 30 minutes. 6-bromoquinoline-2-carbonitrile (185 mg), tris(dibenzylideneacetone)dipalladium (0) (also referred to as Pd$_2$(dba)$_3$) (13 mg), and 2-dicyclohexylphosphino-2',6'-dimethoxybiphenyl (Sphos) (12 mg) were added to the solution which was then stirred for 4 hours under a nitrogen atmosphere at 60° C. The insolubles were removed by filtration through celite, the solvent of the filtrate was distilled off, and the residue was purified by column chromatography (silica gel, ethyl acetate/hexane=0/100→15/85) to give 90 mg of the title compound as a pale yellow oil.

MS(ESI m/z): 398.2 (M+H)

RT(min): 1.72

The synthesis of the compounds shown in Table 2 below was carried out in the same manner as the synthesis of tert-butyl (S)-2-((tert-butoxycarbonyl)amino)-3-(2-cyanoquinolin-6-yl)propanoate.

TABLE 2

| R | Compound name | Observed MS | RT/min |
|---|---|---|---|
| quinoline-6-yl (2-CN) | tert-butyl (S)-2-((tert-butoxycarbonyl)amino)-3-(2-cyanoquinolin-6-yl)propanoate | 398.2 | 1.72 |
| quinoline-2-yl (6-CN) | tert-butyl (S)-2-((tert-butoxycarbonyl)amino)-3-(6-cyanoquinolin-2-yl)propanoate | 398.1 | 1.70 |
| pyridin-3-yl (6-CN) | tert-butyl (S)-2-((tert-butoxycarbonyl)amino)-3-(6-cyanopyridin-3-yl)propanoate | 348.0 | 1.55 |
| pyrimidin-5-yl (2-CN) | tert-butyl (S)-2-((tert-butoxycarbonyl)amino)-3-(2-cyanopyrimidin-5-yl)propanoate | 349.0 | 1.57 |
| pyrazin-2-yl (5-CN) | tert-butyl (S)-2-((tert-butoxycarbonyl)amino)-3-(5-cyanopyrazine-2-yl)propanoate | 349.0 | 1.58 |
| pyridazin-3-yl (6-CN) | tert-butyl (S)-2-((tert-butoxycarbonyl)amino)-3-(6-cyanopyridazin-3-yl)propanoate | 349.0 | 1.48 |
| pyridin-2-yl (5-CN) | tert-butyl (S)-2-((tert-butoxycarbonyl)amino)-3-(5-cyanopyridin-2-yl)propanoate | 348.0 | 1.56 |

TABLE 2-continued

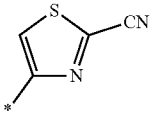 [SMILES: *c1csc(C#N)n1]

| R | Compound name | Observed MS | RT/min |
|---|---|---|---|
| 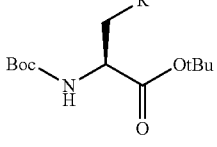 | tert-butyl (S)-2-((tert-butoxycarbonyl)amino)-3-(2-cyanothiazol-4-yl)propanoate | 354.0 | 1.64 |
|  | tert-butyl (S)-2-((tert-butoxycarbonyl)amino)-3-(5-cyanothiophen-3-yl)propanoate | 353.2 | 1.75 |
| 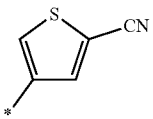 | tert-butyl (S)-2-((tert-butoxycarbonyl)amino)-3-(6-cyano-5-methylpyridin-3-yl)propanoate | 362.1 | 1.62 |
| 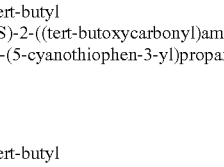 | tert-butyl (S)-2-((tert-butoxycarbonyl)amino)-3-(6-cyano-5-methoxypyridin-3-yl)propanoate | 378.1 | 1.58 |
| 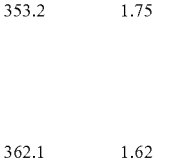 | tert-butyl (S)-2-((tert-butoxycarbonyl)amino)-3-(6-cyano-5-fluoropyridin-3-yl)propanoate | 366.4 | 1.70 |
| 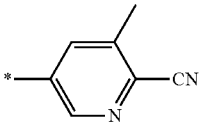 [SMILES: *c1cnc(C#N)c(C)c1] | tert-butyl (S)-2-((tert-butoxycarbonyl)amino)-3-(4-cyanopyridin-2-yl)propanoate | 348.1 | 1.57 |
| 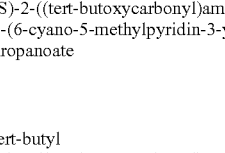 | tert-butyl (S)-2-((tert-butoxycarbonyl)amino)-3-(6-cyanopyridin-2-yl)propanoate | 348.1 | 1.60 |
| 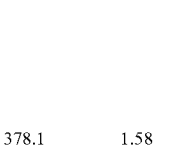 | tert-butyl (S)-2-((tert-butoxycarbonyl)amino)-3-(2-cyanopyridin-3-yl)propanoate | 348.1 | 1.57 |
| 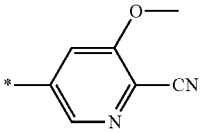 | tert-butyl (S)-2-((tert-butoxycarbonyl)amino)-3-(4-cyanothiazol-2-yl)propanoate | 354.1 | 1.60 |
| 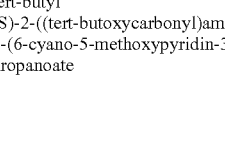 | tert-butyl (S)-2-((tert-butoxycarbonyl)amino)-3-(5-cyanofuran-3-yl)propanoate | 337.1 | 1.67 |

TABLE 2-continued

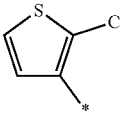

| R | Compound name | Observed MS | RT/min |
|---|---|---|---|
| thiophene-CN | tert-butyl (S)-2-((tert-butoxycarbonyl)amino)-3-(2-cyanothiophen-3-yl)propanoate | 353.1 | 1.69 |
| benzothiophene-CN | tert-butyl (S)-2-((tert-butoxycarbonyl)amino)-3-(2-cyanobenzo[b]thiophen-6-yl)propanoate | 403.0 | 1.89 |
| benzofuran-CN | tert-butyl (S)-2-((tert-butoxycarbonyl)amino)-3-(2-cyanobenzofuran-6-yl)propanoate | 387.1 | 1.86 |
| indole-CN | tert-butyl (S)-2-((tert-butoxycarbonyl)amino)-3-(2-cyano-1H-indol-5-yl)propanoate | 386.1 | 1.71 |
| O$_2$N-phenyl-CN | tert-butyl (S)-2-((tert-butoxycarbonyl)amino)-3-(5-cyano-2-nitrophenyl))propanoate | 392.0 | 1.72 |
| MeO-phenyl-NH$_2$ | tert-butyl (S)-3-(5-amino-2-methoxyphenyl)-2-((tert-butoxycarbonyl)amino)propanoate | 367.1 | 1.13 |
| NH$_2$/NO$_2$-phenyl | tert-butyl (S)-3-(4-amino-3-nitrophenyl)-2-((tert-butoxycarbonyl)amino)propanoate | 382.0 | 1.64 |
| NO$_2$/OH-phenyl | tert-butyl (S)-2-((tert-butoxycarbonyl)amino)-3-(3-hydroxy-4-nitrophenyl)propanoate | 383.1 | 1.74 |

Synthesis of tert-butyl (S)-2-((tert-butoxycarbonyl)amino)-3-(2-cyanobenzo[d]thiazol-6-yl)propanoate

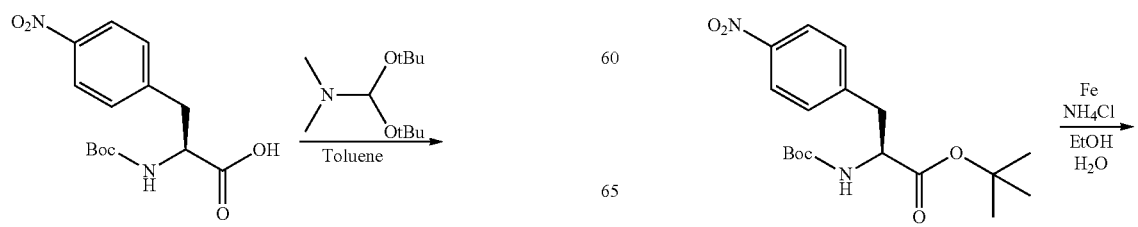

-continued

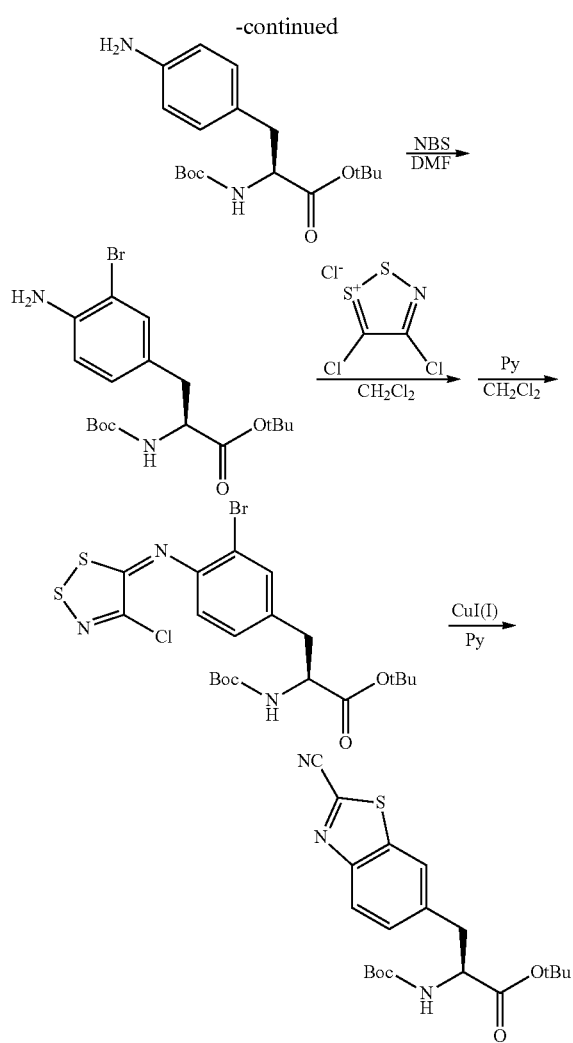

(1) Synthesis of tert-butyl (S)-2-((tert-butoxycarbonyl)amino)-3-(4-nitrophenyl)propanoate (S)-2-((tert-butoxycarbonyl)amino)-3-(4-nitrophenyl) propanoic acid (Boc-Phe(pNO$_2$)—OH) (318 mg) was dissolved in toluene (10 mL) which was then heated to 80° C. To the solution was added dropwise N,N-dimethylformamide-di-tert-butyl acetal (1.0 mL). After completion of dropwise addition, the reaction solution was stirred at 80° C. for 1 hour. The disappearance of the raw materials was confirmed by liquid chromatography mass spectrometry (LC-MS), followed by cooling to room temperature. The solvent was distilled off under reduced pressure, and the residue was purified by column chromatography (silica gel, ethyl acetate/hexane=0/100→15/85) to give 349 mg of the title compound as a transparent liquid.
MS(ESI m/z): 367.9 (M+H)
RT(min): 1.75

(2) Synthesis of tert-butyl (S)-2-((tert-butoxycarbonyl)amino)-3-(4-aminophenyl)propanoate 1.0 g of reduced iron and ammonium chloride (300 mg) were dissolved in ethanol (EtOH) (15 mL) and distilled water (15 mL), which was then heated at 80° C. for 20 minutes. To the solution was added an ethanol solution (5 mL) of tert-butyl (S)-2-((tert-butoxycarbonyl)amino)-3-(4-nitrophenyl)propanoate (349 mg), followed by stirring at 80° C. for 1.5 hours. The insolubles were removed by filtration through celite, and the filtrate was distilled off under reduced pressure. Distilled water and ethyl acetate were added to the resulting residue, followed by extraction with ethyl acetate. The organic layer was washed with saturated saline and dried over magnesium sulfate, and the solvent was distilled off under reduced pressure to give 327 mg of the title compound as a brown oil.
MS(ESI m/z): 337.0 (M+H)
RT(min): 1.20

(3) Synthesis of tert-butyl (S)-2-((tert-butoxycarbonyl)amino)-3-(4-amino-3-bromophenyl)propanoate 173 mg of N-bromosuccinimide (NBS) was added to a DMF solution (10 mL) of tert-butyl (S)-2-((tert-butoxycarbonyl)amino)-3-(4-aminophenyl)propanoate (300 mg) which was then stirred at room temperature for 1 hour. Distilled water and ethyl acetate were added to the reaction solution, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=0/100→15/85→20/80) to give 280 mg of the title compound as a transparent liquid.
MS(ESI m/z): 416.9 (M+H)
RT(min): 1.72

(4) Synthesis of tert-butyl (S,E)-3-(3-bromo-4-((4-chloro-5H-1,2,3-dithiazol-5-ylidene)amino)phenyl)-2-((tert-butoxycarbonyl)amino)propanoate 170 mg of Appel's salt (4,5-dichloro-1,2,3-dithiazolium chloride) was added to a dichloromethane solution (10 mL) of tert-butyl (S)-2-((tert-butoxycarbonyl)amino)-3-(4-amino-3-bromophenyl)propanoate (280 mg) which was then stirred at room temperature for 3.5 hours. To the solution was added 110 µL of pyridine (Py), followed by further stirring at room temperature for 1 hour. The solvent was distilled off under reduced pressure, and the residue was purified by column chromatography (silica gel, ethyl acetate/hexane=0/100→10/90→15/85) to give 280 mg of the title compound as a yellow oil.
MS(ESI m/z): 551.7 (M+H)
RT(min): 2.09

(5) Synthesis of tert-butyl (S)-2-((tert-butoxycarbonyl)amino)-3-(2-cyanobenzo[d]thiazol-6-yl)propanoate 110 mg of copper (I) iodide was added to a pyridine solution (5 mL) of tert-butyl (S,E)-3-(3-bromo-4-((4-chloro-5H-1,2,3-dithiazol-5-ylidene)amino)phenyl)-2-((tert-butoxycarbonyl)amino)propanoate (280 mg), followed by microwave irradiation (Initiator™, 100° C., 1.0 hour, 2.45 GHz, 0 to 240 W). Distilled water and ethyl acetate were added to the reaction solution, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=0/100→15/85) to give 159 mg of the title compound as a pale yellow oil.
MS(ESI m/z): 403.9 (M+H)
RT(min): 1.82

Synthesis of tert-butyl (S)-2-((tert-butoxycarbonyl)amino)-3-(2-cyano-6-methoxybenzo[d]thiazol-5-yl)propanoate

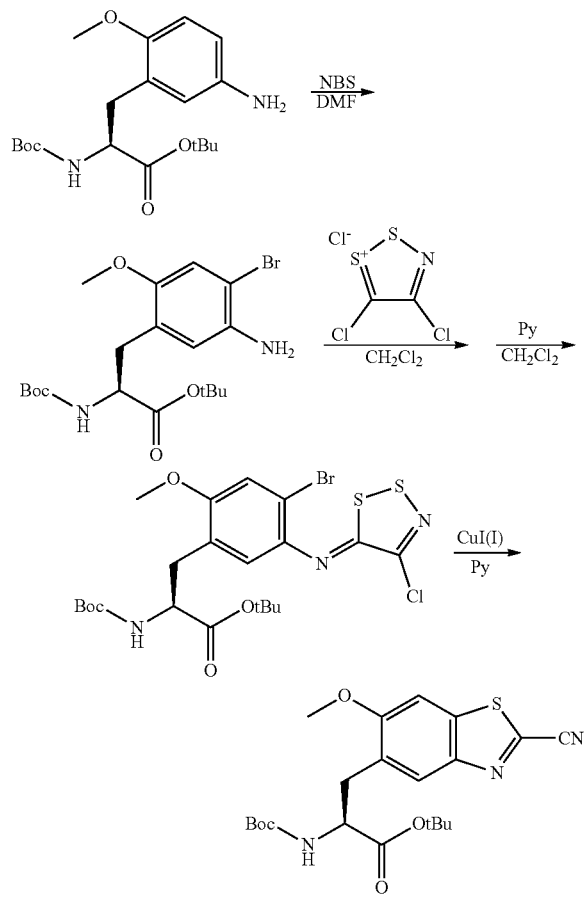

(1) Synthesis of tert-butyl (S)-3-(5-amino-4-bromo-2-methoxyphenyl)-2-((tert-butoxycarbonyl)amino)propanoate The procedure was carried out in the same manner as the synthesis of tert-butyl (S)-2-((tert-butoxycarbonyl)amino)-3-(4-amino-3-bromophenyl)propanoate.
MS(ESI m/z): 446.0 (M+H)
RT(min): 1.73

(2) Synthesis of tert-butyl (S,Z)-3-(4-bromo-5-((4-chloro-5H-1,2,3-dithiazol-5-ylidene)amino)-2-methoxyphenyl)-2-((ter t-butoxycarbonyl)amino)propanoate The procedure was carried out in the same manner as the synthesis of tert-butyl (S,E)-3-(3-bromo-4-((4-chloro-5H-1,2,3-dithiazol-5-ylidene)amino)phenyl)-2-((tert-butoxycarbonyl)amino)propanoate).
MS(ESI m/z): 581.8 (M+H)
RT(min): 2.13

(3) Synthesis of tert-butyl (S)-2-((tert-butoxycarbonyl)amino)-3-(2-cyano-6-methoxybenzo[d]thiazol-5-yl)propanoate The procedure was carried out in the same manner as the synthesis of tert-butyl (S)-2-((tert-butoxycarbonyl)amino)-3-(2-cyanobenzo[d]thiazol-6-yl)propanoate.
MS(ESI m/z): 434.0 (M+H)
RT(min): 1.84

Synthesis of tert-butyl (S)-2-((tert-butoxycarbonyl)amino)-3-(2-cyano-1-methyl-1H-indol-5-yl)propanoate 5 mL of DMF, 180 mg of potassium carbonate, and 50 μL of methyl methanesulfonate (MeOMs) were added to 179 mg of tert-butyl (S)-2-((tert-butoxycarbonyl)amino)-3-(2-cyano-1H-indol-5-yl)propanoate, which was then stirred at room temperature for 3 hours. Distilled water and ethyl acetate were added to the reaction solution, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=0/100→20/80) to give 163 mg of the title compound as a colorless oil.
MS(ESI m/z): 400.1 (M+H)
RT(min): 1.85

Synthesis of mixture of tert-butyl (S)-2-((tert-butoxycarbonyl)amino)-3-(2-cyano-1-methyl-1H-benzo[d]imidazol-6-yl)propanoate and tert-butyl (S)-2-((tert-butoxycarbonyl)amino)-3-(2-cyano-1-methyl-1H-benzo[d]imidazol-5-yl)propanoate

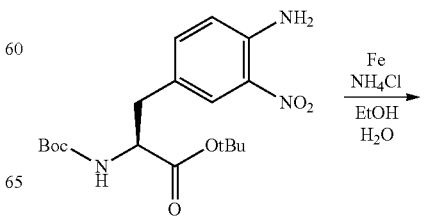

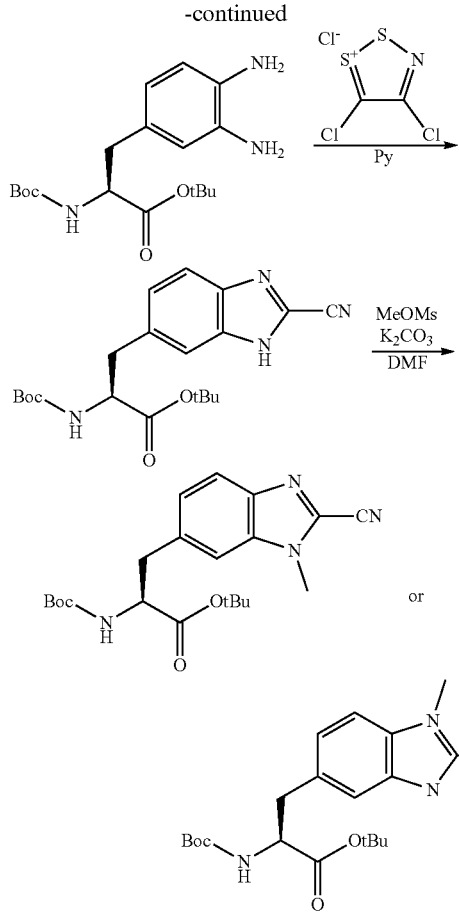

(1) Synthesis of tert-butyl (S)-2-((tert-butoxycarbonyl)amino)-3-(3,4-diaminophenyl)propanoate 10 mL of ethanol and 10 mL of distilled water were added to 110 mg of reduced iron and 210 mg of ammonium chloride, which was then heated to reflux for 20 minutes. Thereafter, an ethanol solution (5 mL) of tert-butyl (S)-3-(4-amino-3-nitrophenyl)-2-((tert-butoxycarbonyl)amino) propanoate (150 mg) was added thereto, followed by heating to reflux for 2 hours. The reaction solution was cooled to room temperature and filtered through celite, and the resulting filtrate was distilled off under reduced pressure. Distilled water and ethyl acetate were added to the resulting residue, followed by extraction with ethyl acetate. The organic layer was washed with saturated saline and dried over magnesium sulfate, the solvent was distilled off under reduced pressure, and the residue was purified by column chromatography (silica gel, ethyl acetate/hexane=0/100→30/70→60/40) to give 81.2 mg of the title compound as a brown oil.
MS(ESI m/z): 352.1 (M+H)
RT(min): 1.10

(2) Synthesis of tert-butyl (S)-2-((tert-butoxycarbonyl)amino)-3-(2-cyano-1H-benzo[d]imidazol-6-yl)propanoate 5 mL of pyridine and 58 mg of Appel's salt were added to 81 mg of tert-butyl (S)-2-((tert-butoxycarbonyl)amino)-3-(3,4-diaminophenyl)propanoate, which was then stirred at room temperature for 30 minutes, followed by microwave irradiation (Initiator™, 150° C., 30 minutes, 2.45 GHz, 0 to 240 W). The solvent was distilled off under reduced pressure, and the residue was purified by column chromatography (silica gel, ethyl acetate/hexane=0/100→30/70→60/40) to give 25.2 mg of the title compound as a brown oil.
MS(ESI m/z): 387.1 (M+H)
RT(min): 1.51

(3) Synthesis of mixture of tert-butyl (S)-2-((tert-butoxycarbonyl)amino)-3-(2-cyano-1-methyl-1H-benzo[d]imidazol-6-yl)propanoate and tert-butyl (S)-2-((tert-butoxycarbonyl)amino)-3-(2-cyano-1-methyl-1H-benzo[d]imidazol-5-yl)propanoate The procedure was carried out in the same manner as the synthesis of tert-butyl (S)-2-((tert-butoxycarbonyl)amino)-3-(2-cyano-1-methyl-1H-indol-5-yl)propanoate.

It continued to the next step with a mixture of regioisomers.
MS(ESI m/z): 401.1 (M+H)
RT(min): 1.62

Synthesis of tert-butyl (S)-2-((tert-butoxycarbonyl)amino)-3-(2-cyanobenzo[d]oxazol-6-yl)propanoate

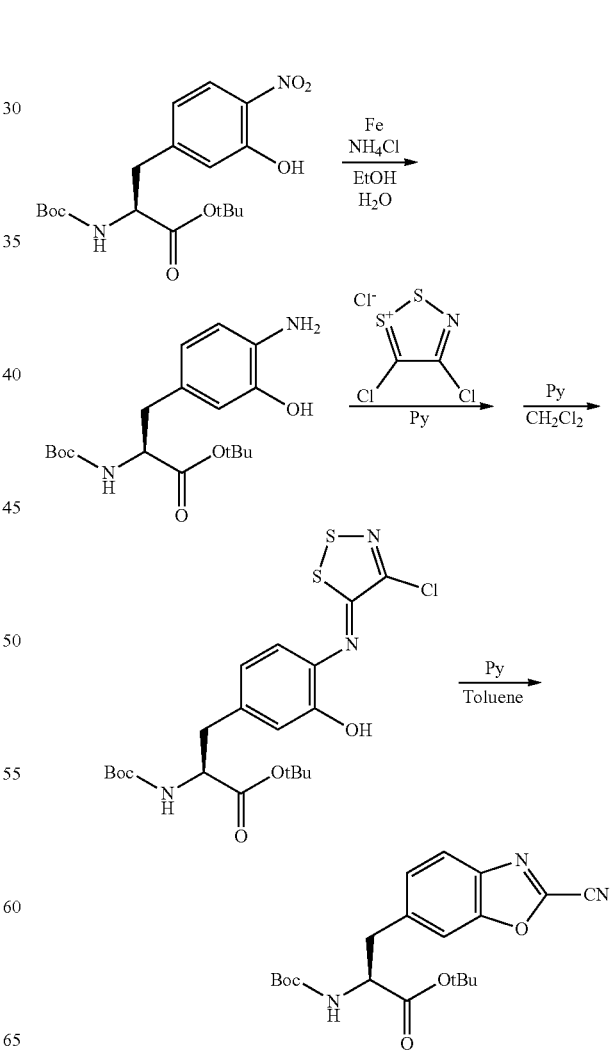

(1) Synthesis of tert-butyl (S)-3-(4-amino-3-hydroxyphenyl)-2-((tert-butoxycarbonyl)amino)propanoate The procedure was carried out in the same manner as the synthesis of tert-butyl (S)-2-((tert-butoxycarbonyl)amino)-3-(3,4-diaminophenyl)propanoate.
MS(ESI m/z): 353.3 (M+H)
RT(min): 1.11

(2) Synthesis of tert-butyl (S,Z)-2-((tert-butoxycarbonyl)amino)-3-(4-((4-chloro-5H-1,2,3-dithiazol-5-ylidene)amino)-3-hydroxyphenyl)propanoate The procedure was carried out in the same manner as the synthesis of tert-butyl (S,E)-3-(3-bromo-4-((4-chloro-5H-1,2,3-dithiazol-5-ylidene)amino)phenyl)-2-((tert-butoxycarbonyl)amino)propanoate.
MS(ESI m/z): 488.3 (M+H)
RT(min): 1.97

(3) Synthesis of tert-butyl (S)-2-((tert-butoxycarbonyl)amino)-3-(2-cyanobenzo[d]oxazol-6-yl)propanoate 4 mL of toluene and 0.5 mL of pyridine were added to 51 mg of tert-butyl (S,Z)-2-((tert-butoxycarbonyl)amino)-3-(4-((4-chloro-5H-1,2,3-dithiazol-5-ylidene)amino)-3-hydroxyphenyl)propanoate, followed by microwave irradiation (Initiator™, 150° C., 30 minutes, 2.45 GHz, 0 to 240 W). The solvent was distilled off under reduced pressure, and the residue was purified by column chromatography (silica gel, ethyl acetate/hexane=0/100→5/95→10/90) to give 22.2 mg of the title compound as a yellow oil.
MS(ESI m/z): 388.1 (M+H)
RT(min): 1.18

Synthesis of mixture of tert-butyl (S)-2-((tert-butoxycarbonyl)amino)-3-(6-cyano-1-methyl-1H-benzo[d]imidazol-2-yl)propanoate and tert-butyl (S)-2-((tert-butoxycarbonyl)amino)-3-(5-cyano-1-methyl-1H-benzo[d]imidazol-2-yl)propanoate

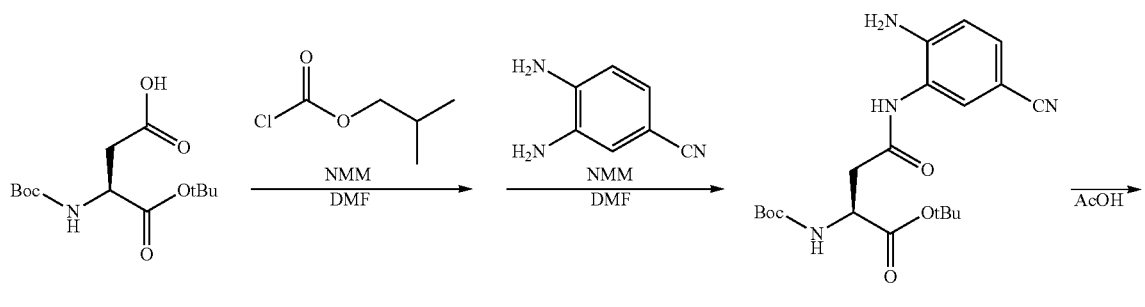

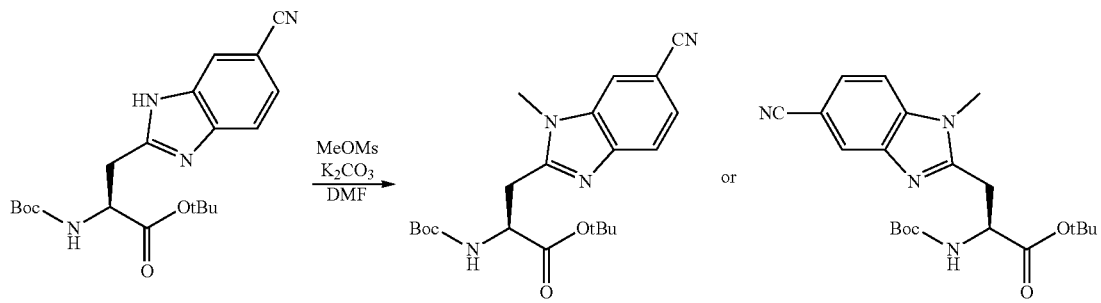

(1) Synthesis of tert-butyl N⁴-(2-amino-5-cyanophenyl)-N²-(tert-butoxycarbonyl)-L-asparaginate 5 mL of DMF and 120 μL of N-methylmorpholine were added to 300 mg of (S)-4-(tert-butoxy)-3-((tert-butoxycarbonyl)amino)-4-oxobutanoic acid. Under an ice bath, 135 μL of isobutyl chloroformate was added thereto, followed by stirring for 30 minutes. Thereafter, 138 mg of 3,4-diaminobenzonitrile was added thereto, followed by stirring at room temperature for 18 hours. Distilled water and ethyl acetate were added to the reaction solution, followed by extraction with ethyl acetate. The organic layer was washed with distilled water and saturated saline and dried over magnepressure, and the residue was purified by column chromatography (silica gel, ethyl acetate/hexane=0/100→50/50) to give 321 mg of the title compound as a brown oil.

MS(ESI m/z): 405.1 (M+H)
RT(min): 1.39

(2) Synthesis of tert-butyl (S)-2-((tert-butoxycarbonyl)amino)-3-(6-cyano-1H-benzo[d]imidazol-2-yl)propanoate 5 mL of acetic acid (AcOH) was added to 321 mg of tert-butyl N⁴-(2-amino-5-cyanophenyl)-N²-(tert-butoxycarbonyl)-L-asparaginate, which was then stirred at 60° C. for 24 hours. Distilled water and ethyl acetate were added to the reaction solution, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=0/100→35/65) to give 321 mg of the title compound as a red oil.

MS(ESI m/z): 387.1 (M+H)
RT(min): 1.36

(3) Synthesis of mixture of tert-butyl (S)-2-((tert-butoxycarbonyl)amino)-3-(6-cyano-1-methyl-1H-benzo[d]imidazol-2-yl)propanoate and tert-butyl (S)-2-((tert-butoxycarbonyl)amino)-3-(5-cyano-1-methyl-1H-benzo[d]imidazol-2-yl)propanoate The procedure was carried out in the same manner as the synthesis of tert-butyl (S)-2-((tert-butoxycarbonyl)amino)-3-(2-cyano-1-methyl-1H-indol-5-yl)propanoate. The title compound was obtained as a brown oil.

It continued to the next step with a mixture of regioisomers.

MS(ESI m/z): 401.1 (M+H)
RT(min): 1.49

Synthesis of cyanomethyl (S)-2-((tert-butoxycarbonyl)amino)-3-(2-cyanoquinolin-6-yl)propanoate

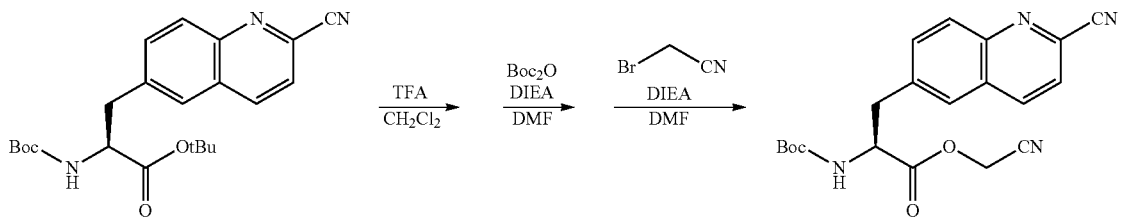

5 mL of trifluoroacetic acid (TFA) was added to a dichloromethane solution (1 mL) of tert-butyl (S)-2-((tert-butoxycarbonyl)amino)-3-(2-cyanoquinolin-6-yl)propanoate (90 mg) which was then stirred at room temperature for 4 hours. The solvent was distilled off, and 5 mL of DMF, 2 mL of N,N-diisopropylethylamine (DIEA), and 80 μL of di-tert-butyl dicarbonate (Boc₂O) were added thereto, followed by stirring at room temperature for 2 hours. After confirming the disappearance of the raw materials, 30 μL of bromoacetonitrile was added thereto, followed by further stirring at room temperature for 5 hours. The solvent was distilled off under reduced pressure, and the residue was purified by column chromatography (silica gel, ethyl acetate/hexane=0/100→20/80→40/60) to give 20.4 mg of the title compound as a white amorphous substance.

¹H-NMR (CDCl₃) δ: 8.29 (1H, d, J=8.6 Hz), 8.15 (1H, d, J=8.6 Hz), 7.77-7.63 (3H, m), 5.04-4.93 (1H, m), 4.89-4.64 (3H, m), 3.47-3.21 (2H, m), 1.41 (9H, s).

MS(ESI m/z): 381.1 (M+H)
RT(min): 1.41

The synthesis of the compounds shown in Table 3 below was carried out in the same manner as the synthesis of cyanomethyl (S)-2-((tert-butoxycarbonyl)amino)-3-(2-cyanoquinolin-6-yl)propanoate.

TABLE 3

| R | Compound | Observed MS | RT/min | ¹H-NMR |
|---|---|---|---|---|
| 2-cyanobenzo[d]thiazol-6-yl | Cyanomethyl (S)-2-((tert-butoxycarbonyl)amino)-3-(2-cyanobenzo[d]thiazol-6-yl)propanoate | 387.2 | 1.55 | ¹H-NMR (CDCl₃) δ: 8.19 (1H, d, J = 8.6 Hz), 7.81 (1H, d, J = 1.3 Hz), 7.47 (1H, dd, J = 8.6, 1.3 Hz), 5.06-4.92 (1H, m), 4.91-4.60 (3H, m), 3.42-3.20 (2H, m), 1.41 (9H, s). |
| 2-cyanoquinolin-6-yl | Cyanomethyl (S)-2-((tert-butoxycarbonyl)amino)-3-(2-cyanoquinolin-6-yl)propanoate | 381.1 | 1.41 | ¹H-NMR (CDCl₃) δ: 8.29 (1H, d, J = 8.6 Hz), 8.15 (1H, d, J = 8.6 Hz), 7.77-7.63 (3H, m), 5.04-4.93 (1H, m), 4.89-4.64 (3H, m), 3.47-3.21 (2H, m), 1.41 (9H, s). |
| 6-cyanoquinolin-2-yl | Cyanomethyl (S)-2-((tert-butoxycarbonyl)amino)-3-(6-cyanoquinolin-2-yl)propanoate | 381.1 | 1.43 | ¹H-NMR (CDCl₃) δ: 8.55 (1H, s), 7.70-7.67 (2H, m), 5.08-4.94 (1H, m), 4.91-4.60 (3H, m), 3.32 (1H, dd, J = 14.2, 5.6 Hz), 3.11 (1H, dd, J = 13.9, 7.3 Hz), 1.41 (9H, s). |
| 6-cyanopyridin-3-yl | Cyanomethyl (S)-2-((tert-butoxycarbonyl)amino)-3-(6-cyanopyridin-3-yl)propanoate | 331.0 | 1.24 | ¹H-NMR (CDCl₃) δ: 8.55 (1H, s), 7.68 (2H, s), 5.09-4.94 (1H, m), 4.91-4.59 (3H, m), 3.32 (1H, dd, J = 14.2, 5.6 Hz), 3.17-3.05 (1H, m), 1.41 (9H, s). |
| 2-cyanopyrimidin-5-yl | Cyanomethyl (S)-2-((tert-butoxycarbonyl)amino)-3-(2-cyanopyrimidin-5-yl)propanoate | 332.0 | 1.27 | ¹H-NMR (CDCl₃) δ: 8.70 (2H, s), 5.17-5.00 (1H, m), 4.83 (2H, q, J = 14.8 Hz), 4.73-4.58 (1H, m), 3.40-3.31 (1H, m), 3.09 (1H, dd, J = 14.5, 7.9 Hz), 1.41 (9H, s). |
| 5-cyanopyrazin-2-yl | Cyanomethyl (S)-2-((tert-butoxycarbonyl)amino)-3-(5-cyanopyrazin-2-yl)propanoate | 332.0 | 1.27 | ¹H-NMR (CDCl₃) δ: 8.83 (1H, s), 8.61 (1H, s), 5.46-5.33 (1H, m), 4.95-4.70 (3H, m), 3.55 (2H, d, J = 5.3 Hz), 1.43 (9H, s). |
| 6-cyanopyridazin-3-yl | Cyanomethyl (S)-2-((tert-butoxycarbonyl)amino)-3-(6-cyanopyridazin-3-yl)propanoate | 332.0 | 1.18 | ¹H-NMR (CDCl₃) δ: 7.82 (1H, d, J = 8.6 Hz), 7.58 (1H, d, J = 8.6 Hz), 5.72-5.59 (1H, m), 4.98-4.92 (1H, m), 4.81 (2H, s), 3.75-3.61 (2H, m), 1.44 (9H, s). |
| 5-cyanopyridin-2-yl | Cyaomethyl (S)-2-((tert-butoxycarbonyl)amino)-3-(5-cyanopyridin-2-yl)propanoate | 331.0 | 1.26 | ¹H-NMR (CDCl₃) δ: 8.80 (1H, d, J = 2.0 Hz), 7.91 (1H, dd, J = 8.3, 2.3 Hz), 7.32 (1H, d, J = 7.9 Hz), 5.69-5.58 (1H, m), |

TABLE 3-continued

| R | Compound | Observed MS | RT/min | ¹H-NMR |
|---|---|---|---|---|
| | | | | 4.88-4.70 (3H, m), 3.55 (1H, dd, J = 15.9, 5.3 Hz), 3.46-3.36 (1H, m), 1.44 (9H, s). |
| thiazole-CN (4-yl, 2-CN) | Cyanomethyl (S)-2-((tert-butoxy-carbonyl)amino)-3-(2-cyanothiazol-4-yl)propanoate | 336.9 | 1.33 | ¹H-NMR (CDCl₃) δ: 7.43 (1H, s), 5.51-5.40 (1H, m), 4.88-4.69 (3H, m), 3.47-3.34 (2H, m), 1.45 (9H, s). |
| thiophene-CN | Cyaomethyl (S)-2-((tert-butoxy-carbonyl)amino)-3-(5-cyanothiophen-3-yl)propanoate | 336.0 | 1.40 | ¹H-NMR (CDCl₃) δ: 7.45 (1H, s), 7.34 (1H, s), 5.04-4.92 (1H, m), 4.91-4.59 (3H, m), 3.23 (1H, dd, J = 14.5, 5.9 Hz), 3.15-3.03 (1H, m), 1.44 (9H, s). |
| 3-methyl-6-cyanopyridine | Cyanomethyl (S)-2-((tert-butoxy-carbonyl)amino)-3-(6-cyano-5-methylpyridin-3-yl)propanoate | 345.1 | 1.32 | ¹H-NMR (CDCl₃) δ: 8.36 (1H, s), 7.51 (1H, s), 5.06-4.93 (1H, m), 4.91-4.61 (3H, m), 3.26 (1H, dd, J = 14.5, 5.9 Hz), 3.16-3.04 (1H, m), 2.55 (3H, s), 1.42 (9H, s). |
| 3-methoxy-6-cyanopyridine | Cyanomethyl (S)-2-((tert-butoxy-carbonyl)amino)-3-(6-cyano-5-methoxypyridin-3-yl)propanoate | 361.1 | 1.31 | ¹H-NMR (CDCl₃) δ: 8.10 (1H, s), 7.18 (1H, s), 5.06-4.95 (1H, m), 4.93-4.65 (3H, m), 3.98 (3H, s), 3.30 (1H, dd, J = 13.9, 5.9 Hz), 3.18-3.05 (1H, m), 1.42 (9H, s). |
| 3-fluoro-6-cyanopyridine | Cyanomethyl (S)-2-((tert-butoxy-carbonyl)amino)-3-(6-cyano-5-fluoropyridin-3-yl)propanoate | 349.0 | 1.37 | ¹H-NMR (CDCl₃) δ: 8.38 (1H, s), 7.48 (1H, dd, J = 8.9, 1.7 Hz), 5.11-4.99 (1H, m), 4.81 (2H, q, J = 15.9 Hz), 4.72-4.60 (1H, m), 3.36 (1H, dd, J = 14.2, 5.6 Hz), 3.20-3.07 (1H, m), 1.42 (9H, s). |
| 4-cyanopyridine-2-yl | Cyanomethyl (S)-2-((tert-butoxy-carbonyl)amino)-3-(4-cyanopyridin-2-yl)propanoate | 331.0 | 1.27 | ¹H-NMR (CDCl₃) δ: 8.71 (1H, d, J = 4.6 Hz), 7.44-7.39 (2H, m), 5.66-5.53 (1H, m), 4.92-4.66 (3H, m), 3.54 (1H, dd, J = 15.9, 5.3 Hz), 3.40 (1H, dd, J = 15.9, 4.6 Hz), 1.44 (9H, s). |
| 6-cyanopyridine-2-yl | Cyanomethyl (S)-2-((tert-butoxy-carbonyl)amino)-3-(6-cyanopyridin-2-yl)propanoate | 331.1 | 1.30 | ¹H-NMR (CDCl₃) δ: 7.80 (1H, t, J = 7.9 Hz), 7.60 (1H, d, J = 7.9 Hz), 7.41 (1H, d, J = 7.9 Hz), 5.59-5.46 (1H, m), 4.89-4.71 (3H, m), 3.55-3.33 (2H, m), 1.44 (9H, s). |

TABLE 3-continued

| R | Compound | Observed MS | RT/min | $^1$H-NMR |
|---|---|---|---|---|
| 2-cyanopyridin-3-yl | Cyanomethyl (S)-2-((tert-butoxy-carbonyl)amino)-3-(2-cyanopyridin-3-yl)propanoate | 331.1 | 1.22 | $^1$H-NMR (CDCl$_3$) δ: 8.64 (1H, d, J = 4.0 Hz), 7.76 (1H, d, J = 7.3 Hz), 7.51 (1H, dd, J = 7.9, 4.6 Hz), 5.17-5.05 (1H, m), 4.84 (2H, d, J = 1.3 Hz), 4.78-4.66 (1H, m), 3.46 (1H, dd, J = 14.2, 5.6 Hz), 3.35-3.21 (1H, m), 1.39 (9H, s). |
| 4-cyanothiazol-2-yl | Cyanomethyl (S)-2-((tert-butoxy-carbonyl)amino)-3-(4-cyanothiazol-2-yl)propanoate | 337.0 | 1.26 | $^1$H-NMR (CDCl$_3$) δ: 7.94 (1H, s), 5.63-5.51 (1H, m), 4.91-4.77 (3H, m), 3.69-3.54 (2H, m), 1.46 (9H, s). |
| 5-cyanofuran-3-yl | Cyanomethyl (S)-2-((tert-butoxy-carbonyl)amino)-3-(5-cyanofuran-3-yl)propanoate | 320.0 | 1.37 | $^1$H-NMR (CDCl$_3$) δ: 7.45 (1H, s), 6.98 (1H, s), 5.05-4.94 (1H, m), 4.92-4.52 (3H, m), 3.07 (1H, dd, J = 14.9, 5.6 Hz), 2.92 (1H, dd, J = 15.2, 6.6 Hz), 1.45 (9H, s). |
| 2-cyanothiophen-3-yl | Cyanomethyl (S)-2-((tert-butoxy-carbonyl)amino)-3-(2-cyanothiophen-3-yl)propanoate | 336.0 | 1.39 | $^1$H-NMR (CDCl$_3$) δ: 7.57 (1H, d, J = 5.3 Hz), 7.02 (1H, d, J = 5.3 Hz), 5.11-5.01 (1H, m), 4.85-4.81 (2H, m), 4.77-4.67 (1H, m), 3.40 (1H, dd, J = 14.2, 5.6 Hz), 3.27 (1H, dd, J = 14.2, 6.3 Hz), 1.44 (9H, s). |
| 2-cyano-6-methoxybenzo[d]thiazol-5-yl | Cyanomethyl (S)-2-((tert-butoxy-carobnyl)amino)-3-(2-cyano-6-methoxybenzo[d]thiazol-5-yl)propanoate | 416.9 | 1.55 | $^1$H-NMR (CDCl$_3$) δ: 7.93 (1H, s), 7.36 (1H, s), 5.10-4.99 (1H, m), 4.89-4.64 (3H, m), 3.99 (3H, s), 3.40-3.28 (1H, m), 3.15 (1H, dd, J = 13.5, 8.3 Hz), 1.35 (9H, s). |
| 2-cyanobenzo[d]oxazol-6-yl | Cyanomethyl (S)-2-((tert-butoxy-carbonyl)amino)-3-(2-cyanobenzo[d]oxazol-6-yl)propanoate | 371.1 | 1.51 | $^1$H-NMR (CDCl$_3$) δ: 7.84 (1H, d, J = 8.6 Hz), 7.49 (1H, s), 7.34 (1H, dd, J = 8.3, 1.7 Hz), 5.04-4.92 (1H, m), 4.89-4.63 (3H, m), 3.35 (1H, dd, J = 13.9, 5.9 Hz), 3.24 (1H, dd, J = 13.9, 6.6 Hz), 1.41 (9H, s). |

TABLE 3-continued

| R | Compound | Observed MS | RT/min | ¹H-NMR |
|---|---|---|---|---|
| (6-benzimidazole with N-CH₃ and 2-CN) or (5-benzimidazole isomer) | Cyanomethyl (S)-2-((tert-butoxycarbonyl)amino)-3-(2-cyano-1-methyl-1H-benzo[d]imidazol-6-yl)propanoate or Cyanomethyl(S)-2-((tert-butoxycarbonyl)amino)-3-(2-cyano-1-methyl-1H-benzo[d]imidazol-5-yl)propanote | 384.1 | 1.33 | |
| (benzothiophene-2-CN, 6-yl) | Cyanomethyl (S)-2-((tert-butoxycarbonyl)amino)-3-(2-cyanobenzo[d]thiophen-6-yl)propanoate | 386.0 | 1.57 | ¹H-NMR (CDCl₃) δ: 7.91-7.82 (2H, m), 7.68 (1H, s), 7.32-7.26 (3H, m), 5.03-4.91 (1H, m), 4.90-4.64 (3H, m), 3.37-3.16 (2H, m), 1.41 (9H, s). |
| (benzofuran-2-CN, 6-yl) | Cyanomethyl (S)-2-((tert-butoxycarbonyl)amino)-3-(2-cyanobenzofuran-6-yl)propanoate | 370.0 | 1.55 | ¹H-NMR (CDCl₃) δ: 7.64 (1H, d, J = 8.6 Hz), 7.44 (1H, s), 7.38 (1H, s), 7.18 (1H, d, J = 8.6 Hz), 5.01-4.90 (1H, m), 4.88-4.64 (3H, m), 3.36-3.15 (2H, m), 1.41 (9H, s). |
| (1-methylindole-2-CN, 5-yl) | Cyanomethyl (S)-2-((tert-butoxycarbonyl)amino)-3-(2-cyano-1-methyl-1H-indol-5-yl)propanoate | 383.1 | 1.55 | ¹H-NMR (CDCl₃) δ: 7.44 (1H, s), 7.33 (1H, d, J = 8.6 Hz), 7.20 (1H, d, J = 8.6 Hz), 7.12 (1H, s), 4.97-4.87 (1H, m), 4.87-4.60 (3H, m), 3.90 (3H, s), 3.26-3.15 (2H, m), 1.41 (9H, s). |
| (6-CN-1-methylbenzimidazol-2-yl) or (5-CN-1-methylbenzimidazol-2-yl) | Cyanomethyl (S)-2-((tert-butoxycarbonyl)amino)-3-(6-cyano-1-methyl-1H-benzo[d]imidazol-2-yl)propanoate or Cyanomethyl(S)-2-((tert-butoxycarbonyl)amino)-3-(5-cyano-1-methyl-1H-benzo[d]imidazol-2-yl)propanoate | 384.1 | 1.25 | |

TABLE 3-continued

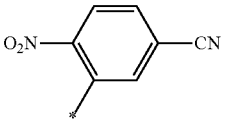 [SMILES: *c1cc(C#N)ccc1[N+](=O)[O-]]

| R | Compound | Observed MS | RT/min | ¹H-NMR |
|---|---|---|---|---|
| $O_2N$—⟨ ⟩—CN (with * marker) | Cyanomethyl (S)-2-((tert-butoxycarbonyl)amino)-3-(5-cyano-2-nitrophenyl)propanote | 375.0 | 1.43 | ¹H-NMR (CDCl₃) δ: 8.08 (1H, d, J = 8.6 Hz), 7.80-7.70 (2H, m), 5.22-5.12 (1H, m), 4.90-4.70 (3H, m), 3.66-3.57 (1H, m), 3.22 (1H, dd, J = 13.9, 9.2 Hz), 1.38 (9H, s). |

Synthesis of cyanomethyl (S)-2-((tert-butoxycarbonyl)amino)-3-(4-cyanophenyl)propanoate

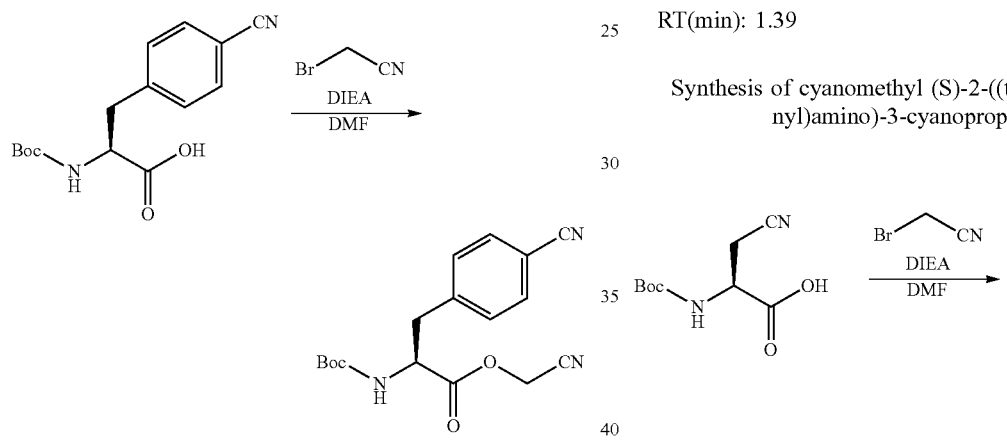

0.9 mL of N,N'-diisopropylethylamine and 0.18 mL of bromoacetonitrile were added to a DMF solution (10 mL) of Boc-4-cyano-L-phenylalanine (Boc-Phe(4-CN)—OH) (0.5 g) which was then stirred at room temperature for 2 hours. The solvent was distilled off under reduced pressure, and the residue was purified by column chromatography (silica gel, ethyl acetate/hexane=0/100→40/60) to give 599 mg of a white solid.

¹H-NMR (CDCl₃) δ: 7.63 (2H, d, J=7.9 Hz), 7.30 (2H, d, J=7.9 Hz), 4.99-4.89 (1H, m), 4.89-4.61 (3H, m), 3.24 (1H, dd, J=13.9, 5.9 Hz), 3.13-3.08 (1H, m), 1.42 (9H, s).

MS(ESI m/z): 330.0 (M+H)

RT(min): 1.39

Synthesis of cyanomethyl (S)-2-((tert-butoxycarbonyl)amino)-3-cyanopropanoate

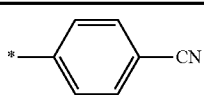

The procedure was carried out in the same manner as the synthesis of cyanomethyl (S)-2-((tert-butoxycarbonyl)amino)-3-(4-cyanophenyl)propanoate.

TABLE 4

| R | Compound | Observed MS | RT/min | ¹H-NMR |
|---|---|---|---|---|
| *—⟨ ⟩—CN | Cyanomethyl (S)-2-((tert-butoxycarbonyl)amino)-3-(4-cyanophenyl)propanoate | 330.0 | 1.39 | ¹H-NMR (CDCl₃) δ: 7.63 (2H, d, J = 7.9 Hz), 7.30 (2H, d, J = 7.9 Hz), 4.99-4.89 (1H, m), 4.89-4.61 (3H, m), 3.24 (1H, dd, J = 13.9, 5.9 Hz), |

TABLE 4-continued

| R | Compound | Observed MS | RT/min | $^1$H-NMR |
|---|---|---|---|---|
| | | | | 3.13-3.08 (1H, m), 1.42 (9H, s). |
| *—CN | Cyanomethyl (S)-2-((tert-butoxycarbonyl)amino)-3-cyanopropanoate | | 2.04 | $^1$H-NMR (CDCl$_3$) δ: 5.48-5.35 (1H, m), 4.86 (2H, dd, J = 19.5, 15.5 Hz), 4.65-4.53 (1H, m), 3.09-2.93 (2H, m), 1.47 (9H, s). |

Synthesis of tert-butyl (tert-butoxycarbonyl)-L-asparaginate

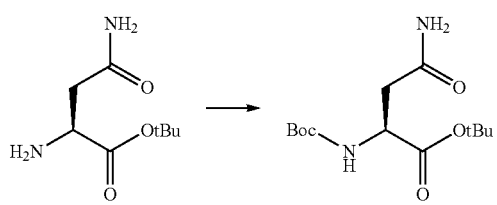 [SMILES: CC(C)(C)OC(=O)[C@@H](N)CC(N)=O ; CC(C)(C)OC(=O)N[C@@H](CC(N)=O)C(=O)OC(C)(C)C]

815 μL of triethylamine and 1.34 mL of di-tert-butyl dicarbonate (Boc$_2$O) were added to an ethyl acetate solution (20 mL) of L-asparagine-t-butyl ester (1.0 g) which was then stirred at room temperature for 15 hours. The organic layer was washed with distilled water and saturated saline and dried over magnesium sulfate. The solvent was distilled off under reduced pressure to give 1.41 g of the title compound as a white solid.
MS(ESI m/z): 289.0
RT(min): 1.10

Synthesis of tert-butyl (S)-4-amino-2-((tert-butoxycarbonyl)amino)-4-thioxobutanoate

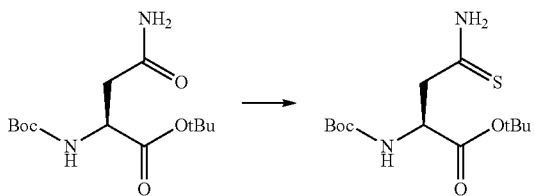 [SMILES: CC(C)(C)OC(=O)N[C@@H](CC(N)=O)C(=O)OC(C)(C)C ; CC(C)(C)OC(=O)N[C@@H](CC(N)=S)C(=O)OC(C)(C)C]

1.03 g of Lawesson's reagent (2,4-bis(4-methoxyphenyl)-1,3-dithia-2,4-diphosphetane 2,4-disulfide) was added to a THF solution (20 mL) of tert-butyl (tert-butoxycarbonyl)-L-asparaginate (1.41 g) which was then stirred at room temperature for 3 hours. The solvent was distilled off under reduced pressure, and the residue was purified by column chromatography (silica gel, ethyl acetate/hexane=0/100→30/70→40/60) to give 1.39 g of the title compound as a white solid.
MS(ESI m/z): 305.0
RT(min): 1.31

Synthesis of ethyl (S)-2-(3-(tert-butoxy)-2-((tert-butoxycarbonyl)amino)-3-oxopropyl)thiazole-4-carboxylate

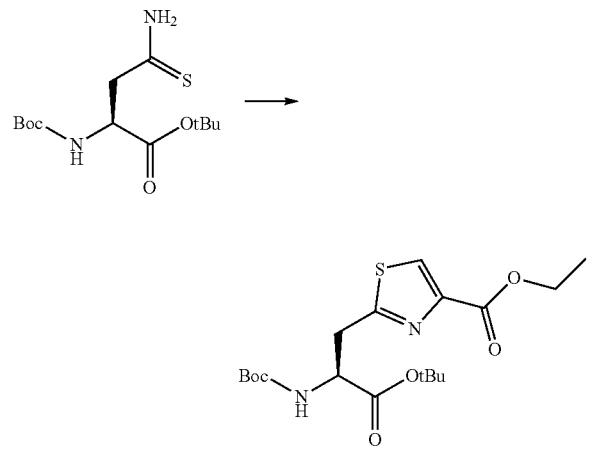

1.1 mL of pyridine and 635 μL of ethyl bromopyruvate were added to an ethanol solution (20 mL) of tert-butyl (S)-4-amino-2-((tert-butoxycarbonyl)amino)-4-thioxobutanoate (1.39 g) which was then heated to reflux for 3.5 hours. Another 310 μL of bromopyruvic acid was added thereto, followed by heating to reflux for 2 hours. The solvent was distilled off under reduced pressure, and distilled water and ethyl acetate were added to the residue, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=0/100→20/80) to give the title compound (680 mg) as a brown oil.
MS(ESI m/z): 401.0
RT(min): 1.62

Synthesis of tert-butyl (S)-2-((tert-butoxycarbonyl)amino)-3-(4-carbamoylthiazol-2-yl)propanoate

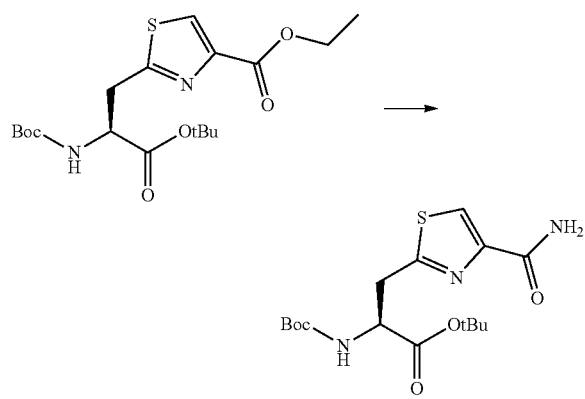

6.5 mL of 25% aqueous ammonia was added to a methanol solution (5 mL) of ethyl (S)-2-(3-(tert-butoxy)-2-((tert-butoxycarbonyl)amino)-3-oxopropyl)thiazole-4-carboxylate (680 mg) which was then stirred at room temperature for 24 hours. Distilled water and ethyl acetate were added to the reaction solution, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=30/70→40/60→80/20) to give 473 mg of the title compound as a transparent oil.
MS(ESI m/z): 372.0
RT(min): 1.30

Synthesis of tert-butyl (S)-2-((tert-butoxycarbonyl)amino)-3-(4-cyanothiazol-2-yl)propanoate

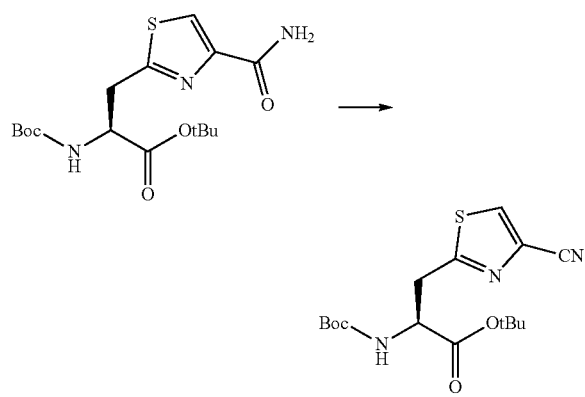

240 µL of triethylamine was added to a dichloromethane solution (5 mL) of tert-butyl (S)-2-((tert-butoxycarbonyl)amino)-3-(4-carbamoylthiazol-2-yl)propanoate (312 mg). 130 µL of trifluoroacetic anhydride was added dropwise thereto on an ice bath, followed by stirring at room temperature for 14 hours. The solvent was distilled off under reduced pressure, and the residue was purified by column chromatography (silica gel, ethyl acetate/hexane=0/100→10/90→20/80) to give 193 mg of the title compound as a transparent oil.
MS(ESI m/z): 354.0
RT(min): 1.58

Synthesis of 4-bromo-1-methyl-1H-pyrrole-2-carbonitrile

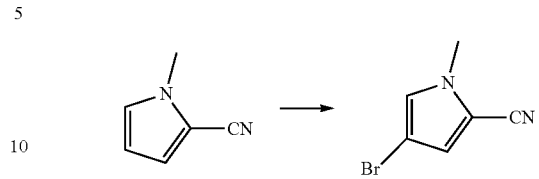

1.02 g of NBS was added to a DMF solution (5 mL) of 1-methyl-1H-pyrrole-2-carbonitrile (605 mg) which was then stirred for 5 hours. Distilled water and ethyl acetate were added to the reaction solution, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=0/100→5/95) to give 405 mg of the title compound as a white solid.
MS(ESI m/z): 186.0 (M+H)
RT(min): 1.26

Synthesis of methyl (4-bromobenzoyl)-L-serinate

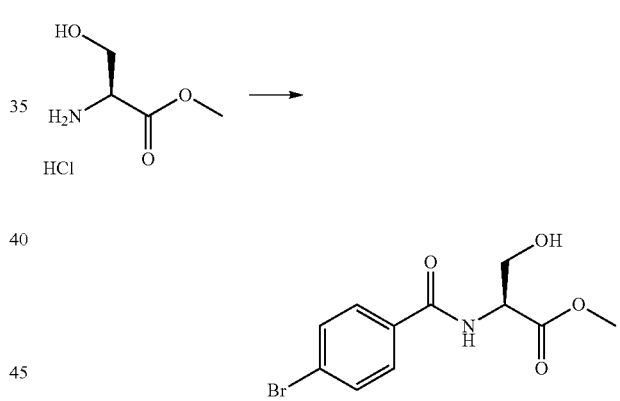

20 mL of dichloromethane and 1.51 mL of triethylamine were added to 0.84 g of methyl-L-serinate hydrochloride. 1.19 g of 4-bromobenzoyl chloride was added dropwise thereto under an ice bath. After completion of dropwise addition, the reaction solution was stirred at room temperature for 2 hours. The solvent was distilled off under reduced pressure, and distilled water and ethyl acetate were added to the residue, followed by extraction with ethyl acetate. The organic layer was washed with a saturated aqueous sodium hydrogen carbonate solution and saturated saline and dried over magnesium sulfate. The solvent was distilled off under reduced pressure, and the residue was purified by column chromatography (silica gel, ethyl acetate/hexane=50/50→100/0) to give 1.49 g of the title compound as a colorless oil.
MS(ESI m/z): 303.8 (M+H)
RT(min): 0.98

Synthesis of methyl 2-(4-bromophenyl)oxazole-4-carboxylate

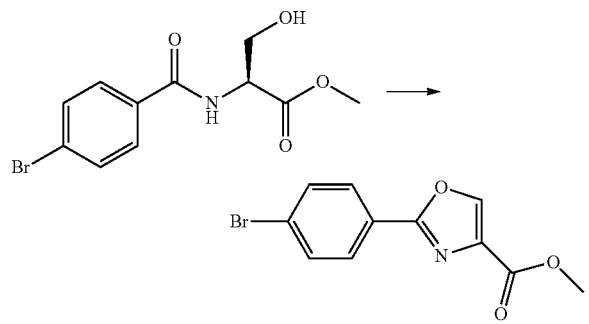

15 mL of THF and 1.41 g of Burgess reagent (methyl N-(triethylammoniosulfonyl)carbamate) were added to methyl (4-bromobenzoyl)-L-serinate, which was then stirred at 80° C. for 2 hours. Thereafter, the solvent was distilled off under reduced pressure, and distilled water and ethyl acetate were added to the residue, followed by extraction with ethyl acetate. The organic layer was washed with distilled water and saturated saline and dried over magnesium sulfate. The solvent was distilled off under reduced pressure, and 15 mL of dichloromethane, 1.51 mL of bromotrichloromethane and 2.29 mL of diazabicycloundecene were added thereto, followed by stirring at room temperature for 2 hours. The solvent was distilled off under reduced pressure, and ethyl acetate was added to the residue, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=0/100→10/90→30/70) to give 775 mg of the title compound as a white solid.
MS(ESI m/z): 283.8 (M+H)
RT(min): 1.45

Synthesis of ethyl 1-(4-nitrophenyl)-1H-imidazole-4-carboxylate

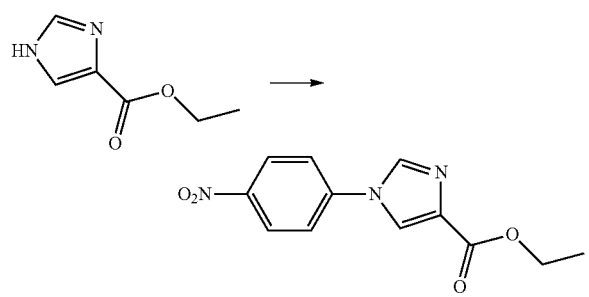

1.3 g of 1-fluoro-4-nitrobenzene and 1.5 g of potassium carbonate were added to a solution of 1.2 g of ethyl 1H-imidazole-4-carboxylate in 15 mL of acetonitrile which was then stirred at 60° C. for 17 hours. Distilled water and ethyl acetate were added to the residue, followed by extraction with ethyl acetate. The organic layer was washed with distilled water and saturated saline and dried over magnesium sulfate. The solvent was distilled off under reduced pressure, 5 mL of ethyl acetate and 30 mL of hexane were added thereto, and the solid was filtered off. The resulting solid was washed with hexane to give 977 mg of the title compound as a white solid.
MS(ESI m/z): 262.9 (M+H)
RT(min): 1.10

Synthesis of ethyl 1-(4-aminophenyl)-1H-imidazole-4-carboxylate

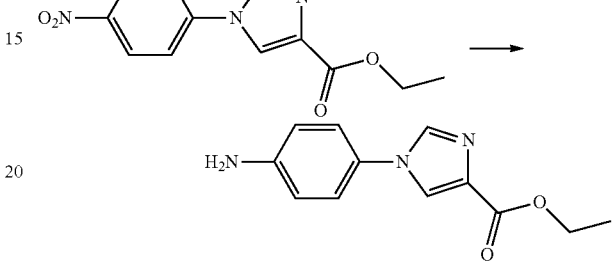

18 mL of ethanol and 2 mL of distilled water were added to 1.05 g of reduced iron and 200 mg of ammonium chloride, which was then heated to reflux for 20 minutes. Thereafter, 970 mg of ethyl 1-(4-nitrophenyl)-1H-imidazole-4-carboxylate was added thereto, followed by heating to reflux for 1 hour. The reaction solution was cooled to room temperature and filtered through celite, and the resulting filtrate was distilled off under reduced pressure. The residue was purified by column chromatography (silica gel, ethyl acetate/methanol=100/0→95/5) to give 819 mg of the title compound as a yellow oil.
MS(ESI m/z): 232.0 (M+H)
RT(min): 0.72

Synthesis of ethyl 1-(4-bromophenyl)-1H-imidazole-4-carboxylate

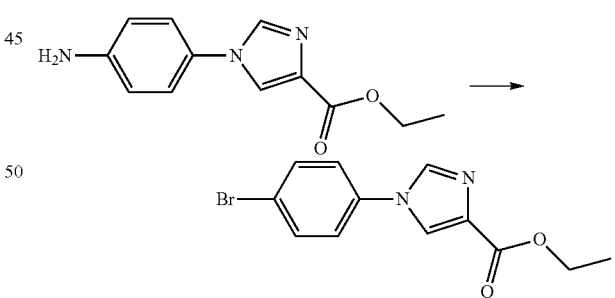

10 mL of acetonitrile and copper bromide 875 mg were added to 819 mg of ethyl 1-(4-aminophenyl)-1H-imidazole-4-carboxylate. To the solution was added dropwise 1.1 mL of t-butyl nitrite at room temperature, followed by stirring at room temperature for 4 hours. Distilled water and ethyl acetate were added to the reaction solution, followed by extraction with ethyl acetate. The organic layer was washed with distilled water and saturated saline and dried over magnesium sulfate. The solvent was distilled off under reduced pressure, 5 mL of ethyl acetate and 30 mL of hexane were added thereto, and the solid was filtered off. The resulting solid was washed with hexane to give 746 mg of the title compound as a yellow solid.
MS(ESI m/z): 296.8 (M+H)
RT(min): 1.29

Synthesis of ethyl 6-bromoimidazo[1,2-a]pyrimidine-2-carboxylate

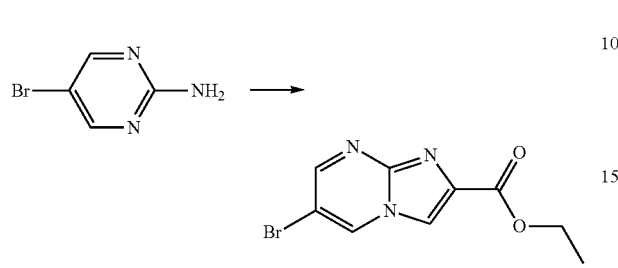

30 mL of ethanol and 2.9 mL of ethyl 3-bromopyruvate were added to 2.0 g of 2-amino-5-bromopyrimidine, which was then heated to reflux for 6 hours. The solvent was distilled off under reduced pressure, and the residue was purified by column chromatography (silica gel, ethyl acetate/hexane=0/100→15/85→30/70) to give 804 mg of the title compound as a yellow solid.
MS(ESI m/z): 271.9 (M+H)
RT(min): 1.06

Synthesis of ethyl 6-bromoimidazo[1,2-a]pyrazine-2-carboxylate

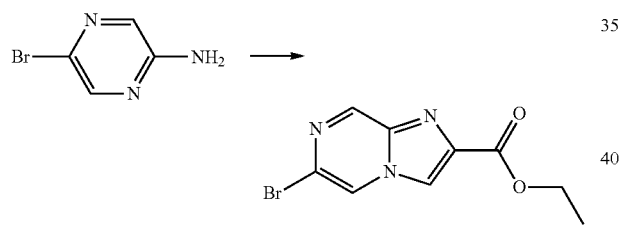

The procedure was carried out in the same manner as the synthesis of ethyl 6-bromoimidazo[1,2-a]pyrimidine-2-carboxylate.
MS(ESI m/z): 271.9 (M+H)
RT(min): 0.92

Synthesis of ethyl 6-bromoimidazo[1,2-b]pyridazine-2-carboxylate


The procedure was carried out in the same manner as the synthesis of ethyl 6-bromoimidazo[1,2-a]pyrimidine-2-carboxylate.

MS(ESI m/z): 271.9 (M+H)
RT(min): 1.09

Synthesis of 5-bromo-1-methyl-1H-indazole-3-carbonitrile

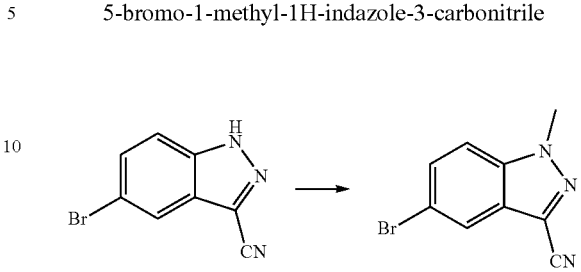

The procedure was carried out in the same manner as the synthesis of tert-butyl (S)-2-((tert-butoxycarbonyl)amino)-3-(2-cyano-1-methyl-1H-indol-5-yl)propanoate.
MS(ESI m/z): 237.9 (M+H)
RT(min): 1.48

Synthesis of 4-bromo-1-methyl-1H-pyrazole-3-carbonitrile

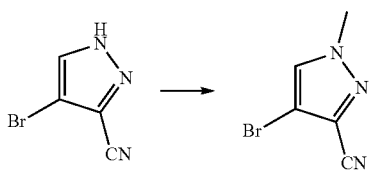

The procedure was carried out in the same manner as the synthesis of tert-butyl (S)-2-((tert-butoxycarbonyl)amino)-3-(2-cyano-1-methyl-1H-indol-5-yl)propanoate.
MS(ESI m/z): 187.0 (M+H)
RT(min): 1.10

Synthesis of ethyl 6-(3-bromophenyl)pyrazolo[1,5-a]pyrimidine-2-carboxylate

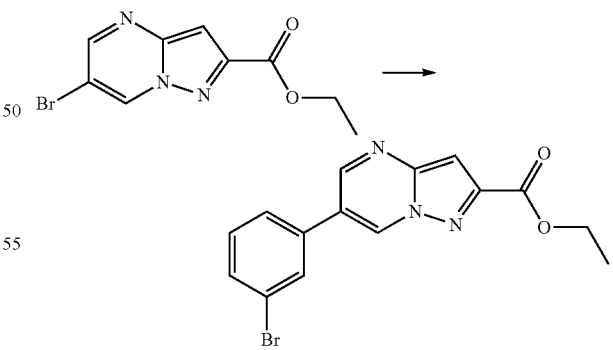

495 mg of (3-bromophenyl)boronic acid, 20 mL of THF, and 5.9 mL of an aqueous sodium carbonate solution (1.0 mol/L) were added to 600 mg of ethyl 6-bromopyrazolo[1,5-a]pyrimidine-2-carboxylate, followed by nitrogen substitution. 81.4 mg of tetrakis(triphenylphosphine)palladium (0) was added to the solution which was then stirred at 80° C. for 9 hours. The solvent was distilled off under reduced pressure, and ethyl acetate was added to the residue, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=10/90→30/70) to give 622 mg of the title compound as a yellow solid.

MS(ESI m/z): 347.8 (M+H)
RT(min): 1.57

Synthesis of 6-(3-bromophenyl)pyrazolo[1,5-a]pyrimidine-2-carboxamide

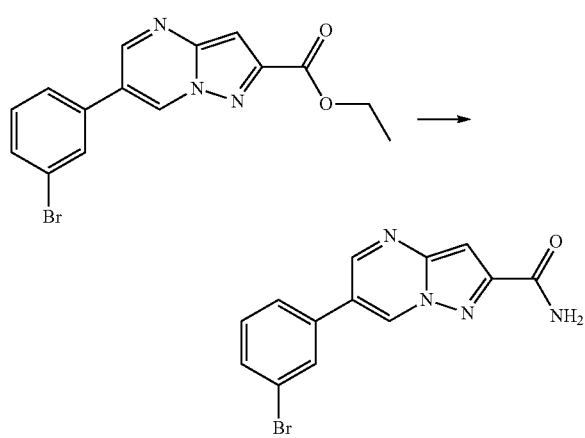

The procedure was carried out in the same manner as the synthesis of tert-butyl (S)-2-((tert-butoxycarbonyl)amino)-3-(4-carbamoylthiazol-2-yl)propanoate.

MS(ESI m/z): 318.9 (M+H)
RT(min): 1.17

Synthesis of 6-(3-bromophenyl)pyrazolo[1,5-a]pyrimidine-2-carbonitrile

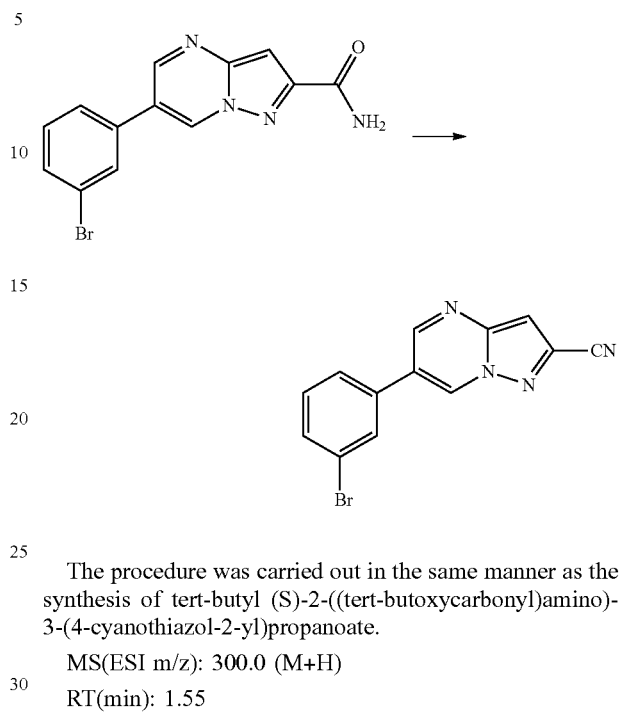

The procedure was carried out in the same manner as the synthesis of tert-butyl (S)-2-((tert-butoxycarbonyl)amino)-3-(4-cyanothiazol-2-yl)propanoate.

MS(ESI m/z): 300.0 (M+H)
RT(min): 1.55

The synthesis of the compounds shown in Table 5 below was carried out in the same manner as the synthesis of tert-butyl (S)-2-(((((9H-fluoren-9-yl)methoxy)carbonyl)amino)-3-(5-cyanothiophen-3-yl)propanoate, using tert-butyl (R)-2-((tert-butoxycarbonyl)amino)-3-iodopropanoate as a raw material.

TABLE 5

| R | Compound name | Observed MS | RT/min |
|---|---|---|---|
| 4-cyanopyridin-3-yl | tert-butyl (S)-2-((tert-butoxycarbonyl)amino)-3-(4-cyanopyridin-3-yl)propanoate | 348.1 | 1.47 |
| 3-cyanopyridin-2-yl | tert-butyl (S)-2-((tert-butoxycarbonyl)amino)-3-(3-cyanopyridin-2-yl)propanote | 348.1 | 1.54 |

TABLE 5-continued

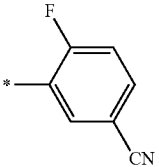

| R | Compound name | Observed MS | RT/min |
|---|---|---|---|
| 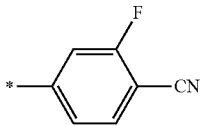 | tert-butyl (S)-2-((tert-butoxycarbonyl)amino)-3-(5-cyano-2-fluorophenyl)propanoate | 365.0 | 1.73 |
| 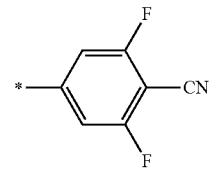 | tet-butyl (S)-2-((tert-butoxycarbonyl)amino)-3-(5-cyano-3-fluorophenyl)propanoate | 365.0 | 1.90 |
| 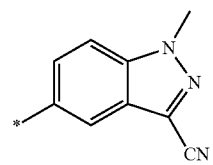 | tert-butyl (S)-2-((tert-butoxycarbonyl)amino)-3-(4-cyano-3,5-difluorophenyl)propanoate | 419.0 | 1.96 |
| 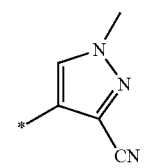 | tert-butyl (S)-2-((tert-butoxycarbonyl)amino)-3-(3-cyano-1-methyl-1H-indazol-5-yl)propanoate | 401.0 | 1.75 |
| 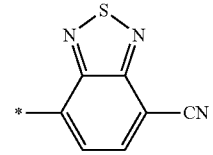 | tert-butyl (S)-2-((tert-butoxycarbonyl)amino)-3-(3-cyano-1-methyl-1H-pyrazol-4-yl)propanoate | 351.2 | 1.58 |
| 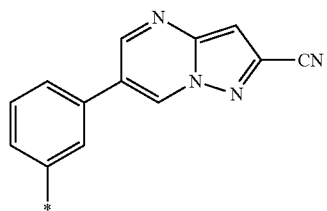 | tert-butyl (S)-2-((tert-butoxycarobnyl)amino)-3-(7-cyanobenzo[c][1,2,5]thiadiazol-4-yl)propanoate | 405.0 | 1.71 |
|  | tert-butyl (S)-2-((tert-butoxycarbonyl)amino)-3-(3-(2-cyanopyrazolo[1,5-a]pyrimidin-6-yl)phenyl)propanoate | 464.2 | 1.80 |

TABLE 5-continued

| R | Compound name | Observed MS | RT/min |
|---|---|---|---|
| 1-methyl-5-cyano-1H-pyrrol-3-yl | tert-butyl (S)-2-((tert-butoxycarbonyl)amino)-3-(5-cyano-1-methyl-1H-pyrrol-3-yl)propanoate | 350.1 | 1.64 |
| 4-(4-(methoxycarbonyl)oxazol-2-yl)phenyl | methyl (S)-2-(4-(3-(tert-butoxy)-2-((tert-butoxycarbonyl)amino)-3-oxopropyl)phenyl)oxazol-4-carboxylate | 447.2 | 1.62 |
| 4-(4-(ethoxycarbonyl)-1H-imidazol-1-yl)phenyl | ethyl (S)-1-(4-(3-(tert-butoxy)-2-((tert-butoxycarbonyl)amino)-3-oxopropyl)phenyl)-1H-imidazole-4-carboxylate | 460.1 | 1.60 |
| 2-(ethoxycarbonyl)imidazo[1,2-a]pyrimidin-6-yl | tert-butyl (S)-2-((tert-butoxycarbonyl)amino)-3-(2-cyanoimidazo[1,2-a]pyrimidin-6-yl)propanoate | 435.0 | 1.51 |
| 2-(ethoxycarbonyl)imidazo[1,2-a]pyrazin-6-yl | tert-butyl (S)-2-((tert-butoxycarbonyl)amino)-3-(2-cyanoimidazo[1,2-a]pyrazin-6-yl)propanoate | 435.0 | 1.43 |
| 2-(ethoxycarbonyl)imidazo[1,2-b]pyridazin-6-yl | tert-butyl (S)-2-((tert-butoxycarbonyl)amino)-3-(2-cyanoimidazo[1,2-a]pyridazin-6-yl)propanoate | 435.0 | 1.52 |
| 2-(ethoxycarbonyl)-2,3-dihydroimidazo[1,2-a]pyridin-6-yl | tert-butyl (S)-2-((tert-butoxycarbonyl)amion)-3-(2-cyanoimidazo[1,2-a]pyridin-6-yl)propanoate | 434.0 | 1.37 |

The synthesis of the compounds shown in Table 6 below was carried out in the same manner as the synthesis of cyanomethyl (S)-2-((tert-butoxycarbonyl)amino)-3-(2-cyanoquinolin-6-yl)propanoate.

TABLE 6

| R | Compound name | Observed MS | Rt/min | ¹H-NMR |
|---|---|---|---|---|
| 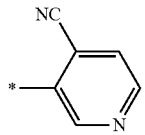 | cyanomethyl (S)-2-((tert-butoxycarbonyl)amino)-3-(4-cyanopyridin-3-yl)propanoate | 331.1 | 1.15 | ¹H-NMR (CDCl₃) δ: 8.76-8.65 (2H, m), 7.53 (1H, d, J = 5.3 Hz), 5.16-5.05 (1H, m), 4.90-4.70 (3H, m), 3.55-3.43 (1H, m), 3.29-3.18 (1H, m), 1.39 (9H, s). |
| 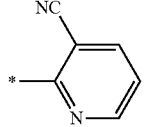 | cyanomethyl (S)-2-((tert-butoxycarbonyl)amino)-3-(3-cyanopyridin-2-yl)propanoate | 331.0 | 1.24 | ¹H-NMR (CDCl₃) δ: 8.72 (1H, d, J = 5.0 Hz), 7.96 (1H, dd, J = 7.9, 2.0 Hz), 7.37-7.30 (1H, m), 5.73-5.63 (1H, m), 5.03-4.92 (1H, m), 4.84-4.68 (2H, m), 3.82-3.72 (1H, m), 3.58 (1H, dd, J = 16.5, 4.0 Hz), 1.45 (9H, s). |
| 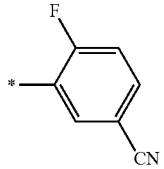 | cyanomethyl (S)-2-((tert-butoxycarbonyl)amino)-3-(5-cyano-2-fluorophenyl)propanoate | 348.0 | 1.42 | ¹H-NMR (CDCl₃) δ: 7.66-7.57 (1H, m), 7.53 (1H, dd, J = 6.6, 2.0 Hz), 7.19 (1H, t, J = 8.9 Hz), 5.07-4.95 (1H, m), 4.80 (2H, dd, J = 25.8, 15.9 Hz), 4.71-4.59 (1H, m), 3.35-3.23 (1H, m), 3.15-3.04 (1H, m), 1.41 (9H, s). |
| 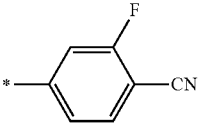 | cyanomethyl (S)-2-((tert-butoxycarbonyl)amino)-3-(4-cyano-3-fluorophenyl)propanoate | 348.0 | 1.59 | ¹H-NMR (CDCl₃) δ: 7.65-7.56 (1H, m), 7.13-7.04 (2H, m), 5.03-4.93 (1H, m), 4.90-4.61 (3H, m), 3.32-3.21 (1H, m), 3.16-3.04 (1H, m), 1.42 (9H, s). |
| 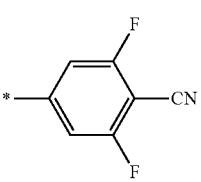 | cyanomethyl (S)-2-((tert-butoxycarbonyl)amino)-3-(4-cyano-3,5-difluorophenyl)propanoate | 366.9 | 1.66 | ¹H-NMR (CDCl₃) δ: 6.93 (1H, s), 6.90 (1H, s), 5.07-4.96 (1H, m), 4.90-4.70 (2H, m), 4.70-4.59 (1H, m), 3.32-3.21 (1H, m), 3.14-3.02 (1H, m), 1.43 (9H, s). |
| 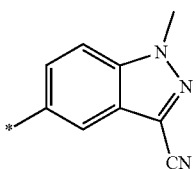 | cyanomethyl (S)-2-((tert-butoxycarbonyl)amino)-3-(3-cyano-1-methyl-1H-indazol-5-yl)propanoate | 384.1 | 1.49 | ¹H-NMR (CDCl₃) δ: 7.61 (1H, s), 7.50 (1H, d, J = 8.6 Hz), 7.33 (1H, d, J = 8.6 Hz), 5.00-4.90 (1H, m), 4.89-4.61 (3H, m), 4.16 (3H, s), 3.38-3.15 (2H, m), 1.41 (9H, s). |

TABLE 6-continued

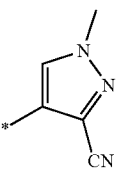

| R | Compound name | Observed MS | Rt/min | ¹H-NMR |
|---|---|---|---|---|
| 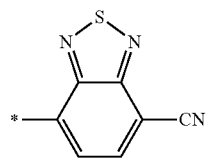 | cyanomethyl (S)-2-((tert-butoxy-carbonyl)amino)-3-(3-cyano-1-methyl-1H-pyrazol-4-yl)propanoate | 334.1 | 1.27 | ¹H-NMR (CDCl₃) δ: 7.33 (1H, s), 5.11-5.00 (1H, m), 4.87-4.80 (2H, m), 4.70-4.58 (1H, m), 3.95 (3H, s), 3.24-3.03 (2H, m), 1.45 (9H, s). |
| 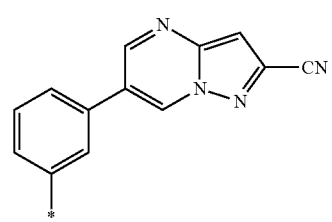 | cyanomethyl (S)-2-((tert-butoxy-carbonyl)amino)-3-(7-cyanobenzo[c][1,2,5]thiadiazol-4-yl)propanoate | 388.0 | 1.42 | ¹H-NMR (CDCl₃) δ: 8.01 (1H, d, J = 7.3 Hz), 7.52 (1H, d, J = 7.3 Hz), 5.26-5.14 (1H, m), 4.97-4.66 (3H, m), 3.82-3.71 (1H, m), 3.69-3.60 (1H, m), 1.36 (9H, s). |
| 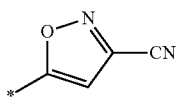 | cyanomethyl (S)-2-((tert-butoxy-carbonyl)amino)-3-(3-(2-cyanopyrazolo[1,5-a]pyrimidin-6-yl)phenyl)propanoate | 447.1 | 1.54 | ¹H-NMR (CDCl₃) δ: 8.91-8.83 (2H, m), 7.56-7.50 (2H, m), 7.40 (1H, s), 7.36-7.29 (1H, m), 7.17 (1H, s), 5.04-4.62 (4H, m), 3.33-3.13 (2H, m), 1.42 (9H, s). |
| 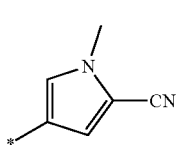 | cyanomethyl (S)-2-((tert-butoxy-carbonyl)amino)-3-(3-cyanoisoxazol-5-yl)propanoate | 321.1 | 1.21 | ¹H-NMR (CDCl₃) δ: 6.51 (1H, s), 5.22-5.10 (1H, m), 4.92-4.68 (3H, m), 3.60-3.46 (1H, m), 3.46-3.33 (1H, m), 1.45 (9H, s). |
| 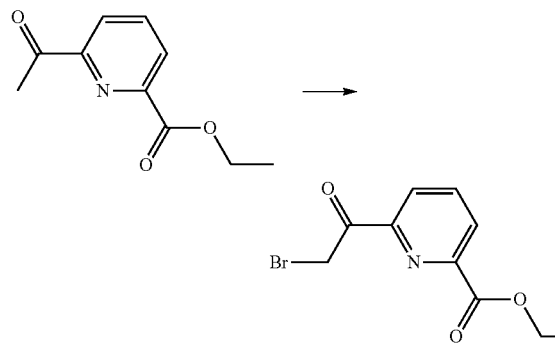 | cyanomethyl (S)-2-((tert-butoxy-carbonyl)amino)-3-(5-cyano-1-methyl-1H-pyrrol-3-yl)propanoate | 333.1 | 1.36 | ¹H-NMR (CDCl₃) δ: 6.65 (1H, s), 6.59 (1H, s), 5.00-4.49 (4H, m), 3.73 (3H, s), 3.02-2.88 (2H, m), 1.45 (9H, s). |

Synthesis of ethyl 6-(2-bromoacetyl)picolinate

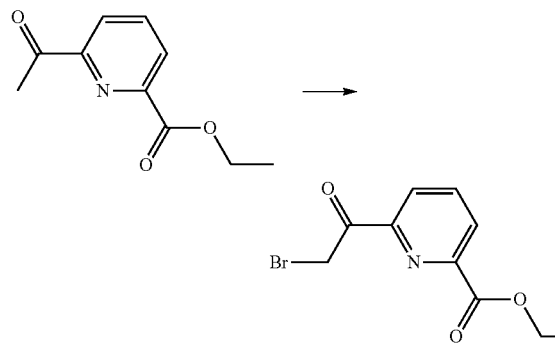

3.1 mL of hydrogen bromide (30% acetic acid solution) was added to 990 mg of ethyl 6-acetylpicolinate. Then, 300 µL of bromine was added dropwise thereto, followed by stirring at room temperature for 9 hours. Distilled water and ethyl acetate were added to the reaction solution, followed by extraction with ethyl acetate. The organic layer was washed with a saturated aqueous sodium hydrogen carbonate solution and saturated saline and dried over magnesium sulfate. The solvent was distilled off under reduced pressure, and the residue was purified by column chromatography (silica gel, ethyl acetate/hexane=0/100→20/80) to give 1.49 g of the title compound as a colorless oil.

MS(ESI m/z): 273.8 (M+H)

RT(min): 1.29

Synthesis of methyl 2-(2-bromoacetyl)thiazole-4-carboxylate

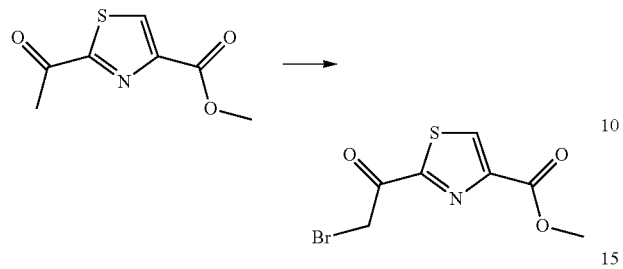

The procedure was carried out in the same manner as the synthesis of ethyl 6-(2-bromoacetyl)picolinate.
MS(ESI m/z): 265.8 (M+H)
RT(min): 1.08

Synthesis of ethyl 2-(2-bromoacetyl)nicotinate

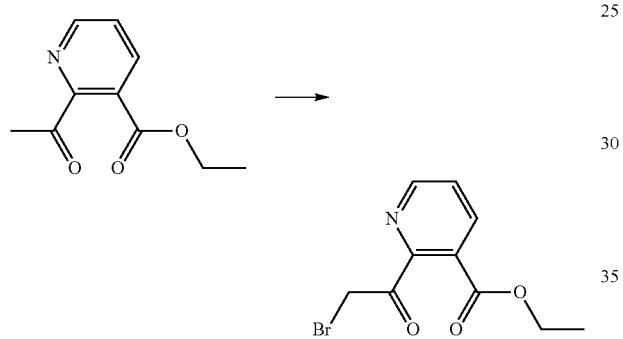

The procedure was carried out in the same manner as the synthesis of ethyl 6-(2-bromoacetyl)picolinate.
MS(ESI m/z): 273.9 (M+H)
RT(min): 1.24

Synthesis of methyl 6-acetylnicotinate

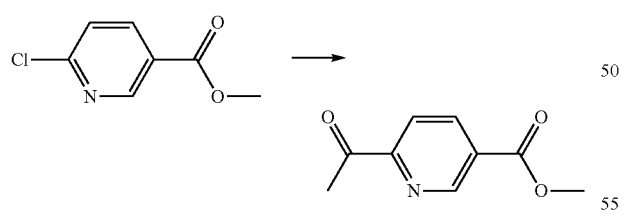

20 mL of toluene was added to 1.5 g of methyl 6-chloronicotinate, followed by nitrogen substitution. 3.65 mL of tributyl (1-ethoxyvinyl)tin and 308 mg of dichlorobis(triphenylphosphine)palladium (II) were added to the solution which was then stirred at 105° C. for 5 hours and 40 minutes under a nitrogen atmosphere. The solvent was distilled off under reduced pressure, and 10 mL of methanol and 5 mL of concentrated hydrochloric acid were added thereto, followed by stirring at room temperature for 16 hours. The solvent was distilled off under reduced pressure, and 5 mL of distilled water was added to the residue, followed by a neutralization treatment with a saturated aqueous sodium hydrogen carbonate solution. Ethyl acetate was added thereto, followed by extraction with ethyl acetate. The organic layer was washed with saturated saline and dried over magnesium sulfate. The solvent was distilled off under reduced pressure, and the residue was purified by column chromatography (silica gel, ethyl acetate/hexane=0/100→40/60) to give 927 mg of the title compound as a white solid.
MS(ESI m/z): 180.0 (M+H)
RT(min): 0.97

Synthesis of methyl 6-(2-bromoacetyl)nicotinate

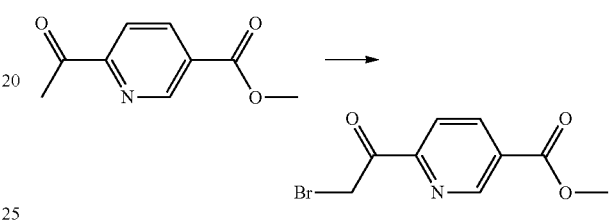

The procedure was carried out in the same manner as the synthesis of ethyl 6-(2-bromoacetyl)picolinate.
MS(ESI m/z): 259.0 (M+H)
RT(min): 1.26

Synthesis of ethyl 6-acetylpyrazolo[1,5-a]pyrimidine-2-carboxylate

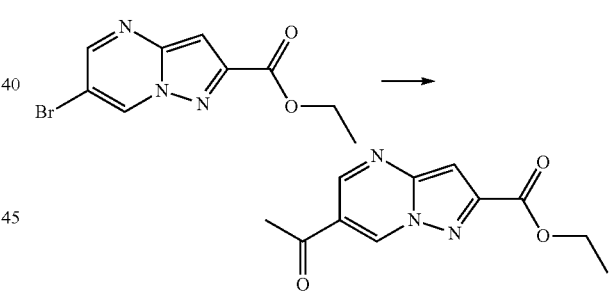

The procedure was carried out in the same manner as the synthesis of methyl 6-acetylnicotinate.
MS(ESI m/z): 234.0 (M+H)
RT(min): 0.95

Synthesis of ethyl 6-(2-bromoacetyl)pyrazolo[1,5-a]pyrimidine-2-carboxylate

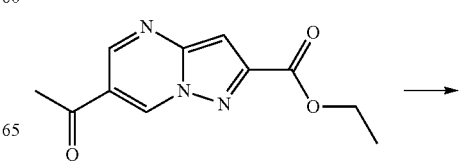

-continued

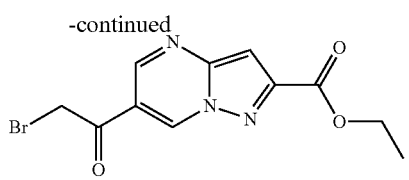

The procedure was carried out in the same manner as the synthesis of ethyl 6-(2-bromoacetyl)picolinate.
MS(ESI m/z): 313.9 (M+H)
RT(min): 1.13

Synthesis of 3-bromo-2,2-dimethoxypropanoic acid

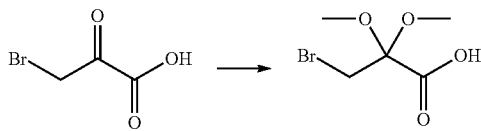

10 mL of trimethyl orthoformate and 400 µL of sulfuric acid were added to 5.0 g of 3-bromopyruvic acid, which was then stirred at room temperature for 9 hours. 100 mL of dichloromethane was added to the reaction solution which was then washed with 100 mL of a 10% aqueous hydrochloric acid solution. Ethyl acetate was added to the aqueous layer, followed by extraction with ethyl acetate. The organic layer was washed with saturated saline and dried over magnesium sulfate. The solvent was distilled off under reduced pressure to give 3.43 g of the title compound as a white solid.
$^1$H-NMR (CDCl$_3$) δ: 3.62 (2H, s), 3.38 (6H, s).

Synthesis of methyl O-benzyl-N-(3-bromo-2,2-dimethoxypropanoyl)-L-serinate

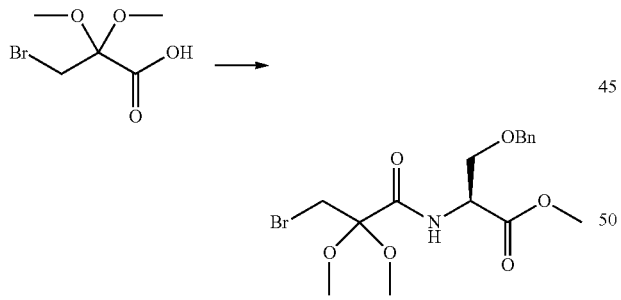

50 mL of dichloromethane, 17 mL of diisopropylethylamine, 7.35 g of HATU (1-[bis(dimethylamino)methylene]-1H-1,2,3-triazolo[4,5-b]pyridinium 3-oxide hexafluorophosphate), and 4.35 g of O-methyl O-benzyl-L-serinate hydrochloride were added to 3.43 g of 3-bromo-2,2-dimethoxypropanoic acid, which was then stirred at room temperature for 7 hours. The solvent was distilled off under reduced pressure, and an aqueous hydrochloric acid solution (1 mol/L) and ethyl acetate were added to the residue, followed by extraction with ethyl acetate. The organic layer was washed with an aqueous hydrochloric acid solution (1 mol/L), a saturated aqueous sodium hydrogen carbonate solution and saturated saline, and dried over magnesium sulfate. The solvent was distilled off under reduced pressure, and the residue was purified by column chromatography (silica gel, ethyl acetate/hexane=0/100→40/60) to give 5.77 g of the title compound as a colorless oil.
MS(ESI m/z): 405.9 (M+H)
RT(min): 1.46

Synthesis of methyl (3-bromo-2,2-dimethoxypropanoyl)-L-serinate

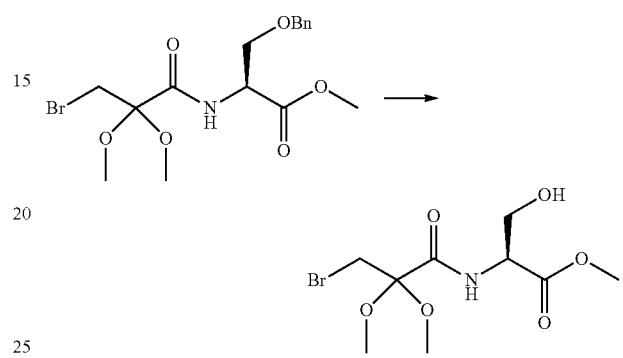

30 mL of methanol was added to 5.77 g of methyl O-benzyl-N-(3-bromo-2,2-dimethoxypropanoyl)-L-serinate and the reaction is carried out by a flow hydrogenation reactor (H-Cube, available from ThalesNano, Inc.) (10% palladium hydroxide/carbon, 40 bar, 60° C., 2.0 mL/mL). After the reaction was completed, the solvent was distilled off under reduced pressure to give 4.41 g of the title compound as a yellow oil.
MS(ESI m/z): 315.9 (M+H)
RT(min): 0.75

Synthesis of methyl 2-(2-bromo-1,1-dimethoxyethyl)oxazole-4-carboxylate

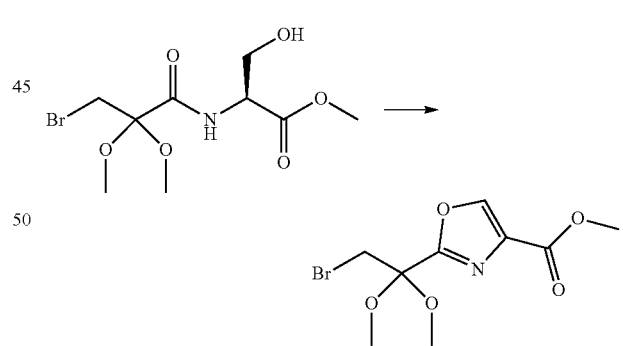

50 mL of dichloromethane was added to 4.41 g of methyl (3-bromo-2,2-dimethoxypropanoyl)-L-serinate, which was then cooled to −78° C. 2.05 mL of (diethylamino) sulfur trifluoride was added dropwise to the solution which was then stirred at −78° C. for 1 hour. Thereafter, 3.75 g of potassium carbonate was added thereto, followed by stirring at −78° C. for 1 hour and at room temperature for 2 hours. After filtering off the insolubles, the filtrate was distilled off under reduced pressure, and 50 mL of dichloromethane and 4.2 mL of diazabicycloundecene were added thereto. On an ice bath, 3.72 mL of bromotrichloromethane was added dropwise thereto, followed by stirring at room temperature for 4 hours and 30 minutes. The solvent was distilled off under reduced pressure, and distilled water and ethyl acetate were added to the residue, followed by extraction with ethyl acetate. The organic layer was washed with an aqueous hydrochloric acid solution (1 mol/L), a saturated aqueous sodium hydrogen carbonate solution and saturated saline, and dried over magnesium sulfate. The solvent was distilled off under reduced pressure, and the residue was purified by column chromatography (silica gel, ethyl acetate/hexane=12/88→100/0) to give 2.57 g of the title compound as a yellow oil.

MS(ESI m/z): 295.9 (M+H)

RT(min): 1.05

Synthesis of methyl 2-(2-bromoacetyl)oxazole-4-carboxylate

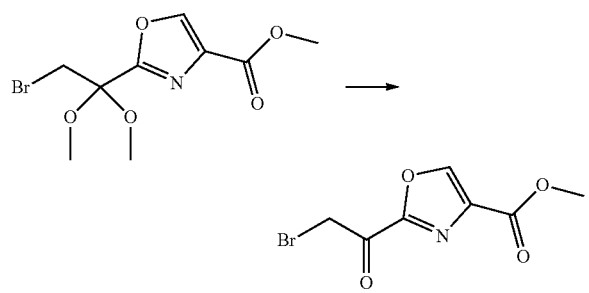

15 mL of formic acid was added to 2.57 g of methyl 2-(2-bromo-1,1-dimethoxyethyl)oxazole-4-carboxylate and stirred at 60° C. for 3 hours and 30 minutes. A saturated aqueous sodium hydrogen carbonate solution was added to the reaction solution, followed by extraction with ethyl acetate. The organic layer was washed with saturated saline and dried over magnesium sulfate. The solvent was distilled off under reduced pressure, and the residue was purified by column chromatography (silica gel, ethyl acetate/hexane=0/100→20/80→40/60) to give 1.46 g of the title compound as a white solid.

MS(ESI m/z): 249.9 (M+H)

RT(min): 0.93

Synthesis of methyl N-(2-(benzyloxy)propanoyl)-O-(tert-butyl)-L-allothreoninate

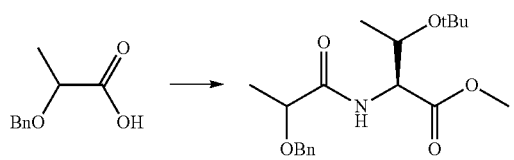 [SMILES: CC(OCc1ccccc1)C(=O)O ; COC(=O)[C@@H](NC(=O)C(C)OCc1ccccc1)C(C)OC(C)(C)C]

The procedure was carried out in the same manner as the synthesis of methyl O-benzyl-N-(3-bromo-2,2-dimethoxypropanoyl)-L-serinate.

MS(ESI m/z): 352.2 (M+H)

RT(min): 1.66

Synthesis of methyl (2-(benzyloxy)propanoyl)-L-allothreoninate

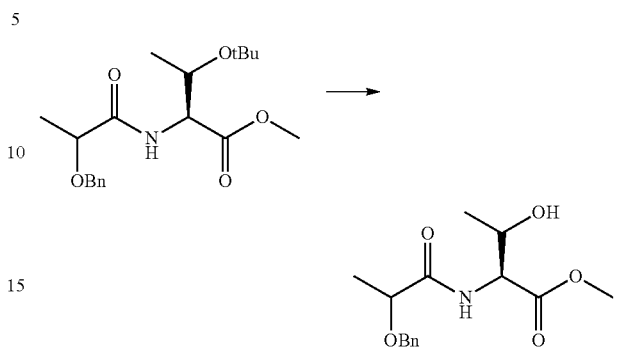

10 mL of TFA was added to 3.91 g of methyl N-(2-(benzyloxy)propanoyl)-O-(tert-butyl)-L-allothreoninate, which was then stirred at room temperature for 2 hours. The solvent was distilled off under reduced pressure, and a saturated aqueous sodium hydrogen carbonate solution and ethyl acetate were added to the residue, followed by extraction with ethyl acetate. The organic layer was washed with a saturated aqueous sodium hydrogen carbonate solution and saturated saline and dried over magnesium sulfate. The solvent was distilled off under reduced pressure, and the residue was purified by column chromatography (silica gel, ethyl acetate/hexane=50/50→100/0) to give 2.30 g of the title compound as a colorless oil.

MS(ESI m/z): 296.1 (M+H)

RT(min): 1.06

Synthesis of methyl (2S)-2-(2-(benzyloxy)propanamide)-3-oxobutanoate

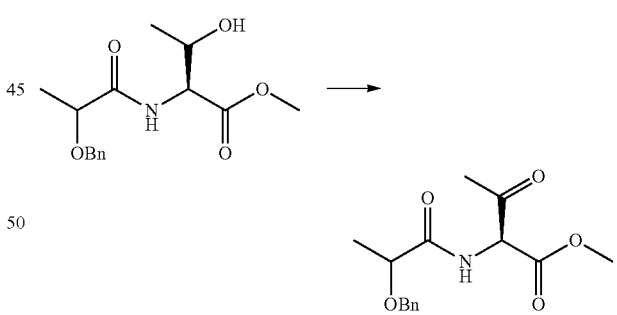

15 mL of dichloromethane was added to 2.30 g of methyl (2-(benzyloxy)propanoyl)-L-allothreoninate. 4.29 g of Dess-Martin periodinane was added thereto on an ice bath, followed by stirring at room temperature for 1 hour. The insolubles were filtered off, the solvent was distilled off under reduced pressure, and the residue was purified by column chromatography (silica gel, ethyl acetate/hexane=0/100→20/80→40/60) to give 2.18 g of the title compound as a colorless oil.

MS(ESI m/z): 294.1 (M+H)

RT(min): 1.26

Synthesis of methyl 2-(1-(benzyloxy)ethyl)-5-methyloxazole-4-carboxylate (DL01721-040)

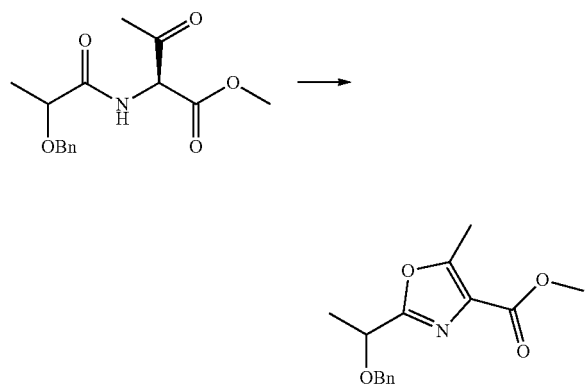

20 mL of dichloromethane and 4.14 mL of triethylamine were added to 2.18 g of methyl (2S)-2-(2-(benzyloxy)propanamide)-3-oxobutanoate. 3.9 g of triphenylphosphine and 3.77 g of iodine were added thereto on an ice bath, followed by stirring at room temperature for 3 hours. The solvent was distilled off under reduced pressure, and distilled water and ethyl acetate were added to the residue, followed by extraction with ethyl acetate. The organic layer was washed with distilled water, an aqueous sodium thiosulfate solution (10%) and saturated saline, and dried over magnesium sulfate. The solvent was distilled off under reduced pressure, and the residue was purified by column chromatography (silica gel, ethyl acetate/hexane=0/100→10/90→20/80) to give 1.55 g of the title compound as a yellow oil.

MS(ESI m/z): 276.1 (M+H)
RT(min): 1.42

Synthesis of 2-(1-(benzyloxy)ethyl)-5-methyloxazole-4-carboxamide

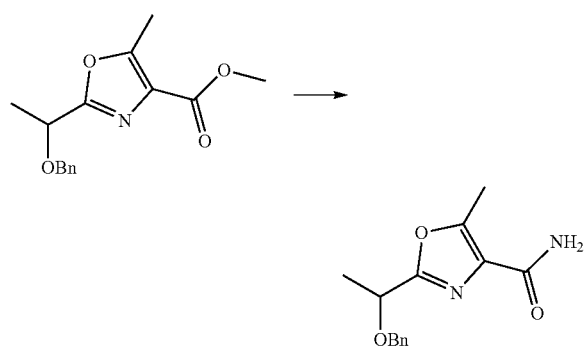

The procedure was carried out in the same manner as the synthesis of tert-butyl (S)-2-((tert-butoxycarbonyl)amino)-3-(4-carbamoylthiazol-2-yl)propanoate MS(ESI m/z): 261.1 (M+H)
RT(min): 1.21

Synthesis of 2-(1-(benzyloxy)ethyl)-5-methyloxazole-4-carbothioamide

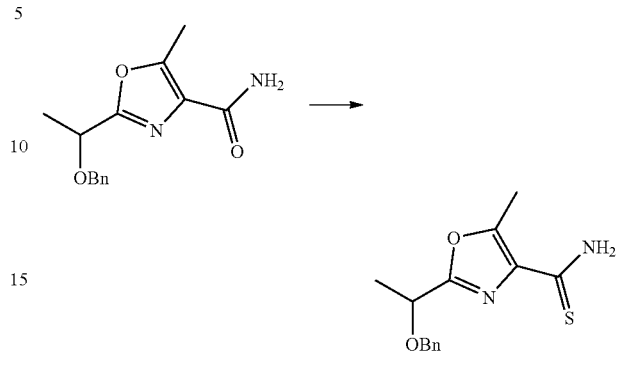

The procedure was carried out in the same manner as the synthesis of tert-butyl (S)-4-amino-2-((tert-butoxycarbonyl)amino)-4-thioxobutanoate.

MS(ESI m/z): 277.1 (M+H)
RT(min): 1.49

Synthesis of ethyl 2-(2-(1-(benzyloxy)ethyl)-5-methyloxazol-4-yl)thiazole-4-carboxylate

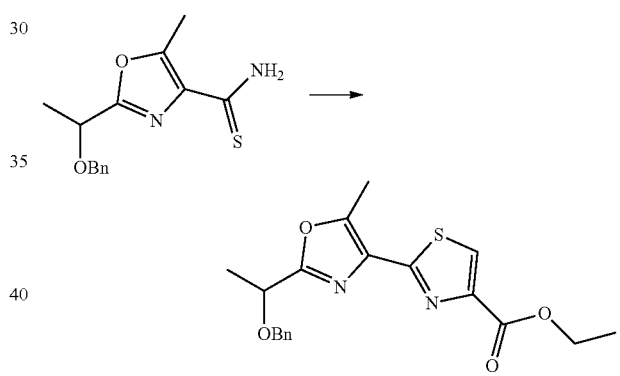

10 mL of ethanol and 335 µL of ethyl bromopyruvate were added to 2-(1-(benzyloxy)ethyl)-5-methyloxazole-4-carbothioamide, which was then heated to reflux for 2 hours. The solvent was distilled off under reduced pressure, and the residue was purified by column chromatography (silica gel, ethyl acetate/hexane=0/100→15/85) to give 650 mg of the title compound as a brown oil.

MS(ESI m/z): 373.1 (M+H)
RT(min): 1.79

Synthesis of ethyl 2-(2-(1-hydroxyethyl)-5-methyloxazol-4-yl)thiazole-4-carboxylate

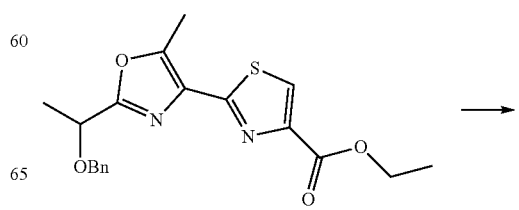

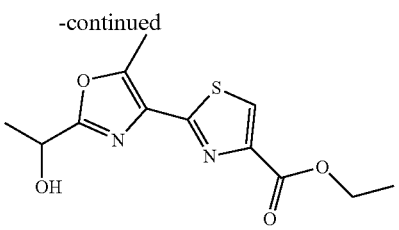

5 mL of dichloromethane was added to 650 mg of ethyl 2-(2-(1-(benzyloxy)ethyl)-5-methyloxazol-4-yl)thiazole-4-carboxylate. 1.65 mL of a dichloromethane solution of boron tribromide (1 mol/L) was added dropwise thereto at −78° C., followed by stirring at −78° C. for 1 hour. Thereafter, another 1.65 mL of a dichloromethane solution of boron tribromide (1 mol/L) was added dropwise thereto at −78° C., followed by stirring at −78° C. for 1 hour. Distilled water was added thereto on an ice bath, followed by extraction with dichloromethane. The organic layer was washed with saturated saline and dried over magnesium sulfate. The solvent was distilled off under reduced pressure, and the residue was purified by column chromatography (silica gel, ethyl acetate/hexane=0/100→25/75→50/50) to give 372 mg of the title compound as a pale yellow solid.

MS(ESI m/z): 283.0 (M+H)
RT(min): 1.09

Synthesis of ethyl 2-(2-acetyl-5-methyloxazol-4-yl)thiazole-4-carboxylate

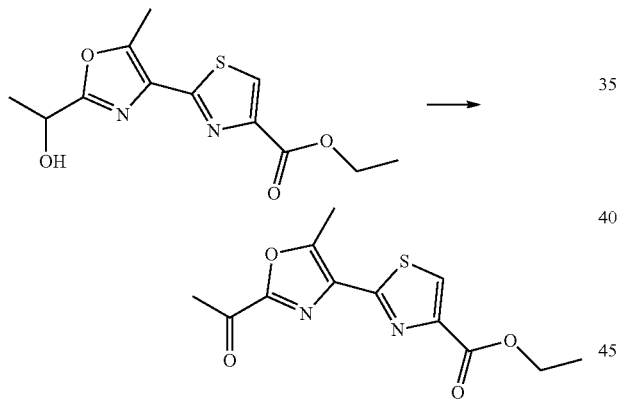

The procedure was carried out in the same manner as the synthesis of methyl (2S)-2-(2-(benzyloxy)propanamido)-3-oxobutanoate.

MS(ESI m/z): 281.0 (M+H)
RT(min): 1.32

Synthesis of ethyl 2-(2-(2-bromoacetyl)-5-methyl-oxazol-4-yl)thiazole-4-carboxylate

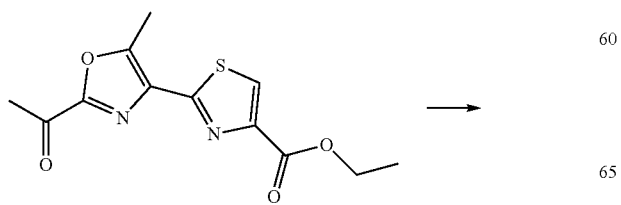

The procedure was carried out in the same manner as the synthesis of ethyl 6-(2-bromoacetyl)picolinate.

MS(ESI m/z): 360.9 (M+H)
RT(min): 1.50

Synthesis of methyl 2-(1-hydroxyethyl)-5-methyloxazole-4-carboxylate

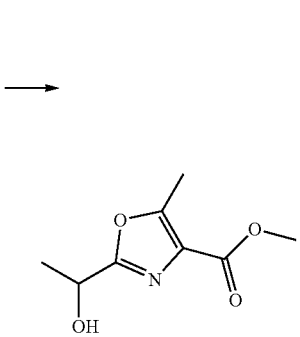

The procedure was carried out in the same manner as the synthesis of ethyl 2-(2-(1-hydroxyethyl)-5-methyloxazol-4-yl)thiazole-4-carboxylate.

MS(ESI m/z): 186.1 (M+H)
RT(min): 0.69

Synthesis of methyl 2-acetyl-5-methyloxazole-4-carboxylate

The procedure was carried out in the same manner as the synthesis of methyl (2S)-2-(2-(benzyloxy)propanamido)-3-oxobutanoate.

MS(ESI m/z): 184.1 (M+H)
RT(min): 0.81

Synthesis of methyl 2-(2-bromoacetyl)-5-methyloxazole-4-carboxylate

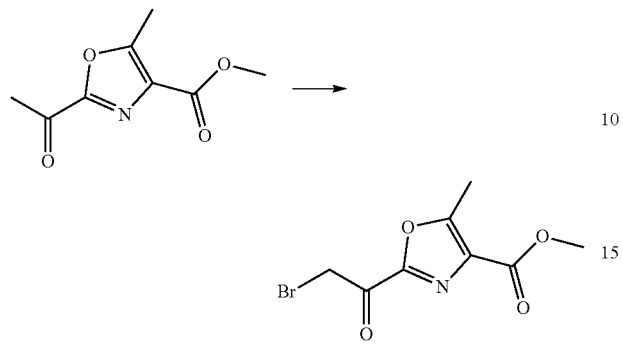

The procedure was carried out in the same manner as the synthesis of ethyl 6-(2-bromoacetyl)picolinate.

MS(ESI m/z): 263.0 (M+H)

RT(min): 1.08

Synthesis of 6-chloropyridine-3-carbothioamide

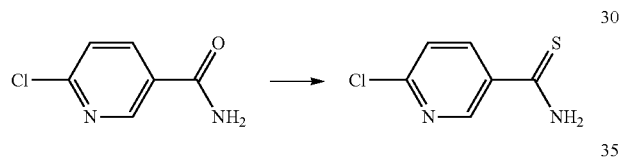

The procedure was carried out in the same manner as the synthesis of tert-butyl (S)-4-amino-2-((tert-butoxycarbonyl)amino)-4-thioxobutanoate.

MS(ESI m/z): 173.0 (M+H)

RT(min): 0.85

Synthesis of ethyl 2-(6-chloropyridin-3-yl)thiazole-4-carboxylate

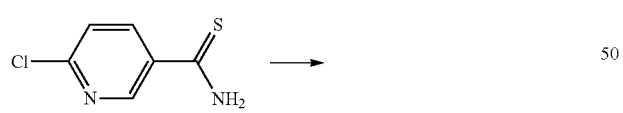

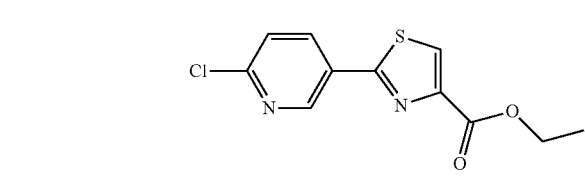

The procedure was carried out in the same manner as the synthesis of ethyl 2-(2-(1-(benzyloxy)ethyl)-5-methyloxazol-4-yl)thiazole-4-carboxylate.

MS(ESI m/z): 269.0 (M+H)

RT(min): 1.31

Synthesis of ethyl 2-(6-acetylpyridin-3-yl)thiazole-4-carboxylate

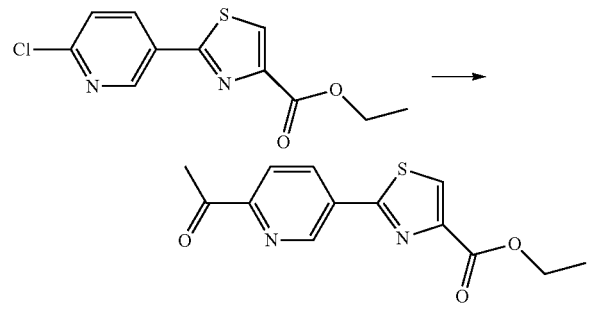

The procedure was carried out in the same manner as the synthesis of methyl 6-acetylnicotinate.

MS(ESI m/z): 277.0 (M+H)

RT(min): 1.23

Synthesis of ethyl 2-(6-(2-bromoacetyl)pyridin-3-yl)thiazole-4-carboxylate

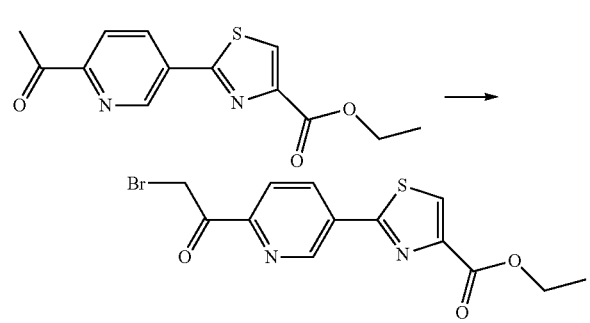

The procedure was carried out in the same manner as the synthesis of ethyl 6-(2-bromoacetyl)picolinate.

MS(ESI m/z): 356.9 (M+H)

RT(min): 1.45

Synthesis of 6-chloropyridine-2-carbothioamide

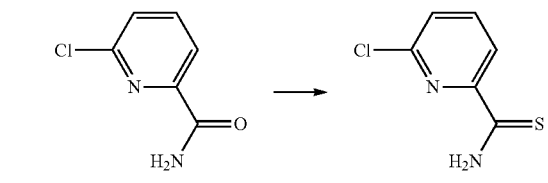 [SMILES: NC(=O)c1cccc(Cl)n1 ; NC(=S)c1cccc(Cl)n1]

The procedure was carried out in the same manner as the synthesis of tert-butyl (S)-4-amino-2-((tert-butoxycarbonyl)amino)-4-thioxobutanoate.

MS(ESI m/z): 173.0 (M+H)

RT(min): 1.08

Synthesis of ethyl 2-(6-chloropyridin-2-yl)thiazole-4-carboxylate

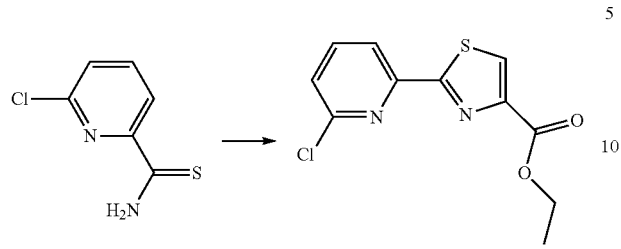

The procedure was carried out in the same manner as the synthesis of ethyl 2-(2-(1-(benzyloxy)ethyl)-5-methyloxazol-4-yl)thiazole-4-carboxylate.

MS(ESI m/z): 269.0 (M+H)
RT(min): 1.51

Synthesis of ethyl 2-(6-acetylpyridin-2-yl)thiazole-4-carboxylate

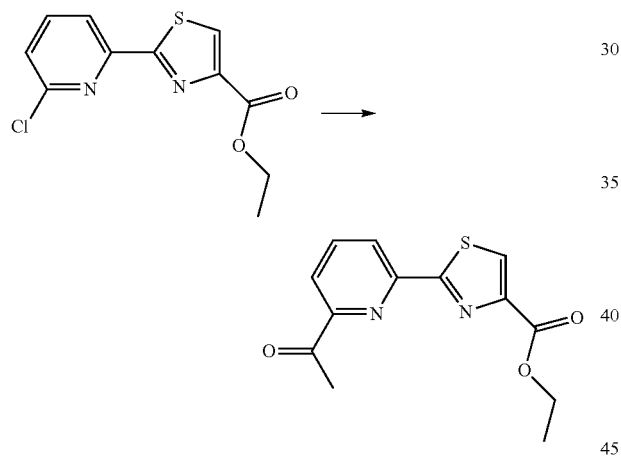

The procedure was carried out in the same manner as the synthesis of methyl 6-acetylnicotinate.

MS(ESI m/z): 277.0 (M+H)
RT(min): 1.41

Synthesis of ethyl 2-(6-(2-bromoacetyl)pyridin-2-yl)thiazole-4-carboxylate

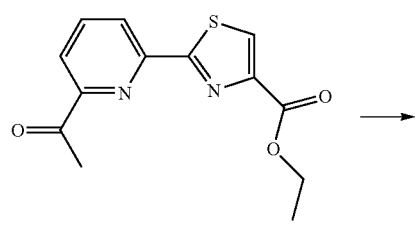

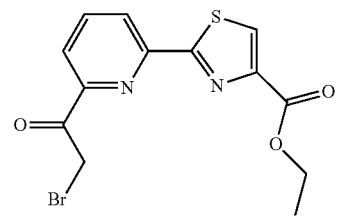

The procedure was carried out in the same manner as the synthesis of ethyl 6-(2-bromoacetyl)picolinate.

MS(ESI m/z): 356.9 (M+H)
RT(min): 1.54

Synthesis of methyl (S)-2'-(3-(tert-butoxy)-2-((tert-butoxycarbonyl)amino)-3-oxopropyl)-[2,4'-bithiazole]-4-carboxylate

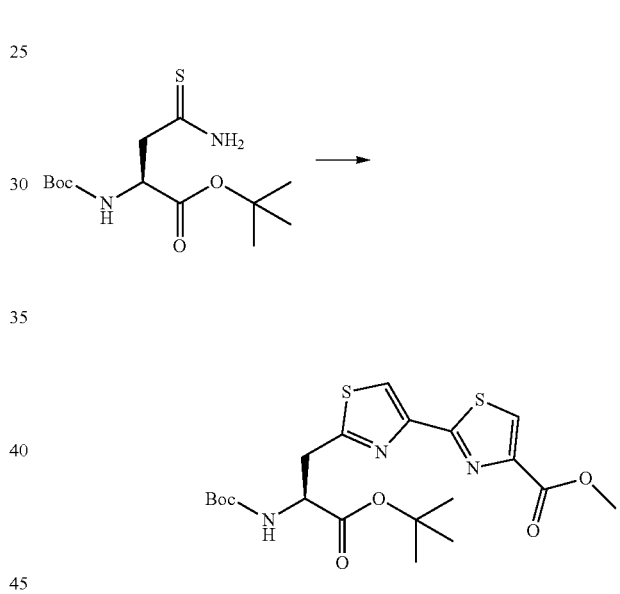

10 mL of ethanol and 342 mg of methyl 2-(2-bromoacetyl)thiazole-4-carboxylate were added to 395 mg of tert-butyl (S)-4-amino-2-((tert-butoxycarbonyl)amino)-4-thioxobutanoate, which was then heated to reflux for 1 hour. The solvent was distilled off under reduced pressure, and 10 mL of dimethylformamide, 1 mL of diisopropylethylamine, and 360 μL of Boc$_2$O were added thereto, followed by stirring at room temperature for 5 hours. The solvent was distilled off under reduced pressure, and the residue was purified by column chromatography (silica gel, ethyl acetate/hexane=0/100→20/80→40/60) to give 489 mg of the title compound as a pale yellow oil.

MS(ESI m/z): 470.0 (M+H)
RT(min): 1.66

The synthesis of the compounds shown in Table 7 below was carried out in the same manner as the synthesis of methyl (S)-2'-(3-(tert-butoxy)-2-((tert-butoxycarbonyl)amino)-3-oxopropyl)-[2,4'-bithiazole]-4-carboxylate.

TABLE 7

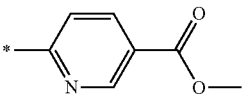

| R | Compound name | Oberved MS | RT/min |
|---|---|---|---|
| 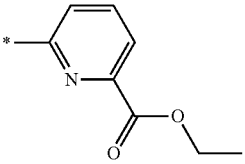 | methyl (S)-6-(2-(3-(tert-butoxy)-2-((tert-butoxycarbonyl)amino)-3-oxopropyl)thiazol-4-yl)nicotinate | 464.0 | 1.79 |
| 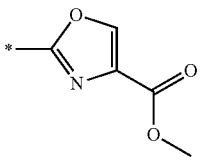 | ethyl (S)-6-(2-(3-(tert-butoxy)-2-((tert-butoxycarbonyl)amino)-3-oxopropyl)thiazol-4-yl)picolinate | 478.1 | 1.81 |
| 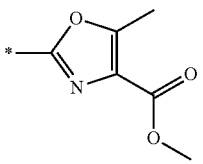 | methyl (S)-2-(2-(3-(tert-butoxy)-2-((tert-butoxycarbonyl)amino)-3-oxopropyl)thiazol-4-yl)oxazol-4-carboxylate | 454.1 | 1.55 |
| 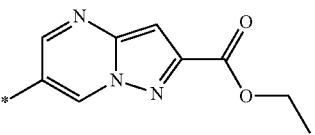 | methyl (S)-2-(2-(3-(tert-butoxy)-2-((tert-butoxycarbonyl)amino)-3-oxopropyl)thiazol-4-yl)-5-methyl-oxazol-4-carboxylate | 468.1 | 1.62 |
|  | ethyl (S)-6-(2-(3-(tert-butoxy)-2-((tert-butoxycarbonyl)amino)-3-oxopropyl)thiazol-4-yl)pyrazolo[1,5-a]pyrimidin-2-carboxylate | 518.1 | 1.74 |

TABLE 7-continued

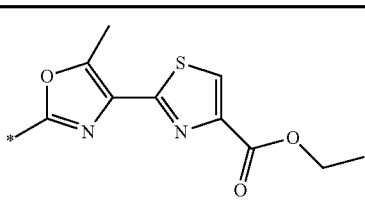

| R | Compound name | Observed MS | RT/min |
|---|---|---|---|
| 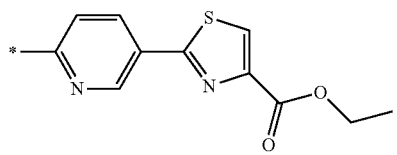 | ethyl (S)-2-(2-(2-(3-(tert-butoxy)-2-((tert-butoxycarbonyl)amino)-3-oxopropyl)thiazol-4-yl)-5-methyloxazol-4-yl)thiazol-4-carboxylate | 565.0 | 1.89 |
| 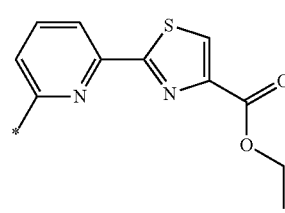 | ethyl (S)-2-(6-(2-(3-(tert-butoxy)-2-((tert-butoxycarbonyl)amino)-3-oxopropyl)thiazol-4-yl)pyridin-3-yl)thiazol-4-carboxylate | 561.1 | 1.89 |
| 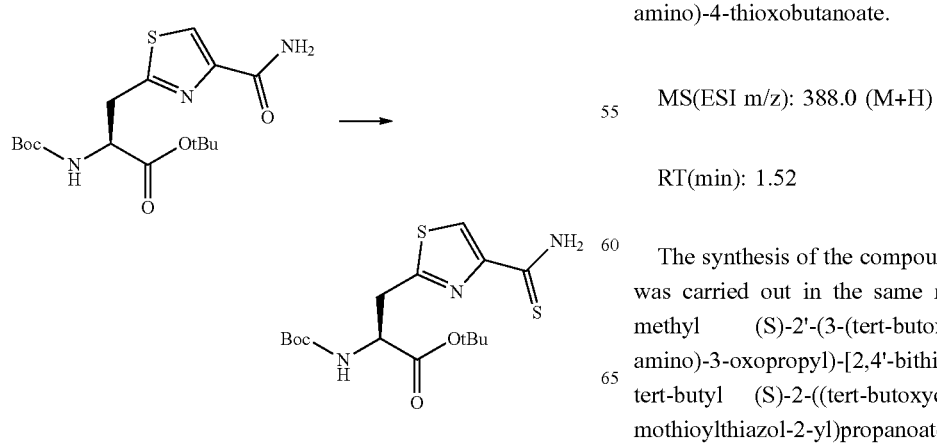 | ethyl (S)-2-(6-(2-(3-(tert-butoxy)-2-((tert-butoxycarbonyl)amino)-3-oxopropyl)thiazol-4-yl)pyridin-2-yl)thiazol-4-carboxylate | 561.1 | 2.01 |

Synthesis of tert-butyl (S)-2-((tert-butoxycarbonyl)amino)-3-(4-carbamothioylthiazol-2-yl)propanoate The procedure was carried out in the same manner as the synthesis of tert-butyl (S)-4-amino-2-((tert-butoxycarbonyl)amino)-4-thioxobutanoate.

MS(ESI m/z): 388.0 (M+H)

RT(min): 1.52

The synthesis of the compounds shown in Table 8 below was carried out in the same manner as the synthesis of methyl (S)-2'-(3-(tert-butoxy)-2-((tert-butoxycarbonyl)amino)-3-oxopropyl)-[2,4'-bithiazole]-4-carboxylate, using tert-butyl (S)-2-((tert-butoxycarbonyl)amino)-3-(4-carbamothioylthiazol-2-yl)propanoate as a raw material.

TABLE 8

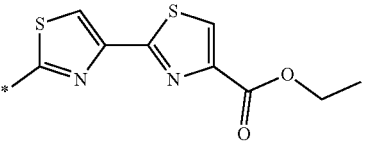 [SMILES: *c1nc(-c2nc(C(=O)OCC)cs2)cs1]

| R | Compound name | Observed MS | RT/min |
|---|---|---|---|
| 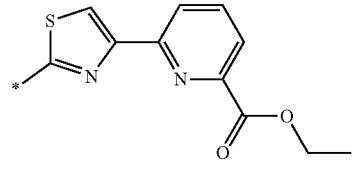 [SMILES: *c1nc(-c2cccc(C(=O)OCC)n2)cs1] | ethyl (S)-2''-(3-(tert-butoxy)-2-((tert-butoxycarbonyl)amino)-3-oxopropyl)-[2,4':2',4''-terthiazole]-4-carboxylate | 553.9 | 1.84 |
| 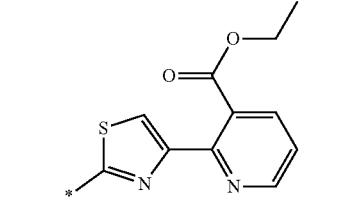 [SMILES: *c1nc(-c2ncccc2C(=O)OCC)cs1] | ethyl (S)-6-(2'-(3-tert-butoxy)-2-((tert-butoxycarbonyl)amino)-3-oxopropyl)-[2,4'-bithiazol]-4-yl)picolinate | 561.0 | 1.95 |
| | ethyl (S)-2-(2'-(3-(tert-butoxy)-2-((tert-butoxycarbonyl)amino)-3-oxopropyl)-[2,4'-bithiazol]-4-yl)nicotinate | 561.0 | 1.84 |

Synthesis of tert-butyl (S)-2-((tert-butoxycarbonyl)amino)-3-(4-carbamoyl-[2,4'-bithiazol]-2'-yl)propanoate

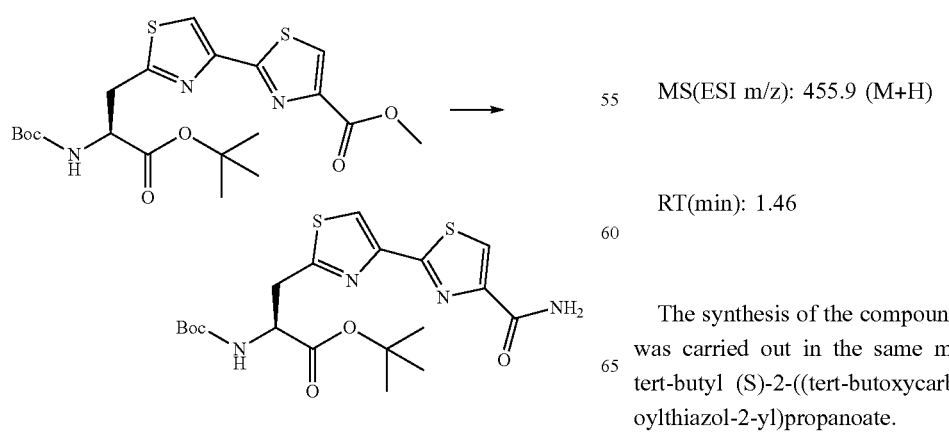

The procedure was carried out in the same manner as the synthesis of tert-butyl (S)-2-((tert-butoxycarbonyl)amino)-3-(4-carbamoylthiazol-2-yl)propanoate.

MS(ESI m/z): 455.9 (M+H)

RT(min): 1.46

The synthesis of the compounds shown in Table 9 below was carried out in the same manner as the synthesis of tert-butyl (S)-2-((tert-butoxycarbonyl)amino)-3-(4-carbamoylthiazol-2-yl)propanoate.

TABLE 9

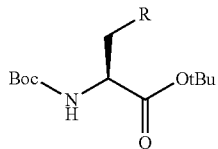

| R | Compound name | Observed MS | RT/min |
|---|---|---|---|
| (4-carbamoyloxazol-2-yl)phenyl | tert-butyl (S)-2-((tert-butoxycarbonyl)amino)-3-(4-(4-carbamoyloxazol-2-yl)phenyl)propanoate | 432.9 | 1.48 |
| (4-carbamoyl-1H-imidazol-1-yl)phenyl | tert-butyl (S)-2-((tert-butoxycarbonyl)amino)-3-(4-(4-carbamoyl-1H-imidazol-1-yl)phenyl)propanoate | 431.0 | 1.36 |
| 2-carbamoylimidazo[1,2-a]pyrimidin-6-yl | tert-butyl (S)-2-((tert-butoxycarbonyl)amino)-3-(2-carbamoylimidazo[1,2-a]pyrimdin-6-yl)propanoate | 406.1 | 1.14 |
| 2-carbamoylimidazo[1,2-a]pyrazin-6-yl | tert-butyl (S)-2-((tert-butoxycarbonyl)amino)-3-(2-carbamoylimidazo[1,2-a]pyrazin-6-yl)propanoate | 406.1 | 1.19 |
| 2-carbamoylimidazo[1,2-b]pyridazin-6-yl | tert-butyl (S)-2-((tert-butoxycarbonyl)amino)-3-(2-carbamoylimidazo[1,2-b]pyridazin-6-yl)propanoate | 406.1 | 1.24 |
| 2-carbamoylimidazo[1,2-a]pyridin-6-yl | tert-butyl (S)-2-((tert-butoxycarbonyl)amino)-3-(2-carbamoylimidazo[1,2-a]pyridin-6-yl)propanoate | 405.1 | 1.17 |
| 4-(5-carbamoylpyridin-2-yl)thiazol-2-yl | tert-butyl (S)-2-((tert-butoxycarobnyl)amino)-3-(4-(5-carbamoylpyridin-2-yl)thiazol-2-yl)propanoate | 449.1 | 1.38 |
| 4-(6-carbamoylpyridin-2-yl)thiazol-2-yl | tert-butyl (S)-2-((tert-butoxycarbonyl)amino)-3-(4-(6-carbamoylpyridin-2-yl)thiazol-2-yl)propanoate | 449.1 | 1.51 |
| 4-(4-carbamoyloxazol-2-yl)thiazol-2-yl | tert-butyl (S)-2-((tert-butoxycarbonyl)amino)-3-(4-(4-carbamoyloxazol-2-yl)thiazol-2-yl)propanoate | 439.1 | 1.33 |

TABLE 9-continued

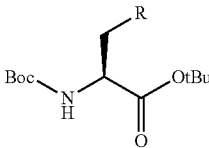

| R | Compound name | Observed MS | RT/min |
|---|---|---|---|
| 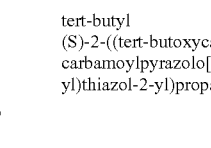 | tert-butyl (S)-2-((tert-butoxycarbonyl)amino)-3-(4-(4-carbamoyl-5-methyloxazol-2-yl)thiazol-2-yl)propanoate | 453.1 | 1.43 |
| 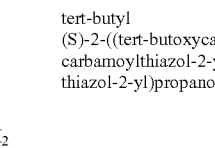 | tert-butyl (S)-2-((tert-butoxycarbonyl)amino)-3-(4-(2-carbamoylpyrazolo[1,5-a]pyrimidin-6-yl)thiazol-2-yl)propanoate | 489.0 | 1.40 |
| 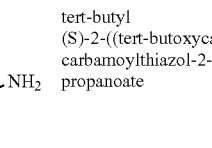 | tert-butyl (S)-2-((tert-butoxycarbonyl)amino)-3-(4-(4-(4-carbamoylthiazol-2-yl)-5-methyloxazol-2-yl-thiazol-2-yl)propanoate | 536.1 | 1.55 |
| 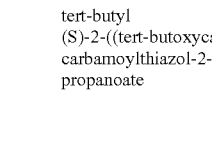 | tert-butyl (S)-2-((tert-butoxycarbonyl)amino)-3-(4-(5-(4-carbamoylthiazol-2-yl)pyridin-2-yl)thiazol-2-yl)propanoate | 532.1 | 1.58 |
| 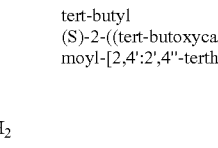 | tert-butyl (S)-2-((tert-butoxycarbonyl)amino)-3-(4-(6-(4-carbamoylthiazol-2-yl)pyridin-2-yl)thiazol-2-yl)propanoate | 532.1 | 1.67 |
| 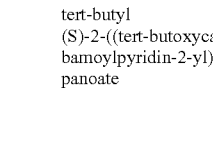 | tert-butyl (S)-2-((tert-butoxycarbonyl)amino)-3-(4-carbamoyl-[2,4':2',4''-terthiazol]-2''-yl)propanoate | 538.2 | 1.59 |
| | tert-butyl (S)-2-((tert-butoxycarbonyl)amino)-3-(4-(6-carbamoylpyridin-2-yl)-[2,4'-bithiazol]-2'-yl)propanoate | 532.0 | 1.65 |

TABLE 9-continued

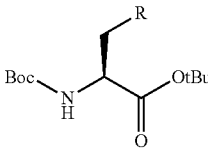

| R | Compound name | Observed MS | RT/min |
|---|---|---|---|
| 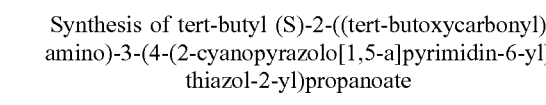 | tert-butyl (S)-2-((tert-butoxycarbonyl)amino)-3-(4-(3-carbamoylpyridin-2-yl)-[2,4'-bithiazol]-2'-yl)propanoate | 532.0 | 1.38 |

Synthesis of tert-butyl (S)-2-((tert-butoxycarbonyl)amino)-3-(4-(2-cyanopyrazolo[1,5-a]pyrimidin-6-yl)thiazol-2-yl)propanoate

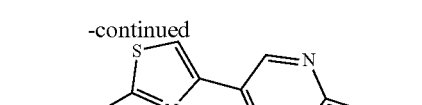

The procedure was carried out in the same manner as the synthesis of tert-butyl (S)-2-((tert-butoxycarbonyl)amino)-3-(4-cyanothiazol-2-yl)propanoate.

MS(ESI m/z): 471.1 (M+H)

RT(min): 1.74

Synthesis of cyanomethyl (S)-2-((tert-butoxycarbonyl)amino)-3-(4-(2-cyanopyrazolo[1,5-a]pyrimidin-6-yl)thiazol-2-yl)propanoate

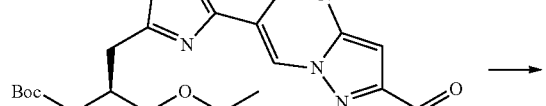

The procedure was carried out in the same manner as the synthesis of cyanomethyl (S)-2-((tert-butoxycarbonyl)amino)-3-(2-cyanoquinolin-6-yl)propanoate.

MS(ESI m/z): 454.2 (M+H)

RT(min): 1.44

$^1$H-NMR (CDCl$_3$) δ: 9.21 (1H, s), 9.05 (1H, s), 7.63 (1H, s), 7.16 (1H, s), 5.59 (1H, d, J=8.6 Hz), 4.97-4.68 (3H, m), 3.78-3.57 (2H, m), 1.46 (9H, s).

Synthesis of tert-butyl (S)-2-((tert-butoxycarbonyl)amino)-3-(4-carbamothioyl[2,4'-bithiazol]-2'-yl)propanoate

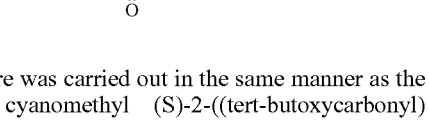

The procedure was carried out in the same manner as the synthesis of tert-butyl (S)-4-amino-2-((tert-butoxycarbonyl)amino)-4-thioxobutanoate.

MS(ESI m/z): 471.1 (M+H)

RT(min): 1.68

Synthesis of methyl (S)-2'''-(3-(tert-butoxy)-2-((tert-butoxycarbonyl)amino)-3-oxopropyl)-[2,4':2',4'':2'',4'''-quaterthiazole]-4-carboxylate

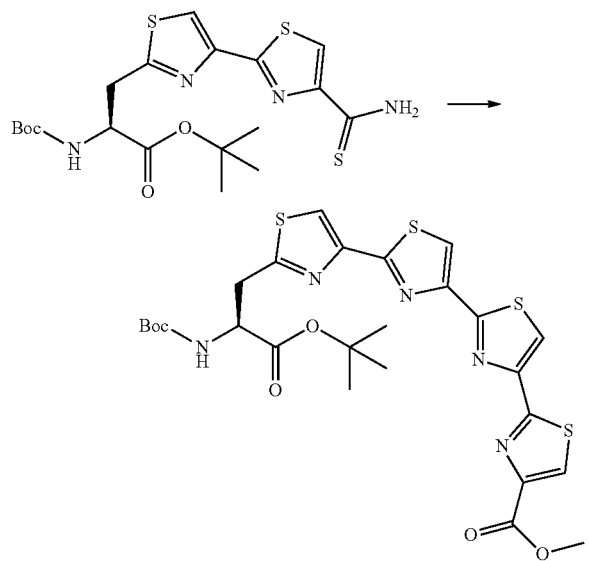

The procedure was carried out in the same manner as the synthesis of methyl (S)-2'-(3-(tert-butoxy)-2-((tert-butoxycarbonyl)amino)-3-oxopropyl)-[2,4'-bithiazole]-4-carboxylate.

MS(ESI m/z): 636.7 (M+H)
RT(min): 1.99

Synthesis of tert-butyl (S)-2-((tert-butoxycarbonyl)amino)-3-(4-(4-carbamothioyloxazol-2-yl)thiazol-2-yl)propanoate

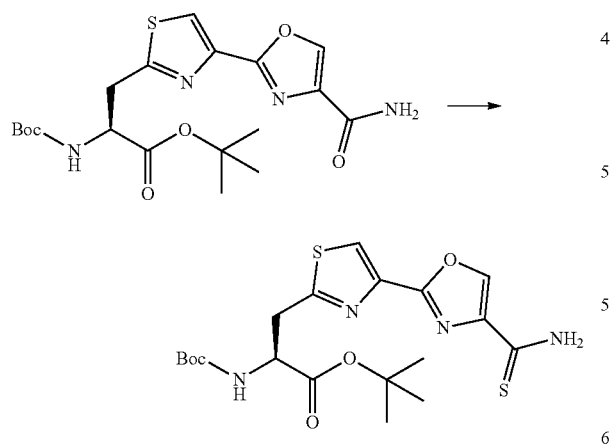

The procedure was carried out in the same manner as the synthesis of tert-butyl (S)-4-amino-2-((tert-butoxycarbonyl)amino)-4-thioxobutanoate.

MS(ESI m/z): 455.0 (M+H)
RT(min): 1.52

Synthesis of ethyl (S)-2-(2-(2-(3-(tert-butoxy)-2-((tert-butoxycarbonyl)amino)-3-oxopropyl)thiazol-4-yl)oxazol-4-yl)thiazole-4-carboxylate

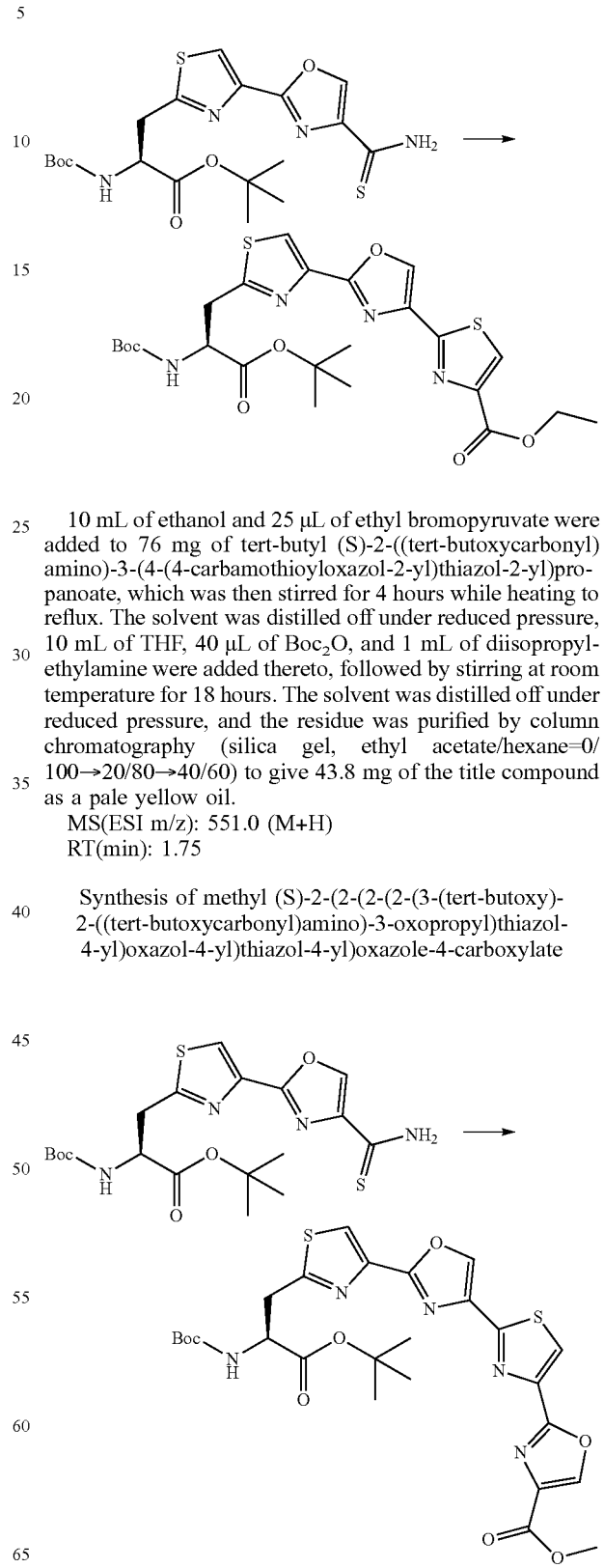

10 mL of ethanol and 25 μL of ethyl bromopyruvate were added to 76 mg of tert-butyl (S)-2-((tert-butoxycarbonyl)amino)-3-(4-(4-carbamothioyloxazol-2-yl)thiazol-2-yl)propanoate, which was then stirred for 4 hours while heating to reflux. The solvent was distilled off under reduced pressure, 10 mL of THF, 40 μL of Boc$_2$O, and 1 mL of diisopropylethylamine were added thereto, followed by stirring at room temperature for 18 hours. The solvent was distilled off under reduced pressure, and the residue was purified by column chromatography (silica gel, ethyl acetate/hexane=0/100→20/80→40/60) to give 43.8 mg of the title compound as a pale yellow oil.

MS(ESI m/z): 551.0 (M+H)
RT(min): 1.75

Synthesis of methyl (S)-2-(2-(2-(2-(3-(tert-butoxy)-2-((tert-butoxycarbonyl)amino)-3-oxopropyl)thiazol-4-yl)oxazol-4-yl)thiazol-4-yl)oxazole-4-carboxylate The procedure was carried out in the same manner as the synthesis of methyl (S)-2'-(3-(tert-butoxy)-2-((tert-butoxycarbonyl)amino)-3-oxopropyl)-[2,4'-bithiazole]-4-carboxylate.

MS(ESI m/z): 604.0 (M+H)

RT(min): 1.69

Synthesis of tert-butyl (S)-2-((tert-butoxycarbonyl)amino)-3-(4-(4-(4-carbamoylthiazol-2-yl)oxazol-2-yl)thiazol-2-yl) propanoate

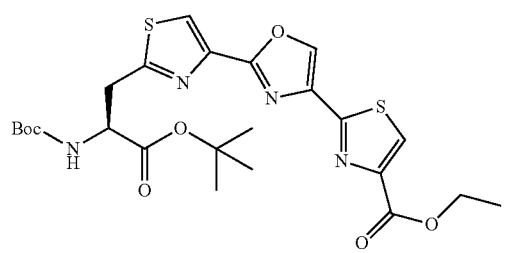

The procedure was carried out in the same manner as the synthesis of tert-butyl (S)-2-((tert-butoxycarbonyl)amino)-3-(4-carbamoylthiazol-2-yl)propanoate.

MS(ESI m/z): 522.1 (M+H)

RT(min): 1.47

Synthesis of tert-butyl (S)-2-((tert-butoxycarbonyl)amino)-3-(4-carbamoyl[2,4':2',4":2",4'''-quaterthiazol]-2'''-yl)propanoate

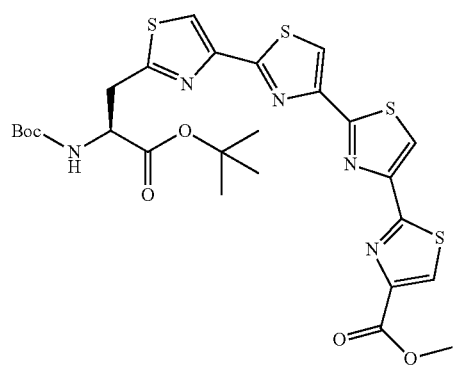

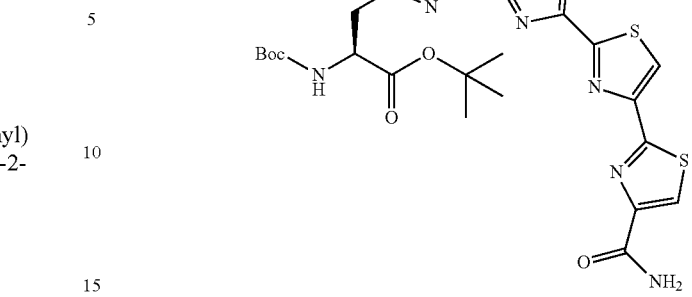

The procedure was carried out in the same manner as the synthesis of tert-butyl (S)-2-((tert-butoxycarbonyl)amino)-3-(4-carbamoylthiazol-2-yl)propanoate.

MS(ESI m/z): 621.9 (M+H)

RT(min): 1.76

Synthesis of tert-butyl (S)-2-((tert-butoxycarbonyl)amino)-3-(4-(4-(4-(4-carbamoyloxazol-2-yl)thiazol-2-yl)oxazol-2-yl)thiazol-2-yl) propanoate

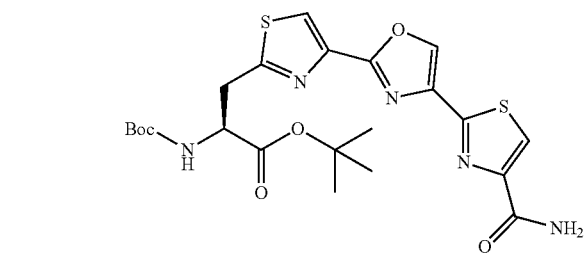

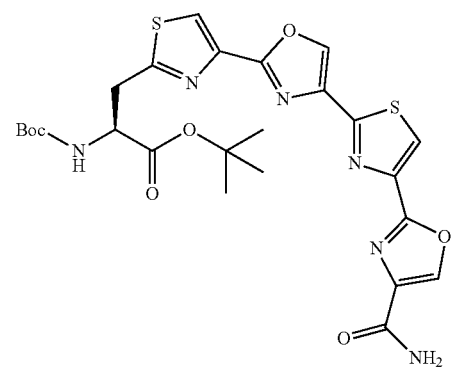

The procedure was carried out in the same manner as the synthesis of tert-butyl (S)-2-((tert-butoxycarbonyl)amino)-3-(4-carbamoylthiazol-2-yl)propanoate.

MS(ESI m/z): 589.0 (M+H)

RT(min): 1.49

Synthesis of cyanomethyl (S)-2-((tert-butoxycarbonyl)amino)-3-(4-carbamoyl-[2,4'-bithiazol]-2'-yl)propanoate

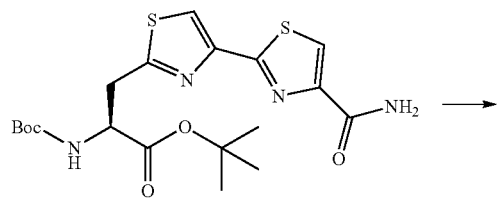

→

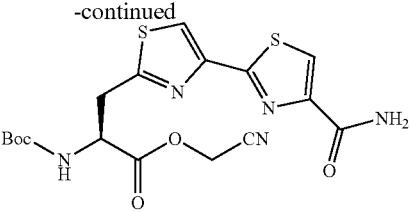

The procedure was carried out in the same manner as the synthesis of cyanomethyl (S)-2-((tert-butoxycarbonyl)amino)-3-(2-cyanoquinolin-6-yl)propanoate.

MS(ESI m/z): 438.0 (M+H)

RT(min): 1.21

The synthesis of the compounds shown in Table 10 below was carried out in the same manner as the synthesis of cyanomethyl (S)-2-((tert-butoxycarbonyl)amino)-3-(2-cyanoquinolin-6-yl)propanoate.

TABLE 10

| R | Compound name | Observed MS | RT/min |
|---|---|---|---|
| 4-(4-carbamoyloxazol-2-yl)phenyl | cyanomethyl (S)-2-((tert-butoxycarbonyl)amino)-3-(4-(4-carbamoyloxazol-2-yl)phenyl)propanoate | 415.0 | 1.21 |
| 4-(4-carbamoyl-1H-imidazol-1-yl)phenyl | cyanomethyl (S)-2-((tert-butoxycarbonyl)amino)-3-(4-(4-carbamoyl-1H-imidazol-1-yl)phenyl)propanoate | 414.3 | 1.08 |
| 2-carbamoylimidazo[1,2-a]pyrimidin-6-yl | cyanomethyl (S)-2-((tert-butoxycarbonyl)amino)-3-(2-carbamoylimidazo[1,2-a]pyrimidin-6-yl)propanoate | 389.9 | 0.88 |
| 2-carbamoylimidazo[1,2-a]pyrazin-6-yl | cyanomethyl (S)-2-((tert-butoxycarbonyl)amino)-3-(2-carbamoylimidazo[1,2-a]pyrazin-6-yl)propanoate | 389.9 | 0.94 |
| 2-carbamoylimidazo[1,2-b]pyridazin-6-yl | cyanomethyl (S)-2-((tert-butoxycarbonyl)amino)-3-(2-carbamoylimidazo[1,2-b]pyridazin-6-yl)propanoate | 389.9 | 0.98 |

TABLE 10-continued

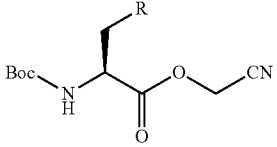

| R | Compound name | Observed MS | RT/min |
|---|---|---|---|
| 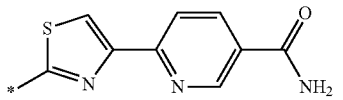 | cyanomethyl (S)-2-((tert-butoxycarbonyl)amino)-3-(2-carbamoylimidazo[1,2-a]pyridin-6-yl)propanoate | 388.1 | 0.89 |
| 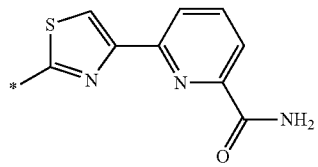 [SMILES: *c1nc(-c2cccc(C(N)=O)n2)cs1] | cyanomethyl (S)-2-((tert-butoxycarbonyl)amino)-3-(4-(5-carbamoylpyridin-2-yl)thiazol-2-yl)propanoate | 432.0 | 1.10 |
| 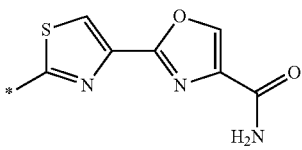 | cyanomethyl (S)-2-((tert-butoxycarbonyl)amino)-3-(4-(6-carbamoylpyridin-2-yl)thiazol-2-yl)propanoate | 432.0 | 1.22 |
| 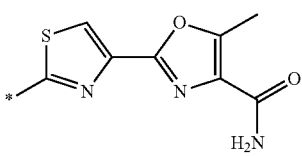 [SMILES: *c1nc(-c2nc(C(N)=O)c(C)o2)cs1] | cyanomethyl (S)-2-((tert-butoxycarbonyl)amino)-3-(4-(4-carbamoyloxazol-2-yl)thiazol-2-yl)propanoate | 422.3 | 1.04 |
| 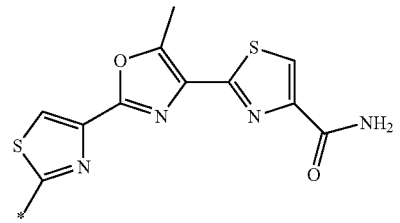 | cyanomethyl (S)-2-((tert-butoxycarbonyl)amino)-3-(4-(4-carbamoyl-5-methyloxazol-2-yl)thiazol-2-yl)propanoate | 436.0 | 1.15 |
| 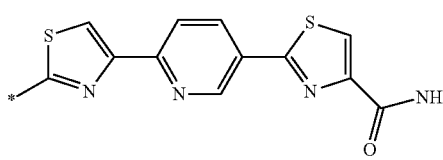 | cyanomethyl (S)-2-((tert-butoxycarbonyl)amino)-3-(4-(4-(4-carbamoylthiazol-2-yl)-5-methyloxazol-2-yl)thiazol-2-yl)propanoate | 519.0 | 1.27 |
|  | cyanomethyl (S)-2-((tert-butoxycarbonyl)amino)-3-(4-(5-(4-carbamoylthiazol-2-yl)pyridin-2-yl)thiazol-2-yl)propanoate | 515.0 | 1.29 |

TABLE 10-continued

| R | Compound name | Observed MS | RT/min |
|---|---|---|---|
| | cyanomethyl (S)-2-((tert-butoxycarbonyl)amino)-3-(4-(6-(4-carbamoylthiazol-2-yl)pyridin-2-yl)thiazol-2-yl)propanoate | 515.0 | 1.38 |
| | cyanomethyl (S)-2-((tert-butoxycarbonyl)amino)-3-(4-carbamoyl-[2,4':2',4''-terthiazol]-2''-yl)propanoate | 521.9 | 1.31 |
| | cyanomethyl (S)-2-((tert-butoxycarbonyl)amino)-3-(4-(4-(4-carbamoylthiazol-2-yl)oxazol-2-yl)thiazol-2-yl)propanoate | 505.0 | 1.20 |
| | cyanomethyl (S)-2-((tert-butoxycarbonyl)amino)-3-(4-(6-carbamoylpyridin-2-yl)-[2,4'-bithiazol]-2'-yl)propanoate | 515.9 | 1.36 |
| | cyanomethyl (S)-2-((tert-butoxycarbonyl)amino)-3-(4-(3-carbamoylpyridin-2-yl)-[2,4'-bithiazol]-2'-yl)propanoate | 515.9 | 1.11 |
| | cyanomethyl (S)-2-((tert-butoxycarbonyl)amino)-3-(4-carbamoyl-[2,4':2'4'':2'',4'''-quaterthiazol]-2'''-yl)propanoate | 604.9 | 1.45 |

TABLE 10-continued

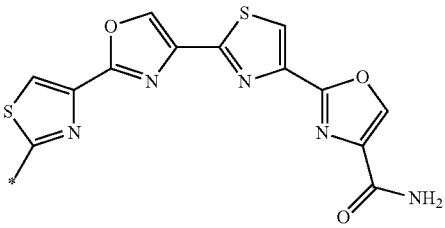

| R | Compound name | Observed MS | RT/min |
|---|---|---|---|
| 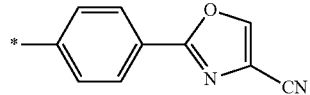 [SMILES: *c1ccc(-c2nc(C#N)co2)cc1] cyanomethyl | (S)-2-((tert-butoxycarbonyl)amino)-3-(4-(4-(4-(4-carbamoyloxazol-2-yl)thiazol-2-yl)oxazol-2-yl)thiazol-2-yl)propanoate | 572.9 | 1.23 |

Synthesis of cyanomethyl (S)-2-((tert-butoxycarbonyl)amino)-3-(4-cyano-[2,4'-bithiazol]-2'-yl)propanoate

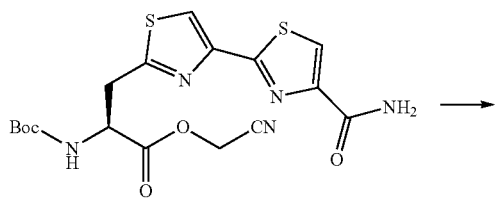

→

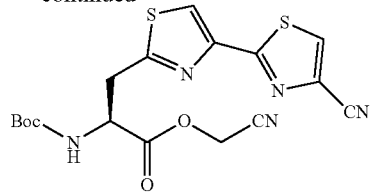

The procedure was carried out in the same manner as the synthesis of tert-butyl (S)-2-((tert-butoxycarbonyl)amino)-3-(4-cyanothiazol-2-yl)propanoate.

MS(ESI m/z): 420.0 (M+H)

RT(min): 1.51

$^{1}$H-NMR (CDCl$_{3}$) δ: 8.01 (1H, s), 7.99 (1H, s), 5.59-5.48 (1H, m), 4.93-4.75 (3H, m), 3.72-3.55 (2H, m), 1.45 (9H, s).

The synthesis of the compounds shown in Table 11 below was carried out in the same manner as the synthesis of tert-butyl (S)-2-((tert-butoxycarbonyl)amino)-3-(4-cyanothiazol-2-yl)propanoate.

TABLE 11

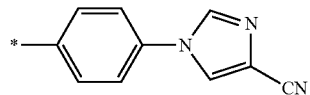 [SMILES: *c1ccc(-n2cnc(C#N)c2)cc1]

| R | Compound name | Observed MS | RT/min | $^{1}$H-NMR |
|---|---|---|---|---|
| *–⟨phenyl⟩–oxazole-CN | cyanomethyl (S)-2-((tert-butoxycarbonyl)amino)-3-(4-(4-cyanooxazol-2-yl)phenyl)propanoate | 397.9 | 1.50 | $^{1}$H-NMR (CDCl$_{3}$) δ: 8.21 (1H, s), 8.02 (2H, d, J = 8.6 Hz), 7.32 (2H, d, J = 7.9 Hz), 5.02-4.62 (4H, m), 3.29-3.07 (2H, m), 1.42 (9H, s). |
| *–⟨phenyl⟩–imidazole-CN | cyanomethyl (S)-2-((tert-butoxycarbonyl)amino)-3-(4-(4-cyano-1H-imidazol-1-yl)phenyl)propanoate | 396.0 | 1.32 | $^{1}$H-NMR (CDCl$_{3}$) δ: 7.84 (1H, s), 7.78 (1H, s), 7.40-7.32 (4H, m), 5.03-4.61 (4H, m), 3.26-3.12 (2H, m), 1.43 (9H, s). |

TABLE 11-continued

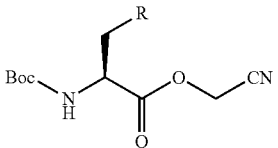

| R | Compound name | Observed MS | RT/ min | ¹H-NMR |
|---|---|---|---|---|
| 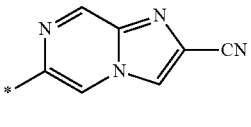 [SMILES: *c1cn2cc(C#N)nc2cn1] | cyanomethyl (S)-2-((tert-butoxy carbonyl)amino)-3-(2-cyanoimidazo[1,2-a]pyrimidin-6-yl)propanoate | 371.9 | 1.09 | ¹H-NMR (CDCl₃) δ: 8.65 (1H, d, J = 2.6 Hz), 8.51 (1H, d, J = 2.6 Hz), 8.33 (1H, s), 5.32-5.19 (1H, m), 4.97-4.63 (3H, m), 3.49-3.35 (1H, m), 3.25-3.11 (1H, m), 1.41 (9H, s). |
| 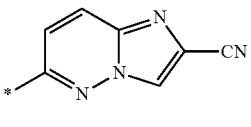 [SMILES: *c1ccc2nc(C#N)cn2n1] | cyanomethyl (S)-2-((tert-butoxy carbonyl)amino)-3-(2-cyanoimidazo[1,2-a]pyrazin-6-yl)propanoate | 371.9 | 1.18 | ¹H-NMR (CDCl₃) δ: 9.12 (1H, s), 8.07 (1H, s), 7.97 (1H, s), 5.74-5.63 (1H, m), 4.91-4.66 (3H, m), 3.44-3.27 (2H, m), 1.43 (9H, s). |
| 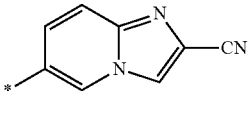 | cyanomethyl (S)-2-((tert-butoxy carbonyl)amino)-3-(2-cyanoimidazo[1,2-b]pyridazin-6-yl)propanoate | 371.9 | 1.23 | ¹H-NMR (CDCl₃) δ: 8.39 (1H, s), 7.95 (1H, d, J = 9.2 Hz), 7.09 (1H, d, J = 9.2 Hz), 5.40-5.31 (1H, m), 4.94-4.72 (3H, m), 3.58-3.41 (2H, m), 1.43 (9H, s). |
| 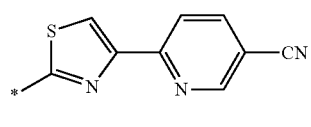 [SMILES: *c1nc(-c2ccc(C#N)cn2)cs1] | cyanomethyl (S)-2-((tert-butoxy carbonyl)amino)-3-(2-cyanoimidazo[1,2-a]pyridin-6-yl)propanoate | 370.1 | 1.20 | ¹H-NMR (CDCl₃) δ: 8.05-7.96 (2H, m), 7.63 (1H, d, J = 9.2 Hz), 7.19 (1H, d, J = 9.2 Hz), 5.10-5.00 (1H, m), 4.93-4.66 (3H, m), 3.27-3.03 (2H, m), 1.42 (9H, s). |
| 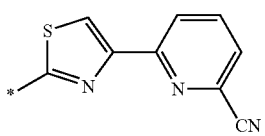 [SMILES: *c1nc(-c2cccc(C#N)n2)cs1] | cyanomethyl (S)-2-((tert-butoxy carbonyl)amino)-3-(4-(5-cyanopyridin-2-yl)thiazol-2-yl)propanoate | 414.0 | 1.45 | ¹H-NMR (CDC 13) δ: 8.84 (1H, s), 13.21-8.14 (2H, m), 8.07-7.99 (1H, m), 5.64-5.53 (1H, m), 4.97-4.75 (3H, m), 3.76-3.54 (2H, m), 1.45 (9H, s). |
| 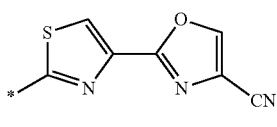 [SMILES: *c1nc(-c2nc(C#N)co2)cs1] | cyanomethyl (S)-2-((tert-butoxy carbonyl)amino)-3-(4-(6-cyanopyridin-2-yl)thiazol-2-yl)propanoate | 414.0 | 1.49 | ¹H-NMR (CDCl₃) δ: 8.26 (1H, d, J = 7.9 Hz), 8.15 (1H, s), 7.91 (1H, t, J = 7.9 Hz), 7.61 (1H, d, J = 7.9 Hz), 5.64-5.55 (1H, m), 4.97-4.73 (3H, m), 3.76-3.54 (2H, m), 1.45 (9H, s). |
| 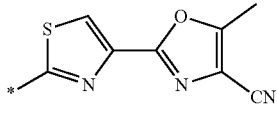 [SMILES: *c1nc(-c2nc(C#N)c(C)o2)cs1] | cyanomethyl (S)-2-((tert-butoxy carbonyl)amino)-3-(4-(4-cyanooxazol-2-yl)thiazol-2-yl)propanoate | 404.0 | 1.32 | ¹H-NMR (CDCl₃) δ: 8.23 (1H, s), 8.05 (1H, s), 5.59-5.46 (1H, m), 4.93-4.78 (3H, m), 3.73-3.57 (2H, m), 1.45 (9H, s). |
|  | cyanomethyl (S)-2-((tert-butoxy carbonyl)amino)-3-(4-(4-cyano-5-methyloxazol-2-yl)thiazol-2-yl)propanoate | 418.0 | 1.38 | ¹H-NMR (CDCl₃) δ: 7.96 (1H, s), 5.59-5.44 (1H, m), 4.94-4.72 (3H, m), 3.71-3.56 (2H, m), 2.61 (3H, s), 1.45 (9H, s). |

TABLE 11-continued

| R | Compound name | Observed MS | RT/ min | ¹H-NMR |
|---|---|---|---|---|
| (5-methyl-oxazole linked to thiazoles) | cyanomethyl (S)-2-((tert-butoxy carbonyl)amino)-3-(4-(4-(4-cyanothiazol-2-yl)-5-methyloxazol-2-yl)thiazol-2-yl)propanoate | 501.0 | 1.58 | ¹H-NMR (CDCl₃) δ: 7.98 (1H, s), 7.95 (1H, s), 5.59-5.46 (1H, m), 4.93-4.79 (3H, m), 3.71-3.57 (2H, m), 2.83 (3H, s), 1.45 (9H, s). |
| (2,5-pyridine linked to thiazoles) | cyanomethyl (S)-2-((tert-butoxy carbonyl)amino)-3-(4-(5-(4-cyanothiazol-2-yl)pyridin-2-yl)thiazol-2-yl)propanoate | 497.3 | 1.53 | ¹H-NMR (CDCl₃) δ: 9.17 (1H, s), 8.33 (1H, d, J = 8.3 Hz), 8.21-8.11 (2H, m), 8.05 (1H, s), 5.73-5.60 (1H, m), 4.98-4.73 (3H, m), 3.77-3.54 (2H, m), 1.46 (9H, s). |
| (2,6-pyridine linked to thiazoles) | cyanomethyl (S)-2-((tert-butoxy carbonyl)amino)-3-(4-(6-(4-cyanothiazol-2-yl)pyridin-2-yl)thiazol-2-yl)propanoate | 497.0 | 1.69 | ¹H-NMR (CDCl₃) δ: 8.18-8.05 (4H, m), 7.95 (1H, t, J = 7.9 Hz), 5.74-5.64 (1H, m), 4.97-4.73 (3H, m), 3.78-3.52 (2H, m), 1.46 (9H, s). |
| (terthiazole) | cyanomethyl (S)-2-((tert-butoxy carbonyl)amino)-3-(4-cyano-[2,4':2',4''-terthiazol]-2''-yl)propanoate | 503.9 | 1.60 | ¹H-NMR (CDCl₃) δ: 8.10 (1H, s), 8.02-8.00 (2H, m), 5.66-5.56 (1H, m), 4.96-4.82 (3H, m), 3.74-3.54 (2H, m), 1.46 (9H, s). |
| (oxazole linked to thiazoles) | cyanomethyl (S)-2-((tert-butoxy carbonyl)amino)-3-(4-(4-(4-cyanothiazol-2-yl)oxazol-2-yl)thiazol-2-yl)propanoate | 487.0 | 1.45 | ¹H-NMR (CDCl3) δ: 8.36 (1H, s), 8.07-8.01 (2H, m), 5.60-5.46 (1H, m), 4.93-4.81 (3H, m), 3.73-3.59 (2H, m), 1.45 (9H, s). |
| (bithiazole linked to cyanopyridine) | cyanomethyl (S)-2-((tert-butoxy carbonyl)amino)-3-(4-(6-cyanopyridin-2-yl)-[2,4'-bithiazol]-2'-yl)propanoate | 497.9 | 1.63 | ¹H-NMR (CDCl₃) δ: 8.43 (1H, d, J = 7.3 Hz), 8.26 (1H, s), 7.98-7.88 (2H, m), 7.63 (1H, d, J = 8.6 Hz), 5.69-5.60 (1H, m), 4.94-4.83 (3H, m), 3.74-3.54 (2H, m), 1.46 (9H, s). |

TABLE 11-continued

| R | Compound name | Observed MS | RT/min | ¹H-NMR |
|---|---|---|---|---|
| (thiazole-thiazole-cyanopyridine) | cyanomethyl (S)-2-((tert-butoxycarbonyl)amino)-3-(4-(3-cyanopyridin-2-yl)-[2,4'-bithiazol]-2'-yl)propanoate | 497.9 | 1.52 | ¹H-NMR (CDCl₃) δ: 8.82 (1H, dd, J = 4.6, 2.0 Hz), 8.27 (1H, s), 8.15-8.09 (2H, m), 7.41-7.36 (1H, m), 5.65-5.56 (1H, m), 4.93-4.82 (3H, m), 3.74-3.54 (2H, m), 1.46 (9H, s). |
| (quaterthiazole with CN) | cyanomethyl (S)-2-((tert-butoxycarbonyl)amino)-3-(4-cyano-[2,4':2',4":2",4'''-quaterthiazol]-2'''-yl)propanoate | 586.9 | 1.76 | ¹H-NMR (DMSO-D₆) δ: 8.95 (1H, s), 8.56 (1H, s), 8.46 (1H, s), 8.33 (1H, s), 7.69 (1H, d, J = 8.6 Hz), 5.06 (2H, s), 4.64-4.53 (1H, m), 3.62-3.37 (2H, m), 1.37 (9H, s). |
| (thiazole-oxazole-thiazole-cyanooxazole) | cyanomethyl (S)-2-((tert-butoxycarbonyl)amino)-3-(4-(4-(4-cyanooxazol-2-yl)thiazol-2-yl)oxazol-2-yl)thiazol-2-yl)propanoate | 554.2 | 1.48 | ¹H-NMR (DMSO-D₆) δ: 9.25 (1H, s), 9.03 (1H, s), 8.69 (1H, s), 8.47 (1H, s), 7.70 (1H, d, J = 7.9 Hz), 5.06 (2H, s), 4.62-4.52 (1H, m), 3.63-3.39 (2H, m), 1.36 (9H, s). |

Synthesis of tert-butyl (S)-3-(4-(2-((((9H-fluoren-9-yl)methoxy)carbonyl)amino)acetamido)phenyl)-2-((tert-butoxycarbonyl)amino)propanoate

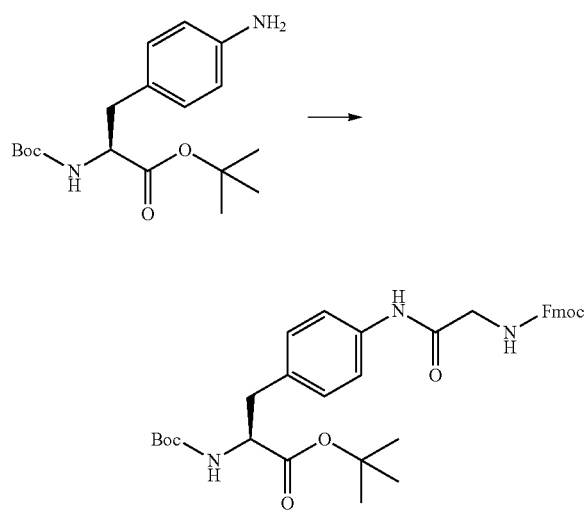

5 mL of DMF, 97.3 mg of (((9H-fluoren-9-yl)methoxy)carbonyl)glycine, 100 µL of diisopropylethylamine, and 170 mg of HATU (1-[bis(dimethylamino)methylene]-1H-1,2,3-triazolo[4,5-b]pyridinium 3-oxide hexafluorophosphate) were added to 100 mg of tert-butyl (S)-2-((tert-butoxycarbonyl)amino)-3-(4-aminophenyl)propanoate, which was then stirred at room temperature for 2 hours. Distilled water and ethyl acetate were added to the reaction solution, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=0/100→30/70→60/40) to give 183 mg of the title compound as a pale yellow oil.

MS(ESI m/z): 616.0 (M+H)

RT(min): 1.91

The synthesis of the compounds shown in Table 12 below was carried out in the same manner as the synthesis of tert-butyl (S)-3-(4-(2-((((9H-fluoren-9-yl)methoxy)carbonyl)amino)acetamido)phenyl)-2-(tert-butoxycarbonyl)amino)propanoate.

TABLE 12

| R | Compound name | Observed MS | RT/min |
|---|---|---|---|
| (structure 1) | tert-butyl (S)-3-(4-(2-(2-((((9H-fluoren-9-yl)methoxy)carbonyl)amino)acetamido)acetamido)phenyl)-2-((tert-butoxycarbonyl)amino)propanoate | 673.1 | 1.76 |
| (structure 2) | tert-butyl (S)-3-(4-(1-(9H-fluoren-9-yl)-3,6,9-trioxo-2-oxa-4,7,10-triazidodecane-12-amido)phenyl)-2-((tert-butoxycarbonyl)amino)propanoate | 730.2 | 1.69 |

Synthesis of tert-butyl (S)-3-(4-(2-aminoacetamido)phenyl)-2-((tert-butoxycarbonyl)amino)propanoate

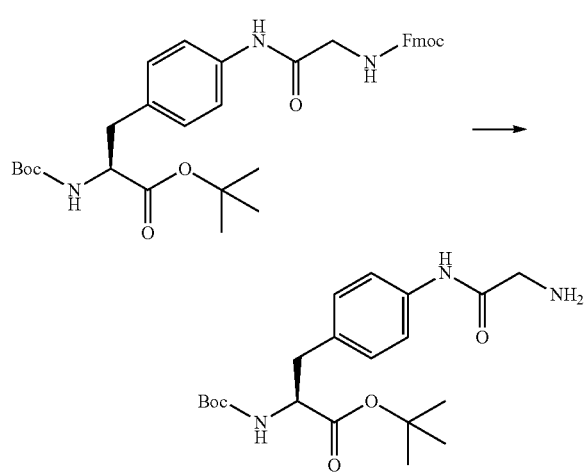

6 mL of dichloromethane and 1.2 mL of piperidine were added to 183 mg of tert-butyl (S)-3-(4-(2-((((9H-fluoren-9-yl)methoxy)carbonyl)amino)acetamido)phenyl)-2-((tert-butoxycarbonyl)amino)propanoate, which was then stirred at room temperature for 1 hour and 30 minutes. The solvent was distilled off under reduced pressure, and the residue was purified by column chromatography (NH silica gel, methanol/ethyl acetate/hexane/=0/50/50→0/100/0→20/80/0) to give 117 mg of the title compound as a pale yellow oil.

MS(ESI m/z): 394.0 (M+H)

RT(min): 1.08

The synthesis of the compounds shown in Table 13 below was carried out in the same manner as the synthesis of tert-butyl (S)-3-(4-(2-aminoacetamido)phenyl)-2-((tert-butoxycarbonyl)amino)propanoate.

TABLE 13

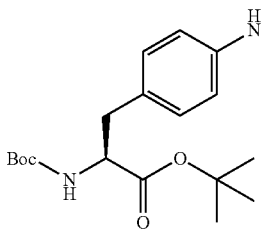

| R | Compound name | Observed MS | RT/min |
|---|---|---|---|
| 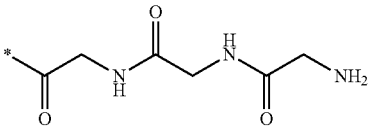 [SMILES: *C(=O)CNC(=O)CNC(=O)CN] | tert-butyl (S)-3-(4-(2-(2-aminoacetamido)acetamido)phenyl)-2-((tert-butoxycarbonyl)amino)propanoate | 451.0 | 1.11 |
| | tert-butyl (S)-3-(4-(2-(2-(2-aminoacetamido)acetamido)acetamido)phenyl)-2-((tert-butoxycarbonyl)amino)propanoate | 508.0 | 1.08 |

Synthesis of tert-butyl (S)-2-((tert-butoxycarbonyl)amino)-3-(4-(2-(5-cyanothiophene-2-carboxamido)acetamido)phenyl)propanoate

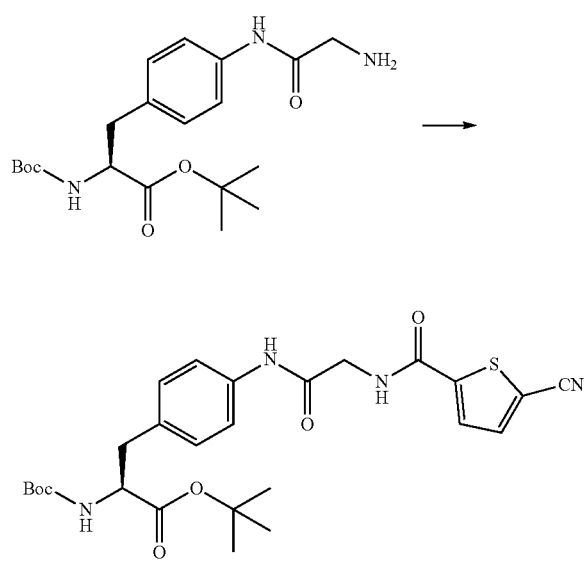 [SMILES: CC(C)(C)OC(=O)N[C@@H](Cc1ccc(NC(=O)CN)cc1)C(=O)OC(C)(C)C ; CC(C)(C)OC(=O)N[C@@H](Cc1ccc(NC(=O)CNC(=O)c2ccc(C#N)s2)cc1)C(=O)OC(C)(C)C]

5 mL of DMF, 300 μL of diisopropylethylamine, 50 mg of 5-cyanothiophene-2-carboxylic acid, and 170 mg of HATU (1-[bis(dimethylamino)methylene]-1H-1,2,3-triazolo[4,5-b]pyridinium 3-oxide hexafluorophosphate) were added to 117 mg of tert-butyl (S)-3-(4-(2-aminoacetamido)phenyl)-2-((tert-butoxycarbonyl)amino)propanoate, which was then stirred at room temperature for 12 hours. Distilled water and ethyl acetate were added to the reaction solution, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=0/100→30/70→60/40) to give 120 mg of the title compound as a pale yellow oil.

MS(ESI m/z): 529.2 (M+H)

RT(min): 1.58

The synthesis of the compounds shown in Table 14 below was carried out in the same manner as the synthesis of tert-butyl (S)-2-((tert-butoxycarbonyl)amino)-3-(4-(2-(5-cyanothiophene-2-carboxamido)acetamido)phenyl)propanoate.

TABLE 14

| R | Compound name | Observed MS | RT/min |
|---|---|---|---|
| (structure: *-CH2-C(O)-NH-CH2-C(O)-NH-thiophene-CN) | tert-butyl (S)-2-((tert-butoxycarbonyl)amino)-3-(4-(2-(2-(5-cyanothiophene-2-carboxamido)acetamido)acetamido)phenyl)propanoate | 586.1 | 1.47 |
| (structure: *-CH2-C(O)-NH-CH2-C(O)-NH-CH2-C(O)-NH-thiophene-CN) | tert-butyl (S)-2-((tert-butoxycarbonyl)amino)-3-(4-(2-(2-(2-(5-cyanothiophene-2-carboxamido)acetamido)acetamido)acetamido)phenyl)propanoate | 643.1 | 1.40 |

Synthesis of cyanomethyl (S)-2-((tert-butoxycarbonyl)amino)-3-(4-(2-(5-cyanothiophene-2-carboxamido)acetamido)phenyl)propanoate The procedure was carried out in the same manner as the synthesis of cyanomethyl (S)-2-((tert-butoxycarbonyl)amino)-3-(2-cyanoquinolin-6-yl)propanoate.

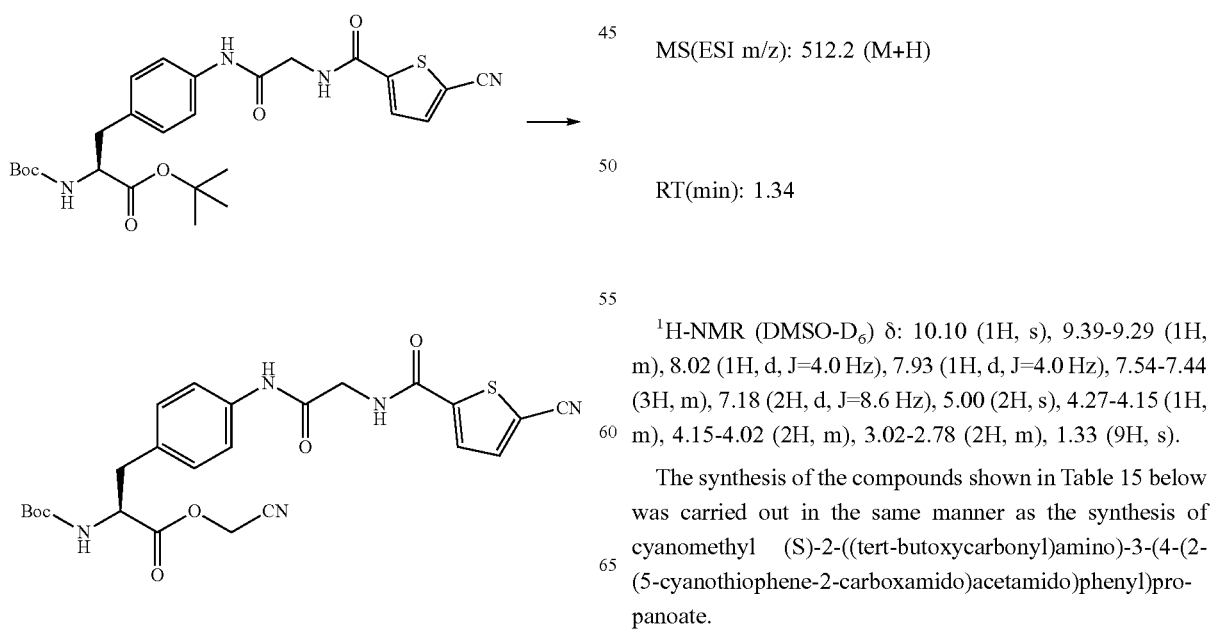

MS(ESI m/z): 512.2 (M+H)

RT(min): 1.34

$^1$H-NMR (DMSO-D$_6$) δ: 10.10 (1H, s), 9.39-9.29 (1H, m), 8.02 (1H, d, J=4.0 Hz), 7.93 (1H, d, J=4.0 Hz), 7.54-7.44 (3H, m), 7.18 (2H, d, J=8.6 Hz), 5.00 (2H, s), 4.27-4.15 (1H, m), 4.15-4.02 (2H, m), 3.02-2.78 (2H, m), 1.33 (9H, s).

The synthesis of the compounds shown in Table 15 below was carried out in the same manner as the synthesis of cyanomethyl (S)-2-((tert-butoxycarbonyl)amino)-3-(4-(2-(5-cyanothiophene-2-carboxamido)acetamido)phenyl)propanoate.

TABLE 15

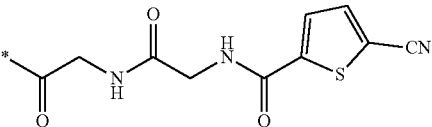 [SMILES: *C(=O)CNC(=O)CNC(=O)c1ccc(C#N)s1]

| R | Compound name | Observed MS | RT/min | ¹H-NMR |
|---|---|---|---|---|
| 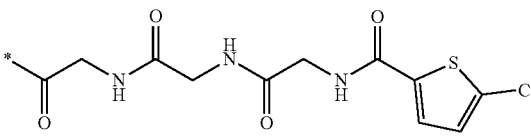 | cyanomethyl (S)-2-((tert-butoxycarbonyl)amino)-3-(4-(2-(2-(5-cyanothiophene-2-carboxamido)acetamido)acetamido)phenyl)propanoate | 569.9 | 1.23 | ¹H-NMr (DMSO-D₆) δ: 9.81 (1H, s), 9.33 (1H, t, J = 5.6 Hz), 8.43 (1H, t, J = 5.6 Hz), 8.02 (1H, d, J = 4.0 Hz), 7.91 (1H, d, J = 4.0 Hz), 7.56-7.44 (3H, m), 7.18 (2H, d, J = 7.9 Hz), 5.00 (2H, s), 4.27-4.16 (1H, m), 4.01-3.86 (4H, m), 3.02-2.78 (2H, m), 1.33 (9H, s). |
| 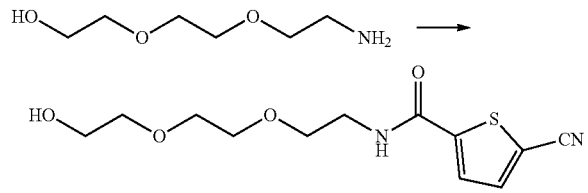 | cyanomethyl (S)-2-((tert-butoxycarbonyl)amino)-3-(4-(2-(2-(2-(5-cyanothiophene-2-carboxamido)acetamido)acetamido)acetamido)phenyl)propanoate | 626.0 | 1.27 | ¹H-NMR (DMSO-D₆) δ: 9.77 (1H, s), 9.27 (1H, t, J = 5.9 Hz), 8.48-8.40 (1H, m), 8.31-8.23 (1H, m), 8.00 (1H, d, J = 4.0 Hz), 7.90 (1H, d, J = 4.0 Hz), 7.55-7.44 (3H, m), 7.14 (2H, d, J = 8.6 Hz), 5.00 (2H, s), 4.26-4.14 (1H, m), 4.01-3.75 (4H, m), 3.71-3.54 (2H, m), 2.98-2.80 (2H, m), 1.33 (9H, s). |

Synthesis of 5-cyano-N-(2-(2-(2-hydroxyethoxy)ethoxy)ethyl)thiophene-2-carboxamide

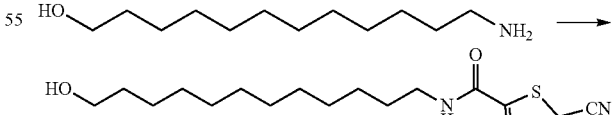

The procedure was carried out in the same manner as the synthesis of tert-butyl (S)-2-((tert-butoxycarbonyl)amino)-3-(4-(2-(5-cyanothiophene-2-carboxamido)acetamido)phenyl)propanoate.

MS(ESI m/z): 285.0 (M+H)

RT(min): 0.78

Synthesis of 5-cyano-N-(2-(2-(2-(2-hydroxyethoxy)ethoxy)ethoxy)ethyl)thiophene-2-carboxamide

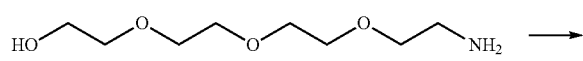

The procedure was carried out in the same manner as the synthesis of tert-butyl (S)-2-((tert-butoxycarbonyl)amino)-3-(4-(2-(5-cyanothiophene-2-carboxamido)acetamido)phenyl)propanoate.

MS(ESI m/z): 329.0 (M+H)

RT(min): 0.82

Synthesis of 5-cyano-N-(12-hydroxydodecyl)thiophene-2-carboxamide

The procedure was carried out in the same manner as the synthesis of tert-butyl (S)-2-((tert-butoxycarbonyl)amino)-3-(4-(2-(5-cyanothiophene-2-carboxamido)acetamido)phenyl)propanoate.

MS(ESI m/z): 337.1 (M+H)

RT(min): 1.54

Synthesis of 12-(5-cyanothiophene-2-carboxamido)dodecyl 4-methylbenzenesulfonate

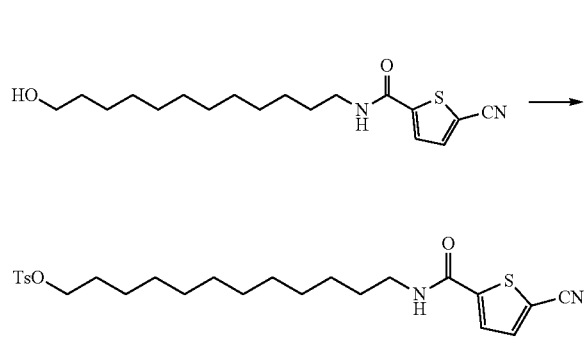 [SMILES: N#Cc1ccc(C(=O)NCCCCCCCCCCCCO)s1 ; Cc1ccc(S(=O)(=O)OCCCCCCCCCCCCNC(=O)c2ccc(C#N)s2)cc1]

380 µL of triethylamine was added to a chloroform solution (10 mL) of 5-cyano-N-(12-hydroxydodecyl)thiophene-2-carboxamide (230 mg). 195 mg of para-toluenesulfonyl chloride was added thereto on an ice bath, followed by stirring for 2 hours under an ice bath. 380 µL of triethylamine and 195 mg of para-toluenesulfonyl chloride were further added thereto, followed by stirring for 3 hours in an ice bath. The solvent was distilled off under reduced pressure, and the residue was purified by column chromatography (silica gel, ethyl acetate/hexane=5/95→15/85→30/70) to give 267 mg of the title compound as a yellow oil.

MS(ESI m/z): 491.2 (M+H)
RT(min): 2.01

Synthesis of 2-(2-(2-(2-hydroxyethoxy)ethoxy)ethoxy)ethyl 4-methylbenzenesulfonate

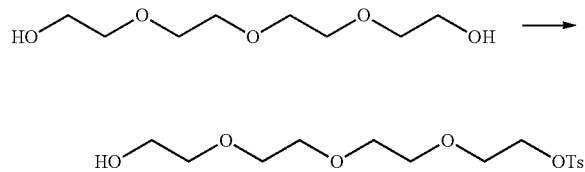

5 mL of THF and an aqueous solution (5 mL) of 1.92 g of sodium hydroxide were added to 11 g of 2,2'-((oxybis(ethane-2,1-diyl))bis(oxy))bis(ethan-1-ol). A THF solution (10 mL) of para-toluenesulfonyl chloride (4.32 g) was added dropwise thereto on an ice bath. After completion of dropwise addition, the reaction solution was stirred at room temperature for 2 hours. Distilled water and ethyl acetate were added to the reaction solution, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=50/50→100/0) to give 1.30 g of the title compound as a colorless oil.

MS(ESI m/z): 349.0 (M+H)
RT(min): 1.08

Synthesis of 5-(2-(2-(2-(2-hydroxyethoxy)ethoxy)ethoxy)ethoxy)picolinonitrile

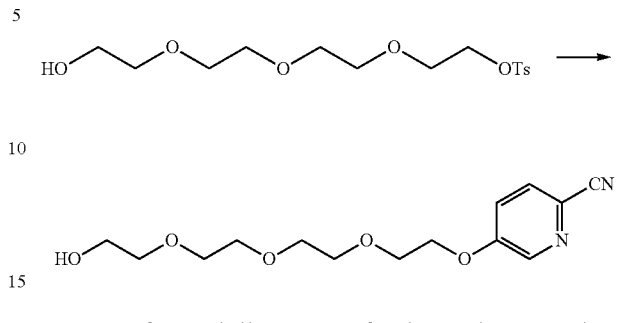

10 mL of acetonitrile, 371 mg of cesium carbonate, and 82 mg of 5-hydroxypicolinonitrile were added to 231 mg of 2-(2-(2-(2-hydroxyethoxy)ethoxy)ethoxy)ethyl 4-methylbenzenesulfonate, which was then stirred at 60° C. for 5 hours and at 90° C. for 3 hours. The solvent was distilled off under reduced pressure, and the residue was purified by column chromatography (NH silica gel, ethyl acetate/hexane=60/40→100/0) to give 116 mg of the title compound as a colorless oil.

MS(ESI m/z): 297.1 (M+H)
RT(min): 0.80

Synthesis of N-(2-(2-(2-bromoethoxy)ethoxy)ethyl)-5-cyanothiophene-2-carboxamide

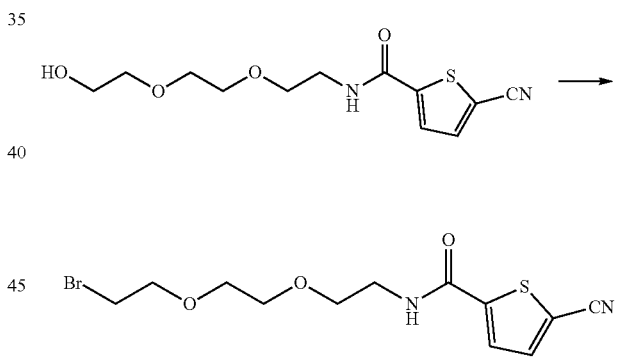

312 mg of triphenylphosphine and 396 mg of carbon tetrabromide were added to a dichloromethane solution (10 mL) of 5-cyano-N-(2-(2-(2-hydroxyethoxy)ethoxy)ethyl)thiophene-2-carboxamide (233 mg) on an ice bath. This was followed by stirring at room temperature for 24 hours. The solvent was distilled off under reduced pressure, and the residue was purified by column chromatography (silica gel, ethyl acetate/hexane=35/65→70/30) to give 141 mg of the title compound as a colorless oil.

MS(ESI m/z): 348.9 (M+H)
RT(min): 1.14

The synthesis of compounds shown in Table 16 below were carried out in the same manner as the synthesis of N-(2-(2-(2-bromoethoxy)ethoxy)ethyl)-5-cyanothiophene-2-carboxamide.

TABLE 16

| Structure | Compound name | Observed MS | RT/min |
|---|---|---|---|
| 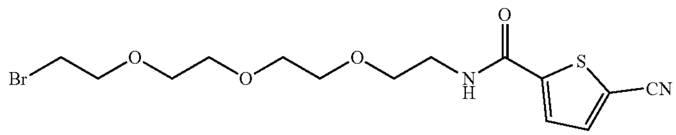 [SMILES: N#Cc1ccc(C(=O)NCCOCCOCCOCCBr)s1] | N-(2-(2-(2-(2-bromoethoxy)ethoxy)ethoxy)ethyl)-5-cyanothiophene-2-carboxamide | 392.9 | 1.17 |
| 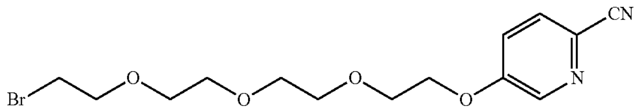 [SMILES: N#Cc1ccc(OCCOCCOCCOCCBr)cn1] | 5-(2-(2-(2-(2-bromoethoxy)ethoxy)ethoxy)ethoxy)picolinonitrile | 360.0 | 1.19 |

Synthesis of tert-butyl (tert-butoxycarbonyl)-L-tyrosinate

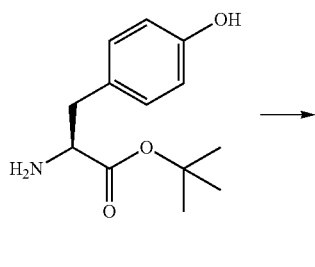

50 mL of dichloromethane, 6.2 mL of triethylamine, and 6.1 mL of Boc₂O were added to 5.19 g of tert-butyl L-tyrosinate, which was then stirred at room temperature for 1 hour and 30 minutes. The solvent was distilled off under reduced pressure, and an aqueous hydrochloric acid solution (1 mol/L) and ethyl acetate were added to the residue, followed by extraction with ethyl acetate. The organic layer was washed with an aqueous hydrochloric acid solution (1 mol/L), a saturated aqueous sodium hydrogen carbonate solution and saturated saline, and dried over magnesium sulfate. The solvent was distilled off under reduced pressure, and the residue was purified by column chromatography (silica gel, ethyl acetate/hexane=0/100→30/70) to give 6.52 g of the title compound as a colorless oil.

MS(ESI m/z): 338.1 (M+H)

RT(min): 1.51

Synthesis of tert-butyl (S)-2-((tert-butoxycarbonyl)amino)-3-(4-(2-(2-(2-(5-cyanothiophene-2-carboxamido)ethoxy)ethoxy)ethoxy)phenyl)propanoate

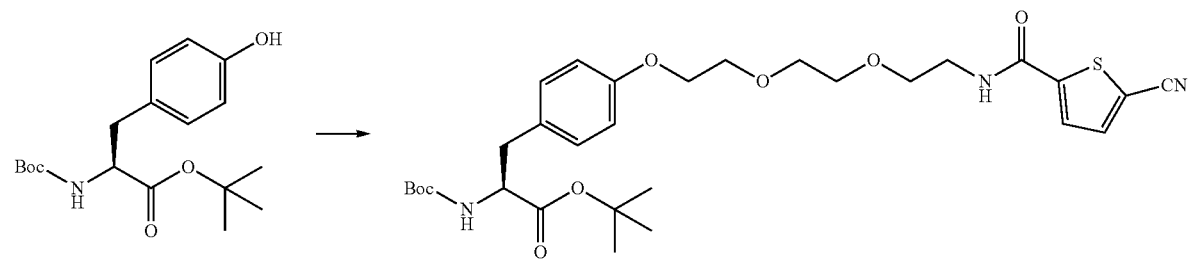 [SMILES: CC(C)(C)OC(=O)N[C@@H](Cc1ccc(O)cc1)C(=O)OC(C)(C)C ; CC(C)(C)OC(=O)N[C@@H](Cc1ccc(OCCOCCOCCNC(=O)c2ccc(C#N)s2)cc1)C(=O)OC(C)(C)C]

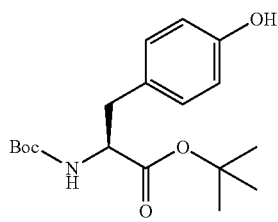

10 mg of DMF, 151 mg of potassium carbonate, and 141 mg of N-(2-(2-(2-(2-bromoethoxy)ethoxy)ethoxy)ethyl)-5-cyanothiophene-2-carboxamide were added to 123 mg of tert-butyl (tert-butoxycarbonyl)-L-tyrosinate, which was then stirred at room temperature for 24 hours. Distilled water and ethyl acetate were added to the reaction solution, followed by extraction with ethyl acetate. The organic layer was washed with distilled water and saturated saline and dried over magnesium sulfate. The solvent was distilled off under reduced pressure, and the residue was purified by column chromatography (silica gel, ethyl acetate/hexane=30/70→60/40) to give 178 mg of the title compound as a colorless oil.

MS(ESI m/z): 604.1 (M+H)

RT(min): 1.72

The synthesis of the compounds shown in Table 17 below was carried out in the same manner as the synthesis of tert-butyl (S)-2-((tert-butoxycarbonyl)amino)-3-(4-(2-(2-(2-(5-cyanothiophene-2-carboxamido)ethoxy)ethoxy)ethoxy)phenyl)propanoate.

TABLE 17

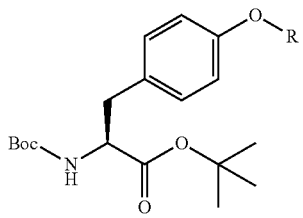

| R | Compound name | Observed MS | RT/min |
|---|---|---|---|
| *~O~O~O~NH-C(O)-thiophene-CN | tert-butyl (S)-2-((tert-butoxycarbonyl)amino)-3-(4-((1-(5-cyanothiophen-2-yl)-1-oxo-5,8,11-trioxa-2-azatridecan-13-yl)oxy)phenyl)propanoate | 648.1 | 1.72 |
| *~O~O~O~O-pyridine-CN | tert-butyl (S)-2-((tert-butoxycarbonyl)amino)-3-(4-(2-(2-(2-(2-((6-cyanopyridin-3-yl)oxy)ethoxy)ethoxy)ethoxy)ethoxy)phenyl)propanoate | 616.2 | 1.76 |
| *~(CH2)11~NH-C(O)-thiophene-CN | tert-butyl (S)-2-((tert-butoxycarbonyl)amino)-3-(4-((12-(5-cyanothiophene-2-carboxamido)dodecyl)oxy)phenyl)propanoate | 656.3 | 2.31 |

Synthesis of cyanomethyl (S)-2-((tert-butoxycarbonyl)amino)-3-(4-(2-(2-(2-(5-cyanothiophene-2-carboxamido)ethoxy)ethoxy)ethoxy)phenyl)propanoate

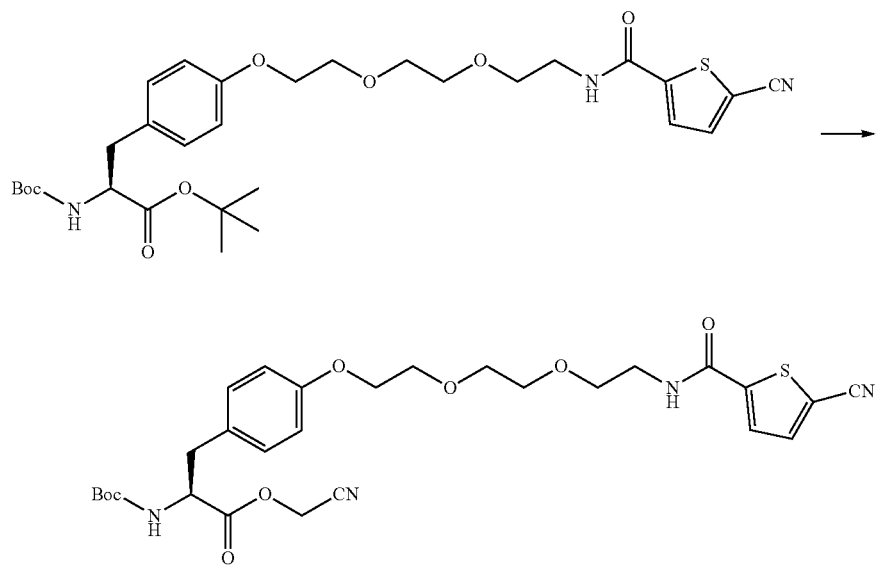 [SMILES: CC(C)(C)OC(=O)N[C@@H](Cc1ccc(OCCOCCOCCNC(=O)c2ccc(C#N)s2)cc1)C(=O)OC(C)(C)C ; CC(C)(C)OC(=O)N[C@@H](Cc1ccc(OCCOCCOCCNC(=O)c2ccc(C#N)s2)cc1)C(=O)OCC#N]

The procedure was carried out in the same manner as the synthesis of cyanomethyl (S)-2-((tert-butoxycarbonyl)amino)-3-(2-cyanoquinolin-6-yl)propanoate.

MS(ESI m/z): 587.0 (M+H)
RT(min): 1.47
¹H-NMR: (CDCl₃) δ: 7.46-7.42 (2H, m), 7.06 (2H, d, J=8.6 Hz), 6.82 (2H, d, J=8.6 Hz), 4.98-4.54 (4H, m), 4.13-4.08 (2H, m), 3.89-3.84 (2H, m), 3.76-3.61 (9H, m), 3.06 (2H, d, J=5.9 Hz), 1.43 (9H, s).

The synthesis of the compounds shown in Table 18 below was carried out in the same manner as the synthesis of cyanomethyl (S)-2-((tert-butoxycarbonyl)amino)-3-(4-(2-(2-(2-(5-cyanothiophene-2-carboxamido)ethoxy) ethoxy) ethoxy)phenyl)propanoate.

TABLE 18

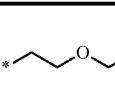

| R | Compound name | Observed MS | RT/min | ¹H-NMR |
|---|---|---|---|---|
| 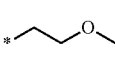 | cyanomethyl (S)-2-((tert-butoxycarbonyl)amino)-3-(4-((1-(5-cyanothiophen-2-yl)-1-oxo-5,8,11-trioxa-2-azatridecan-13-yl)oxy)phenyl)propanoate | 631.1 | 1.48 | ¹H-NMR (CDCl₃) δ: 7.54 (1H, d, J = 4.0 Hz), 7.43 (1H, d, J = 4.0 Hz), 7.04 (2H, d, J = 8.6 Hz), 6.81 (2H, d, J = 8.6 Hz), 4.97-4.55 (4H, m), 4.11-4.05 (2H, m), 3.86-3.79 (2H, m), 3.15-3.58 (13H, m), 3.05 (2H, d, J = 6.6 Hz), 1.43 (9H, s). |
| 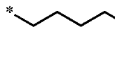 | cyanomethyl (S)-2-((tert-butoxycarbonyl)amino)-3-(4-(2-(2-(2-(2-(6-cyanopyridin-3-yl)oxy)ethoxy)ethoxy)ethoxy)ethoxy)phenyl)propanoate | 599.1 | 1.51 | ¹H-NMR (CDCl₃) δ: 8.38 (1H, d, J = 2.6 Hz), 7.62 (1H, d, J = 8.6 Hz), 7.30-7.24 (1H, m), 7.04 (2H, d, J = 8.6 Hz), 6.86 (2H, d, J = 8.6 Hz), 4.97-4.52 (4H, m), 4.23 (2H, t, J = 4.6 Hz), 4.10 (2H, t, J = 4.6 Hz), 3.91-3.82 (4H, m), 3.74-3.66 (8H, m), 3.04 (2H, d, J = 5.9 Hz), 1.42 (9H, s). |
|  | cyanomethyl (S)-2-((tert-butoxycarbonyl)amino)-3-(4-((12-(5-cyanothiophene-2-carboxamido)dodecyl)oxy)phenyl)propanoate | 639.2 | 2.09 | ¹H-NMR (CDCl₃) δ: 7.57 (1H, d, J = 4.0 Hz), 7.39 (1H, d, J = 4.0 Hz), 7.04 (2H, d, J = 8.6 Hz), 6.84 (2H, d, J = 8.6 Hz), 6.08-5.97 (1H, m), 4.94-4.53 (4H, m), 3.93 (2H, t, J = 6.6 Hz). 3.48-3.38 (2H, m), 3.04 (2H, d, J = 5.9 Hz). 1.81-1.72 (2H, m), 1.66-1.56 (6H, m), 1.42-1.26 (21H, m). |

Synthesis of tert-butyl (R)-2-((((9H-fluoren-9-yl)methoxy)carbonyl)amino)-3-iodopropanoate (2) Synthesis of allyl 2-(6-iodopyridin-2-yl)thiazole-4-carboxylate

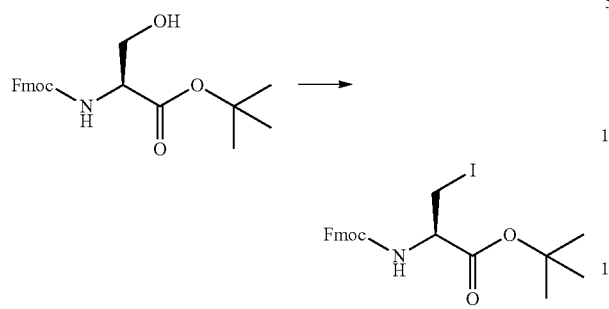

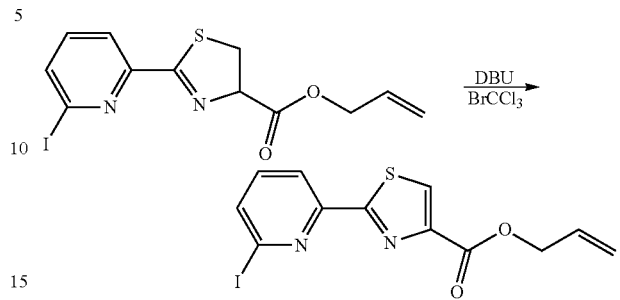

The procedure was carried out in the same manner as the synthesis of tert-butyl (R)-2-(((tert-butoxycarbonyl)amino)-3-iodopropanoate. In the present specification, Fmoc represents a 9-fluorenylmethyloxycarbonyl group.

MS(ESI m/z): 494.0 (M+H)
RT(min): 2.02

Synthesis of allyl 2-(6-iodopyridin-2-yl)thiazole-4-carboxylate (1) Synthesis of allyl (R)-2-(6-iodopyridin-2-yl)-4,5-dihydrothiazole-4-carboxylate Bromotrichloromethane (5 mL) and diazabicycloundecene (DBU) (0.3 mL) were added to allyl (R)-2-(6-iodopyridin-2-yl)-4,5-dihydrothiazole-4-carboxylate (0.5 g), which was then stirred at room temperature for 10 minutes. An aqueous citric acid solution and ethyl acetate were added to the reaction solution to carry out an extraction operation. The organic layer was dried over anhydrous magnesium sulfate, and the solvent was distilled off under reduced pressure to give 0.31 g of the title compound as a white solid.

MS(ESI m/z): 372.4 (M+H)
RT(min): 1.67

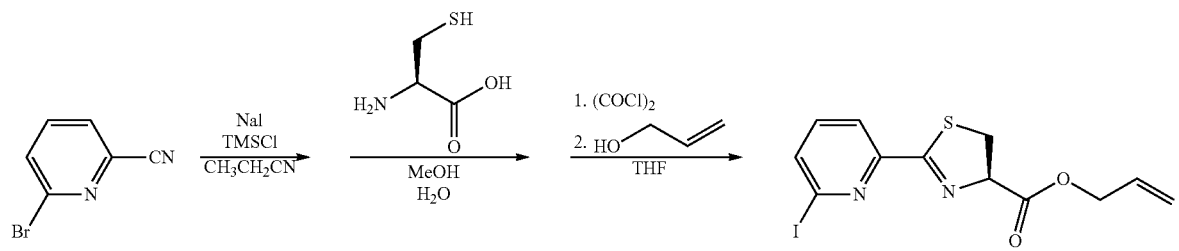

Sodium iodide (12.3 g), trimethylsilyl chloride (TMSCl) (3.5 mL), and propionitrile (30 mL) were added to 2-cyano-6-bromopyridine (5.0 g), which was then stirred at 90° C. for 2 hours. An aqueous sodium hydroxide solution and ethyl acetate were added to the reaction solution to carry out an extraction operation. The organic layer was washed with an aqueous sodium thiosulfate solution and dried over anhydrous magnesium sulfate, and the solvent was concentrated under reduced pressure. 3.63 g of L-cysteine, methanol (20 mL), and distilled water (10 mL) were added to the resulting residue which was then stirred at 80° C. for 3.5 hours. The solvent was distilled off under reduced pressure, a methanol/ethyl acetate mixed solvent was added to the resulting residue, and the solid was filtered off. THF (100 mL) and oxalyl chloride (2.4 mL) were added to the resulting solid which was then stirred for 45 minutes. Thereafter, allyl alcohol (3.4 mL) was added to the reaction solution which was then stirred for 4 hours. A saturated aqueous sodium hydrogen carbonate solution and ethyl acetate were added to the reaction solution to carry out an extraction operation. The organic layer was dried over anhydrous magnesium sulfate and the solvent was distilled off under reduced pressure to give 3.2 g of the title compound as a yellow solid.

MS(ESI m/z): 335.8 (M+H)
RT(min): 1.56

Synthesis of tert-butyl (S)-2-((((9H-fluoren-9-yl)methoxy)carbonyl)amino)-3-(5-cyanothiophen-3-yl)propanoate

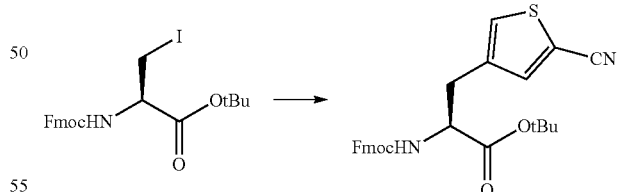

Iodine (46 mg) was added to a solution of zinc powder (2.4 g) in DMF (2.6 mL), which was then stirred at room temperature for 5 minutes under a nitrogen atmosphere. A solution of tert-butyl (R)-2-((((9H-fluoren-9-yl)methoxy)carbonyl)amino)-3-iodopropanoate (600 mg) in DMF (1.4 mL) and iodine (46 mg) were added at room temperature to the reaction mixture which was then stirred for 2 hours and 40 minutes. 4-bromo-2-cyanothiophene (298 mg), 2-dicyclohexylphosphino-2',4',6'-triisopropyl-1,1'-biphenyl (29 mg), and tris(dibenzylideneacetone)dipalladium (28 mg)

were added at room temperature to the reaction mixture which was then stirred at room temperature for 3 hours under a nitrogen atmosphere and filtered through celite. Ethyl acetate was added to the filtrate which was then washed with an aqueous sodium thiosulfate solution. The organic layer was dried over anhydrous magnesium sulfate and concentrated under reduced pressure. The resulting residue was purified by silica gel chromatography (n-hexane:ethyl acetate=90:10→30:70) to give tert-butyl (S)-2-((((9H-fluoren-9-yl)methoxy)carbonyl)amino)-3-(5-cyanothiophen-3-yl)propanoate (127 mg).

MS(ESI m/z): 475.1 (M+H)

RT(min): 1.95

The synthesis of the compounds shown in Table 19 below was carried out in the same manner as the synthesis of tert-butyl (S)-2-((((9H-fluoren-9-yl)methoxy)carbonyl)amino)-3-(5-cyanothiophen-3-yl)propanoate.

TABLE 19

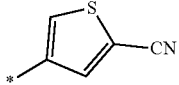

| R | Compound Name | Observed MS | RT/min |
|---|---|---|---|
| 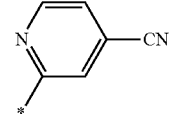 [SMILES: *c1cc(C#N)ccn1] | tert-butyl (S)-2-((((9H-fluoren-9-yl)methoxy)carbonyl)amino)-3-(5-cyanothiophen-3-yl)propanoate | 475.1 | 1.95 |
| 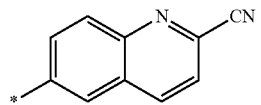 | tert-butyl (S)-2-((((9H-fluoren-9-yl)methoxy)carbonyl)amino)-3-(4-cyanopyridin-2-yl)propanoate | 470.1 | 1.85 |
| 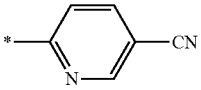 [SMILES: *c1ccc(C#N)cn1] | tert-butyl (S)-2-((((9H-fluoren-9-yl)methoxy)carbonyl)amino)-3-(2-cyanoquinolin-6-yl)propanoate | 520.1 | 1.98 |
| 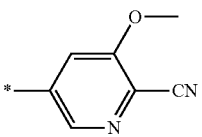 [SMILES: *c1cnc(C#N)c(OC)c1] | tert-butyl (S)-2-((((9H-fluoren-9-yl)methoxy)carbonyl)amino)-3-(5-cyanopyridin-2-yl)propanoate | 470.1 | 1.85 |
| 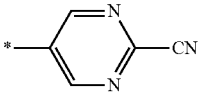 | tert-butyl (S)-2-((((9H-fluoren-9-yl)methoxy)carbonyl)amino)-3-(6-cyano-5-methoxypyridin-3-yl)propanoate | 500.1 | 1.85 |
| 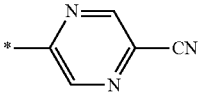 [SMILES: *c1cnc(C#N)cn1] | tert-butyl (S)-2-((((9H-fluoren-9-yl)methoxy)carbonyl)amino)-3-(2-cyanopyrimidin-5-yl)propanoate | 471.1 | 1.85 |
| 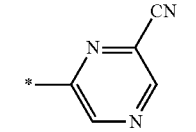 [SMILES: *c1cncc(C#N)n1] | tert-butyl (S)-2-((((9H-fluoren-9-yl)methoxy)carbonyl)amino)-3-(5-cyanopyrazin-2-yl)propanoate | 471.1 | 1.85 |
| 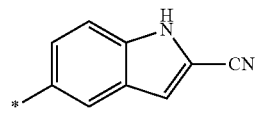 [SMILES: *c1ccc2[nH]c(C#N)cc2c1] | tert-butyl (S)-2-((((9H-fluoren-9-yl)methoxy)carbonyl)amino)-3-(6-cyanopyrazin-2-yl)propanoate | 471.1 | 1.84 |
|  | tert-butyl (S)-2-((((9H-fluoren-9-yl)methoxy)carbonyl)amino)-3-(2-cyano-1H-indol-5-yl)propanoate | 508.0 | 1.90 |

TABLE 19-continued

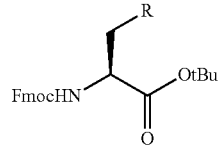

| R | Compound Name | Observed MS | RT/ min |
|---|---|---|---|
| 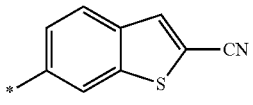 [SMILES: *c1ccc2cc(C#N)sc2c1] | tert-butyl (S)-2-((((9H-fluoren-9-yl)methoxy)carbonyl)amino)-3-(3-cyanoquinolin-7-yl)propanoate | 520.0 | 1.88 |
| 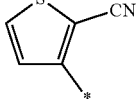 | tert-butyl (S)-2-((((9H-fluoren-9-yl)methoxy)carbonyl)amino)-3-(2-cyanobenzo[b]thiophen-6-yl)propanoate | 525.9 | 2.06 |
|  | tert-butyl (S)-2-((((9H-fluoren-9-yl)methoxy)carbonyl)amino)-3-(2-cyanothiophen-3-yl)propanoate | 475.1 | 1.95 |
| 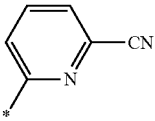 [SMILES: *c1cccc(C#N)n1] | tert-butyl (S)-2-((((9H-fluoren-9-yl)methoxy)carbonyl)amino)-3-(5-cyanothiophen-2-yl)propanoate | 475.1 | 1.95 |
| 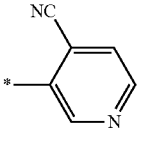 | tert-butyl (S)-2-((((9H-fluoren-9-yl)methoxy)carbonyl)amino)-3-(6-cyanopyridin-2-yl)propanoate | 470.2 | 1.87 |
| 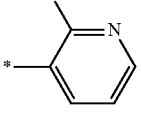 | tert-butyl (S)-2-((((9H-fluoren-9-yl)methoxy)carbonyl)amino)-3-(4-cyanopyridin-3-yl)propanoate | 470.3 | 1.78 |
| 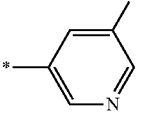 | tert-butyl (S)-2-((((9H-fluoren-9-yl)methoxy)carbonyl)amino)-3-(2-cyanopyridin-3-yl)propanoate | 470.1 | 1.82 |
| 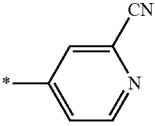 [SMILES: *c1ccnc(C#N)c1] | tert-butyl (S)-2-((((9H-fluoren-9-yl)methoxy)carbonyl)amino)-3-(5-cyanopyridin-3-yl)propanoate | 470.1 | 1.78 |
| 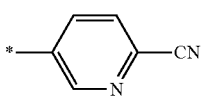 | tert-butyl (S)-2-((((9H-fluoren-9-yl)methoxy)carbonyl)amino)-3-(2-cyanopyridin-4-yl)propanoate | 470.1 | 1.83 |
|  | tert-butyl (S)-2-((((9H-fluoren-9-yl)methoxy)carbonyl)amino)-3-(6-cyanopyridin-3-yl)propanoate | 470.1 | 1.83 |

TABLE 19-continued

| R | Compound Name | Observed MS | RT/min |
|---|---|---|---|
| 3-methyl-6-cyanopyridin-3-yl | tert-butyl (S)-2-((((9H-fluoren-9-yl)methoxy)carbonyl)amino)-3-(6-cyano-5-methylpyridin-3-yl)propanoate | 484.1 | 1.88 |
| 3-cyanopyridin-2-yl | tert-butyl (S)-2-((((9H-fluoren-9-yl)methoxy)carbonyl)amino)-3-(3-cyanopyridin-2-yl)propanoate | 470.1 | 1.86 |
| 6-cyanopyridazin-3-yl | tert-butyl (S)-2-((((9H-fluoren-9-yl)methoxy)carbonyl)amino)-3-(6-cyanopyridazin-3-yl)propanoate | 471.2 | 1.75 |
| 3-cyano-1-(tetrahydro-2H-pyran-2-yl)-1H-pyrazol-4-yl | tert-butyl (2S)-2-((((9H-fluoren-9-yl)methoxy)carbonyl)amino)-3-(3-cyano-1-(tetrahydro-2H-pyran-2-yl)-1H-pyrazol-4-yl)propanoate | 543.3 | 1.99 |
| 2-cyanobenzo[b]thiophen-4-yl | tert-butyl (S)-2-((((9H-fluoren-9-yl)methoxy)carbonyl)amino)-3-(2-cyanobenzo[b]thiophen-4-yl)propanoate | 525.2 | 2.08 |
| 2-cyanothiazol-4-yl | tert-butyl (S)-2-((((9H-fluoren-9-yl)methoxy)carbonyl)amino)-3-(2-cyanothiazol-4-yl)propanoate | 476.9 | 1.88 |
| 6-(pyridin-2-yl)thiazol-4-carboxylate-allyl | allyl (S)-2-(6-(2-((((9H-fluoren-9-yl)methoxy)carbonyl)amino)-3-(tert-butoxy)-3-oxopropyl)pyridin-2-yl)thiazol-4-carboxylate | 612.0 | 1.99 |

Synthesis of (S)-2-((((9H-fluoren-9-yl)methoxy)carbonyl)amino)-3-(5-cyanothiophen-3-yl)propanoic acid

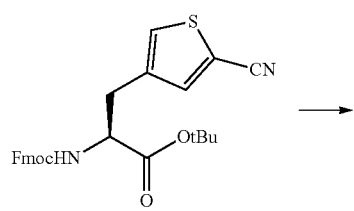

→

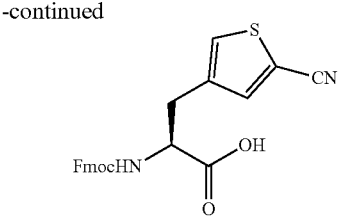

TFA (1.0 mL)) was added to tert-butyl (S)-2-((((9H-fluoren-9-yl)methoxy)carbonyl)amino)-3-(5-cyanothiophen-3-yl)propanoate (127 mg), followed by stirring at room temperature for 30 minutes, and then the solvent was distilled off under reduced pressure. The resulting residue was purified by silica gel chromatography (n-hexane:ethyl acetate=70:30→0:100) to give 63 mg of the title compound as a white solid.

¹H-NMR (MeOD) δ: 7.78 (2H, d, J=7.3 Hz), 7.59 (2H, d, J=7.3 Hz), 7.53-7.24 (6H, m), 4.53-4.43 (1H, m), 4.36-4.11 (3H, m), 3.25-2.93 (2H, m).

MS(ESI m/z): 419.0 (M+H)
RT(min): 1.55

The synthesis of the compounds shown in Table 20 below was carried out in the same manner as the synthesis of (S)-2-((((9H-fluoren-9-yl)methoxy)carbonyl)amino)-3-(5-cyanothiophen-3-yl)propanoic acid.

TABLE 20

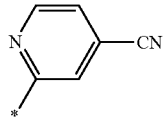 [SMILES: *c1cc(C#N)ccn1]

| R | Compound name | Observed MS | RT/ min | ¹H-NMR |
|---|---|---|---|---|
| 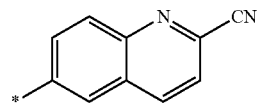 [SMILES: *c1ccc2nc(C#N)ccc2c1] | (S)-2-((((9H-fluoren-9-yl)methoxy)carbonyl)amino)-3-(4-cyanopyridin-2-yl)propanoic acid | 414.1 | 1.44 | ¹H-NMR (CDCl₃) δ: 8.73 (1H, d, J = 5.3 Hz), 7.78 (2H, d, J = 7.3 Hz), 7.63-7.54 (4H, m), 7.47-7.29 (4H, m), 6.15-6.06 (1H, m), 4.66-4.55 (1H, m), 4.51-4.38 (2H, m), 4.23 (1H, t, J = 6.9 Hz), 3.52-3.37 (2H, m). |
| 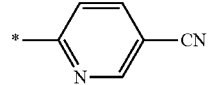 [SMILES: *c1ccc(C#N)cn1] | (S)-2-((((9H-fluoren-9-yl)methoxy)carbonyl)amino)-3-(2-cyanoquinolin-6-yl)propanoic acid | 464.1 | 1.56 | ¹H-NMR (CDCl₃) δ: 8.18 (1H, d, J = 7.9 Hz), 8.08 (1H, d, J = 9.2 Hz), 7.77 (2H, d, J = 7.3 Hz), 7.70-7.49 (5H, m), 7.40 (2H, t, J = 7.3 Hz), 7.34-7.25 (2H, m), 5.29 (1H, d, J = 6.6 Hz), 4.87-4.75 (1H, m), 4.54-4.35 (2H, m), 4.22-4.14 (1H, m), 3.52-3.40 (1H, m), 3.38-3.26 (1H, m). |
| 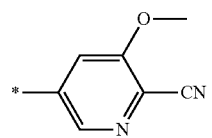 | (S)-2-((((9H-fluoren-9-yl)methoxy)carbonyl)amino)-3-(5-cyanopyridin-2-yl)propanoic acid | 414.1 | 1.43 | ¹H-NMR (CDCl₃) δ: 8.84 (1H, s), 7.97 (1H, d, J = 7.3 Hz), 7.78 (2H, d, J = 7.3 Hz), 7.59 (2H, d, J = 7.3 Hz), 7.42 (2H, t, J = 7.3 Hz), 7.36-7.29 (3H, m), 6.00-5.88 (1H, m), 4.73-4.61 (1H, m), 4.56-4.39 (2H, m), 4.22 (1H, t, J = 6.6 Hz), 3.56-3.43 (2H, m). |
| 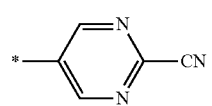 | (S)-2-((((9H-fluoren-9-yl)methoxy)carbonyl)amino)-3-(6-cyano-5-methoxypyridin-3-yl)propanoic acid | 444.1 | 1.46 | ¹H-NMR (CDCl₃) δ: 8.05 (1H, s), 7.76 (2H, d, J = 7.9 Hz), 7.55 (2H, d, J = 7.3 Hz), 7.41 (2H, t, J = 7.3 Hz), 7.36-7.18 (3H, m), 5.66-5.54 (1H, m), 4.76-4.62 (1H, m), 4.54-4.35 (2H, m), 4.21 (1H, t, J = 6.6 Hz), 3.84 (3H, s), 3.33-3.22 (2H, m). |
|  | (S)-2-((((9H-fluoren-9-yl)methoxy)carbonyl)amino)-3-(2-cyanopyrimidin-5-yl)propanoic acid | 415.1 | 1.46 | ¹H-NMR (CDCl₃) δ: 8.59 (1H, s), 7.78 (2H, d, J = 6.6 Hz), 7.56 (2H, d, J = 7.9 Hz), 7.47-7.29 (5H, m), 5.45-5.34 (1H, m), 4.73-4.39 (3H, m), 4.20 (1H, t, J = 5.6 Hz), 3.37-3.24 (1H, m), 3.21-3.09 (1H, m). |

TABLE 20-continued

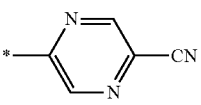

| R | Compound name | Observed MS | RT/min | ¹H-NMR |
|---|---|---|---|---|
| 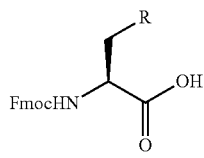 | (S)-2-((((9H-fluoren-9-yl)methoxy)carbonyl)amino)-3-(5-cyanopyrazin-2-yl)propanoic acid | 415.0 | 1.45 | ¹H-NMR (CDCl₃) δ: 8.80 (1H, s), 8.59 (1H, s), 7.76 (2H, d, J = 7.3 Hz), 7.55 (2H, d, J = 7.3 Hz), 7.41 (2H, t, J = 7.3 Hz), 7.31 (2H, t, J = 7.6 Hz), 5.83-5.72 (1H, m), 4.91-4.79 (1H, m), 4.44 (2H, d, J = 6.6 Hz), 4.20 (1H, t, J = 6.3 Hz), 3.58-3.46 (2H, m). |
| 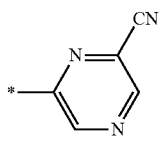 | (S)-2-((((9H-fluoren-9-yl)methoxy)carbonyl)amino)-3-(6-cyanopyrazin-2-yl)propanoic acid | 415.0 | 1.42 | ¹H-NMR (CDC 13) δ: 8.80 (1H, s), 8.67 (1H, s), 7.75 (2H, d, J = 7.9 Hz), 7.56 (2H, d, J = 7.9 Hz), 7.40 (2H, t, J = 7.6 Hz), 7.31 (2H, t, J = 7.3 Hz), 5.75 (1H, d, J = 7.3 Hz), 4.90-4.78 (1H, m), 4.41 (2H, d, J = 7.3 Hz), 4.20 (1H, t, J = 6.6 Hz). 3.59-3.41 (2H, m). |
| 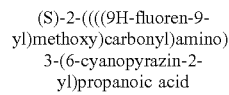 | (S)-2-((((9H-fluoren-9-yl)methoxy)carbonyl)amino)-3-(2-cyano-1H-indol-5-yl)propanoic acid | 452.3 | 1.56 | ¹H-NMR (MeOD) δ: 7.76 (2H d, J = 7.9 Hz), 7.58-7.48 (3H, m), 7.42-7.31 (3H, m), 7.30-7.14 (3H, m), 7.05 (1H, s), 4.46 (1H, dd, J = 9.2, 4.6 Hz), 4.31-4.22 (1H, m), 4.19-4.04 (2H, m), 3.34-3.28 (1H, m), 3.06-2.95 (1H, m). |
| 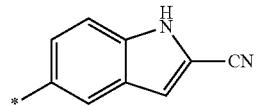 [SMILES: *c1ccc2[nH]c(C#N)cc2c1] | (S)-2-((((9H-fluoren-9-yl)methoxy)carbonyl)amino)-3-(3-cyanoquinolin-7-yl)propanoic acid | 464.3 | 1.54 | ¹H-NNIR (DMSO-D₆) δ: 9.14 (1H, s), 9.04 (1H, s), 8.07-8.00 (2H, m), 7.91-7.82 (3H, m).7.73 (1H, d, J = 8.6 Hz), 7.56 (2H, dd, J = 7.3, 2.6 Hz), 7.37 (2H, t, J = 7.3 Hz). 7.29-7.13 (2H, m), 4.44-4.31 (1H, m), 4.22-4.06 (3H, m), 3.44-3.36 (1H, m), 3.22-3.09 (1H, m). |
| 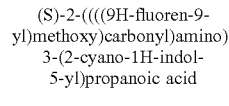 | (S)-2-((((9H-fluoren-9-yl)methoxy)carbonyl)amino)-3-(2-cyanobenzo[b]thiophen-6-yl)propanoic acid | 469.0 | 1.64 | ¹H-NMR (DMSO-D₆) δ: 8.41-8.33 (1H, m), 8.03-7.77 (5H, m), 7.60 (2H, t, J = 6.3 Hz), 7.51-7.35 (3H, m), 7.31-7.17 (2H, m), 4.33-4.10 (4H, m), 3.29-3.17 (1H, m), 3.09-2.97 (1H, m). |
| 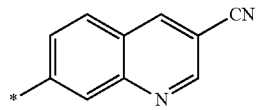 [SMILES: *c1ccc2cc(C#N)cnc2c1] | (S)-2-((((9H-fluoren-9-yl)methoxy)carbonyl)amino)-3-(2-cyanothiophen-3-yl)propanoic acd | 418.9 | 1.54 | ¹H-N1R.(MeOD) δ: 7.83-7.25 (9H, m), 7.01 (1H, d, J = 5.3 Hz), 5.52 (1H, d, J = 5.52), 4.68-4.12 (4H, m), 3.45-3.15 (2H, m). |
| 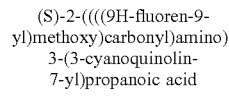 | (S)-2-((((9H-fluoren-9-yl)methoxy)carbonyl)amino)-3-(5-cyanothiophen-2-yl)propanoic acid | 418.9 | 1.54 | ¹H-NMR (CDCl₃) δ: 7.77 (2H, d, J = 7.3 Hz), 7.58 (2H, d, J = 7.3), 7.47-7.26 (5H, m), |

TABLE 20-continued

| R | Compound name | Observed MS | RT/min | $^1$H-NMR |
|---|---|---|---|---|
| | | | | 6.80-6.71 (1H, m), 5.51 (1H, d, J = 7.9) 4.56-4.16 (3H, m), 3.49-3.24 (2H, m). |
| 6-cyanopyridin-2-yl | (S)-2-((((9H-fluoren-9-yl)methoxy)carbonyl)amino)-3-(6-cyanopyridin-2-yl)propionic acid | 414.1 | 1.46 | $^1$H-NMR (CDCl$_3$) δ: 7.81 (t, 1H, 1-7.9 Hz), 7.76 (d, 2H, J = 7.6 Hz), 7.65-7.55 (m, 3H), 7.46 (d, 1H, J = 7.9 Hz), 7.40 (t, 2H, J = 7.4 Hz), 7.31 (td, 2H, J = 7.4, 1.2 Hz), 6.08 (d, 1H, J = 6.9 Hz), 4.76 (d, 1H, J = 6.3 Hz), 4.41-4.35 (m, 2H), 4.22 (t, 1H, J = 6.9 Hz), 3.47-3.43 (m, 2H). |
| 4-cyanopyridin-3-yl | (S)-2-((((9H-fluoren-9-yl)methoxy)carbonyl)amino)-3-(4-cyanopyridin-3-yl)propionic acid | 414.1 | 1.38 | $^1$H-NMR (CDCl$_3$) δ: 8.70-8.63 (m, 2H), 7.77 (d, 2H, J = 7.6 Hz), 7.62-7.55 (m, 3H), 7.41 (t, 2H, J = 7.3 Hz), 7.35-7.28 (m, 2H), 5.48 (d, 1H, J = 7.3 Hz), 4.84 (d, 1H, J = 6.3 Hz), 4.50-4.38 (m, 2H), 4.24 (d, 1H, J = 5.6 Hz), 3.64-3.56 (m, 1H), 3.45-3.36 (m, 1H). |
| 2-cyanopyridin-3-yl | (S)-2-((((9H-fluoren-9-yl)methoxy)carbonyl)amino)-3-(2-cyanopyridin-3-yl)propionic acid | 414.0 | 1.42 | $^1$H-NMR (DMSO-D$_6$) δ: 8.55 (d, 1H, J = 3.3 Hz), 7.94-7.85 (m, 3H), 7.62-7.54 (m, 3H), 7.41 (t, 2H, J = 7.3 Hz), 7.31 (t, 2H, J = 7.3 Hz), 6.88 (br, 1H), 4.23-4.06 (m, 4H), 3.42-3.36 (m, 1H), 3.10-3.01 (m, 1H). |
| 5-cyanopyridin-3-yl | (S)-2-((((9H-fluoren-9-yl)methoxy)carbonyl)amino)-3-(5-cyanopyridin-3-yl)propionic acid | 414.1 | 1.39 | $^1$H-NMR (DMSO-D$_6$) δ: 8.90 (d, 1H, J = 2.0 Hz), 8.77 (d, 1H, J = 2.0 Hz), 8.23 (t, 1H, J = 2.0 Hz), 7.88 (d, 2H, J = 7.5 Hz), 7.82 (d, 1H, J = 8.6 Hz), 7.62-7.60 (m, 2H), 7.41 (t, 2H, J = 7.5 Hz), 7.32-7.28 (m, 2H), 4.27-4.20 (m, 4H), 3.23-3.18 (m, 1H), 2.98-2.93 (m, 1H). |
| 2-cyanopyridin-4-yl | (S)-2-((((9H-fluoren-9-yl)methoxy)carbonyl)amino)-3-(2-cyanopyridin-4-yl)propionic acid | 414.0 | 1.43 | $^1$H-NMR (DMSO-D$_6$) δ: 8.63 (d, 1H, J = 5.0 Hz), 7.96 (s, 1H), 7.88 (d, 2H, J = 7.9 Hz), 7.65-7.55 (m, 3H), 7.41 (t, 2H, J = 7.3 Hz), 7.33-7.25 (m, 3H), 4.26-4.14 (m, 5H), 3.01-2.91 (m, 1H). |
| 6-cyanopyridin-3-yl | (S)-2-((((9H-fluoren-9-yl)methoxy)carbonyl)amino)-3-(6-cyanopyridin-3-yl)propionic acid | 414.0 | 1.43 | $^1$H-NMR (DMSO-D$_6$) δ: 8.51 (s, 1H), 7.89-7.87 (m, 3H), 7.73 (d, 1H, J = 9.2 Hz), 7.62-7.60 (m, 2H), 7.42 (t, 2H, J = 7.1 Hz), |

… TABLE 20-continued

| R | Compound name | Observed MS | RT/min | ¹H-NMR |
|---|---|---|---|---|
| | | | | 7.32 (t, 2H, J = 7.1 Hz), 6.61 (br, 1H), 4.33-4.32 (m, 1H), 4.19-4.14 (m, 2H), 3.90 (d, 1H, J = 5.3 Hz), 3.20-3.16 (m, 1H), 3.05-3.00 (m, 1H). |
| 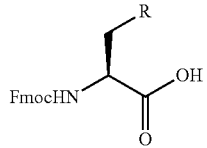 | (S)-2-((((9H-fluoren-9-yl)methoxy)carbonyl)amino)-3-(6-cyano-5-methyl pyridin-3-yl)propionic acid | 428.1 | 1.49 | ¹H-NMR (DMSO-D₆) δ: 8.38 (s, 1H), 7.89 (d, 2H, J = 7.3 Hz), 7.65-7.60 (m, 3H), 7.41 (t, 2H, J = 7.3 Hz), 7.30 (t, 2H, J = 7.3 Hz), 6.80 (d, 1H, J = 7.3 Hz), 4.34-3.96 (m, 4H), 3.19-3.17 (m, 1H), 3.01-2.97 (m, 1H), 2.37 (s, 3H). |
| 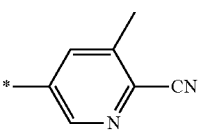 [SMILES: *c1cnc(C#N)c(C)c1] | (S)-2-((((9H-fluoren-9-yl)methoxy)carbonyl)amino)-3-(3-cyanopyridin-2-yl)propionic acid | 414.0 | 1.43 | ¹H-NMR (DMSO-D₆) δ: 8.77 (dd, 1H, J = 5.0, 1.7 Hz), 8.27 (dd, 1H, J = 7.9, 1.7 Hz), 7.88 (d, 2H, J = 7.3 Hz), 7.84 (d, 1H, J = 8.3 Hz), 7.65 (d, 2H, J = 7.3 Hz), 7.47 (dd, 1H, J = 7.9, 5.0 Hz), 7.41 (t, 2H, J = 7.3 Hz), 7.30 (t, 2H, J = 7.3 Hz), 4.72 (dd, 1H, J = 14.7, 8.3 Hz), 4.26-4.16 (m, 3H), 3.53-3.47 (m, 1H), 3.30-3.28 (m, 1H). |
| 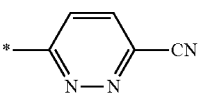 [SMILES: *c1ccc(C#N)nn1] | (S)-2-((((9H-fluoren-9-yl)methoxy)carbonyl)amino)-3-(6-cyanopyridazin-3-yl)propionic acid | 415.1 | 1.37 | ¹H-NMR (MeOD) δ: 8.03 (1H, d, J = 8.7 Hz), 7.84-7.70 (3H, m), 7.59 (2H, d, J = 5.1 Hz), 7.38 (2H, d, J = 6.6 Hz), 7.29 (2H, d, J = 6.6 Hz), 4.74 (1H, m), 4.30 (2H, br s), 4.17 (1H, br s), 3.75-3.60 (2H, m). |
| 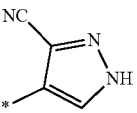 [SMILES: *c1c[nH]nc1C#N] | (S)-2-((((9H-fluoren-9-yl)methoxy)carbonyl)amino)-3-(3-cyano-1H-pyrazol-4-yl)propionic acid | 403.1 | 1.31 | ¹H-NMR (MeOD) δ: 7.78 (2H, br s), 7.61 (3H, br s), 7.37 (2H, d, J = 5.1 Hz), 7.30 (2H, d, J = 5.1 Hz), 4.37-4.01 (4H, m), 3.25-2.91 (2H, m). |
| 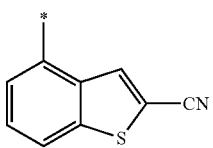 [SMILES: *c1cccc2sc(C#N)cc12] | (S)-2-((((9H-fluoren-9-yl)methoxy)carbonyl)amino)-3-(2-cyanobenzo[b]thiophen-4-yl)propionic acid | 469.1 | 1.70 | ¹H-NMR (MeOD) δ: 8.31 (1H, s), 7.86 (2H, d, J = 7.8 Hz), 7.78 (2H, d, J = 7.8 Hz), 7.59-7.52 (1H, m), 7.48 (2H, t, J = 8.1 Hz), 7.32 (2H, t, J = 8.1 Hz), 7.32-7.20 (2H, m), 4.52 (1H, m), 4.35-4.13 (2H, m.), 4.13-4.04 (1H, m), 3.70-3.50 (2H, m). |
| 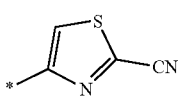 | (S)-2-((((9H-fluoren-9-yl)methoxy)carbonyl)amino)-3-(2-cyanothiazol-4-yl)propanoic acid | 420.8 | 1.48 | ¹H-NMR (DMSO-D₆) δ: 7.90 (2H, t, J = 7.9 Hz), 7.76 (1H, d, J = 7.9 Hz), 7.64 (2H, d, J = 7.3 Hz), 7.47-7.26 (5H, m), 4.44-4.30 (1H, m), 4.29-4.14 (3H, m), 3.34-3.09 (2H, m). |

TABLE 20-continued

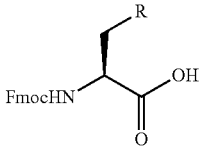

| R | Compound name | Observed MS | RT/min | ¹H-NMR |
|---|---|---|---|---|
| [structure: 6-(pyridin-2-yl)-thiazole with allyloxycarbonyl] | (S)-2-((((9H-fluoren-9-yl)methoxy)carbonyl)amino)-3-(6-(4-((allyloxy)carbonyl)thiazol-2-yl)pyridin-2-yl)propanoic acid | 556.0 | 1.66 | ¹H-NMR (DMSO-D₆) δ: 8.68 (1H.s), 8.01 (1H, d, J = 7.3 Hz), 7.96-7.83 (3H, m), 7.73 (1H, d, J = 7.9 Hz), 7.60 (2H, d, J = 7.9 Hz), 7.47-7.34 (5H, m), 6.14-5.98 (1H, m), 5.48-5.38 (1H, m), 5.30 (1H, d, J = 11.9 Hz), 4.83 (2H, d, J = 5.3 Hz), 4.63-4.53 (1H, m), 4.26-4.12 (3H, m), 3.31-3.10 (2H, m). |

Synthesis of (S)-2-((((9H-fluoren-9-yl)methoxy)carbonyl)amino)-3-(4-cyanothiazol-2-yl)propanoic acid

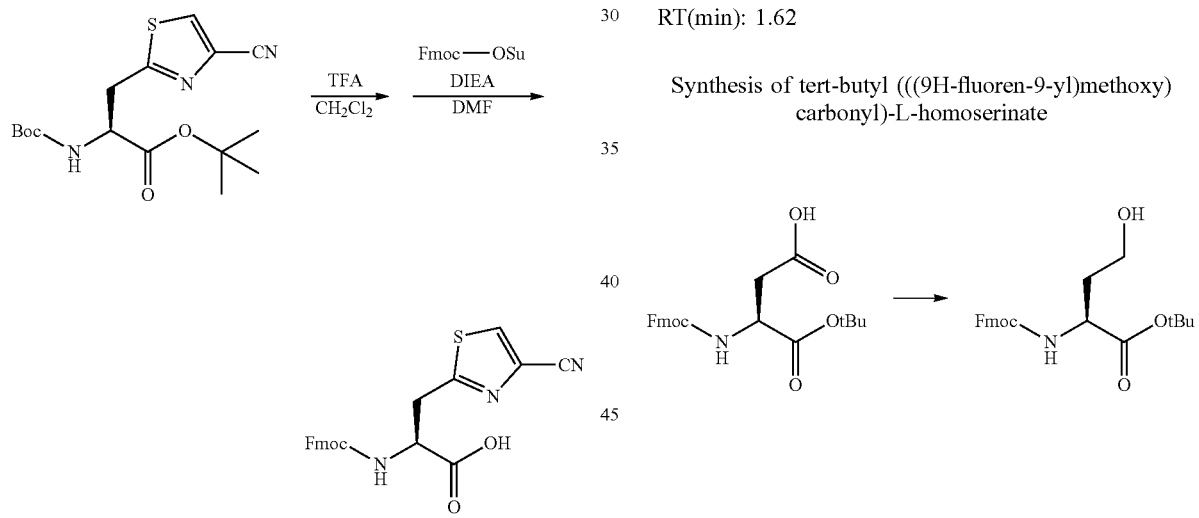

10 mL of TFA was added to a dichloromethane solution (2 mL) of tert-butyl (S)-2-((tert-butoxycarbonyl)amino)-3-(4-cyanothiazol-2-yl)propanoate (193 mg) which was then stirred at room temperature for 3 hours. The solvent was distilled off under reduced pressure, and 10 mL of DMF, 0.48 mL of N,N-diisopropylethylamine, and 204 mg of 9-fluorenylmethyl N-succinimidyl carbonate (Fmoc-OSu) were added thereto, followed by stirring at room temperature for 15 hours. The solvent was distilled off under reduced pressure, and the residue was purified by column chromatography (silica gel, ethyl acetate/hexane=30/70→100/0) to give 121 mg of the title compound as a pale yellow amorphous substance.

¹H-NMR (CDCl₃) δ: 7.78 (2H, d, J=7.3 Hz), 7.68-7.63 (1H, m), 7.60-7.49 (2H, m), 7.45-7.28 (4H, m), 5.34-5.24 (1H, m), 4.80-4.67 (1H, m), 4.55-4.35 (2H, m), 4.18 (1H, t, J=6.9 Hz), 3.42-3.21 (2H, m).

MS(ESI m/z): 454.9 (M+H)

RT(min): 1.62

Synthesis of tert-butyl (((9H-fluoren-9-yl)methoxy)carbonyl)-L-homoserinate

Triethylamine (2.80 mL) was added to a THF solution (30 mL) of (S)-3-((((9H-fluoren-9-yl)methoxy)carbonyl)amino)-4-(tert-butoxy)-4-oxobutanoic acid (5.02 g). A THF solution (10 mL) of ethyl chloroformate (1.43 mL) was added dropwise thereto on an ice bath, followed by stirring at room temperature for 35 minutes. The insolubles were filtered off, and 1.36 g of sodium borohydride was added little by little to the filtrate, followed by stirring at room temperature for 1 hour. 5 mL of distilled water was added to the reaction solution to which an aqueous hydrochloric acid solution (1 mol/L) and ethyl acetate were then added, followed by extraction with ethyl acetate. The organic layer was washed with saturated saline and dried over magnesium sulfate. The solvent was distilled off under reduced pressure to give 1.62 g of the title compound as a colorless oil.

MS(ESI m/z): 398.0 (M+H)

RT(min): 1.61

Synthesis of tert-butyl (S)-2-((((9H-fluoren-9-yl)methoxy)carbonyl)amino)-4-iodobutanoate

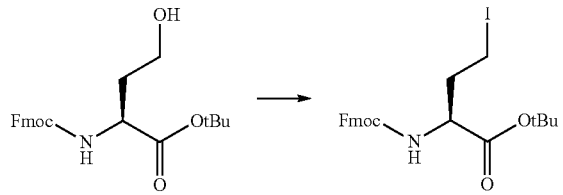

The procedure was carried out in the same manner as the synthesis of tert-butyl (R)-2-((((9H-fluoren-9-yl)methoxy)carbonyl)amino)-3-iodopropanoate.
MS(ESI m/z): 507.8 (M+H)
RT(min): 1.99

Synthesis of (S)-2-((((9H-fluoren-9-yl)methoxy)carbonyl)amino)-3-(4-cyano-1H-1,2,3-triazol-1-yl)propionic acid

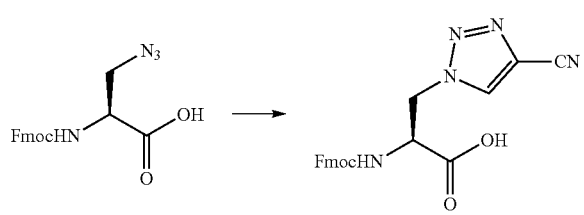

2-chloroacrylonitrile (0.11 mL) was added at room temperature to a water/acetonitrile mixed solvent (=5/2, 7 mL) of (S)-2-((((9H-fluoren-9-yl)methoxy)carbonyl)amino)-3-azidopropanoic acid (230 mg), followed by stirring at 80° C. for 21 hours. Ethyl acetate and saturated saline were added to the reaction solution, followed by extraction with ethyl acetate. The organic layer was dried over anhydrous magnesium sulfate and the solvent was distilled off under reduced pressure. A hexane/acetone mixed solvent (15:1) was added to the resulting residue, and recrystallization was carried out at 50° C. to give the title compound (145 mg) as a white solid.
MS(ESI m/z): 403.9 (M+H)
RT(min): 1.41
$^{1}$H-NMR (CDCl$_3$) δ: 7.87-7.78 (2H, m), 7.65-7.55 (2H, m), 7.49-7.41 (3H, m), 7.40-7.31 (2H, m), 5.44-5.38 (1H, m), 5.03-4.62 (3H, m), 4.56-4.50 (1H, m), 4.23-4.19 (2H, m).

Synthesis of tert-butyl (S)-2-((((9H-fluoren-9-yl)methoxy)carbonyl)amino)-3-(4-nitrophenyl)propanoate

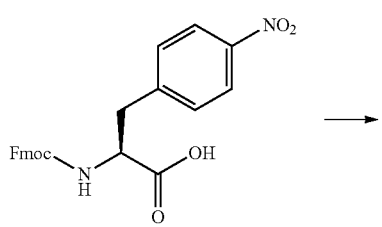

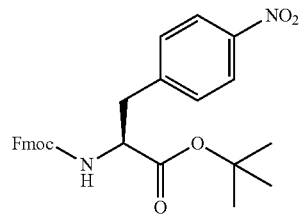

4.5 mL of tert-butyl 2,2,2-trichloroacetimidate was added at room temperature to a THF solution (100 mL) of (S)-2-((((9H-fluoren-9-yl)methoxy)carbonyl)amino)-3-(4-nitrophenyl)propanoic acid (2.5 g) which was then stirred at 70° C. for 24 hours. The solvent was distilled off under reduced pressure, and the residue was purified by column chromatography (silica gel, ethyl acetate/hexane=0/100→10/90→20/80) to give the title compound (3.65 g) as a yellow oil.
MS(ESI m/z): 489.1 (M+H)
RT(min): 1.96

Synthesis of tert-butyl (S)-2-((tert-butoxycarbonyl)amino)pent-4-enoate

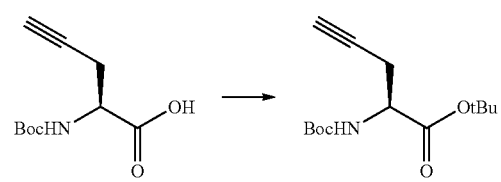 [SMILES: C#CC[C@H](NC(=O)OC(C)(C)C)C(=O)O ; C#CC[C@H](NC(=O)OC(C)(C)C)C(=O)OC(C)(C)C]

Tert-butyl 2,2,2-trichloroacetimidate (4.6 g) was added dropwise to an ethyl acetate solution (5.0 mL) of (S)-2-((tert-butoxycarbonyl)amino)pent-4-enoic acid (1.5 g) which was then stirred at room temperature for 22 hours. The solvent was distilled off under reduced pressure, and the residue was purified by column chromatography (silica gel, ethyl acetate/hexane=0/100→30/70) to give the title compound (1.66 g) as a colorless oil.
MS(ESI m/z): 270.1 (M+H)
RT(min): 1.59

Synthesis of ethyl (S)-5-(3-(tert-butoxy)-2-((tert-butoxycarbonyl)amino)-3-oxopropyl)isoxazole-3-carboxylate

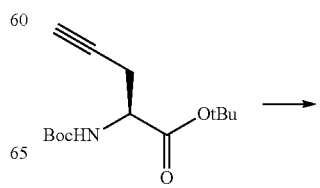

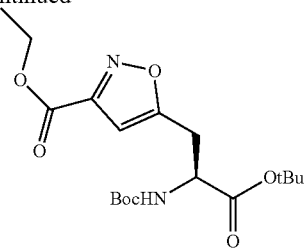

Triethylamine (640 µL) was added at 90° C. to a DMF solution (21 mL) of tert-butyl (S)-2-((tert-butoxycarbonyl)amino)pent-4-enoate (1660 mg) and ethyl 2-chloro-2-(hydroxyimino)acetate (2.8 g), followed by stirring for 15 minutes. Triethylamine (640 µL) was added at 90° C. to the reaction solution which was then stirred for 15 minutes. Triethylamine (1278 µL) was added thereto at 90° C., followed by stirring for 30 minutes. Ethyl acetate and saturated saline were added to the reaction solution, followed by extraction with ethyl acetate. The organic layer was dried over magnesium sulfate. The solvent was distilled off under reduced pressure, and the residue was purified by column chromatography (silica gel, ethyl acetate/hexane=0/100→25/75) to give 818 mg of the title compound as a yellow oil.

MS(ESI m/z): 385.0 (M+H)
RT(min): 1.36

Synthesis of 5-bromo-1-methyl-1H-pyrrolo[2,3-b]pyridine-6-carbonitrile

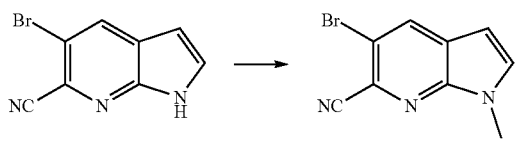

Cesium carbonate (919 mg) and methyl methanesulfonate (115 µL) were added to a THF/acetonitrile solution (=2/1, 6 mL) of 5-bromo-1H-pyrrolo[2,3-b]pyridine-6-carbonitrile (250 mg) which was then stirred at room temperature for 16 hours. Ethyl acetate and an aqueous ammonium chloride solution were added to the reaction solution, followed by extraction with ethyl acetate. The organic layer was dried over magnesium sulfate. The solvent was distilled off under reduced pressure, and the residue was purified by column chromatography (silica gel, ethyl acetate/hexane=0/100→50/50) to give 151 mg of the title compound as a white solid.

MS(ESI m/z): 235.6 (M+H)
RT(min): 1.58

Synthesis of ethyl 6-(3-bromophenyl)imidazo[1,2-a]pyrimidine-2-carboxylate

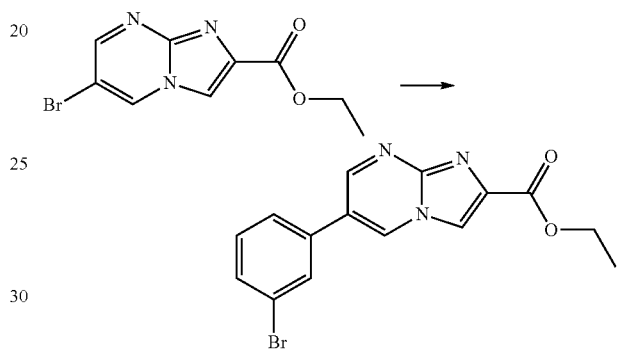

The procedure was carried out in the same manner as the synthesis of ethyl 6-(3-bromophenyl)pyrazolo[1,5-a]pyrimidine-2-carboxylate.

MS(ESI m/z): 347.0 (M+H)
RT(min): 1.45

The synthesis of the compounds shown in Table 21 below was carried out in the same manner as the synthesis of ethyl 6-(3-bromophenyl)pyrazolo[1,5-a]pyrimidine-2-carboxylate.

TABLE 21

| Structure | Compound name | Observed MS | RT/min |
|---|---|---|---|
| 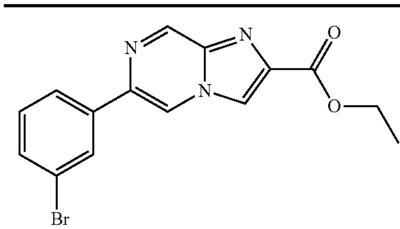 | ethyl 6-(3-bromophenyl)imidazo[1,2-a]pyrazine-2-carboxylate | 347.0 | 1.45 |
| 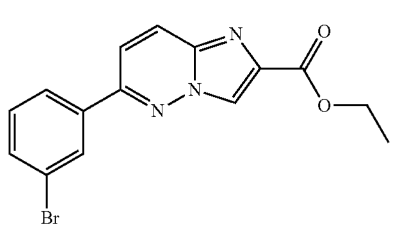 [SMILES: CCOC(=O)c1cn2nc(-c3cccc(Br)c3)ccc2n1] | ethyl 6-(3-bromophenyl)imidazo[1,2-b]pyridazine-2-carboxylate | 347.0 | 1.54 |

169
Synthesis of
1-(4-bromophenyl)-1H-imidazole-4-carboxamide

170
Synthesis of 6-(3-bromophenyl)imidazo[1,2-a]pyrimidine-2-carboxamide

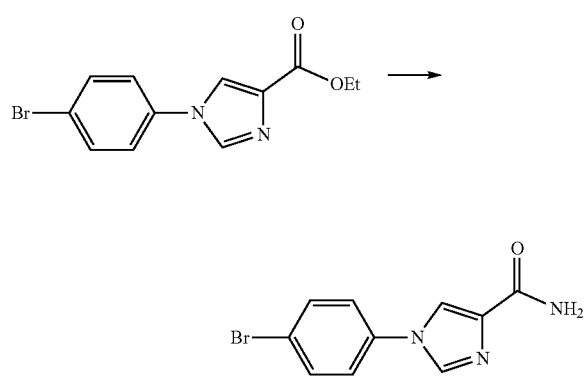

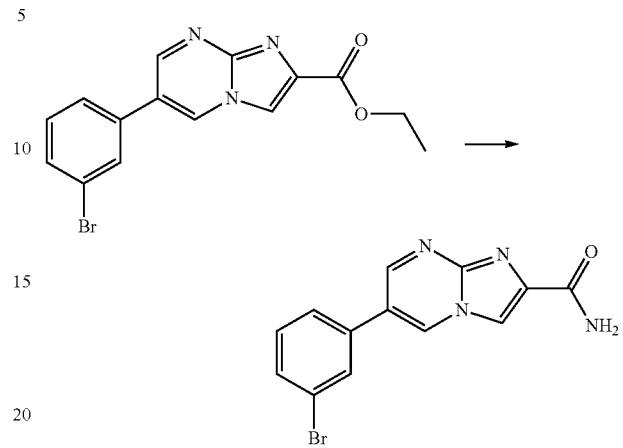

A methanol solution of ammonia (7 mol/L, 10 mL) was added to ethyl 1-(4-bromophenyl)-1H-imidazole-4-carboxylate (746 mg), followed by microwave irradiation (Initiator™, 110° C., 1.0 hour, 2.45 GHz, 0 to 240 W). The reaction solution was further irradiated with microwaves (Initiator™, 120° C., 4.0 hours, 2.45 GHz, 0 to 240 W). The solvent was distilled off under reduced pressure to give 660 mg of the title compound as a white solid.
MS(ESI m/z): 268.0 (M+H)
RT(min): 0.98

The procedure was carried out in the same manner as the synthesis of tert-butyl (S)-2-((tert-butoxycarbonyl)amino)-3-(4-carbamoylthiazol-2-yl)propanoate.
MS(ESI m/z): 318.9 (M+H)
RT(min): 1.00
The synthesis of the compounds shown in Table 22 below was carried out in the same manner as the synthesis of tert-butyl (S)-2-((tert-butoxycarbonyl)amino)-3-(4-carbamoylthiazol-2-yl)propanoate.

TABLE 22

| Structure | Compound name | Observed MS | RT/min |
|---|---|---|---|
| 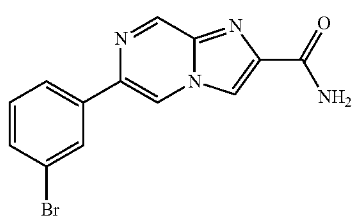 [SMILES: NC(=O)c1cn2cc(-c3cccc(Br)c3)ncc2n1] | 6-(3-bromophenyl)imidazo[1,2-a]pyrazine-2-carboxamide | 318.9 | 1.19 |
| 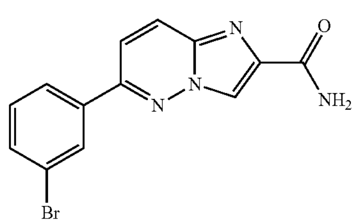 [SMILES: NC(=O)c1cn2nc(-c3cccc(Br)c3)ccc2n1] | 6-(3-bromophenyl)imidazo[1,2-b]pyridazine-2-carboxamide | 318.9 | 1.17 |
| 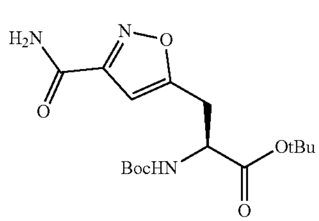 [SMILES: CC(C)(C)OC(=O)N[C@@H](Cc1cc(C(N)=O)no1)C(=O)OC(C)(C)C] | tert-butyl (S)-2-((tert-butoxycarbonyl)amino)-3-(3-carbamoylisoxazol-5-yl)propanoate | 356.1 | 1.31 |

Synthesis of 6-(3-bromophenyl)imidazo[1,2-a]pyrimidine-2-carbonitrile

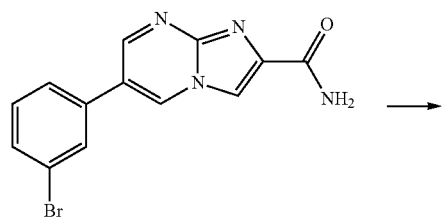

→

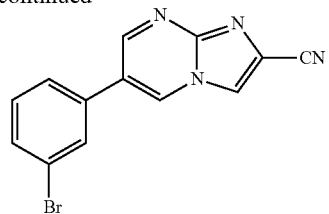

The procedure was carried out in the same manner as the synthesis of tert-butyl (S)-2-((tert-butoxycarbonyl)amino)-3-(4-cyanothiazol-2-yl)propanoate.

MS(ESI m/z): 300.0 (M+H)
RT(min): 1.24

The synthesis of the compounds shown in Table 23 below was carried out in the same manner as the synthesis of tert-butyl (S)-2-((tert-butoxycarbonyl)amino)-3-(4-cyanothiazol-2-yl)propanoate.

TABLE 23

| Structure | Compound name | Observed MS | RT/min |
|---|---|---|---|
| 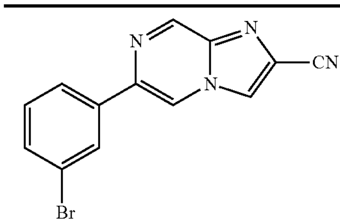 | 6-(3-bromophenyl)imidazo[1,2-a]pyrazine-2-carbonitrile | 300.0 | 1.48 |
| 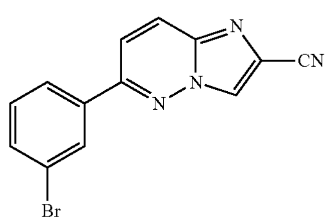 [SMILES: N#Cc1cn2nc(-c3cccc(Br)c3)ccc2n1] | 6-(3-bromophenyl)imidazo[1,2-b]pyridazine-2-carbonitrile | 300.0 | 1.49 |
| 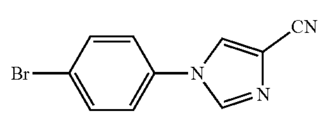 | 1-(4-bromophenyl)-1H-imidazole-4-carbonitrile | 249.9 | 1.25 |
| 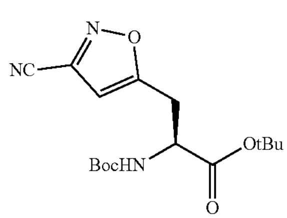 [SMILES: CC(C)(C)OC(=O)N[C@@H](Cc1cc(C#N)no1)C(=O)OC(C)(C)C] | tert-butyl (S)-2-((tert-butoxycarbonyl)amino)-3-(3-cyanoisoxazol-5-yl)propanoate | 338.1 | 1.65 |

The synthesis of the compounds shown in Table 24 below was carried out in the same manner as the synthesis of tert-butyl (S)-2-((((9H-fluoren-9-yl)methoxy)carbonyl)amino)-3-(5-cyanothiophen-3-yl)propanoate.

TABLE 24

| R | Compound name | Observed MS | RT/min |
|---|---|---|---|
| 3-(2-cyanoimidazo[1,2-a]pyrimidin-6-yl)phenyl | tert-butyl (S)-2-((((9H-fluoren-9-yl)methoxy)carbonyl)amino)-3-(3-(2-cyanoimidazo[1,2-a]pyrimidin-6-yl)phenyl)propanoate | 586.2 | 1.80 |
| 3-(2-cyanoimidazo[1,2-a]pyrazin-6-yl)phenyl | tert-butyl (S)-2-((((9H-fluoren-9-yl)methoxy)carbonyl)amino)-3-(3-(2-cyanoimidazo[1,2-a]pyrazin-6-yl)phenyl)propanoate | 586.2 | 1.90 |
| 3-(2-cyanoimidazo[1,2-b]pyridazin-6-yl)phenyl | tert-butyl (S)-2-((((9H-fluoren-9-yl)methoxy)carbonyl)amino)-3-(3-(2-cyanoimidazo[1,2-b]pyridazin-6-yl)phenyl)propanoate | 586.2 | 1.93 |
| 6-aminopyridin-2-yl | tert-butyl (S)-2-((((9H-fluoren-9-yl)methoxy)carbonyl)amino)-3-(6-aminopyridin-2-yl)propanoate | 460.7 | 1.32 |
| 5-cyanothiophen-3-yl (butanoate chain) | tert-butyl (S)-2-((((9H-fluoren-9-yl)methoxy)carbonyl)amino)-4-(5-cyanothiophen-3-yl)butanoate | 489.1 | 1.94 |
| 3-cyano-1-methyl-1H-indazol-5-yl | tert-butyl (S)-2-((((9H-fluoren-9-yl)methoxy)carbonyl)amino)-3-(3-cyano-1-methyl-1H-indazol-5-yl)propanoate | 522.9 | 1.97 |
| 6-cyano-1-methyl-1H-pyrrolo[2,3-b]pyridin-5-yl | tert-butyl (S)-2-((((9H-fluoren-9-yl)methoxy)carbonyl)amino)-3-(6-cyano-1-methyl-1H-pyrrolo[2,3-b]pyridin-5-yl)propanoate | 522.8 | 1.90 |

TABLE 24-continued

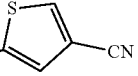

| R | Compound name | Observed MS | RT/min |
|---|---|---|---|
| 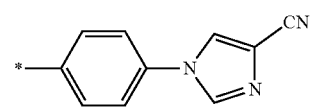 | tert-butyl (S)-2-((((9H-fluoren-9-yl)methoxy)carbonyl)amino)-3-(4-cyanothiophen-2-yl)propanoate | 475.0 | 1.90 |
| 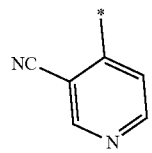 | tert-butyl 2-((((9H-fluoren-9-yl)methoxy)carbonyl)amino)-3-(4-(4-cyano-1H-imidazol-1-yl)phenyl)propanoate | 535.1 | 1.85 |
| 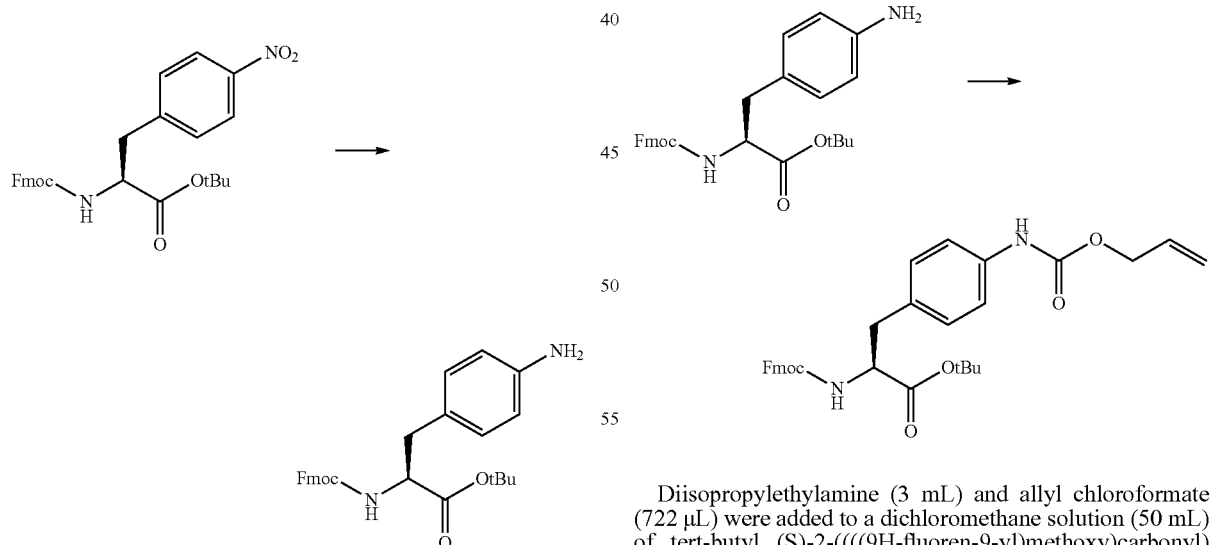 | tert-butyl (S)-2-((((9H-fluoren-9-yl)methoxy)carbonyl)amino)-3-(3-cyanopyridin-4-yl)propanoate | 470.0 | 1.74 |

Synthesis of tert-butyl (S)-2-(((((9H-fluoren-9-yl)methoxy)carbonyl)amino)-3-(4-aminophenyl)propanoate

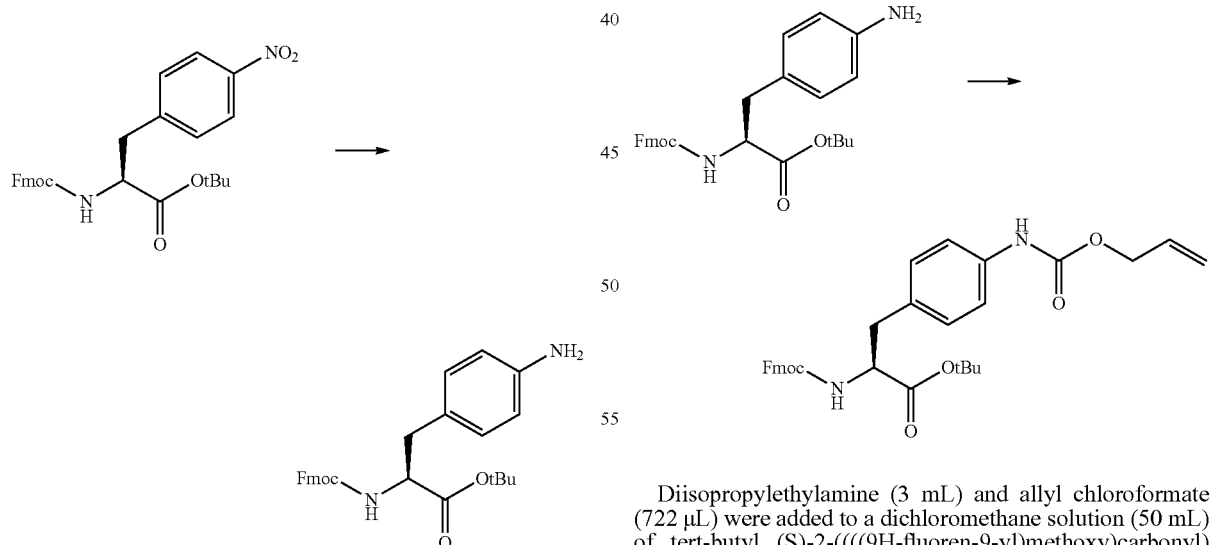

The procedure was carried out in the same manner as the synthesis of tert-butyl (S)-2-((tert-butoxycarbonyl)amino)-3-(3,4-diaminophenyl)propanoate.

MS(ESI m/z): 459.1 (M+H)

RT(min): 1.55

Synthesis of tert-butyl (S)-2-(((((9H-fluoren-9-yl)methoxy)carbonyl)amino)-3-(4-((allyloxy)carbonyl)amino)phenyl)propanoate Diisopropylethylamine (3 mL) and allyl chloroformate (722 µL) were added to a dichloromethane solution (50 mL) of tert-butyl (S)-2-(((((9H-fluoren-9-yl)methoxy)carbonyl)amino)-3-(4-aminophenyl)propanoate (2.83 g) which was then stirred at room temperature for 2 hours. The solvent was distilled off under reduced pressure, and the residue was purified by column chromatography (silica gel, ethyl acetate/hexane=0/100→20/80) to give 2.52 g of the title compound as a yellow oil.

MS(ESI m/z): 543.1 (M+H)

RT(min): 1.93

The synthesis of the compounds shown in Table 25 below was carried out in the same manner as the synthesis of (S)-2-((((9H-fluoren-9-yl)methoxy)carbonyl)amino)-3-(5-cyanothiophen-3-yl)propanoic acid.

TABLE 25

| R | Compound name | Observed MS | RT/min | ¹H-NMR |
|---|---|---|---|---|
| 3-(2-cyanoimidazo[1,2-a]pyrimidin-6-yl)phenyl | (S)-2-((((9H-fluoren-9-yl)methoxy)carbonyl)amino)-3-(3-(2-cyanoimidazo[1,2-a]pyrimidin-6-yl)phenyl)propanoic acid | 530.1 | 1.41 | ¹H-NMR (DMSO-D$_6$) δ: 9.18-9.01 (2H, m), 8.58 (1H, s), 7.86-7.12 (13H, m), 4.40-4.16 (1H, m), 4.16-3.90 (3H, m), 3.54-3.45 (1H, m), 3.12-2.95 (1H, m). |
| 3-(2-cyanoimidazo[1,2-a]pyrazin-6-yl)phenyl | (S)-2-((((9H-fluoren-9-yl)methoxy)carbonyl)amino)-3-(3-(2-cyanoimidazo[1,2-a]pyrazin-6-yl)phenyl)propanoic acid | 530.1 | 1.51 | ¹H-NMR (CDCl$_3$) δ: 9.09 (1H, s), 8.21 (1H, s), 7.91 (1H, s), 7.83-7.13 (12H, m), 5.40 (1H, d, J = 7.9 Hz), 4.89-4.75 (1H, m), 4.59-4.43 (1H, m), 4.18-4.05 (2H, m), 3.48-3.35 (1H, m), 3.31-3.18 (1H, m). |
| 3-(2-cyanoimidazo[1,2-b]pyridazin-6-yl)phenyl | (S)-2-((((9H-fluoren-9-yl)methoxy)carbonyl)amino)-3-(3-(2-cyanoimidazo[1,2-b]pyridazin-6-yl)phenyl)propanoic acid | 530.1 | 1.53 | ¹H-NMR (CDCl$_3$) δ: 8.06 (1H, s), 7.91-7.64 (5H, m), 7.61-7.15 (9H, m), 5.43 (1H, d, J = 7.3 Hz), 4.87-4.74 (1H, m), 4.62-4.49 (1H, m), 4.33-4.07 (2H, m), 3.50-3.22 (2H, m). |
| 4-(((allyloxy)carbonyl)amino)phenyl | (S)-2-((((9H-fluoren-9-yl)methoxy)carbonyl)amino)-3-(4-(((allyloxy)carbonyl)amino)phenyl)propanoic acid | 487.0 | 1.56 | ¹H-NMR (CDCl$_3$) δ: 7.78 (2H, d, J = 7.3 Hz), 7.57 (2H, d, J = 7.3 Hz), 7.46-7.22 (6H, m), 7.07 (2H, d, J = 8.6 Hz), 6.89 (1H, brs), 6.05-5.88 (1H, m), 5.44-5.13 (3H, m), 4.68 (3H, d, J = 5.9 Hz), 4.55-4.34 (2H, m), 4.22 (1H, t, J = 6.9 Hz), 3.13 (2H, d, J = 5.3 Hz). |
| 5-cyanothiophen-3-yl (extended) | (S)-2-((((9H-fluoren-9-yl)methoxy)carbonyl)amino)-4-(5-cyanothiophen-3-yl)butanoic acid | 433.0 | 1.53 | ¹H-NMR (CDCl$_3$) δ: 7.77 (2H, d, J = 7.3 Hz), 7.55 (2H, d, J = 7.3 Hz), 7.46-7.28 (6H, m), 5.21-5.09 (1H, m), 4.54-4.37 (2H, m), 4.26-4.10 (2H, m), 3.02-2.83 (2H, m), 2.67-2.46 (2H, m). |

TABLE 25-continued

| R | Compound name | Observed MS | RT/min | ¹H-NMR |
|---|---|---|---|---|
| (1-methyl-3-cyano-indazol-5-yl) | (S)-2-((((9H-fluoren-9-yl)methoxy)carbonyl)amino)-3-(3-cyano-1-methyl-1H-indazol-5-yl)propanoic acid | 466.8 | 1.56 | ¹H-NMR (CDCl₃) δ: 7.83 (2H, d, J = 7.3 Hz), 7.73 (1H, s), 7.68-7.20 (8H, m), 6.06 (1H, d, J = 7.9 Hz), 4.59-4.42 (1H, m), 4.31-4.19 (2H, m), 4.17-4.09 (4H, m), 3.44-3.33 (1H, m), 3.19-3.03 (1H, m). |
| (6-cyano-1-methyl-pyrrolo[2,3-b]pyridin-5-yl) | (S)-2-((((9H-fluoren-9-yl)methoxy)carbonyl)amino)-3-(6-cyano-1-methyl-1H-pyrrolo[2,3-b]pyridin-5-yl)propanoic acid | 466.8 | 1.53 | ¹H-NMR (CD₃CN) δ: 7.98 (1H, s), 7.83 (2H, d, J = 7.3 Hz), 7.63-7.23 (7H, m), 6.50-6.45 (1H, m), 6.19-6.10 (1H, m), 4.65-4.52 (1H, m), 4.24-4.18 (2H, m), 4.15-4.07 (1H, m), 3.85-3.14 (5H, m). |
| (4-cyanothiophen-2-yl) | (S)-2-((((9H-fluoren-9-yl)methoxy)carbonyl)amino)-3-(4-cyanothiophen-2-yl)propanoic acid | 418.1 | 1.47 | ¹H-NMR (CDCl₃) δ: 7.84-7.27 (9H, m), 6.93 (1H, s), 5.51-5.38 (1H, m), 4.78-4.50 (2H, m), 4.47-4.35 (1H, m), 4.27-4.17 (1H, m), 3.49-3.27 (2H, m). |
| (4-(4-cyano-1H-imidazol-1-yl)phenyl) | (S)-2-((((9H-fluoren-yl)methoxy)carbonyl)amino)-3-(4-(4-cyano-1H-imidazol-1-yl)phenyl)propanoic acid | 479.1 | 1.43 | 8.24-7.02, (m, 14H), 4.68-4.02 (4H, m), 3.38-2.95 (2H, m). |
| (3-cyanopyridin-4-yl) | (S)-2-((((9H-fluoren-9-yl)methoxy)carbonyl)amino)-3-(3-cyanopyridin-4-yl)propanoic acid | 414.0 | 1.35 | ¹H-NMR (MeOD) δ: 8.82 (1H, s), 8.61 (1H, d, J = 5.3 Hz), 7.84-7.23 (9H, m), 4.66-4.57 (1H, m), 4.32-4.11 (3H, m), 3.77-3.15 (2H, m). |

Synthesis of ethyl (S)-5-(2-((((9H-fluoren-9-yl)methoxy)carbonyl)amino)-3-(tert-butoxy)-3-oxopropyl)imidazo[1,2-a]pyridine-2-carboxylate

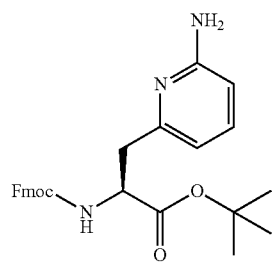

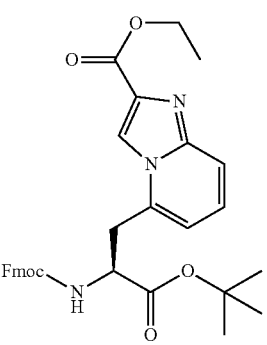

The procedure was carried out in the same manner as the synthesis of ethyl 6-bromoimidazo[1,2-a]pyrimidine-2-carboxylate.

MS(ESI m/z): 556.4 (M+H)

RT(min): 1.70

Synthesis of ethyl (S)-5-(3-(tert-butoxy)-2-((tert-butoxycarbonyl)amino)-3-oxopropyl)imidazo[1,2-a]pyridine-2-carboxylate

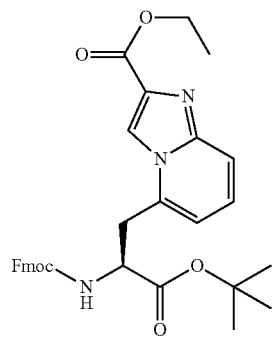

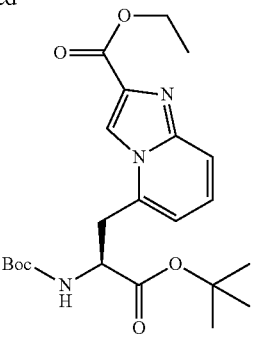

DMF (10 mL) and piperidine (635 µL) were added to ethyl (S)-5-(2-((((9H-fluoren-9-yl)methoxy)carbonyl)amino)-3-(tert-butoxy)-3-oxopropyl)imidazo[1,2-a]pyridine-2-carboxylate (357 mg), which was then stirred at room temperature for 1 hour. After confirming the disappearance of the raw materials, diisopropylethylamine (4 mL) and Boc$_2$O (3 mL) were added thereto, followed by stirring at room temperature for 3 hours. The solvent was distilled off under reduced pressure, and the residue was purified by column chromatography (silica gel, ethyl acetate/hexane=0/100→50/50→100/0) to give the title compound (176 mg) as a brown oil.

MS(ESI m/z): 434.4 (M+H)

RT(min): 1.41

Synthesis of tert-butyl (S)-2-((tert-butoxycarbonyl)amino)-3-(2-carbamoylimidazo[1,2-a]pyridin-5-yl)propanoate

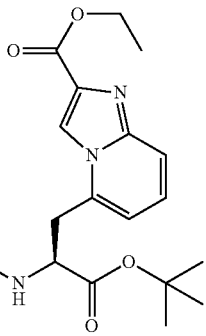

The procedure was carried out in the same manner as the synthesis of tert-butyl (S)-2-((tert-butoxycarbonyl)amino)-3-(4-carbamoylthiazol-2-yl)propanoate.

MS(ESI m/z): 405.9 (M+H)

RT(min): 1.19

Synthesis of tert-butyl (S)-2-((tert-butoxycarbonyl)amino)-3-(4-cyano-[2,4'-bithiazol]-2'-yl)propanoate

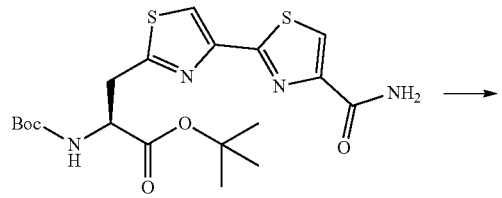

→

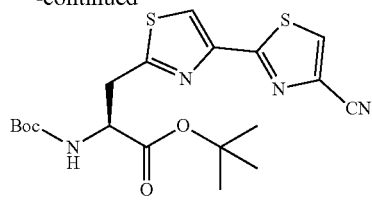

The procedure was carried out in the same manner as the synthesis of tert-butyl (S)-2-((tert-butoxycarbonyl)amino)-3-(4-cyanothiazol-2-yl)propanoate.
MS(ESI m/z): 437.9 (M+H)
RT(min): 1.74

The synthesis of the compounds shown in Table 26 below was carried out in the same manner as the synthesis of tert-butyl (S)-2-((tert-butoxycarbonyl)amino)-3-(4-cyano-[2,4'-bithiazol]-2'-yl)propanoate.

TABLE 26

| R | Compound name | Observed MS | RT/min |
|---|---|---|---|
| thiazole-oxazole-CN | tert-butyl (S)-2-((tert-butoxycarbonyl)amino)-3-(4-(4-cyanooxazol-2-yl)thiazol-2-yl)propanoate | 421.0 | 1.60 |
| cyanoimidazo[1,2-a]pyridine | tert-butyl (S)-2-((tert-butoxycarbonyl)amino)-3-(2-cyanoimidazo[1,2-a]pyridin-5-yl)propanoate | 387.0 | 1.52 |

Synthesis of (S)-2-(((((9H-fluoren-9-yl)methoxy)carbonyl)amino)-3-(4-((1-(5-cyanothiophen-2-yl)-1-oxo-5, 8,11-trioxa-2-azatridecane-13-yl)oxy)phenyl) propanoic acid

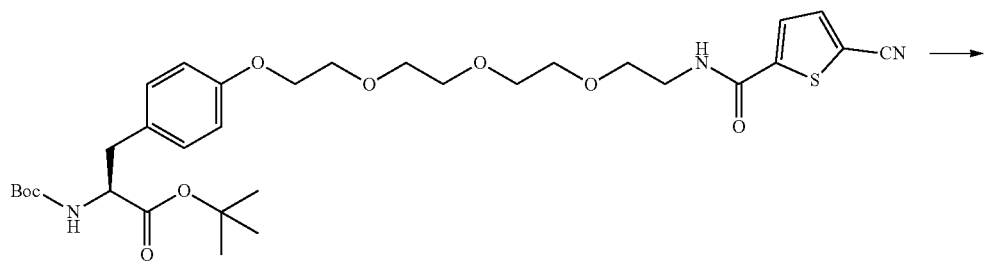 →

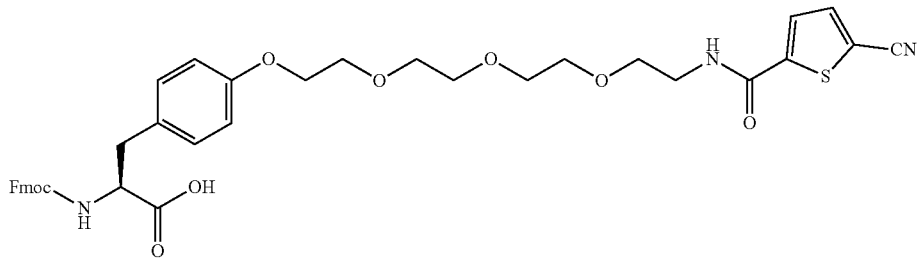

Trifluoroacetic acid (25 mL) was added to a dichloromethane solution (5 mL) of tert-butyl (S)-2-((tert-butoxycarbonyl)amino)-3-(4-((1-(5-cyanothiophen-2-yl)-1-oxo-5,8,11-trioxa-2-aza tridecan-13-yl)oxy)phenyl)propanoate (891 mg) which was then stirred at room temperature for 3 hours. The solvent was distilled off under reduced pressure, and dichloromethane (10 mL), diisopropylethylamine (3 mL), and N-[(9H-fluoren-9-ylmethoxy)carbonyloxy]succinimide (464 mg) were added to the residue, followed by stirring at room temperature for 2 hours. The solvent was distilled off under reduced pressure, and the residue was purified by column chromatography (silica gel, methanol/ethyl acetate=0/100→30/70) to give 921 mg of the title compound as a pale yellow oil.

MS(ESI m/z): 714.4 (M+H)

RT(min): 1.53

Synthesis of (S)-2-((((9H-fluoren-9-yl)methoxy)carbonyl)amino)-3-(4-(2-(2-(2-(2-((6-cyanopyridine-3-yl)o xy)ethoxy)ethoxy)ethoxy)ethoxy)phenyl)propanoic acid

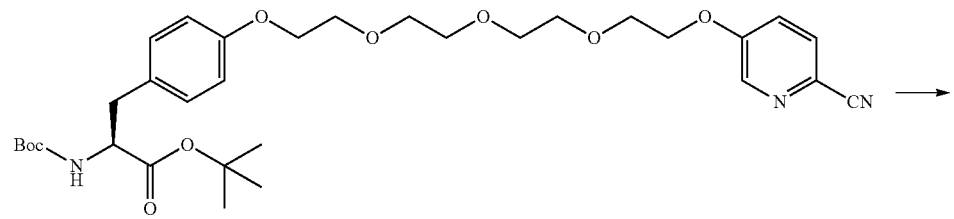

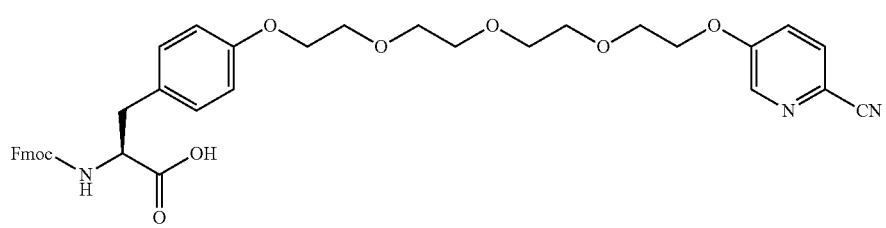

The synthesis of the compounds shown in the following table was carried out in the same manner as the synthesis of (S)-2-((((9H-fluoren-9-yl)methoxy)carbonyl)amino)-3-(4-((1-(5-cyanothiophen-2-yl)-1-oxo-5, 8,11-trioxa-2-azatridecan-13-yl)oxy)phenyl)propanoic acid.

MS(ESI m/z): 682.2 (M+H)
RT(min): 1.58

The synthesis of the compounds shown in Table 27 below was carried out in the same manner as the synthesis of (S)-2-((((9H-fluoren-9-yl)methoxy)carbonyl)amino)-3-(4-((1-(5-cyanothiophen-2-yl)-1-oxo-5, 8,11-trioxa-2-azatridecan-13-yl)oxy)phenyl)propanoic acid.

TABLE 27

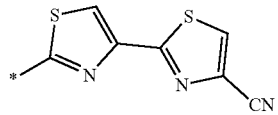 [SMILES: *c1nc(-c2nc(C#N)cs2)cs1]

| R | Compound name | Observed MS | RT/min | ¹H-NMR |
|---|---|---|---|---|
| 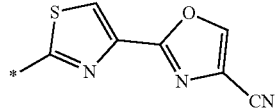 | (S)-2-((((9H-fluoren-9-yl)methoxy)carbonyl)amino)-3-(4-cyano-[2,4'-bithiazol]-2'-yl)propanoic acid | 503.2 | 1.52 | ¹H-NMR (CDCl$_3$) δ: 7.97 (2H, d, J = 10.6 Hz), 7.75 (2H, d, J = 7.3 Hz), 7.62-7.51 (2H, m), 7.44-7.23 (4H, m), 6.08-5.97 (1H, m), 4.90-4.77 (1H, m), 4.44 (2H, d, J = 6.6 Hz), 4.22 (1H, t, J = 6.6 Hz), 3.76-3.52 (2H, m). |
| | (S)-2-((((9H-fluoren-9-yl)methoxy)carbonyl)amino)-3-(4-(4-cyanooxazol-2-yl)thiazol-2-yl)propanoic acid | 487.2 | 1.46 | ¹H-NMR (CDCl$_3$) δ: 8.19 (1H, s), 8.04 (1H, s), 7.76 (2H, d, J = 7.3 Hz), 7.62-7.52 (2H, m), 7.45-7.22 (4H, m), 6.04 (1H, d, J = 6.6 Hz), 4.86-4.74 (1H, m), 4.51-4.33 (2H, m), 4.21 (1H, t, J = 6.9 Hz), 3.78-3.58 (2H, m). |

TABLE 27-continued
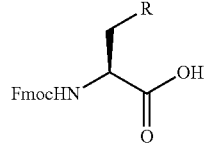
| R | Compound name | Observed MS | RT/min | ¹H-NMR |
|---|---|---|---|---|
| 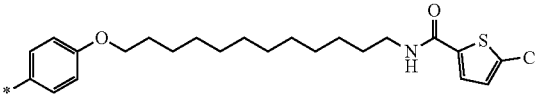 | (S)-2-((((9H-fluoren-9-yl)methoxy)carbonyl)amino)-3-(2-cyanoimidazo[1,2-a]pyridin-5-yl)propanoic acid | 453.3 | 1.37 | ¹H-NMR (CDCl₃) δ: 8.42 (1H, s), 7.82-7.69 (2H, m), 7.63-7.47 (3H, m), 7.45-7.20 (5H, m), 6.82-6.70 (1H, m), 5.80-5.65 (1H, m), 4.81-4.67 (1H, m), 4.55-4.37 (2H, m), 4.24-4.07 (1H, m), 3.56-3.40 (2H, m). |
|  | (S)-2-((((9H-fluoren-9-yl)methoxy)carbonyl)amino)-3-(4-((12-(5-cyanothiophene-2-carboxamido)dodecyl)oxy)phenyl)propanoic acid | 722.2 | 2.13 | ¹H-NMR (CDCl₃) δ: 7.76 (2H, d, J = 7.3 Hz), 7.58-7.50 (2H, m), 7.46-7.23 (6H, m), 7.07-6.93 (2H, m), 6.86-6.69 (2H, m), 6.17-6.05 (1H, m), 5.30-5.18 (1H, m), 4.71-4.59 (1H, m), 4.53-4.29 (2H, m), 4.20 (1H, t, J = 6.9 Hz), 3.91 (2H, t, J = 6.6 Hz), 3.42 (2H, q, J = 6.6 Hz), 3.17-3.02 (2H, m), 1.75 (2H, t, J = 6.9 Hz), 1.60 (2H, t, J = 6.9 Hz), 1.50-1.23 (16H, m). |

TABLE 27-continued
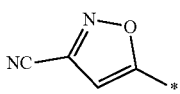 [SMILES: *c1cc(C#N)no1]
| R | Compound name | Observed MS | RT/min | ¹H-NMR |
|---|---|---|---|---|
| NC-isoxazole* | (S)-2-((((9H-fluoren-9-yl)methoxy)carbonyl)amino)-3-(3-cyanoisoxazol-5-yl)propanoic acid | 404.0 | 1.51 | ¹H-NMR (MeOD) δ: 7.82-7.72 (2H, m), 7.65-7.54 (2H, m), 7.43-7.21 (4H, m), 6.63 (1H, s), 4.66-4.47 (1H, m), 4.47-4.29 (2H, m), 4.29-4.13 (1H, m), 3.54-3.24 (2H, m). |
Synthesis of pdCpA amino acid-1
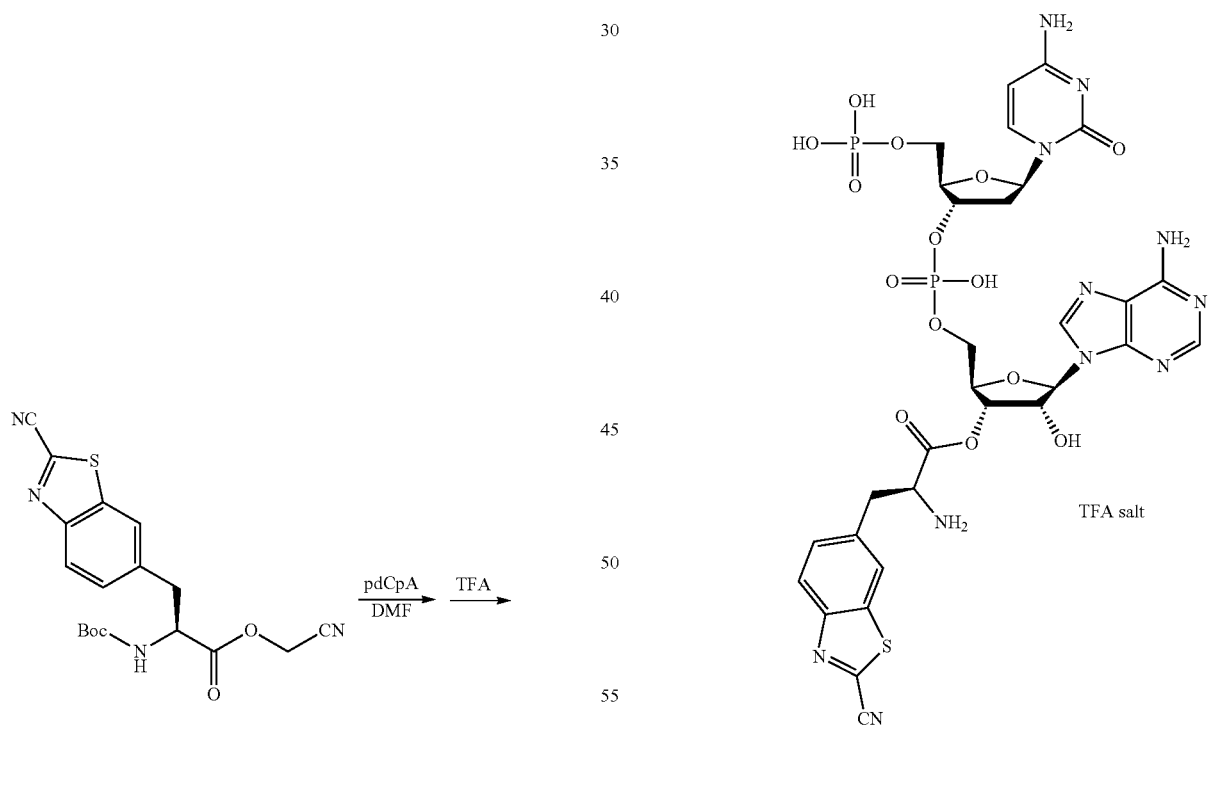

13.7 μL of a DMF solution (1.0 OD/μL) of pdCpA (manufactured by Gene Act, Inc.) (dinucleotide composed of deoxycytidine and adenosine) was added to cyanomethyl (S)-2-((tert-butoxycarbonyl)amino)-3-(2-cyanobenzo[d]thiazol-6-yl)propanoate (1.15 mg), followed by shaking with a vortex for 1 hour. OD indicates an optical density. After the reaction was completed, the reaction solution was diluted with a 0.38% aqueous formic acid solution/acetonitrile (1/1) solution, and purified by high performance liquid chromatography (HPLC) (Agilent 1260 Infinity binary LC system, column: Agilent ZORBAX SB-C18 (9.4×50 mm), column temperature: 40° C., gradient conditions: H$_2$O (0.1% TFA)/acetonitrile (0.1% TFA)=90/10→0/100, flow rate: 4.0 mL/min, detection wavelength: 254 nm). The solvent of the obtained target product solution was distilled off under reduced pressure, and 100 μL of TFA was added to the resulting residue. After shaking at room temperature for 1 hour, the solvent was distilled off under reduced pressure to obtain pdCpA amino acid-1. Identification was carried out by MALDI-TOF MS (manufactured by Bruker Daltonics, Inc., ultrafleXtreme MALDI-TOF/TOF MS, matrix: α-cyano-4-hydroxycinnamic acid).

MS(MALDI-TOF, m/z): 864.5 (M−H)

The synthesis of pdCpA amino acid-2 to 29 shown in Table 28 below was carried out in the same manner as the synthesis of pdCpA amino acid-1.

TABLE 28

| No. | R | Compound | Observed MS |
|---|---|---|---|
| pdCpA amino acid-1 | 2-cyanobenzo[d]thiazol-6-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyanobenzo[d]thiazol-6-yl)propanoate | 864.5 |
| pdCpA amino acid-2 | 2-cyanoquinolin-6-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyanoquinolin-6-yl)propanoate | 858.5 |
| pdCpA amino acid-3 | 6-cyanoquinolin-2-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(6-cyanoquinolin-2-yl)propanoate | 858.4 |
| pdCpA amino acid-4 | 6-cyanopyridin-3-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(6-cyanopyridin-3-yl)propanoate | 808.3 |

TABLE 28-continued

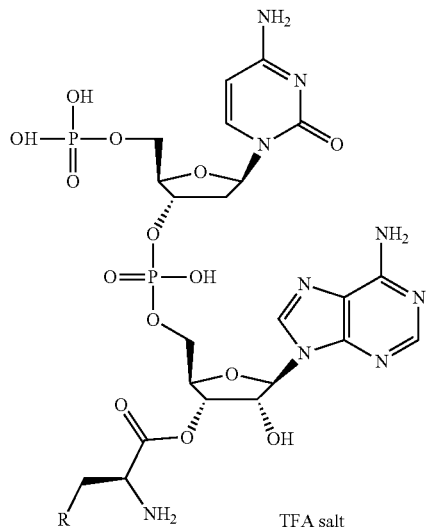

TFA salt

| No. | R | Compound | Observed MS |
|---|---|---|---|
| pdCpA amino acid-5 | *-pyrimidin-5-yl-2-CN | (2R,3S,4R,5R)-2-(((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyanopyrimidin-5-yl)propanoate | 809.3 |
| pdCpA amino acid-6 | *-pyrazin-2-yl-5-CN | (2R,3S,4R,5R)-2-(((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(5-cyanopyrazin-2-yl)propanoate | 809.2 |
| pdCpA amino acid-7 | *-pyridazin-3-yl-6-CN | (2R,3S,4R,5R)-2-(((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(6-cyanopyridazin-3-yl)propanoate | 809.2 |
| pdCpA amino acid-8 | *-pyridin-2-yl-5-CN | (2R,3S,4R,5R)-2-(((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(5-cyanopyridin-2-yl)propanoate | 808.2 |
| pdCpA amino acid-9 | *-thiazol-4-yl-2-CN | (2R,3S,4R,5R)-2-(((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyanothiazol-4-yl)propanoate | 814.2 |
| pdCpA amino acid-10 | *-thiophen-3-yl-5-CN | (2R,3S,4R,5R)-2-(((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(5-cyanothiophen-3-yl)propanoate | 813.2 |

TABLE 28-continued

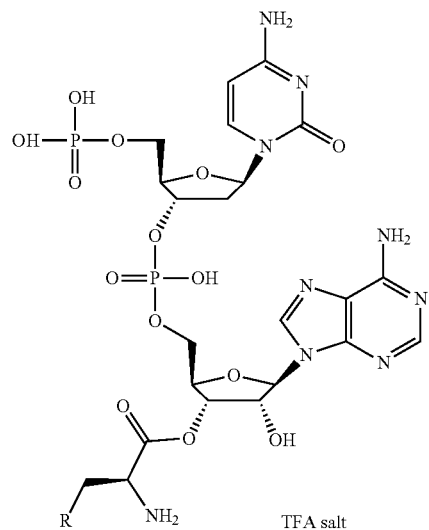

TFA salt

| No. | R | Compound | Observed MS |
|---|---|---|---|
| pdCpA amino acid-11 | 3-methyl-2-cyanopyridin-5-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(6-cyano-5-methylpyridin-3-yl)propanoate | 822.1 |
| pdCpA amino acid-12 | 3-methoxy-2-cyanopyridin-5-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(6-cyano-5-methoxypyridin-3-yl)propanoate | 838.2 |
| pdCpA amino acid-13 | 3-fluoro-2-cyanopyridin-5-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(6-cyano-5-fluoropyridin-3-yl)propanoate | 826.1 |
| pdCpA amino acid-14 | 4-cyanopyridin-2-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-cyanopyridin-2-yl)propanoate | 808.2 |
| pdCpA amino acid-15 | 6-cyanopyridin-2-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(6-cyanopyridin-2-yl)propanoate | 808.1 |
| pdCpA amino acid-16 | 2-cyanopyridin-3-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyanopyridin-3-yl)propanoate | 808.3 |

TABLE 28-continued

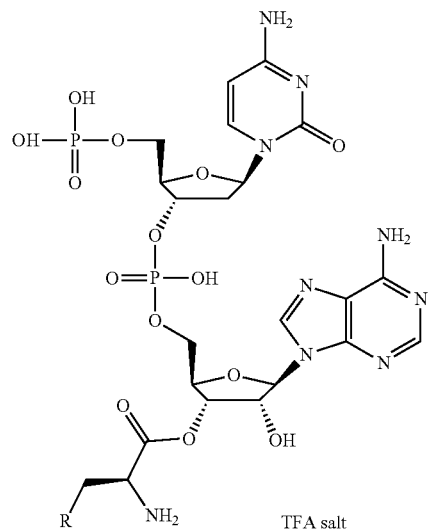

TFA salt

| No. | R | Compound | Observed MS |
|---|---|---|---|
| pdCpA amino acid-17 | thiazole-CN | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-cyanothiazol-2-yl)propanoate | 814.3 |
| pdCpA amino acid-18 | furan-CN | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(5-cyanofuran-3-yl)propanoate | 797.3 |
| pdCpA amino acid-19 | thiophene-CN | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyanothiophen-3-yl)propanoate | 813.1 |
| pdCpA amino acid-20 | methoxybenzothiazole-CN | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyano-6-methoxybenzo[d]thiazol-5-yl)propanoate | 894.2 |
| pdCpA amino acid-21 | benzoxazole-CN | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyanobenzo[d]oxazol-6-yl)propanoate | 848.3 |

TABLE 28-continued

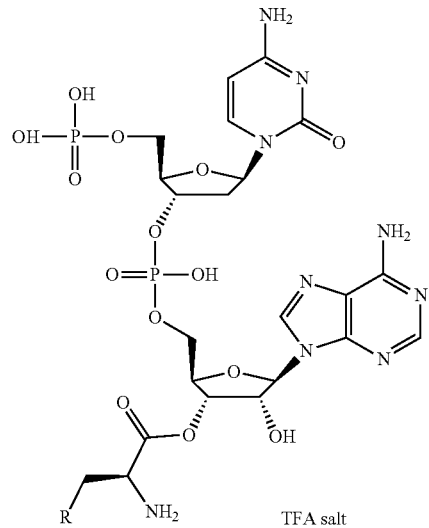

TFA salt

| No. | R | Compound | Observed MS |
|---|---|---|---|
| pdCpA amino acid-22 | benzimidazole with CN (2-cyano-1-methyl or 1-methyl-2-cyano isomer) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyano-1-methyl-1H-benzo[d]imidazol-6-yl)propanoate or (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyano-1-methyl-1H-benzo[d]imidazol-5-yl)propanoate | 861.1 |
| pdCpA amino acid-23 | benzo[b]thiophene-2-CN | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyanobenzo[b]thiophen-6-yl)propanoate | 863.1 |
| pdCpA amino acid-24 | benzofuran-2-CN | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyanobenzofuran-6-yl)propanoate | 847.1 |
| pdCpA amino acid-25 | 1-methylindole-2-CN | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyano-1-methyl-1H-indol-5-yl)propanoate | 860.2 |

TABLE 28-continued

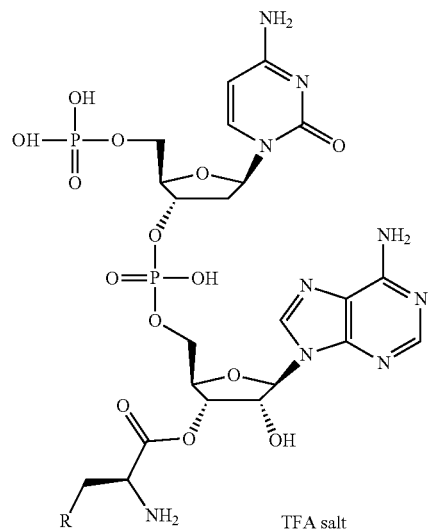

TFA salt

| No. | R | Compound | Observed MS |
|---|---|---|---|
| pdCpA amino acid-26 | [6-cyano-1-methyl-1H-benzo[d]imidazol-2-yl (via CH2)] or [5-cyano-1-methyl-1H-benzo[d]imidazol-2-yl (via CH2)] | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(6-cyano-1-methyl-1H-benzo[d]imidazol-2-yl)propanoate or (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(5-cyano-1-methyl-1H-benzo[d]imidazol-2-yl)propanoate | 861.2 |
| pdCpA amino acid-27 | 5-cyano-2-nitrophenyl (via CH2) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(5-cyano-2-nitrophenyl)propanoate | 852.1 |
| pdCpA amino acid-28 | 4-cyanophenyl (via CH2) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-cyanophenyl)propanoate | 807.2 |
| pdCpA amino acid-29 | *—CN | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-cyanopropanoate | 731.2 |

The synthesis of the pdCpA amino acids shown in Table 29 below was carried out in the same manner as the synthesis of pdChA amino acid-1.

TABLE 29

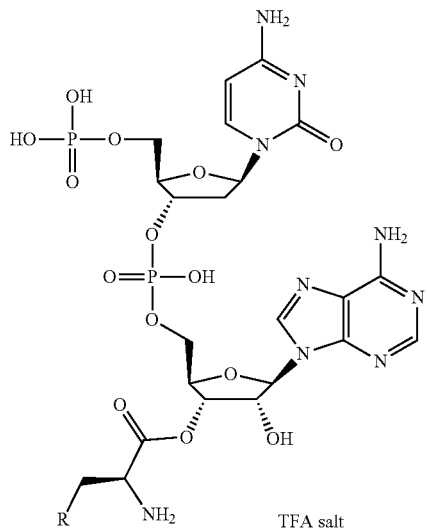

TFA salt

| No. | R | Compound | Observed MS |
|---|---|---|---|
| pdCpA amino acid-30 | 4-cyanopyridin-3-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-cyanopyridin-3-yl)propanoate | 808.2 |
| pdCpA amino acid-31 | 3-cyanopyridin-2-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(3-cyanopyridin-2-yl)propanoate | 808.2 |
| pdCpA amino acid-32 | 5-cyano-2-fluorophenyl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(5-cyano-2-fluorophenyl)propanoate | 825.1 |
| pdCpA amino acid-33 | 4-cyano-3-fluorophenyl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-cyano-3-fluorophenyl)propanoate | 825.3 |
| pdCpA amino acid-34 | 4-cyano-3,5-difluorophenyl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-cyano-3,5-difluorophenyl)propanoate | 843.3 |

TABLE 29-continued

| No. | R | Compound | Observed MS |
|---|---|---|---|
| pdCpA amino acid-35 | 1-methyl-3-cyano-1H-indazol-5-yl (attached at 5-position) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(3-cyano-1-methyl-1H-indazol-5-yl)propanoate | 861.3 |
| pdCpA amino acid-36 | 1-methyl-3-cyano-1H-pyrazol-4-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(3-cyano-1-methyl-1H-pyrazol-4-yl)propanoate | 811.4 |
| pdCpA amino acid-37 | 7-cyanobenzo[c][1,2,5]thiadiazol-4-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(7-cyanobenzo[c][1,2,5]thiadiazol-4-yl)propanoate | 865.2 |
| pdCpA amino acid-38 | 3-(2-cyanopyrazolo[1,5-a]pyrimidin-6-yl)phenyl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(3-(2-cyanopyrazolo[1,5-a]pyrimidin-6-yl)phenyl)propanoate | 924.2 |
| pdCpA amino acid-39 | 3-cyanoisoxazol-5-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(3-cyanoisoxazol-5-yl)propanoate | 798.2 |
| pdCpA amino acid-40 | 5-cyano-1-methyl-1H-pyrrol-3-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(5-cyano-1-methyl-1H- | 810.3 |

TABLE 29-continued

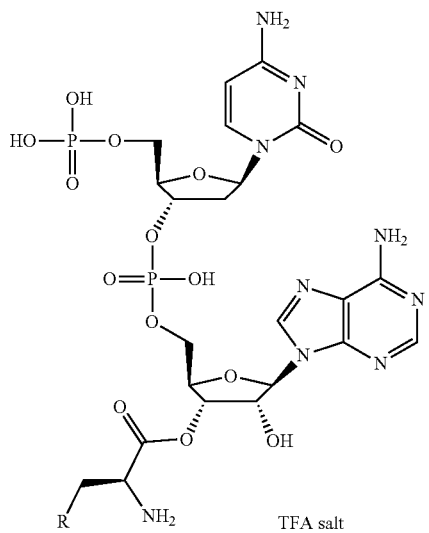

TFA salt

| No. | R | Compound | Observed MS |
|---|---|---|---|
| | | pyrrol-3-yl)propanoate | |
| pdCpA amino acid-41 | *-phenyl-2-(4-cyanooxazol-2-yl) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-(4-cyanooxazol-2-yl)phenyl)propanoate | 874.1 |
| pdCpA amino acid-42 | *-phenyl-1-(4-cyanoimidazol-1-yl) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-(4-cyano-1H-indazol-1-yl)phenyl)propanoate | 873.1 |
| pdCpA amino acid-43 | 2-cyanoimidazo[1,2-a]pyrimidin-6-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyanoimidazo[1,2-a]pyrimidin-6-yl)propanoate | 848.3 |
| pdCpA amino acid-44 | 2-cyanoimidazo[1,2-a]pyrazin-6-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyanoimidazo[1,2-a]pyrazin-6-yl)propanoate | 848.4 |
| pdCpA amino acid-45 | 2-cyanoimidazo[1,2-b]pyridazin-6-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyanoimidazo[1,2-b]pyridazin-6-yl)propanoate | 848.3 |
| pdCpA amino acid-46 | 2-cyanoimidazo[1,2-a]pyridin-6-yl | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(2-cyanoimidazo[1,2-a]pyridin-6-yl)propanoate | 847.3 |

TABLE 29-continued

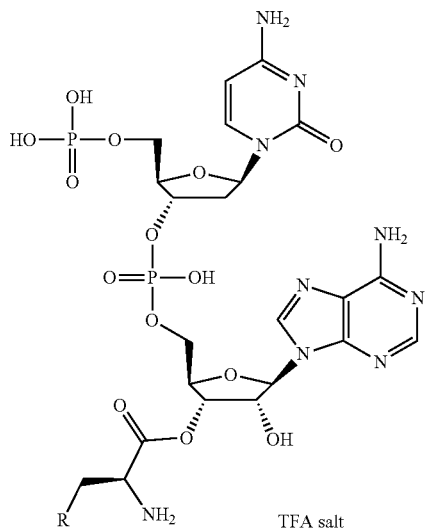

TFA salt

| No. | R | Compound | Observed MS |
|---|---|---|---|
| pdCpA amino acid-47 | thiazole-pyridine-CN | (2R,3S,4R,5R)-2-(((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-(5-cyanopyridin-2-yl)thiazol-2-yl)propanoate | 891.1 |
| pdCpA amino acid-48 | thiazole-pyridine-CN | (2R,3S,4R,5R)-2-(((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-(6-cyanopyridin-2-yl)thiazol-2-yl)propanoate | 891.2 |
| pdCpA amino acid-49 | bithiazole-CN | (2R,3S,4R,5R)-2-(((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-cyano-[2,4'-bithiazol]-2'-yl)propanoate | 897.3 |
| pdCpA amino acid-50 | thiazole-oxazole-CN | (2R,3S,4R,5R)-2-(((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-(4-cyanooxazol-2-yl)thiazol-2-yl)propanoate | 881.2 |
| pdCpA amino acid-51 | thiazole-methyloxazole-CN | (2R,3S,4R,5R)-2-(((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-(4-cyano-5-methyloxazol-2-yl)thiazol-2-yl)propanoate | 895.2 |
| pdCpA amino acid-52 | thiazole-pyrazolopyrimidine-CN | (2R,3S,4R,5R)-2-(((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-(2-cyanopyrazolo[1,5-a]pyrimidin-6-yl)thiazol-2-yl)propanoate | 931.2 |

TABLE 29-continued

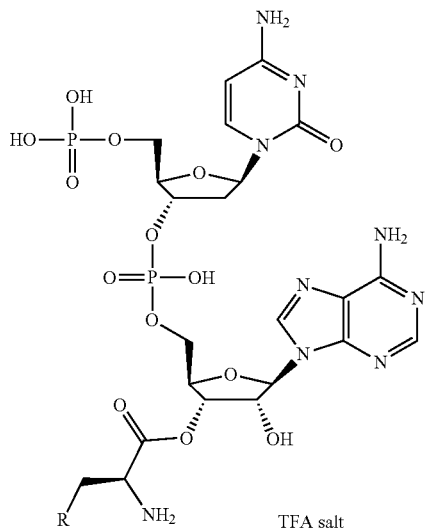

TFA salt

| No. | R | Compound | Observed MS |
|---|---|---|---|
| pdCpA amino acid-53 | (5-methyloxazole-thiazole-cyanothiazole group with *) | (2R,3S,4R,5R)-2-((((((2R,3S,5R)-5-(4-amino-2-oxopyrimidin-1(2H)-yl)-2-((phosphonoxy) methyl)tetrahydrofuran-3-yl)oxy)(hydroxy) phosphoryl)oxy)methyl)-5-(6-amino-9H-purin-9-yl)-4-hydroxytetrahydrofuran-3-yl (2S)-2-amino-3-(4-(4-(4-cyanothiazol-2-yl)-5-methyloxazol-2-yl)thiazol-2-yl)propanoate | 978.2 |
| pdCpA amino acid-54 | (thiazole-pyridine-cyanothiazole group with *) | (2R,3S,4R,5R)-2-((((((2R,3S,5R)-5-(4-amino-2-oxopyrimidin-1(2H)-yl)-2-((phosphonoxy) methyl)tetrahydrofuran-3-yl)oxy)(hydroxy) phosphoryl)oxy)methyl)-5-(6-amino-9H-purin-9-yl)-4-hydroxytetrahydrofuran-3-yl (2S)-2-amino-3-(4-(5-(4-cyanothiazol-2-yl) pyridin-2-yl)thiazol-2-yl)propanoate | 974.1 |
| pdCpA amino acid-55 | (thiazole-pyridine-cyanothiazole group with *) | (2R,3S,4R,5R)-2-((((((2R,3S,5R)-5-(4-amino-2-oxopyrimidin-1(2H)-yl)-2-((phosphonoxy) methyl)tetrahydrofuran-3-yl)oxy)(hydroxy) phosphoryl)oxy)methyl)-5-(6-amino-9H-purin-9-yl)-4-hydroxytetrahydrofuran-3-yl (2S)-2-amino-3-(4-(6-(4-cyanothiazol-2-yl) pyridin-2-yl)thiazol-2-yl)propanoate | 974.2 |
| pdCpA amino acid-56 | (terthiazole with CN group and *) | (2R,3S,4R,5R)-2-((((((2R,3S,5R)-5-(4-amino-2-oxopyrimidin-1(2H)-yl)-2-((phosphonoxy) methyl)tetrahydrofuran-3-yl)oxy)(hydroxy) phosphoryl)oxy)methyl)-5-(6-amino-9H-purin-9-yl)-4-hydroxytetrahydrofuran-3-yl (2S)-2-amino-3-(4-cyano-[2,4':2',4''-terthiazol]-2''-yl)propanoate | 980.3 |
| pdCpA amino acid-57 | (thiazole-oxazole-cyanothiazole group with *) | (2R,3S,4R,5R)-2-((((((2R,3S,5R)-5-(4-amino-2-oxopyrimidin-1(2H)-yl)-2-((phosphonoxy) methyl)tetrahydrofuran-3-yl)oxy)(hydroxy) phosphoryl)oxy)methyl)-5-(6-amino-9H-purin-9-yl)-4-hydroxytetrahydrofuran-3-yl (2S)-2-amino-3-(4-(4-(4-cyanothiazol-2-yl) oxazol-2-yl)thiazol-2-yl)propanoate | 964.1 |

TABLE 29-continued

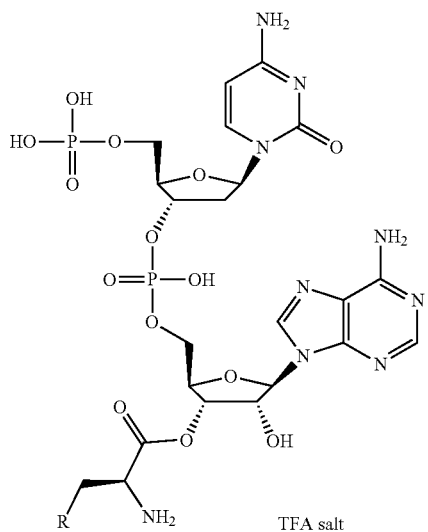

TFA salt

| No. | R | Compound | Observed MS |
|---|---|---|---|
| pdCpA amino acid-58 | (thiazole-thiazole-pyridine-CN) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy) phosphoryl)oxy)methyl)-5-(6-amino-9H-purin-9-yl)-4-hydroxytetrahydrofuran-3-yl (2S)-2-amino-3-(4-(6-cyanopyridin-2-yl)-[2,4'-bithiazol]-2'-yl)propanoate | 974.4 |
| pdCpA amino acid-59 | (thiazole-thiazole-pyridine-CN) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy) phosphoryl)oxy)methyl)-5-(6-amino-9H-purin-9-yl)-4-hydroxytetrahydrofuran-3-yl (2S)-2-amino-3-(4-(3-cyanopyridin-2-yl)-[2,4'-bithiazol]-2'-yl)propanoate | 974.4 |
| pdCpA amino acid-60 | (quaterthiazole-CN) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy) phosphoryl)oxy)methyl)-5-(6-amino-9H-purin-9-yl)-4-hydroxytetrahydrofuran-3-yl (2S)-2-amino-3-(4-cyano-[2,4':2',4'':2'',4'''-quaterthiazol]-2'''-yl)propanoate | 1063.1 |
| pdCpA amino acid-61 | (thiazole-oxazole-thiazole-oxazole-CN) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy) phosphoryl)oxy)methyl)-5-(6-amino-9H-purin-9-yl)-4-hydroxytetrahydrofuran-3-yl (2S)-2-amino-3-(4-(4-(4-cyanooxazol-2-yl)thiazol-2-yl)oxazol-2-yl)thiazol-2-yl) propanoate | 1031.1 |
| pdCpA amino acid-62 | (phenyl-NH-CO-CH2-NH-CO-thiophene-CN) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy) phosphoryl)oxy)methyl)-5-(6-amino-9H-purin-9-yl)-4-hydroxytetrahydrofuran-3-yl (2S)-2-amino-3-(4-(2-(5-cyathiophene-2-carboxamido)acetamido)phenyl)propanoate | 989.4 |

TABLE 29-continued

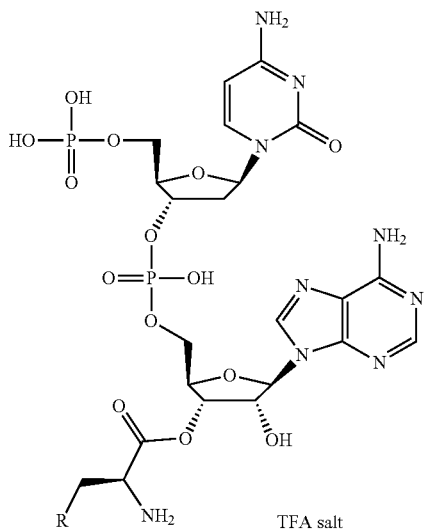

TFA salt

| No. | R | Compound | Observed MS |
|---|---|---|---|
| pdCpA amino acid-63 | (phenyl-NH-CO-CH2-NH-CO-CH2-NH-CO-thiophene-CN) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-(2-(2-(5-cyanothiophene-2-carboxamido)acetamido)acetamido)phenyl)propanoate | 1046.5 |
| pdCpA amino acid-64 | (phenyl-NH-CO-CH2-NH-CO-CH2-NH-CO-CH2-NH-CO-thiophene-CN) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-(2-(2-(2-(5-cyanothiophene-2-carboxamido)acetamido)acetamido)acetamido)phenyl)propanoate | 1103.5 |
| pdCpA amino acid-65 | (phenyl-O-CH2CH2-O-CH2CH2-O-CH2CH2-NH-CO-thiophene-CN) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-(2-(2-(2-(5-cyanothiophene-2-carboxamido)ethoxy)ethoxy)ethoxy)phenyl)propanoate | 1064.2 |
| pdCpA amino acid-66 | (phenyl-O-CH2CH2-O-CH2CH2-O-CH2CH2-O-CH2CH2-NH-CO-thiophene-CN) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-((1-(5-cyanothiophen-2-yl)-1-oxo-5,8,11-trioxa-2-azatridecan-13-yl)oxy)phenyl)propanoate | 1108.2 |
| pdCpA amino acid-67 | (phenyl-O-CH2CH2-O-CH2CH2-O-CH2CH2-O-CH2CH2-O-pyridine-CN) | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-(2-(2-(2-(2-((6-cyanopyridin-3-yl)oxy)ethoxy)ethoxy)ethoxy)ethoxy)phenyl)propanoate | 1076.3 |

TABLE 29-continued

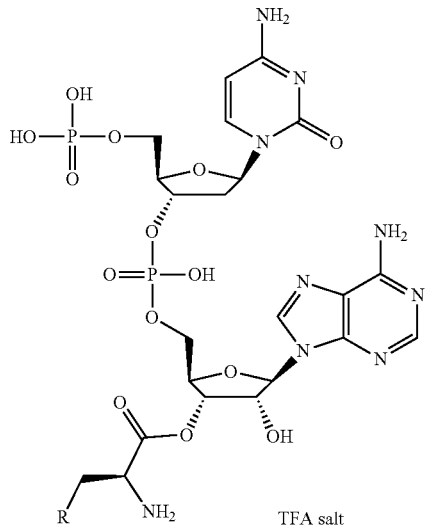

TFA salt

| No. | R | Compound | Observed MS |
|---|---|---|---|
| pdCpA amino acid-68 | | (2R,3S,4R,5R)-2-((((((2R,3S,5R)-5-(4-amino-2-oxopyrimidin-1(2H)-yl)-2-((phosphonoxy)methyl)tetrahydrofuran-3-yl)oxy)(hydroxy)phosphoryl)oxy)methyl)-5-(6-amino-9H-purin-9-yl)-4-hydroxytetrahydrofuran-3-yl (2S)-2-amino-3-(4-((12-(5-cyanothiophene-2-carboxamido)dodecyl)oxy)phenyl)propanoat | 1116.3 |

All water used in the subsequent experiments using DNAs and RNAs is Nuclease-free Water manufactured by QIAGEN GmbH.

Synthesis of mRNA

All mRNA-1 to mRNA-13 used for cell-free translational synthesis were synthesized according to the following method.

Double-stranded DNA having a T7 promoter and a base sequence to which a ribosome binds upstream of an open reading frame was amplified by PCR to construct a template DNA gene of mRNA (template DNA-1 to 13, shown in the table below). The thus-constructed template DNA gene was purified using a QIAquick PCR Purification Kit (manufactured by QIAGEN GmbH).

Next, mRNA was synthesized by a transcription reaction. A solution having the following solution composition 1 was prepared and reacted at 37° C. for 6 hours. 100 µL of 5 M ammonium acetate was added thereto, followed by being mixed gently and left on ice for 20 minutes. After centrifuging the mixture at 13200 rpm and 4° C. for 20 minutes, the supernatant was removed, and the precipitate was dissolved in 200 µL of 1×TE buffer (10 mmol/L Tris-HCl (pH 8.0), 1 mmol/L EDTA (pH 8.0)). Here, Tris represents trishydroxymethylaminomethane, and EDTA represents ethylenediaminetetraacetic acid. An equal volume of phenol/chloroform=1/1 (saturated with 1×TE) was added thereto, followed by stirring and centrifugation. The upper layer was recovered and an equal volume of chloroform was added thereto, followed by stirring and centrifugation. The upper layer was recovered, and 20 µL of 3 mol/L potassium acetate pH 4.5 and 600 µL of ethanol were added thereto, followed by being mixed gently and left at −80° C. for 30 minutes. After centrifuging at 13200 rpm and 4° C. for 30 minutes, the supernatant was removed, 200 µL of 70% cold ethanol stored at −30° C. was added thereto, followed by centrifugation at 13200 rpm and 4° C. for 5 seconds. The supernatant was removed, followed by drying under reduced pressure. The concentration of mRNA was determined with a spectrophotometer and the mRNA was dissolved in water to a concentration of 16 µmol/L.

Solution Composition 1 10× Buffer (400 mmol/L Tris-HCl (pH 8.0), 500 mmol/L NaCl, 80 mmol/L MgCl$_2$, 50 mmol/L Dithiothreitol (DTT): 10 µL 25 mmol/L NTPs (nucleoside triphosphate mixture): 16 µL 100 mmol/L Spermidine: 2 µL 0.1% Bovine serum albumin (BSA): 1 µL Ribonuclease inhibitor (40 unit/µL, manufactured by Takara Bio Inc.): 1 µL Inorganic pyrophosphatase (0.5 unit/µL, manufactured by Sigma-Aldrich LLC): 1 µL Thermo T7 RNA Polymerase (50 unit/µL; manufactured by Toyobo Co., Ltd.): 4 µL Template DNA gene for mRNA (100 ng/µL): 20 µL Water: 45 µL "Sequence Listing"

TABLE 30

| Template DNA No. | Full sequence of template DNA | Synthetic mRNA No. |
|---|---|---|
| Template | CGAAATTAATACGACTCACTATAGGGAGACCACAACGGTTTCCCTCTAGAAATAATTTTGTTTAACTTTAAGAAGGAGATATACATATGTGCAAACAGAAACCGCGGAGCAAAAACTAGAGCGACTACAAAGACGATGACGACAAATAAGCTTGAGTATTCTATAGTGT | mRNA-1 |
| Template | CGAAATTAATACGACTCACTATAGGGAGACCACAACGGTTTCCCTCTAGAAATAATTTTGTTTAACTTTAAGAAGGAGATATACATATGTGCAAATGCAAACCGCGGAGCAAAAACTAGAGCGACTACAAAGACGATGACGACAAATAAGCTTGAGTATTCTATAGTGT | mRNA-2 |
| Template | CGAAATTAATACGACTCACTATAGGGAGACCACAACGGTTTCCCTCTAGAAATAATTTTGTTTAACTTTAAGAAGGAGATATACATATGTGCAAACAGAAACCGCGGTGCAAAAACTAGAGCGACTACAAAGACGATGACGACAAATAAGCTTGAGTATTCTATAGTGT | mRNA-3 |
| Template | CGAAATTAATACGACTCACTATAGGGAGACCACAACGGTTTCCCTCTAGAAATAATTTTGTTTAACTTTAAGAAGGAGATATACATATGTGCGCGCAGGCGCCGCGGAGCGCGAACTAGAGCGACTACAAAGACGATGACGACAAATAAGCTTGAGTATTCTATAGTGT | mRNA-4 |
| Template | CGAAATTAATACGACTCACTATAGGGAGACCACAACGGTTTCCCTCTAGAAATAATTTTGTTTAACTTTAAGAAGGAGATATACATATGTGCAAACAGAAACCGCGGAGCAAATAGAGCGACTACAAAGACGATGACGACAAATAAGCTTGAGTATTCTATAGTGT | mRNA-5 |
| Template | CGAAATTAATACGACTCACTATAGGGAGACCACAACGGTTTCCCTCTAGAAATAATTTTGTTTAACTTTAAGAAGGAGATATACATATGTGCAAACAGAAACCGCGGAGCTAGAGCGACTACAAAGACGATGACGACAAATAAGCTTGAGTATTCTATAGTGT | mRNA-6 |
| Template | CGAAATTAATACGACTCACTATAGGGAGACCACAACGGTTTCCCTCTAGAAATAATTTTGTTTAACTTTAAGAAGGAGATATACATATGTGCAAACAGAAACCGCGGTAGAGCGACTACAAAGACGATGACGACAAATAAGCTTGAGTATTCTATAGTGT | mRNA-7 |
| Template | CGAAATTAATACGACTCACTATAGGGAGACCACAACGGTTTCCCTCTAGAAATAATTTTGTTTAACTTTAAGAAGGAGATATACATATGTGCAAACAGAAACCGTAGAGCGACTACAAAGACGATGACGACAAATAAGCTTGAGTATTCTATAGTGT | mRNA-8 |
| Template | CGAAATTAATACGACTCACTATAGGGAGACCACAACGGTTTCCCTCTAGAAATAATTTTGTTTAACTTTAAGAAGGAGATATACATATGTGCAAACAGAAATAGAGCGACTACAAAGACGATGACGACAAATAAGCTTGAGTATTCTATAGTGT | mRNA-9 |
| Template | CGAAATTAATACGACTCACTATAGGGAGACCACAACGGTTTCCCTCTAGAAATAATTTTGTTTAACTTTAAGAAGGAGATATACATATGTGCAAACAGAAACCGCGGAGCAAAAACCCGTTTTGGTGCCATTAGAGCGACTACAAAGACGATGACGACAAATAAGCTTGAGTATTCTATAGTGT | mRNA-10 |
| Template | CGAAATTAATACGACTCACTATAGGGAGACCACAACGGTTTCCCTCTAGAAATAATTTTGTTTAACTTTAAGAAGGAGATATACATATGTGCAAACAGAAACCGCGGAGCAAAAACCAGAAACGGAACAGCCCGTTTTGGTGCCATTAGAGCGACTACAAAGACGATGACGACAAATAAGCTTGAGTATTCTATAGTGT | mRNA-11 |
| Template | CGAAATTAATACGACTCACTATAGGGAGACCACAACGGTTTCCCTCTAGAAATAATTTTGTTTAACTTTAAGAAGGAGATATACATATGTGCCAGAAACTGGTGTTCTTTGCGGAATAGAGCGAGTACAAAGACGATGACGACAAATAAGCTTGAGTATTCTATAGTGT | mRNA-12 |
| Template | CGAAATTAATACGACTCACTATAGGGAGACCACAACGGTTTCCCTCTAGAAATAATTTTGTTTAACTTTAAGAAGGAGATATACATATGTGCGCGATCATTGGCCTGTGCGTGGGCTAGAGCGACTACAAAGACGATGACGACAAATAAGCTTGAGTATTCTATAGTGT | mRNA-13 |

The entire sequences of template DNA-1 to template DNA-13 are set forth in SEQ ID NOS: 1 to 13 in the "Sequence Listing", respectively.

The mRNA synthesized from the template DNA-1 was defined as mRNA-1, and hereafter, mRNA-2 to 13 were similarly defined.

Synthesis of Amber Suppressor tRNA (-CA)

A tRNA (-CA) gene was constructed by PCR amplification of tRNA in which the CA dinucleotide at the 3' end has been deleted by a *Mycoplasma capricolum*-derived tryptophan tRNA variant described in WO 07/055429A, and purified using a MinElute PCR Purification Kit (manufactured by QIAGEN GmbH).

Next, tRNA (-CA) was synthesized by a transcription reaction. A solution having the following solution composition 2 was prepared and reacted at 37° C. for 12 hours. The tRNA (-CA) was purified by an RNeasy MinElute Cleanup Kit (manufactured by QIAGEN GmbH) and dissolved in water to a concentration of 200 µmol/L.

Solution Composition 2

10× Transcription Buffer (400 mmol/L Tris-HCl (pH 8.0), 200 mmol/L MgCl$_2$, 50 mmol/L DTT): 10 µL 25 mmol/L NTPs: 16 µL 100 mmol/L GMP: 20 µL 100 mmol/L Spermidine: 2 µL 0.10% BSA: 1 µL Ribonuclease inhibitor (40 unit/µL, manufactured by Takara Bio Inc.): 1 µL Inorganic pyrophosphatase (0.5 unit/µL, manufactured by Sigma-Aldrich LLC): 1 µL T7 RNA Polymerase (50 unit/µL; manufactured by New England Biolabs, Inc.): 8 µL tRNA (-CA) gene (100 ng/µL): 41 µL Synthesis of aminoacyl-tRNA-1 (the Base Sequence of the RNA Portion is Shown in SEQ ID NO: 14 of "Sequence Listing")

A solution having the following solution composition 3 was prepared in a 1.5 mL sample tube, and was allowed to stand at 4° C. for 2 hours. Thereafter, 26.7 µL of a 0.6 mol/L aqueous potassium acetate solution (pH 4.5) and 160 µL of ethanol were added to the reaction solution which was then allowed to stand at −80° C. for 30 minutes. This was followed by centrifugation (4° C., 13200 rpm) for 30 minutes to remove the supernatant. 200 µL of a 70% aqueous ethanol solution was gently added thereto, followed by centrifugation (4° C., 13200 rpm) for 1 minute. The supernatant was removed again, followed by drying under reduced pressure to obtain aminoacyl-tRNA-1. The obtained aminoacyl-tRNA was dissolved in a 1 mmol/L aqueous potassium acetate solution immediately before the addition thereof to the translation mixture.

Solution composition 3

Water: 14 µL

5× Ligation Buffer (275 mmol/L HEPES-Na pH 7.5, 75 mmol/L MgCl$_2$, 16.5 mmol/L DTT, 5 mmol/L ATP): 5.34 µL 0.1% BSA: 0.54 µL DMSO solution of pdCpA amino acid-1 (0.73 mmol/L): 2.66 µL Aqueous solution of amber suppressor tRNA (-CA) (200 µmol/L): 3.34 µL T4 RNA Ligase solution (manufactured by Takara Bio Inc., 40 U/µL): 0.80 µL Here, HEPES indicates 2-[4-(2-hydroxyethyl)piperazin-1-yl]ethanesulfonic acid, and DMSO indicates dimethyl sulfoxide.

The synthesis of the aminoacyl-tRNA-2 to 68 shown in Tables 31 and 32 below was carried out in the same manner as the synthesis of aminoacyl-tRNA-1.

GGGAGAGUAGUUCAAUGGUAGAACGUCGGUCUCUAAAACCGAGCGUUGAGGGUUCGAUUCCUUUCUCUCCCAC-CA—O

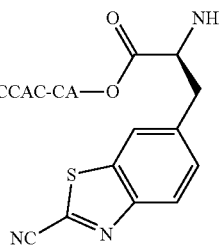

TABLE 31

5'-GGGAGAGUAGUUCAAUGGUAGAACGUCGGUCUCUAAAACCGAGCGUUGAGGGUUCGAUUCCUUUCUCUCCCAC-CA—O—C(=O)—CH(NH)—R

| Aminoacyl-tRNA No. | R |
| --- | --- |
| Aminoacyl-tRNA-1 | 6-benzothiazolyl-2-CN (*at 6-position of benzothiazole, CN at 2-position) |
| Aminoacyl-tRNA-2 | 6-quinolinyl-2-CN |
| Aminoacyl-tRNA-3 | 2-quinolinyl-6-CN |
| Aminoacyl-tRNA-4 | 5-pyridyl-2-CN |
| Aminoacyl-tRNA-5 | 5-pyrimidinyl-2-CN |
| Aminoacyl-tRNA-6 | 5-pyrazinyl-2-CN |
| Aminoacyl-tRNA-7 | 6-pyridazinyl-3-CN |
| Aminoacyl-tRNA-8 | 2-pyridyl-5-CN |
| Aminoacyl-tRNA-9 | 4-thiazolyl-2-CN |
| Aminoacyl-tRNA-10 | 4-thienyl-2-CN |
| Aminoacyl-tRNA-11 | 3-methyl-5-pyridyl-2-CN |
| Aminoacyl-tRNA-12 | 4-methoxy-5-pyridyl-2-CN |

TABLE 31-continued

5'-GGGAGAGUAGUUCAAUGGUAGAACGUCGGUCUCUAAAACCGAGCGUUGAGGGUUCGAUUCCUUUCUCUCCCAC-CA—O—C(=O)—CH(NH—)—R

| Aminoacyl-tRNA No. | R |
|---|---|
| Aminoacyl-tRNA-13 | 5-* , 3-F, 2-CN pyridine |
| Aminoacyl-tRNA-14 | 2-*, 4-CN pyridine |
| Aminoacyl-tRNA-15 | 6-*, 2-CN pyridine |
| Aminoacyl-tRNA-16 | 3-*, 2-CN pyridine |
| Aminoacyl-tRNA-17 | 2-*, 4-CN thiazole |
| Aminoacyl-tRNA-18 | 4-*, 2-CN furan |
| Aminoacyl-tRNA-19 | 3-*, 2-CN thiophene |
| Aminoacyl-tRNA-20 | 6-*, 5-methoxy, 2-CN benzothiazole |
| Aminoacyl-tRNA-21 | 6-*, 2-CN benzoxazole |
| Aminoacyl-tRNA-22 | 6-*, 1-methyl, 2-CN benzimidazole or 5-*, 1-methyl, 2-CN benzimidazole |
| Aminoacyl-tRNA-23 | 6-*, 2-CN benzothiophene |

TABLE 31-continued

5′-GGGAGAGUAGUUCAAUGGUAGAACGUCGGUCUCUAAAACCGAGCGUUGAGGGUUCGAUUCCUUUCUCUCCCAC-CA—O—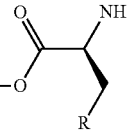

| Aminoacyl-tRNA No. | R |
|---|---|
| Aminoacyl-tRNA-24 | 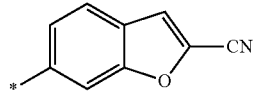 |
| Aminoacyl-tRNA-25 | 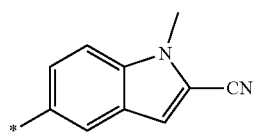 [SMILES: *c1ccc2c(c1)cc(C#N)n2C] |
| Aminoacyl-tRNA-26 | 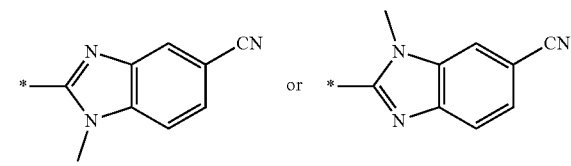 [SMILES: *c1nc2cc(C#N)ccc2n1C ; "or" ; *c1nc2ccc(C#N)cc2n1C] |
| Aminoacyl-tRNA-27 | 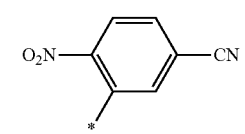 |
| Aminoacyl-tRNA-28 |  |
| Aminoacyl-tRNA-29 | *—CN |

TABLE 32

5′-GGGAGAGUAGUUCAAUGGUAGAACGUCGGUCUCUAAAACCGAGCGUUGAGGGUUCGAUUCCUUUCUCUCCCAC-CA—O—

| Aminoacyl-tRNA No. | R |
|---|---|
| Aminoacyl-tRNA-30 | 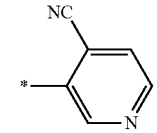 [SMILES: *c1cnccc1C#N] |
| Aminoacyl-tRNA-31 | 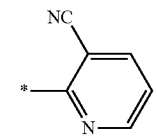 [SMILES: *c1ncccc1C#N] |

TABLE 32-continued

5'-GGGAGAGUAGUUCAAUGGUAGAACGUCGGUCUCUAAAACCGAGCGUUGAGGGUUCGAUUCCUUUCUCUCCCAC-CA—O-C(=O)-CH(NH-)-CH2-R

| Aminoacyl-tRNA No. | R |
|---|---|
| Aminoacyl-tRNA-32 | 5-fluoro-6-cyanopyridin-3-yl (F on pyridine, CN substituent) |
| Aminoacyl-tRNA-33 | 2-fluoro-4-cyanophenyl |
| Aminoacyl-tRNA-34 | 2,6-difluoro-4-cyanophenyl |
| Aminoacyl-tRNA-35 | 1-methyl-3-cyano-1H-indazol-5-yl |
| Aminoacyl-tRNA-36 | 1-methyl-3-cyano-1H-pyrazol-4-yl |
| Aminoacyl-tRNA-37 | 4-cyano-2,1,3-benzothiadiazol-7-yl |
| Aminoacyl-tRNA-38 | 6-(3-substituted-phenyl)-2-cyanopyrazolo[1,5-a]pyrimidine |
| Aminoacyl-tRNA-39 | 3-cyanoisoxazol-5-yl |

TABLE 32-continued

5'-GGGAGAGUAGUUCAAUGGUAGAACGUCGGUCUCUAAAACCGAGCGUUGAGGGUUCGAUUCCUUUCUCUCCCAC-CA—O-C(=O)-CH(NH-)-R

| Aminoacyl-tRNA No. | R |
|---|---|
| Aminoacyl-tRNA-40 | *-( 1-methylpyrrole-2-carbonitrile, attached at 4-position) |
| Aminoacyl-tRNA-41 | *-(phenyl)-(oxazole-4-CN) |
| Aminoacyl-tRNA-42 | *-(phenyl)-(imidazole-4-CN, N-linked) |
| Aminoacyl-tRNA-43 | *-(imidazo[1,2-a]pyrimidine-2-CN) |
| Aminoacyl-tRNA-44 | *-(imidazo[1,2-a]pyrazine-2-CN) |
| Aminoacyl-tRNA-45 | *-(imidazo[1,2-b]pyridazine-2-CN) |
| Aminoacyl-tRNA-46 | *-(imidazo[1,2-a]pyridine-2-CN) |
| Aminoacyl-tRNA-47 | *-(thiazole)-(pyridine-5-CN) |
| Aminoacyl-tRNA-48 | *-(thiazole)-(pyridine-6-CN) |
| Aminoacyl-tRNA-49 | *-(thiazole)-(thiazole-4-CN) |
| Aminoacyl-tRNA-50 | *-(thiazole)-(oxazole-4-CN) |
| Aminoacyl-tRNA-51 | *-(thiazole)-(5-methyloxazole-4-CN) |

TABLE 32-continued
5'-GGGAGAGUAGUUCAAUGGUAGAACGUCGGUCUCUAAAACCGAGCGUUGAGGGUUCGAUUCCUUUCUCUCCCAC-CA—O-C(=O)-CH(NH-)-R
| Aminoacyl-tRNA No. | R |
|---|---|
| Aminoacyl-tRNA-52 | 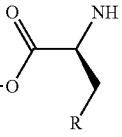 |
| Aminoacyl-tRNA-53 | 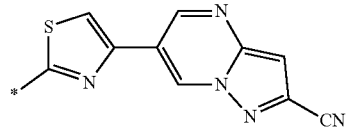 [SMILES: *c1nc(-c2cnc3cc(C#N)nn3c2)cs1] |
| Aminoacyl-tRNA-54 | 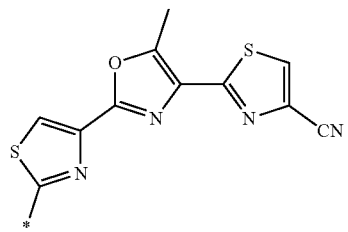 [SMILES: *c1nc(-c2nc(-c3nc(C#N)cs3)c(C)o2)cs1] |
| Aminoacyl-tRNA-55 | 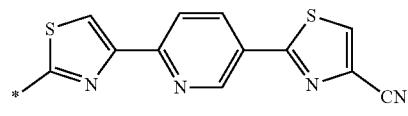 [SMILES: *c1nc(-c2ccc(-c3nc(C#N)cs3)cn2)cs1] |
| Aminoacyl-tRNA-56 | 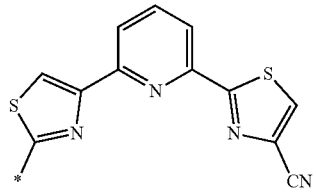 [SMILES: *c1nc(-c2cccc(-c3nc(C#N)cs3)n2)cs1] |
| Aminoacyl-tRNA-57 | 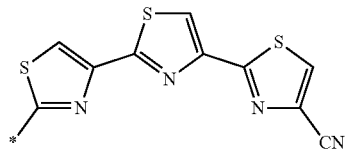 [SMILES: *c1nc(-c2nc(-c3nc(C#N)cs3)cs2)cs1] |
| Aminoacyl-tRNA-58 | 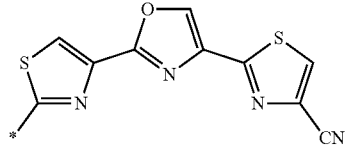 [SMILES: *c1nc(-c2nc(-c3nc(C#N)cs3)co2)cs1] |
| Aminoacyl-tRNA-59 | 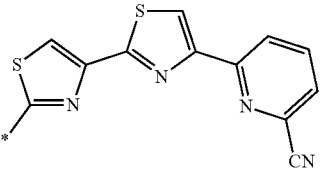 [SMILES: *c1nc(-c2nc(-c3cccc(C#N)n3)cs2)cs1] |

TABLE 32-continued
5′-GGGAGAGUAGUUCAAUGGUAGAACGUCGGUCUCUAAAACCGAGCGUUGAGGGUUCGAUUCCUUUCUCUCCCAC-CA—O— 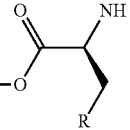
| Aminoacyl-tRNA No. | R |
|---|---|
| Aminoacyl-tRNA-60 | 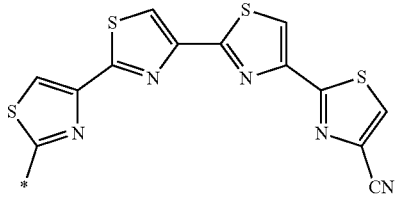 [SMILES: *c1nc(-c2nc(-c3nc(-c4nc(C#N)cs4)cs3)cs2)cs1] |
| Aminoacyl-tRNA-61 | 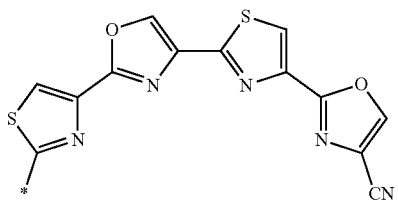 [SMILES: *c1nc(-c2nc(-c3nc(-c4nc(C#N)co4)cs3)co2)cs1] |
| Aminoacyl-tRNA-62 | 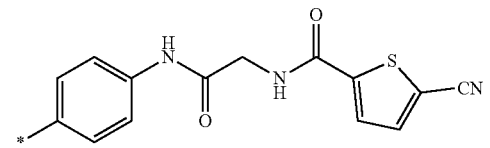 [SMILES: *c1ccc(NC(=O)CNC(=O)c2ccc(C#N)s2)cc1] |
| Aminoacyl-tRNA-63 | 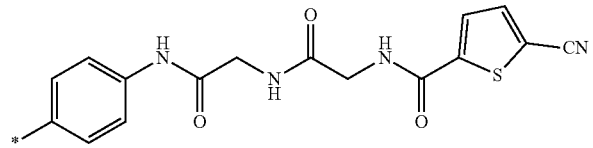 [SMILES: *c1ccc(NC(=O)CNC(=O)CNC(=O)c2ccc(C#N)s2)cc1] |
| Aminoacyl-tRNA-64 | 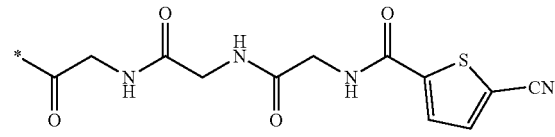 [SMILES: *C(=O)CNC(=O)CNC(=O)CNC(=O)c1ccc(C#N)s1] |
| Aminoacyl-tRNA-65 | 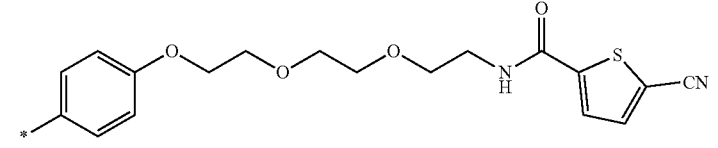 [SMILES: *c1ccc(OCCOCCOCCNC(=O)c2ccc(C#N)s2)cc1] |
| Aminoacyl-tRNA-66 | 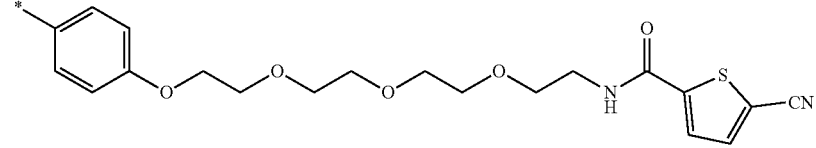 [SMILES: *c1ccc(OCCOCCOCCOCCNC(=O)c2ccc(C#N)s2)cc1] |
| Aminoacyl-tRNA-67 | 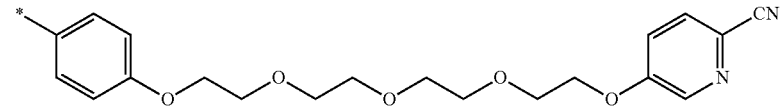 [SMILES: *c1ccc(OCCOCCOCCOCCOc2ccc(C#N)nc2)cc1] |

TABLE 32-continued

5'-GGGAGAGUAGUUCAAUGGUAGAACGUCGGUCUCUAAAACCGAGCGUUGAGGGUUCGAUUCCUUUCUCUCCCAC-CA—O—[aa]

| Aminoacyl-tRNA No. | R |
|---|---|
| Aminoacyl-tRNA-68 | (4-phenoxy linker with C10 chain-NH-C(O)-thiophene-5-CN) |

Cell-free translational synthesis of unnatural amino acid-introduced linear peptide and synthesis of cyclic peptide represented by Formula (1)

As the MALDI-TOF MS in this section, ultrafleXtreme MALDI-TOF/TOF MS (manufactured by Bruker Daltonics, Inc.) was used. As the matrix, α-cyano-4-hydroxycinnamic acid was used.

Synthesis of Cyclic Peptide 1-1 (SEQ ID NO: 25)

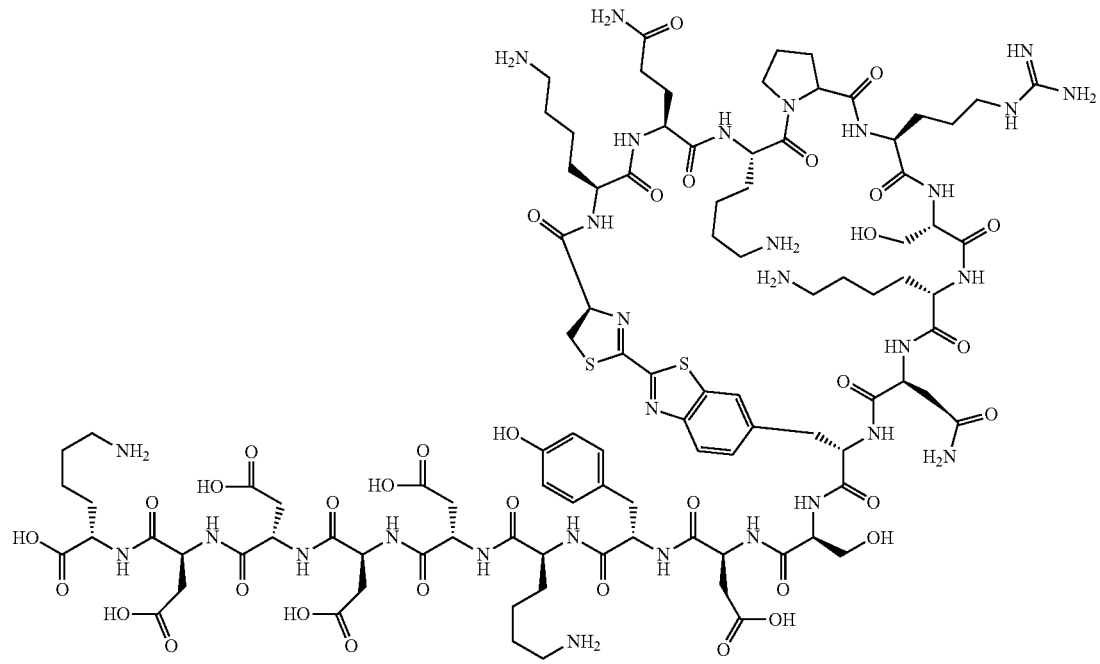 [SMILES: N=C(N)NCCC[C@@H]1NC(=O)C2CCCN2C(=O)[C@H](CCCCN)NC(=O)[C@H](CCC(N)=O)NC(=O)[C@H](CCCCN)NC(=O)[C@@H]2CSC(=N2)C2=Nc3ccc(cc3S2)C[C@@H](C(=O)N[C@@H](CO)C(=O)N[C@@H](CC(=O)O)C(=O)N[C@@H](Cc2ccc(O)cc2)C(=O)N[C@@H](CCCCN)C(=O)N[C@@H](CC(=O)O)C(=O)N[C@@H](CC(=O)O)C(=O)N[C@@H](CC(=O)O)C(=O)N[C@@H](CC(=O)O)C(=O)N[C@@H](CCCCN)C(=O)O)NC(=O)[C@H](CC(N)=O)NC(=O)[C@H](CCCCN)NC(=O)[C@H](CO)NC1=O]

A solution having the following solution composition 4 was prepared in a 1.5 mL sample tube and incubated at 37° C. for 1.5 hours. 31 μL of wash buffer (composition: 20 mmol/L phosphate buffer (pH 7.5), 500 mmol/L NaCl, 5 mM imidazole) and 10 μL of a magnetic bead solution (manufactured by MBL Life Science, Anti-DDDDK-tag mAb-Magnetic Agarose) were added to the reaction solution which was then shaken with a vortex for 30 minutes at room temperature. This was followed by centrifugation to remove the supernatant solution. The washing operation of the obtained magnetic beads (adding 200 μL of wash buffer-→shaking with a vortex→centrifugation→removal of supernatant) was repeated three times. 10 μL of a 2% aqueous formic acid solution was added to the resulting magnetic beads which were then shaken using a vortex for 1 hour at room temperature. Thereafter, the magnetic beads were sedimented by centrifugation, and the supernatant was recovered to obtain cyclic peptide 1-1. Identification of the obtained peptide was carried out by MALDI-TOF MS.

MS(MALDI-TOF, m/z): 2382.0 (M+H)

Solution Composition 4

Water: 2 μL

Aqueous solution of mRNA-1 (0.02 OD/μL): 1 μL

Aqueous solution of aminoacyl-tRNA-1 (0.2 OD/μL): 1 μL

Aqueous solution of amino acids (a mixture of 19 amino acids other than Met, each 0.3 mmol/L): 1.5 μL PUREfrex (registered trademark) custom ver 2 (PFC-Z1802, manufactured by GeneFrontier Corporation)

Solution I: 4 μL

Solution II: 0.5 μL

Solution III: 1 μL

The synthesis of cyclic peptides 1-2 to 27 shown in Table 33 below was carried out in the same manner as the synthesis of cyclic peptide 1-1, using combinations of mRNA and aminoacyl-tRNA shown in Table 33.

TABLE 33

(SEQ ID NO: 25)

| Cyclic peptide No. | mRNA No. | Aminoacyl-tRNA No. | Linker No. | Observed MS |
|---|---|---|---|---|
| 1-1 | mRNA-1 | 1 | thiazoline-benzothiazole | 2382.0 |
| 1-2 | | 2 | thiazoline-quinoline | 2376.0 |
| 1-3 | | 3 | thiazoline-quinoline | 2376.2 |
| 1-4 | | 4 | thiazoline-pyridine | 2326.1 |
| 1-5 | | 5 | thiazoline-pyrimidine | 2327.0 |
| 1-6 | | 6 | thiazoline-pyrazine | 2327.0 |

TABLE 33-continued
(SEQ ID NO: 25)
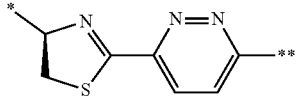
| Cyclic peptide No. | mRNA No. | Aminoacyl-tRNA No. | Linker No. | Observed MS |
|---|---|---|---|---|
| 1-7 | | 7 | 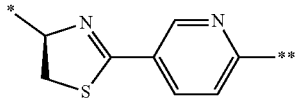 | 2327.1 |
| 1-8 | | 8 | | 2326.1 |
| 1-9 | | 9 | 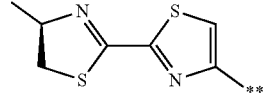 | 2332.0 |
| 1-10 | | 10 | 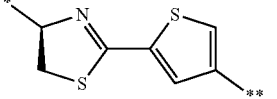 | 2331.1 |
| 1-11 | | 11 | 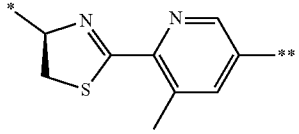 | 2340.1 |

TABLE 33-continued (SEQ ID NO: 25)

| Cyclic peptide No. | mRNA No. | Aminoacyl-tRNA No. | Linker No. | Observed MS |
|---|---|---|---|---|
| 1-12 | 12 | | thiazoline-(3-methoxy)pyridine | 2356.0 |
| 1-13 | 13 | | thiazoline-(3-fluoro)pyridine | 2344.0 |
| 1-14 | 14 | | thiazoline-pyridine | 2326.2 |
| 1-15 | 15 | | thiazoline-pyridine | 2326.0 |
| 1-16 | 16 | | thiazoline-pyridine | 2326.0 |

TABLE 33-continued
(SEQ ID NO: 25)
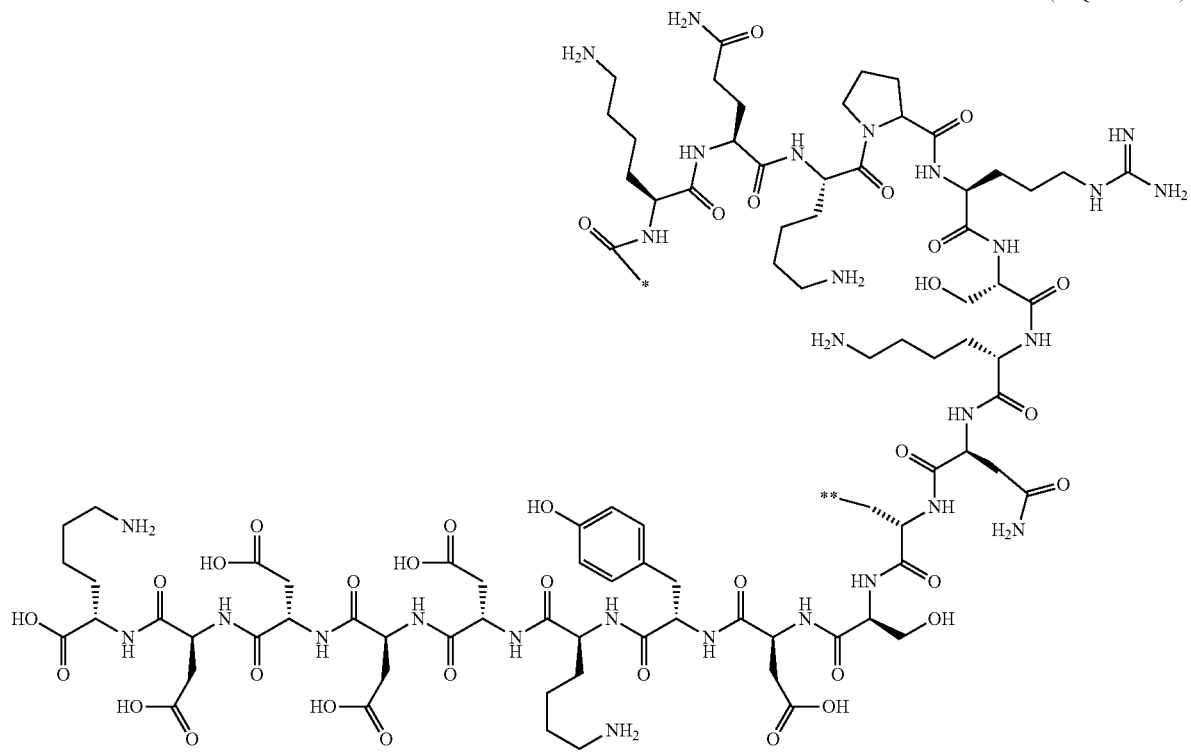
| Cyclic peptide No. | mRNA No. | Aminoacyl-tRNA No. | Linker No. | Observed MS |
|---|---|---|---|---|
| 1-17 | | 17 | | 2332.0 |
| 1-18 | | 18 | | 2315.1 |
| 1-19 | | 19 | | 2330.9 |
| 1-20 | | 20 | | 2412.2 |
| 1-21 | | 21 | | 2366.0 |

TABLE 33-continued (SEQ ID NO: 25)

| Cyclic peptide No. | mRNA No. | Aminoacyl-tRNA No. | Linker No. | Observed MS |
|---|---|---|---|---|
| 1-22 | 22 | | | 2379.4 |
| 1-23 | 23 | | | 2381.3 |
| 1-24 | 24 | | | 2365.3 |
| 1-25 | 25 | | | 2378.4 |

TABLE 33-continued
(SEQ ID NO: 25)
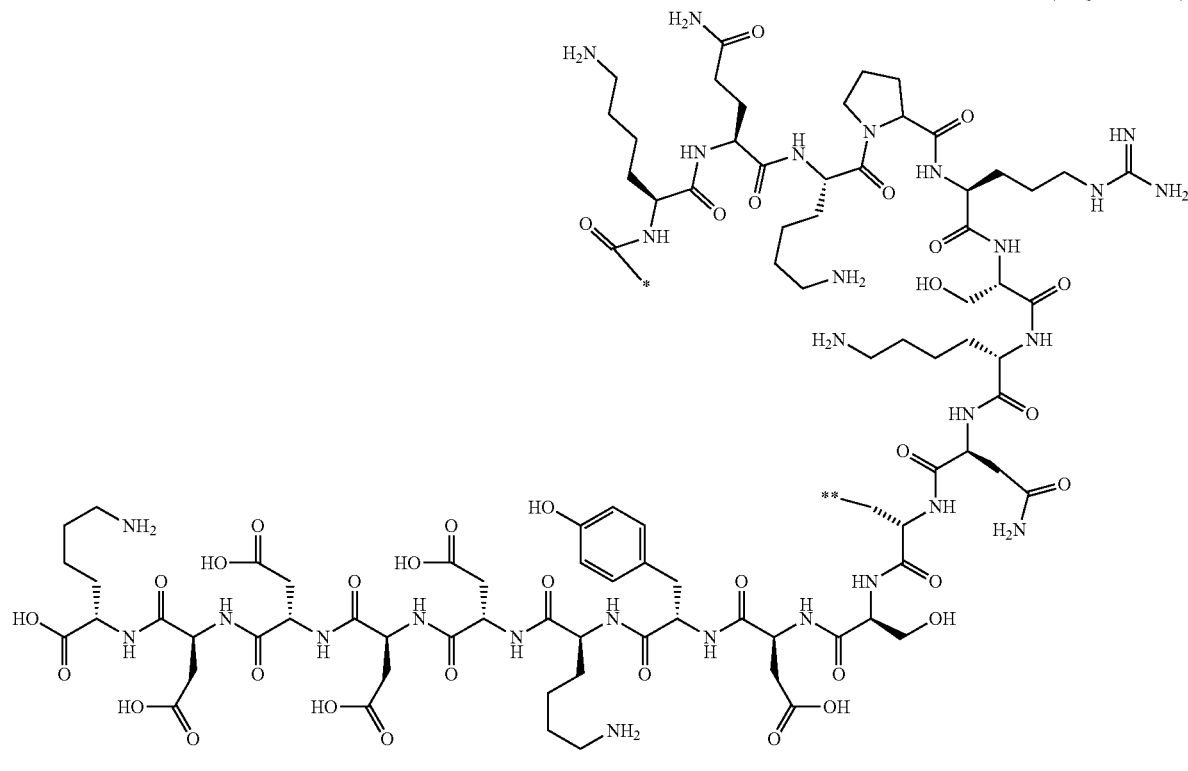
| Cyclic peptide No. | mRNA No. | Aminoacyl-tRNA No. | Linker No. | Observed MS |
|---|---|---|---|---|
| 1-26 | | 26 | (structure) or (structure) | 2379.0 |
| 1-27 | | 27 | (structure) | 2370.0 |

The synthesis of cyclic peptides shown in Table 34 below was carried out in the same manner as the synthesis of cyclic peptide 1-1, using combinations of mRNA and aminoacyl-tRNA shown in Table 34.

TABLE 34

(SEQ ID NO: 25)

| Cyclic peptide No. | mRNA No. | Aminoacyl-tRNA No. | Linker No. | Observed MS |
|---|---|---|---|---|
| A-1 | mRNA-1 | 30 | (thiazoline-pyridine) | 2326.3 |
| A-2 | | 31 | (thiazoline-pyridine isomer) | 2326.3 |
| A-3 | | 32 | (thiazoline-fluorophenyl) | 2343.0 |
| A-4 | | 33 | (thiazoline-fluorophenyl isomer) | 2343.1 |

TABLE 34-continued
(SEQ ID NO: 25)
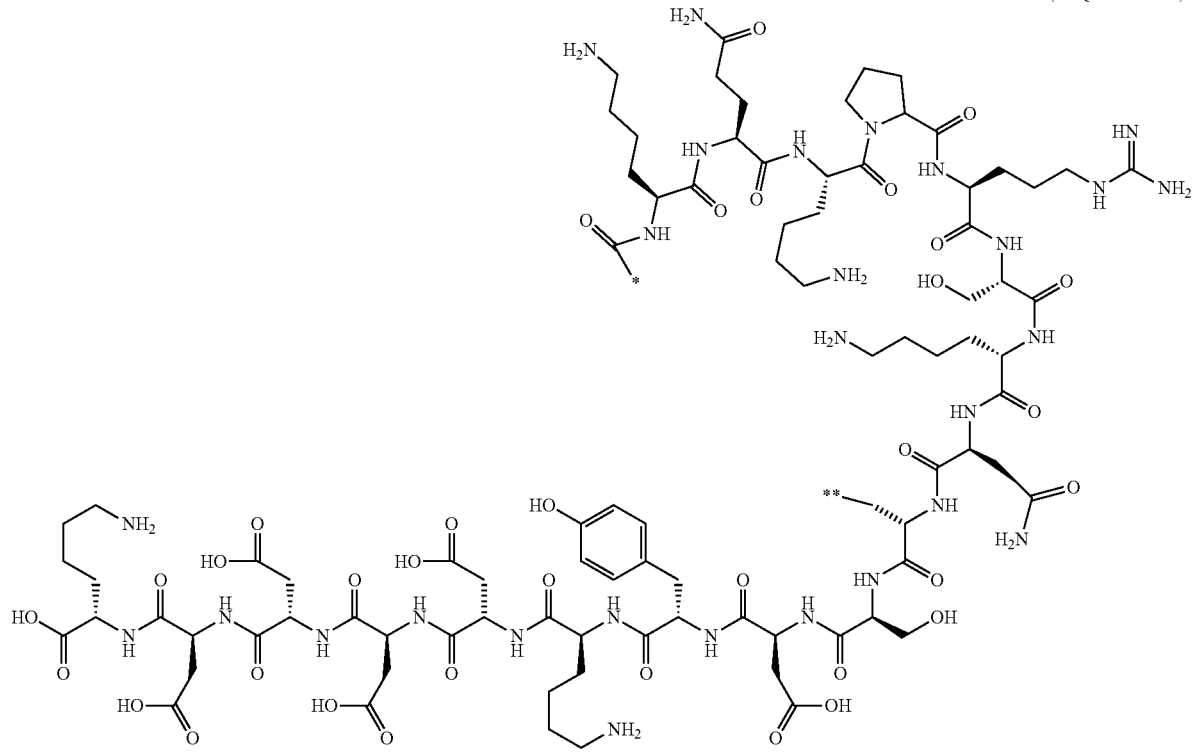
| Cyclic peptide No. | mRNA No. | Aminoacyl-tRNA No. | Linker No. | Observed MS |
|---|---|---|---|---|
| A-5 | | 34 | (thiazoline-2,6-difluorophenyl) | 2361.0 |
| A-6 | | 35 | (thiazoline-N-methylindazole) | 2379.1 |
| A-7 | | 36 | (thiazoline-N-methylpyrazole) | 2329.1 |
| A-8 | | 37 | (thiazoline-benzothiadiazole) | 2383.2 |

TABLE 34-continued
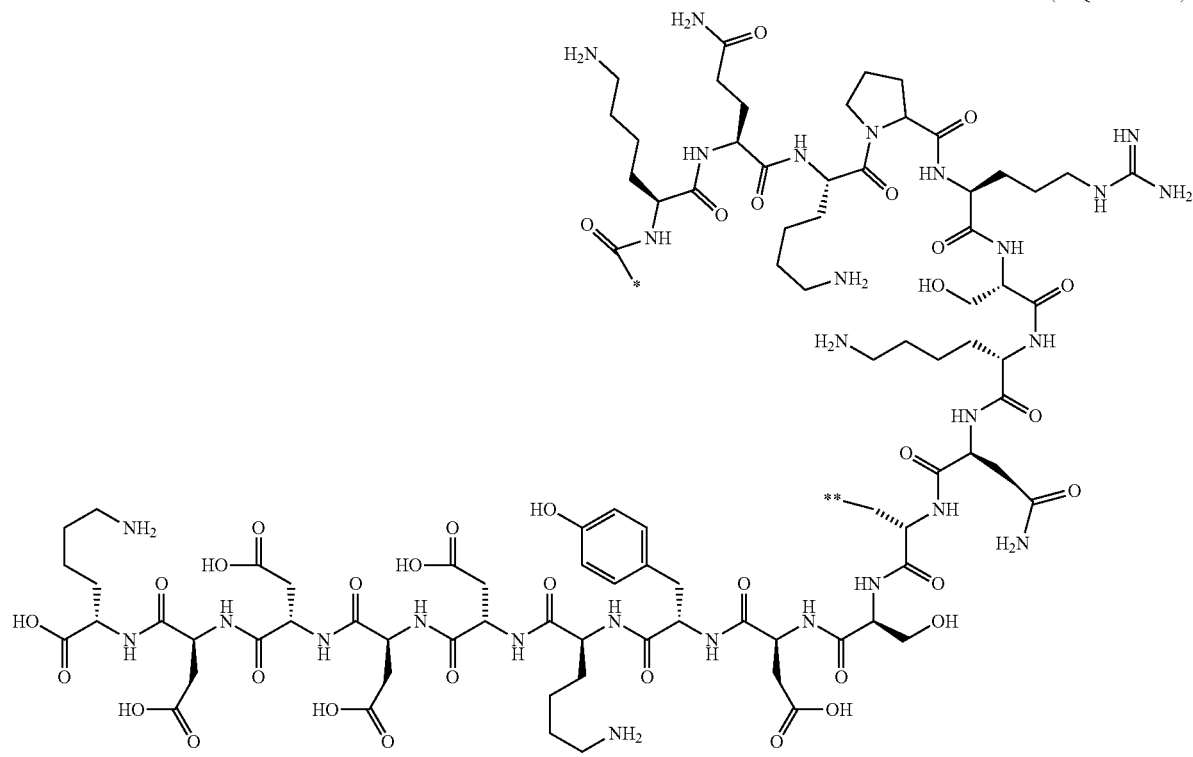
(SEQ ID NO: 25)
| Cyclic peptide No. | mRNA No. | Aminoacyl-tRNA No. | Linker No. | Observed MS |
|---|---|---|---|---|
| A-9 | 38 | | | 2442.3 |
| A-10 | 39 | | | 2316.2 |
| A-11 | 40 | | | 2328.0 |
| A-12 | 41 | | | 2391.8 |

TABLE 34-continued
(SEQ ID NO: 25)
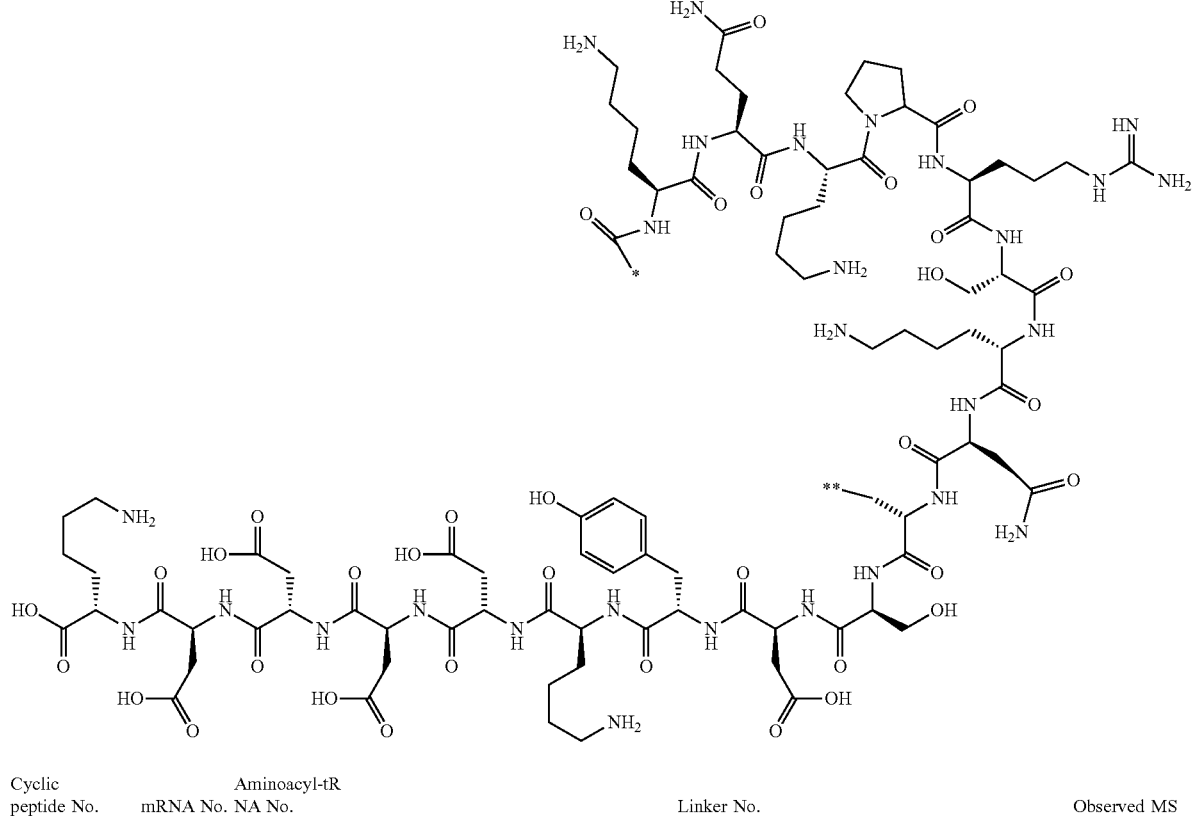
| Cyclic peptide No. | mRNA No. | Aminoacyl-tRNA No. | Linker No. | Observed MS |
|---|---|---|---|---|
| A-13 | | 42 | | 2390.9 |
| A-14 | | 43 | | 2366.1 |
| A-15 | | 44 | | 2366.1 |
| A-16 | | 45 | | 2366.2 |
| A-17 | | 46 | | 2365.1 |
| A-18 | | 47 | | 2409.0 |

TABLE 34-continued
(SEQ ID NO: 25)
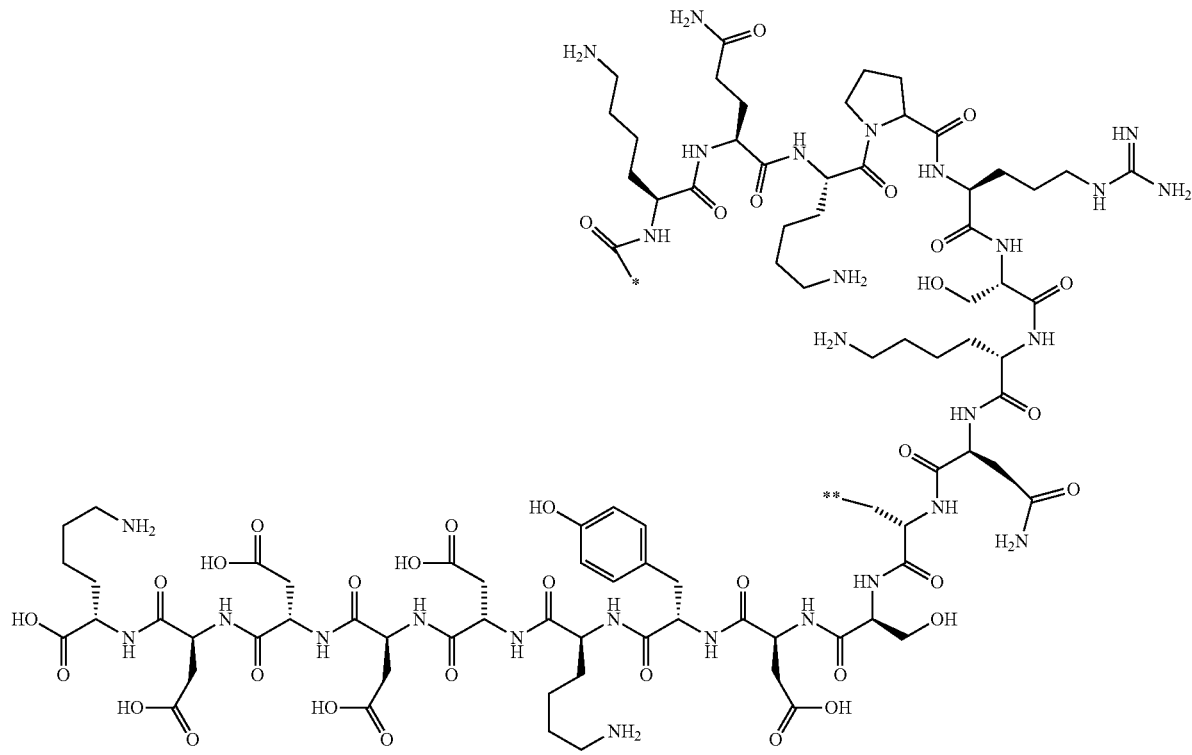
| Cyclic peptide No. | Aminoacyl-tRNA mRNA No. No. | Linker No. | Observed MS |
|---|---|---|---|
| A-19 | 48 | | 2409.2 |
| A-20 | 49 | | 2414.8 |
| A-21 | 50 | | 2399.1 |

TABLE 34-continued
(SEQ ID NO: 25)
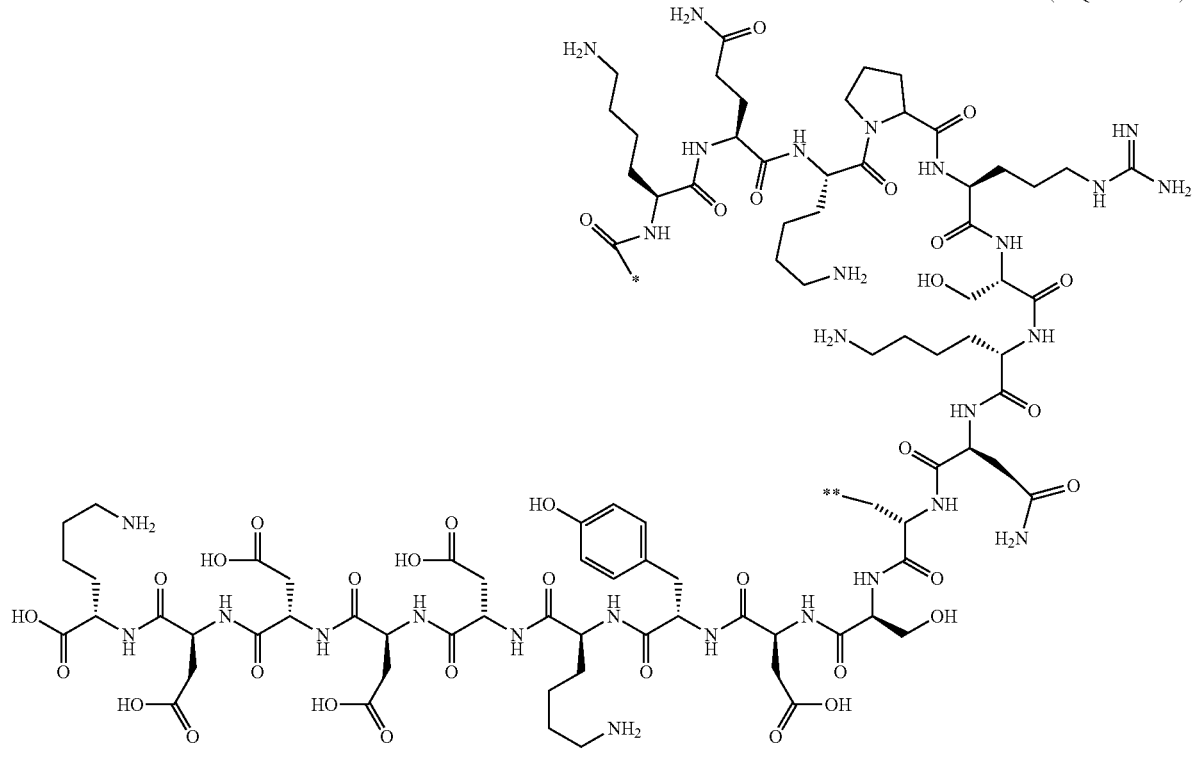
| Cyclic peptide No. | mRNA No. | Aminoacyl-tRNA No. | Linker No. | Observed MS |
|---|---|---|---|---|
| A-22 | 51 | | (structure) | 2413.2 |
| A-23 | 52 | | (structure) | 2449.2 |
| A-24 | 53 | | (structure) | 2496.2 |

TABLE 34-continued
(SEQ ID NO: 25)
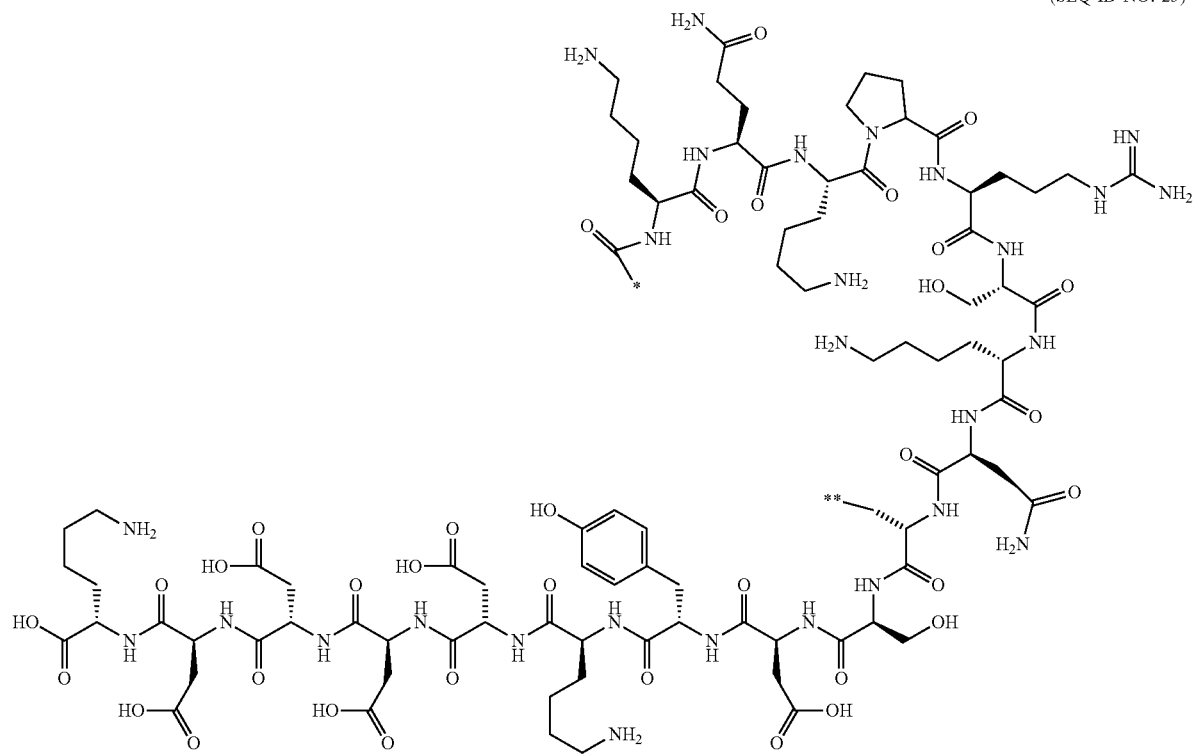
| Cyclic peptide No. | mRNA No. | Aminoacyl-tRNA No. | Linker No. | Observed MS |
|---|---|---|---|---|
| A-25 | 54 | | 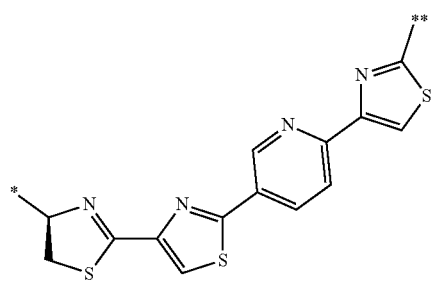 | 2491.9 |
| A-26 | 55 | | 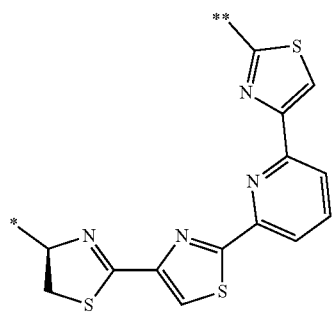 | 2492.1 |

TABLE 34-continued
(SEQ ID NO: 25)
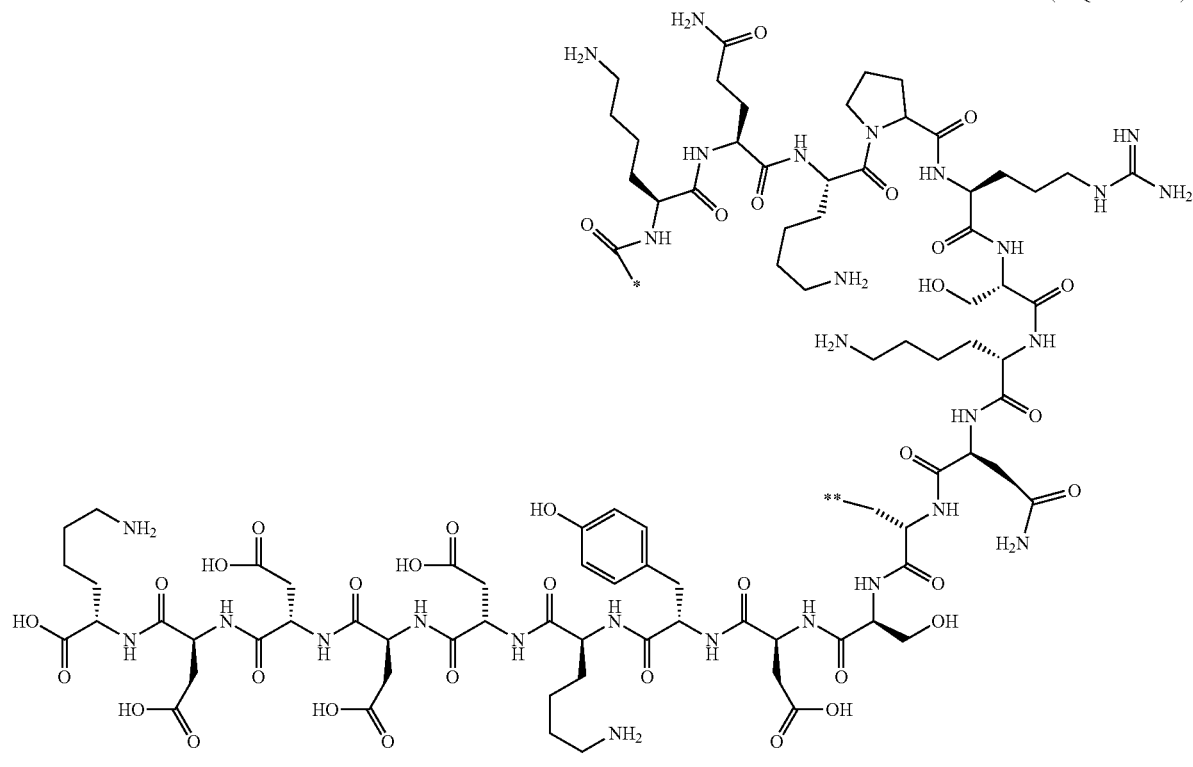
| Cyclic peptide No. | mRNA No. | Aminoacyl-tRNA No. | Linker No. | Observed MS |
|---|---|---|---|---|
| A-27 | 56 | | 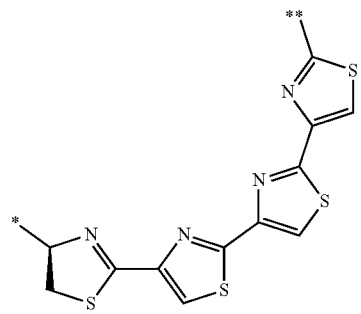 | 2497.9 |
| A-27 | 57 | | 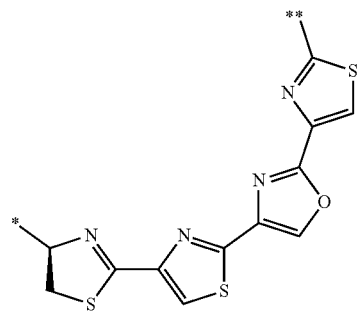 | 2482.2 |

TABLE 34-continued
(SEQ ID NO: 25)
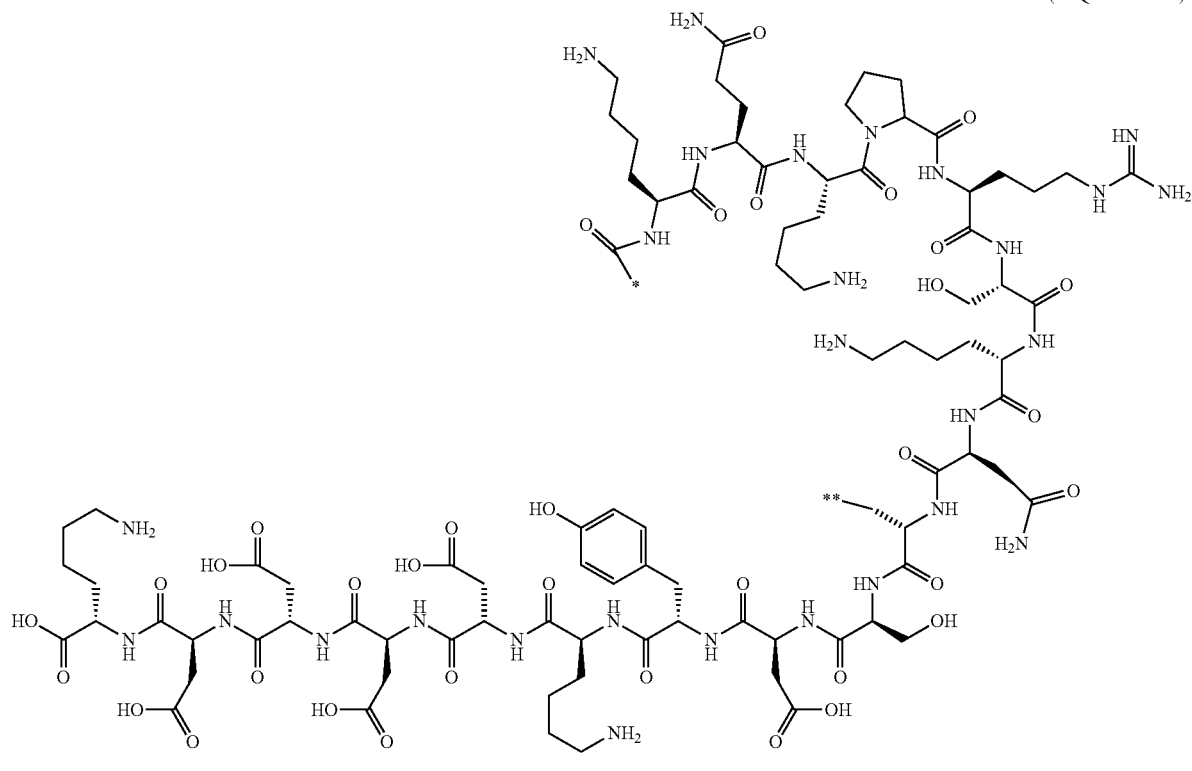
| Cyclic peptide No. | mRNA No. | Aminoacyl-tRNA No. | Linker No. | Observed MS |
|---|---|---|---|---|
| A-28 | 58 | | 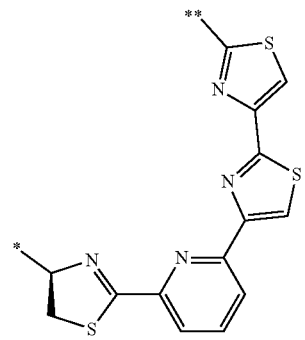 | 2492.1 |
| A-29 | 59 | | 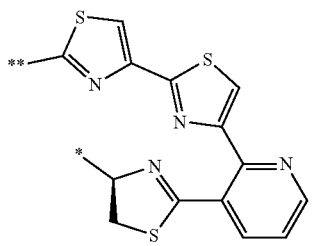 | 2492.1 |

TABLE 34-continued
(SEQ ID NO: 25)
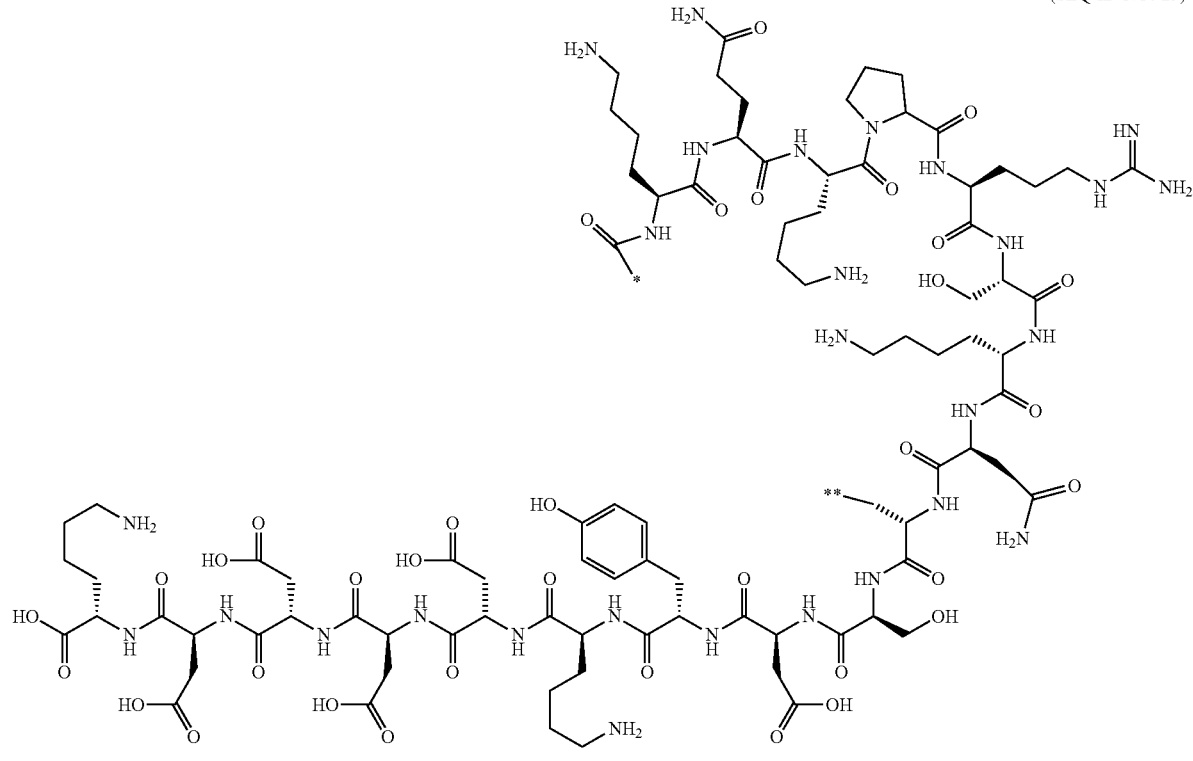
| Cyclic peptide No. | mRNA No. | Aminoacyl-tRNA No. | Linker No. | Observed MS |
|---|---|---|---|---|
| A-30 | 60 | | | 2581.1 |
| A-31 | 61 | | | 2549.3 |

TABLE 34-continued
(SEQ ID NO: 25)
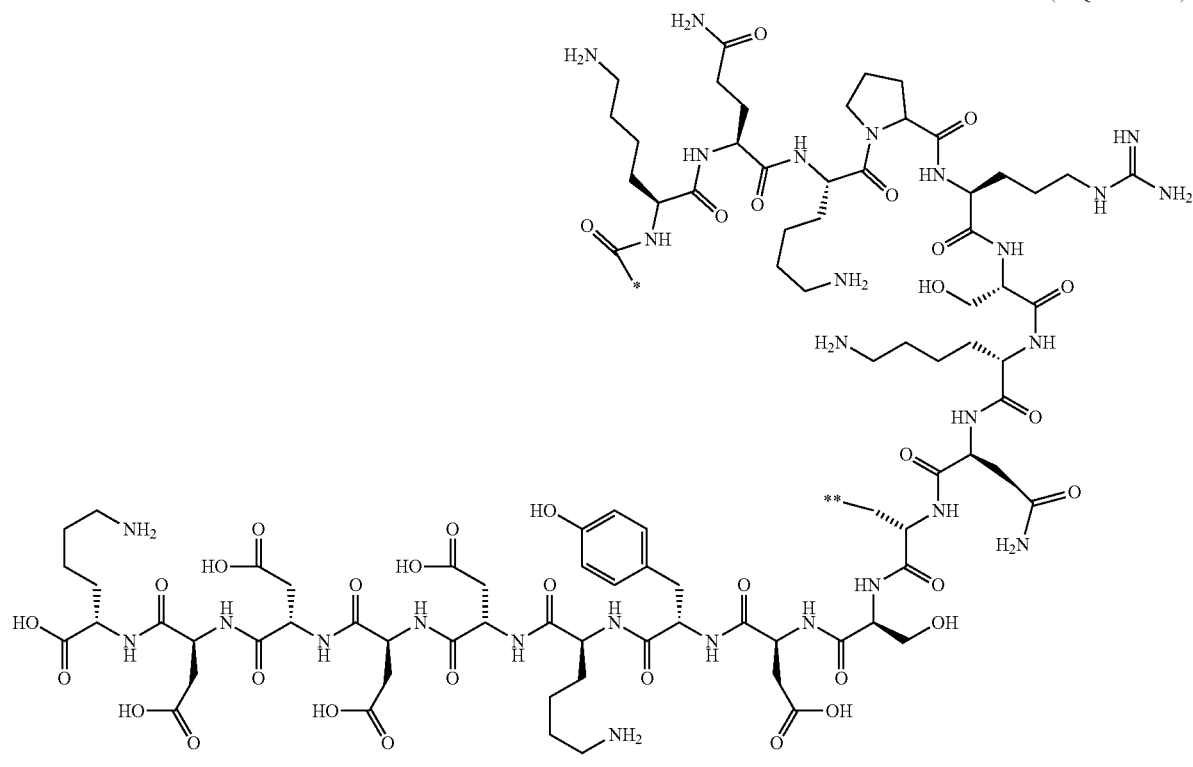
| Cyclic peptide No. | mRNA No. | Aminoacyl-tRNA No. | Linker No. | Observed MS |
|---|---|---|---|---|
| A-32 | 62 | | 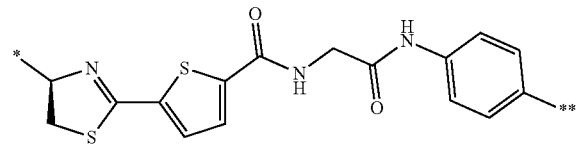 | 2507.1 |
| A-33 | 63 | | 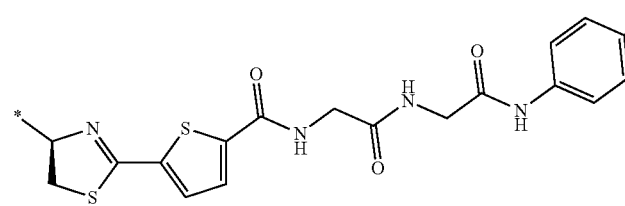 | 2564.2 |
| A-34 | 64 | | 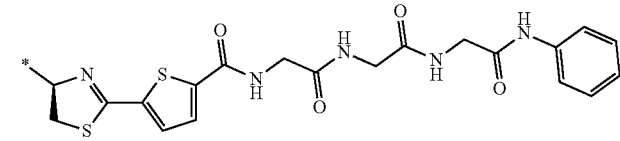 | 2621.2 |
| A-35 | 65 | | 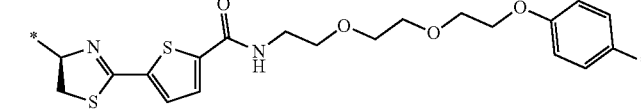 | 2582.1 |

TABLE 34-continued
(SEQ ID NO: 25)
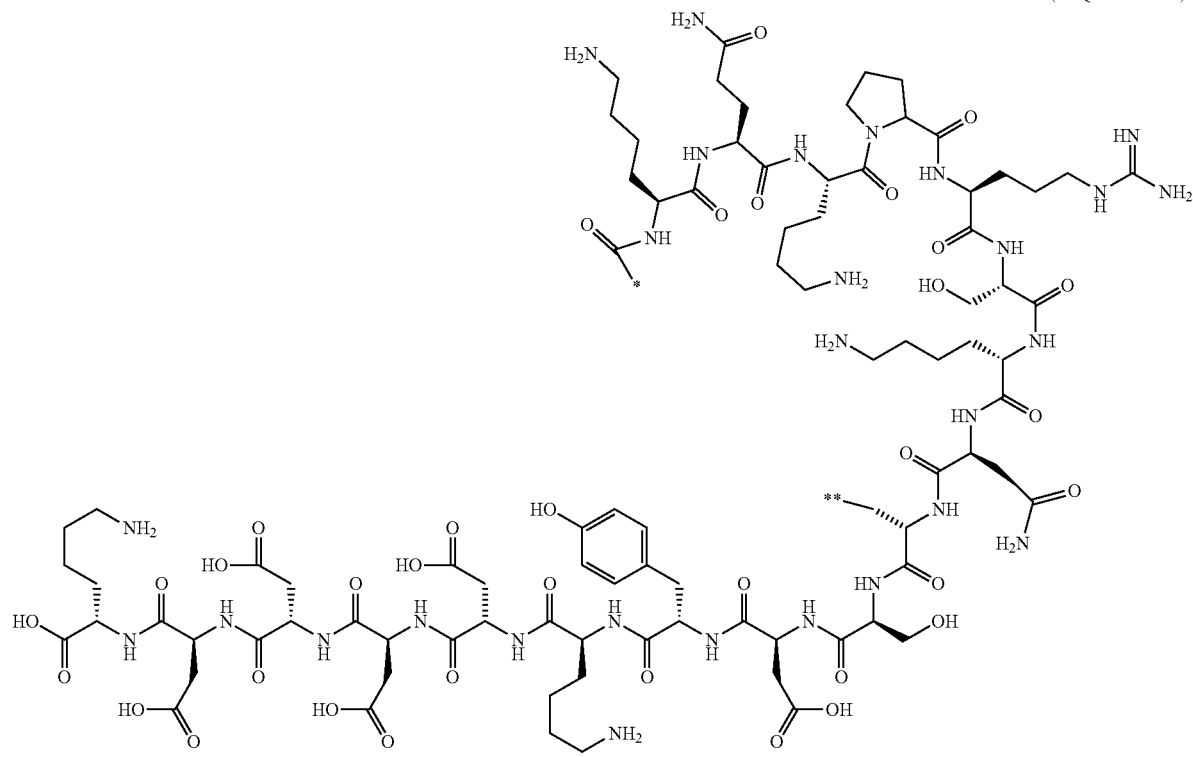
| Cyclic peptide No. | mRNA No. | Aminoacyl-tRNA No. | Linker No. | Observed MS |
|---|---|---|---|---|
| A-36 | 66 | | 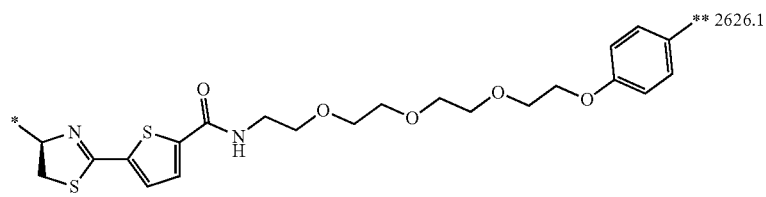 | 2626.1 |
| A-37 | 67 | | 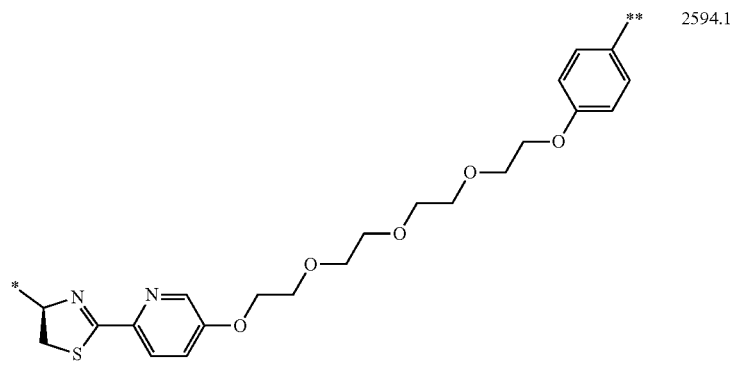 | 2594.1 |
| A-38 | 68 | | 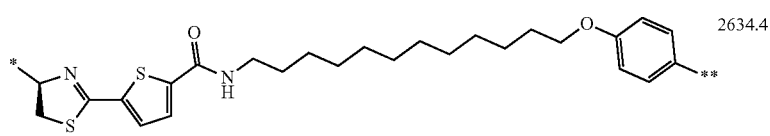 | 2634.4 |

Synthesis of Cyclic Peptide 1-28 (SEQ ID NO: 25)

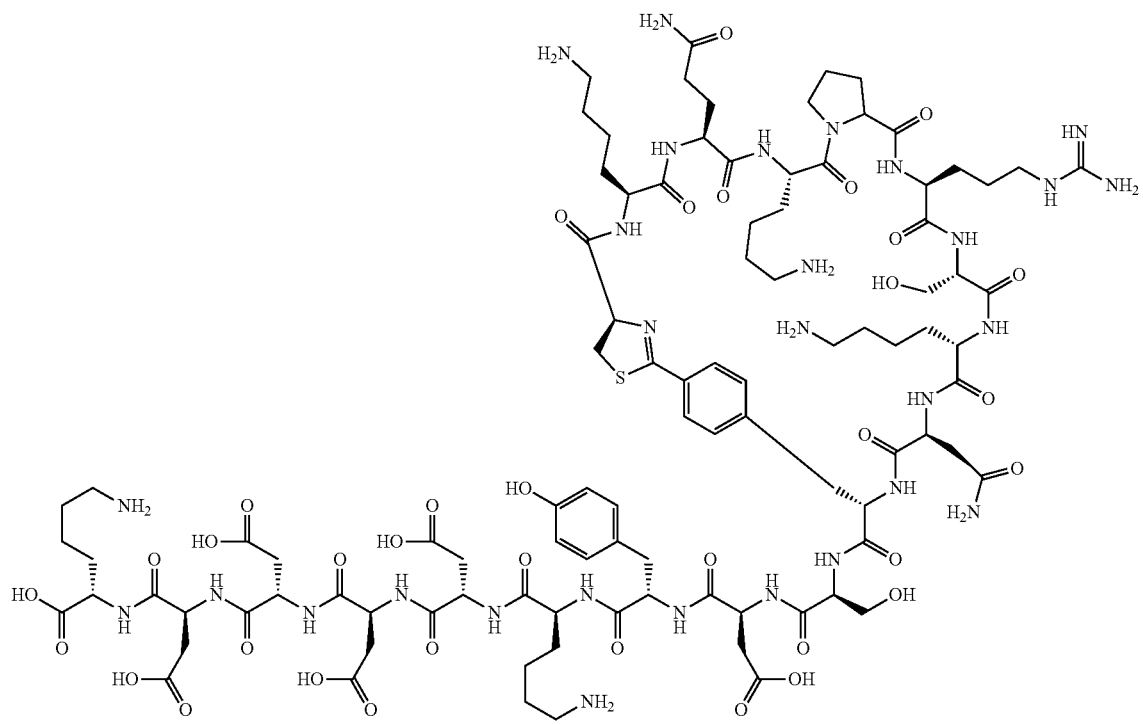 [SMILES: N=C(N)NCCC[C@@H]1NC(=O)C2CCCN2C(=O)[C@H](CCCCN)NC(=O)[C@H](CCC(N)=O)NC(=O)[C@H](CCCCN)NC(=O)[C@@H]2CSC(=N2)c2ccc(cc2)C[C@@H](C(=O)N[C@@H](CO)C(=O)N[C@@H](CC(=O)O)C(=O)N[C@@H](Cc2ccc(O)cc2)C(=O)N[C@@H](CCCCN)C(=O)N[C@@H](CC(=O)O)C(=O)N[C@@H](CC(=O)O)C(=O)N[C@@H](CC(=O)O)C(=O)N[C@@H](CC(=O)O)C(=O)N[C@@H](CCCCN)C(=O)O)NC(=O)[C@H](CC(N)=O)NC(=O)[C@H](CCCCN)NC(=O)[C@H](CO)NC1=O]

A solution having the foregoing solution composition 4 was prepared in a 1.5 mL sample tube and incubated at 37° C. for 30 minutes. 70 μL of 0.1 mol/L phosphate buffer (pH 6.4) was added to the reaction solution which was then incubated at 37° C. for 4 hours. 20 μL of a 0.1 mol/L aqueous sodium hydroxide solution and 10 μL of a magnetic bead solution (manufactured by MBL Life Science, Anti-DDDDK-tag mAb-Magnetic Agarose) were added to the reaction solution which was then shaken using a vortex for 30 minutes at room temperature. This was followed by centrifugation to remove the supernatant solution. The washing operation of the obtained magnetic beads (adding 200 μL of wash buffer→shaking with a vortex→centrifugation→removal of supernatant) was repeated three times. 10 μL of a 2% aqueous formic acid solution was added to the resulting magnetic beads which were then shaken using a vortex for 1 hour at room temperature. Thereafter, the magnetic beads were sedimented by centrifugation, and the supernatant was recovered to obtain cyclic peptide 1-28. Identification of the obtained peptide was carried out by MALDI-TOF MS.

MS(MALDI-TOF, m/z): 2325.1 (M+H)

Synthesis of Cyclic Peptide 1-29

The aminoacyl-tRNA-28 in the synthesis of cyclic peptide 1-28 was changed to aminoacyl-tRNA-29, and the incubation time after addition of buffer was 24 hours to thereby obtain cyclic peptide 1-29 shown in Table 35.

TABLE 35
(SEQ ID NO: 25)
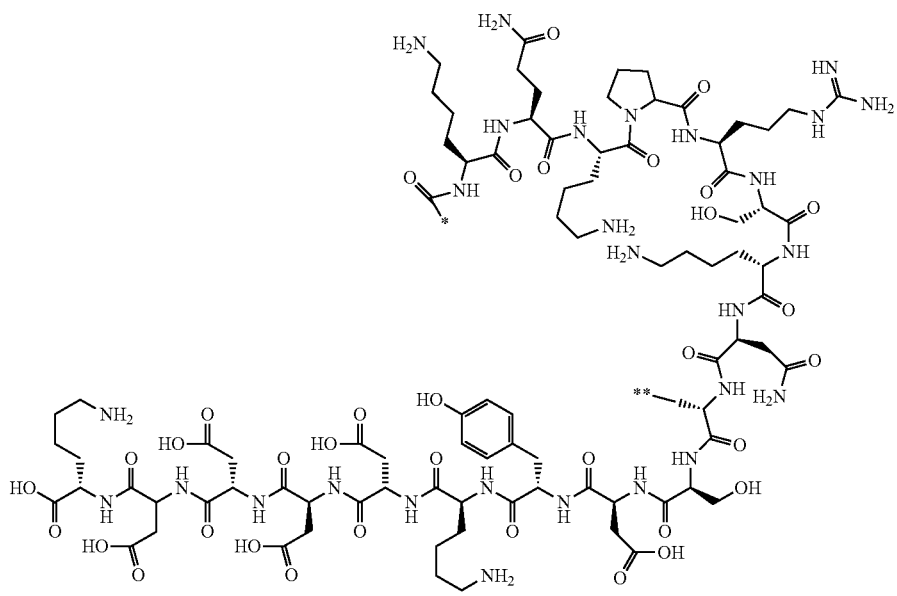
| Cyclic peptide No. | mRNA No. | Aminoacyl-tRNA No. | Linker No. | Observed MS |
|---|---|---|---|---|
| 1-28 | mRNA-1 | 28 | | 2325.1 |
| | | | 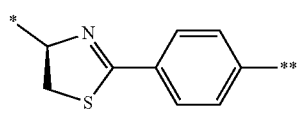 | |
| 1-29 | | 29 | | 2249.1 |
| | | | 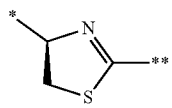 | |

Synthesis of Cyclic Peptides 1-30 to 38

The synthesis of cyclic peptides 1-30 to 38 shown in Table 36 below was carried out in the same manner as the synthesis of cyclic peptide 1-1, using combinations of mRNA and aminoacyl-tRNA shown in Table 36.

TABLE 36

(SEQ ID NO: 25)

| Cyclic peptide No. | mRNA No. | Aminoacyl-tRNA No. | Linker No. | Observed MS |
|---|---|---|---|---|
| 1-30 | mRNA-2 | 1 | | 2357.0 |
| 1-31 | | 2 | | 2351.0 |
| 1-32 | | 4 | | 2301.0 |
| 1-33 | | 5 | | 2301.9 |

TABLE 36-continued
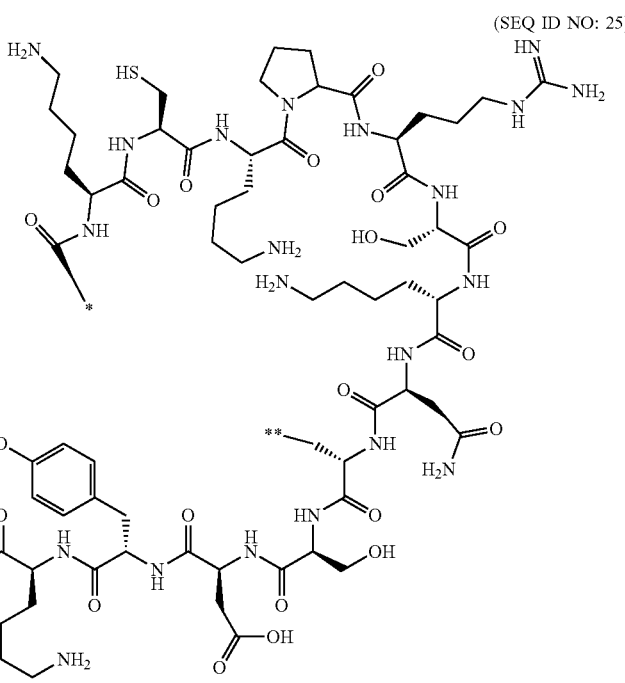
(SEQ ID NO: 25)
| Cyclic peptide No. | mRNA No. | Aminoacyl-tRNA No. | Linker No. | Observed MS |
|---|---|---|---|---|
| 1-34 | | 6 | 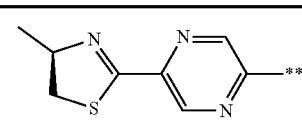 | 2301.9 |
| 1-35 | | 7 | 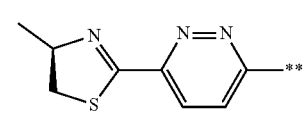 | 2301.9 |
| 1-36 | | 8 | 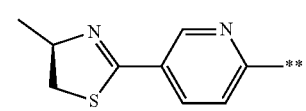 | 2301.0 |
| 1-37 | | 9 | 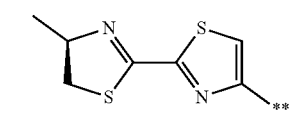 | 2306.9 |
| 1-38 | | 10 | 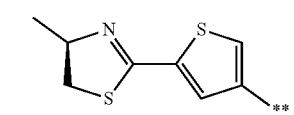 | 2305.9 |

Synthesis of Cyclic Peptides 1-39 to 47
The synthesis of cyclic peptides 1-39 to 47 shown in Table 37 below was carried out in the same manner as the synthesis of cyclic peptide 1-1, using combinations of mRNA and aminoacyl-tRNA shown in Table 37.
TABLE 37
(SEQ ID NO: 26)
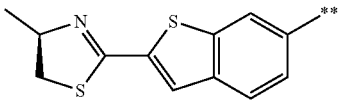
| Cyclic peptide No. | mRNA No. | Aminoacyl-tRNA No. | Linker No. | Observed MS |
|---|---|---|---|---|
| 1-39 | mRNA-3 | 1 | 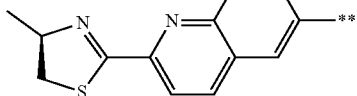 | 2399.0 |
| 1-40 | | 2 | 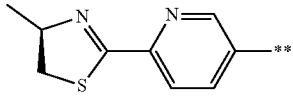 | 2392.0 |
| 1-41 | | 4 | 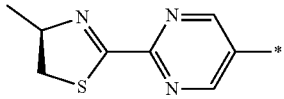 | 2342.0 |
| 1-42 | | 5 | 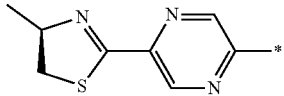 | 2342.9 |
| 1-43 | | 6 | 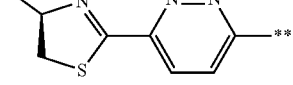 | 2342.9 |
| 1-44 | | 7 | 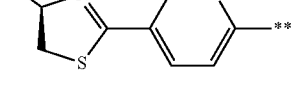 | 2342.9 |
| 1-45 | | 8 |  | 2342.0 |

TABLE 37-continued
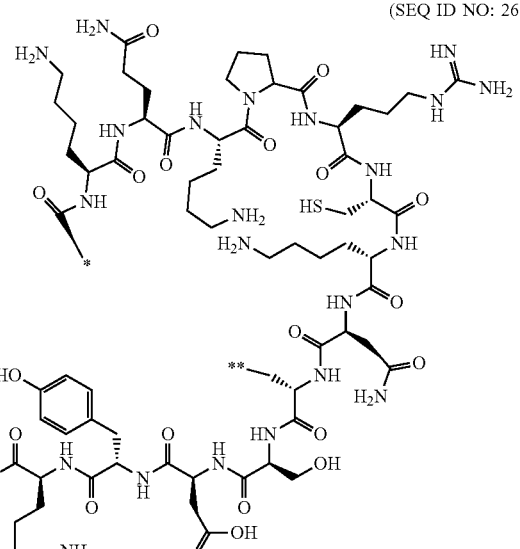
(SEQ ID NO: 26)
| Cyclic peptide No. | mRNA No. | Aminoacyl-tRNA No. | Linker No. | Observed MS |
|---|---|---|---|---|
| 1-46 | | 9 | | 2347.9 |
| 1-47 | | 10 | | 2346.9 |
Synthesis of Cyclic Peptide 1-48 (SEQ ID NO: 27)
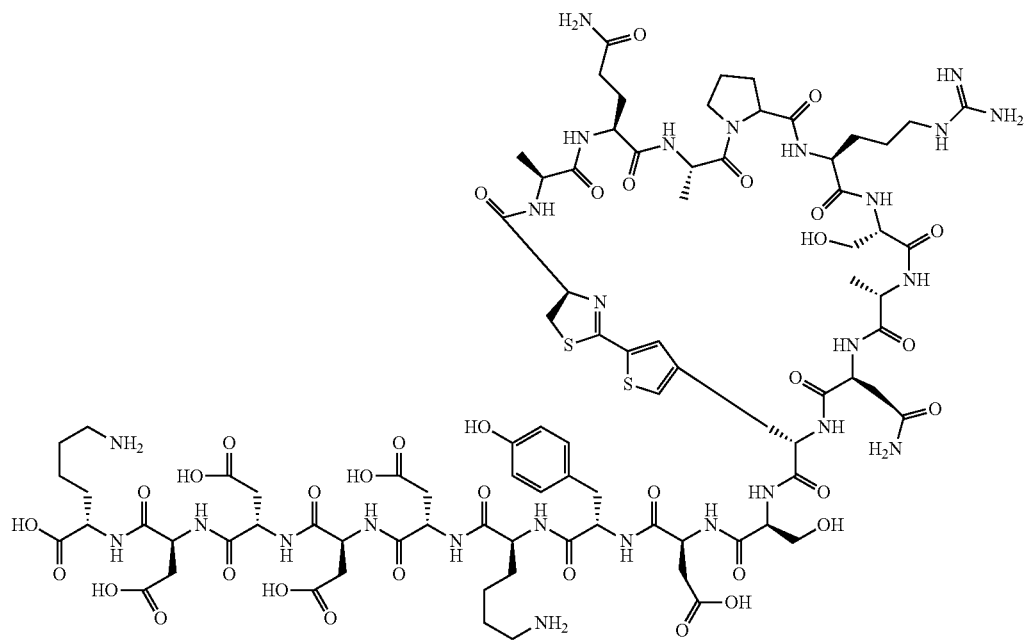 [SMILES: C[C@@H]1NC(=O)[C@@H]2CSC(=N2)c2cc(cs2)C[C@@H](C(=O)N[C@@H](CO)C(=O)N[C@@H](CC(=O)O)C(=O)N[C@@H](Cc2ccc(O)cc2)C(=O)N[C@@H](CCCCN)C(=O)N[C@@H](CC(=O)O)C(=O)N[C@@H](CC(=O)O)C(=O)N[C@@H](CC(=O)O)C(=O)N[C@@H](CC(=O)O)C(=O)N[C@@H](CCCCN)C(=O)O)NC(=O)[C@H](CC(N)=O)NC(=O)[C@H](C)NC(=O)[C@H](CO)NC(=O)[C@H](CCCNC(=N)N)NC(=O)C2CCCN2C(=O)[C@H](C)NC(=O)[C@H](CCC(N)=O)NC1=O]

The synthesis of cyclic peptide 1-48 was carried out in the same manner as the synthesis of cyclic peptide 1-1, using a combination of mRNA-4 and aminoacyl-tRNA-10.
MS(MALDI-TOF, m/z): 2159.9 (M+H)

Synthesis of Cyclic Peptide 1-49 (SEQ ID NO: 28)

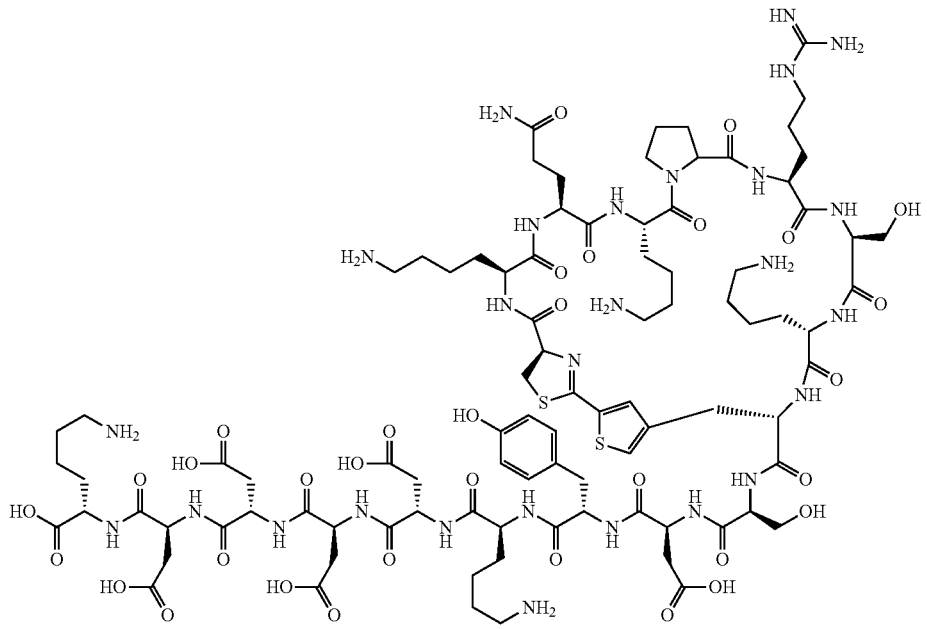 [SMILES: N=C(N)NCCC[C@@H]1NC(=O)C2CCCN2C(=O)[C@H](CCCCN)NC(=O)[C@H](CCC(N)=O)NC(=O)[C@H](CCCCN)NC(=O)[C@@H]2CSC(=N2)c2cc(cs2)C[C@@H](C(=O)N[C@@H](CO)C(=O)N[C@@H](CC(=O)O)C(=O)N[C@@H](Cc2ccc(O)cc2)C(=O)N[C@@H](CCCCN)C(=O)N[C@@H](CC(=O)O)C(=O)N[C@@H](CC(=O)O)C(=O)N[C@@H](CC(=O)O)C(=O)N[C@@H](CC(=O)O)C(=O)N[C@@H](CCCCN)C(=O)O)NC(=O)[C@H](CCCCN)NC(=O)[C@H](CO)NC1=O]

The synthesis of cyclic peptide 1-49 was carried out in the same manner as the synthesis of cyclic peptide 1-1, using a combination of mRNA-5 and aminoacyl-tRNA-10.
MS(MALDI-TOF, m/z): 2217.6 (M+H)

Synthesis of Cyclic Peptide 1-50 (SEQ ID NO: 29)

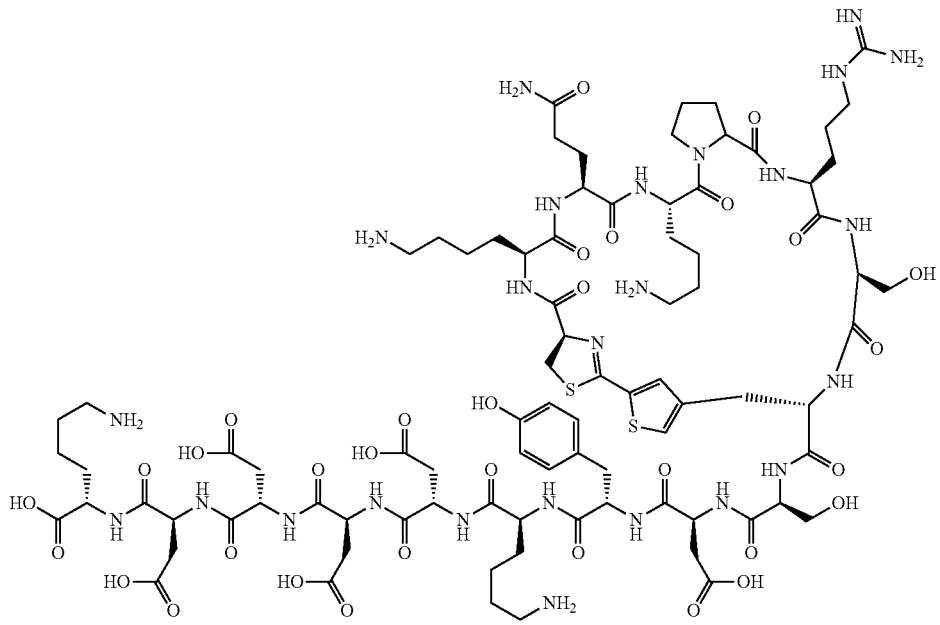 [SMILES: N=C(N)NCCC[C@@H]1NC(=O)C2CCCN2C(=O)[C@H](CCCCN)NC(=O)[C@H](CCC(N)=O)NC(=O)[C@H](CCCCN)NC(=O)[C@@H]2CSC(=N2)c2cc(cs2)C[C@@H](C(=O)N[C@@H](CO)C(=O)N[C@@H](CC(=O)O)C(=O)N[C@@H](Cc2ccc(O)cc2)C(=O)N[C@@H](CCCCN)C(=O)N[C@@H](CC(=O)O)C(=O)N[C@@H](CC(=O)O)C(=O)N[C@@H](CC(=O)O)C(=O)N[C@@H](CC(=O)O)C(=O)N[C@@H](CCCCN)C(=O)O)NC(=O)[C@H](CO)NC1=O]

The synthesis of cyclic peptide 1-50 was carried out in the same manner as the synthesis of cyclic peptide 1-1, using a combination of mRNA-6 and aminoacyl-tRNA-10.
MS(MALDI-TOF, m/z): 2088.9 (M+H)

Synthesis of Cyclic Peptide 1-51 (SEQ ID NO: 30)

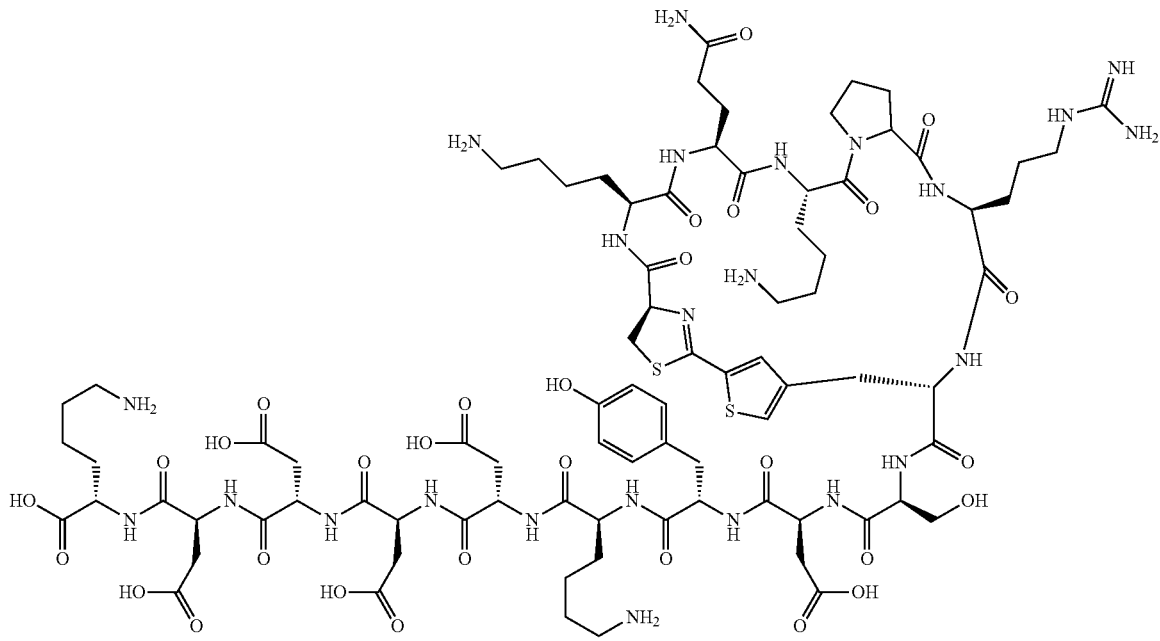 [SMILES: N=C(N)NCCC[C@@H]1NC(=O)C2CCCN2C(=O)[C@H](CCCCN)NC(=O)[C@H](CCC(N)=O)NC(=O)[C@H](CCCCN)NC(=O)[C@@H]2CSC(=N2)c2cc(cs2)C[C@@H](C(=O)N[C@@H](CO)C(=O)N[C@@H](CC(=O)O)C(=O)N[C@@H](Cc2ccc(O)cc2)C(=O)N[C@@H](CCCCN)C(=O)N[C@@H](CC(=O)O)C(=O)N[C@@H](CC(=O)O)C(=O)N[C@@H](CC(=O)O)C(=O)N[C@@H](CC(=O)O)C(=O)N[C@@H](CCCCN)C(=O)O)NC1=O]

The synthesis of cyclic peptide 1-51 was carried out in the same manner as the synthesis of cyclic peptide 1-1, using a combination of mRNA-7 and aminoacyl-tRNA-10.
MS(MALDI-TOF, m/z): 2001.8 (M+H)

Synthesis of Cyclic Peptide 1-52 (SEQ ID NO: 31)

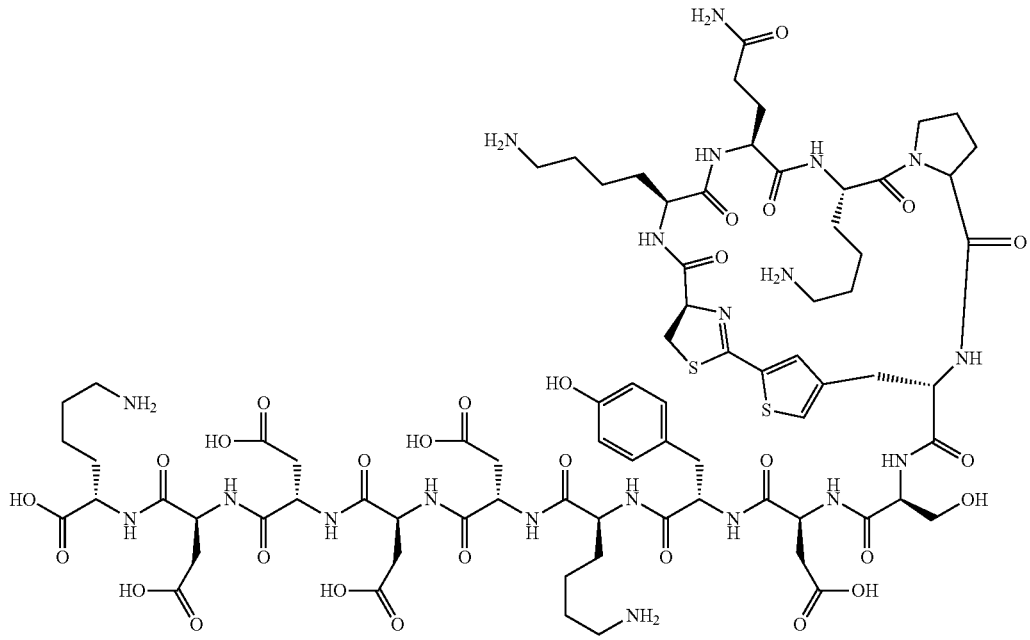 [SMILES: NCCCC[C@H](NC(=O)[C@H](CC(=O)O)NC(=O)[C@H](CC(=O)O)NC(=O)[C@H](CC(=O)O)NC(=O)[C@H](CC(=O)O)NC(=O)[C@H](CCCCN)NC(=O)[C@H](Cc1ccc(O)cc1)NC(=O)[C@H](CC(=O)O)NC(=O)[C@H](CO)NC(=O)[C@@H]1Cc2csc(c2)C2=N[C@@H](CS2)C(=O)N[C@@H](CCCCN)C(=O)N[C@@H](CCC(N)=O)C(=O)N[C@@H](CCCCN)C(=O)N2CCCC2C(=O)N1)C(=O)O]

The synthesis of cyclic peptide 1-52 was carried out in the same manner as the synthesis of cyclic peptide 1-1, using a combination of mRNA-8 and aminoacyl-tRNA-10.
MS(MALDI-TOF, m/z): 1845.7 (M+H)

Synthesis of Cyclic Peptide 1-53 (SEQ ID NO: 32)

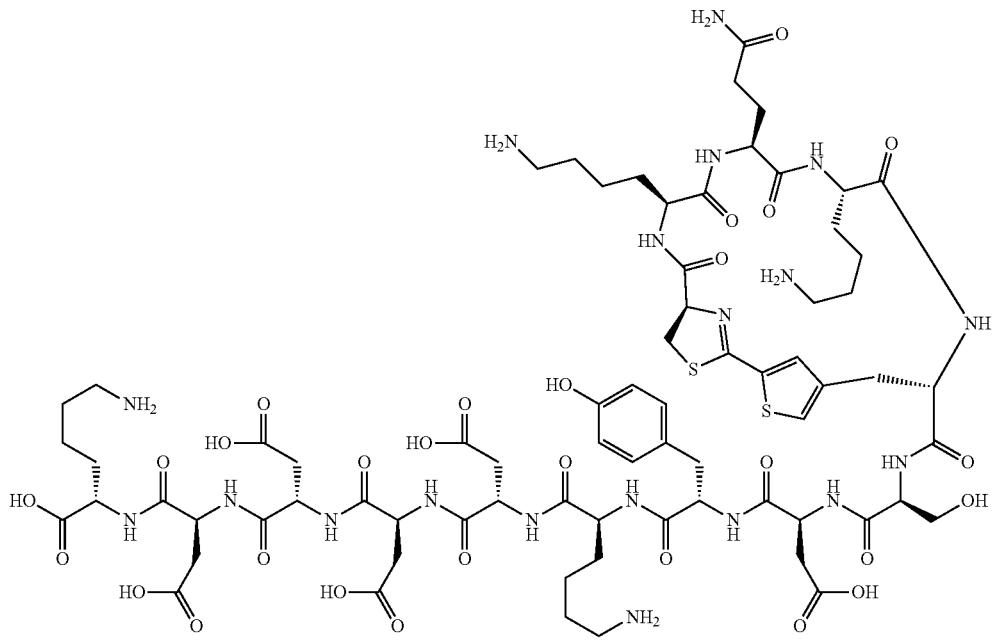 [SMILES: NCCCC[C@H](NC(=O)[C@H](CC(=O)O)NC(=O)[C@H](CC(=O)O)NC(=O)[C@H](CC(=O)O)NC(=O)[C@H](CC(=O)O)NC(=O)[C@H](CCCCN)NC(=O)[C@H](Cc1ccc(O)cc1)NC(=O)[C@H](CC(=O)O)NC(=O)[C@H](CO)NC(=O)[C@@H]1Cc2csc(c2)C2=N[C@@H](CS2)C(=O)N[C@@H](CCCCN)C(=O)N[C@@H](CCC(N)=O)C(=O)N[C@@H](CCCCN)C(=O)N1)C(=O)O]

The synthesis of cyclic peptide 1-53 was carried out in the same manner as the synthesis of cyclic peptide 1-1, using a combination of mRNA-9 and aminoacyl-tRNA-10.
MS(MALDI-TOF, m/z): 1748.7 (M+H)

Synthesis of Cyclic Peptide 1-54 (SEQ ID NO: 33)

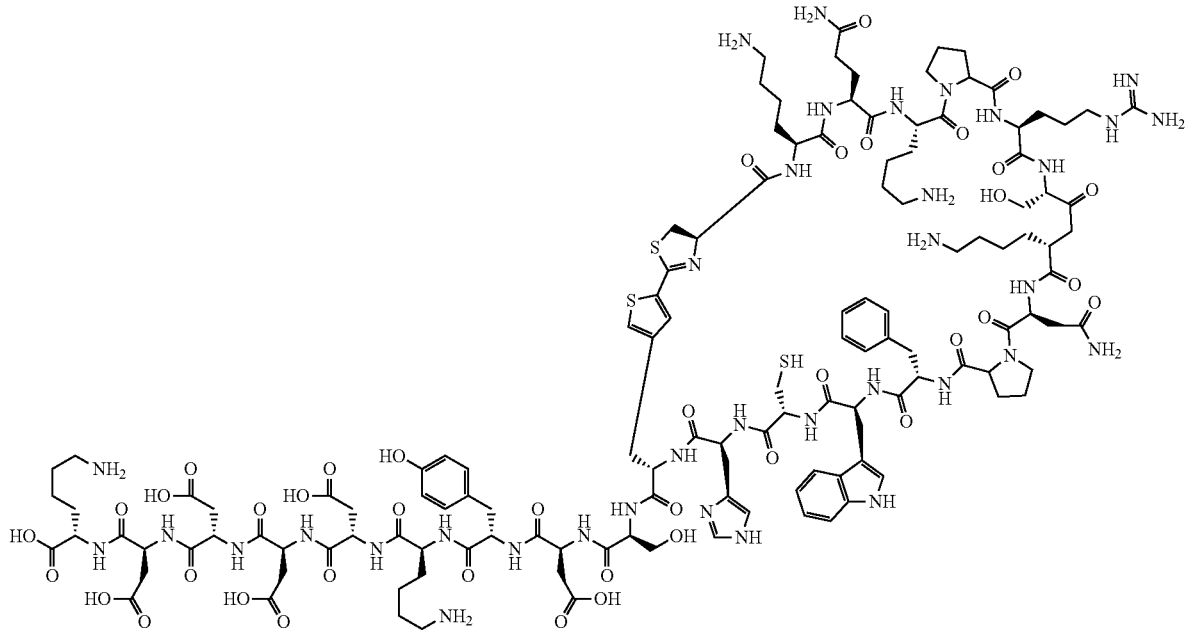 [SMILES: N=C(N)NCCC[C@@H]1NC(=O)C2CCCN2C(=O)[C@H](CCCCN)NC(=O)[C@H](CCC(N)=O)NC(=O)[C@H](CCCCN)NC(=O)[C@@H]2CSC(=N2)c2cc(cs2)C[C@@H](C(=O)N[C@@H](CO)C(=O)N[C@@H](CC(=O)O)C(=O)N[C@@H](Cc2ccc(O)cc2)C(=O)N[C@@H](CCCCN)C(=O)N[C@@H](CC(=O)O)C(=O)N[C@@H](CC(=O)O)C(=O)N[C@@H](CC(=O)O)C(=O)N[C@@H](CC(=O)O)C(=O)N[C@@H](CCCCN)C(=O)O)NC(=O)[C@H](Cc2c[nH]cn2)NC(=O)[C@H](CS)NC(=O)[C@H](Cc2c[nH]c3ccccc23)NC(=O)[C@H](Cc2ccccc2)NC(=O)C2CCCN2C(=O)[C@H](CC(N)=O)NC(=O)[C@H](CCCCN)CC(=O)[C@H](CO)NC1=O]

The synthesis of cyclic peptide 1-54 was carried out in the same manner as the synthesis of cyclic peptide 1-1, using a combination of mRNA-10 and aminoacyl-tRNA-10.
MS(MALDI-TOF, m/z): 3001.3 (M+H)
Synthesis of Cyclic Peptide 1-55 (SEQ ID NO: 34)
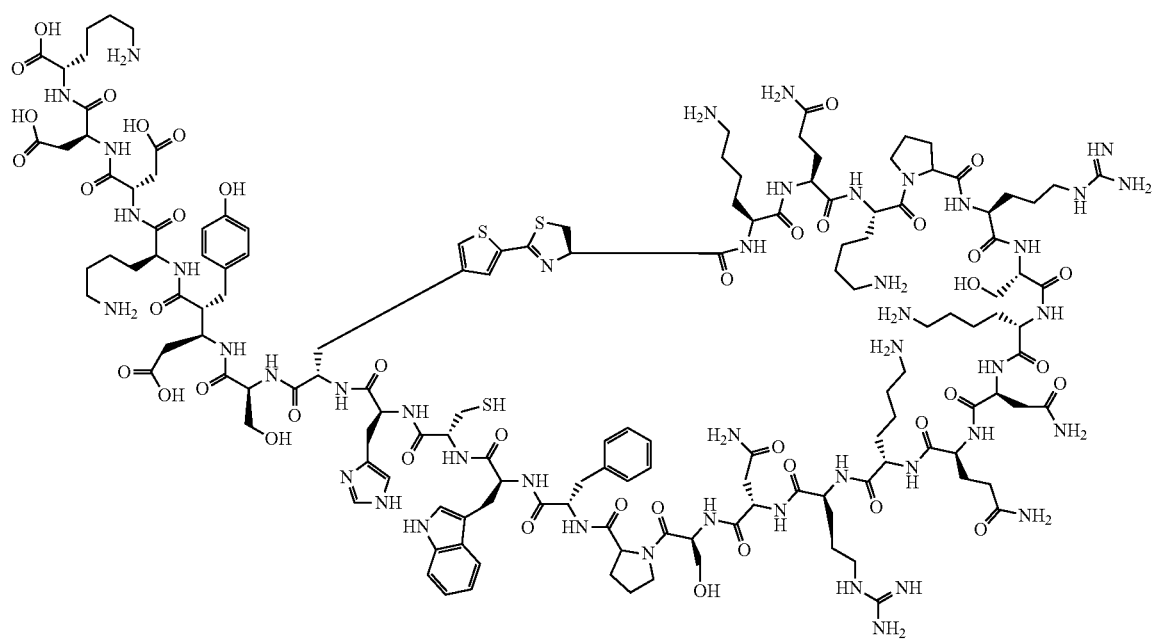

The synthesis of cyclic peptide 1-55 was carried out in the same manner as the synthesis of cyclic peptide 1-1, using a combination of mRNA-11 and aminoacyl-tRNA-10.
MS(MALDI-TOF, m/z): 3614.6 (M+H)
Synthesis of Cyclic Peptide 1-56 (SEQ ID NO: 35)
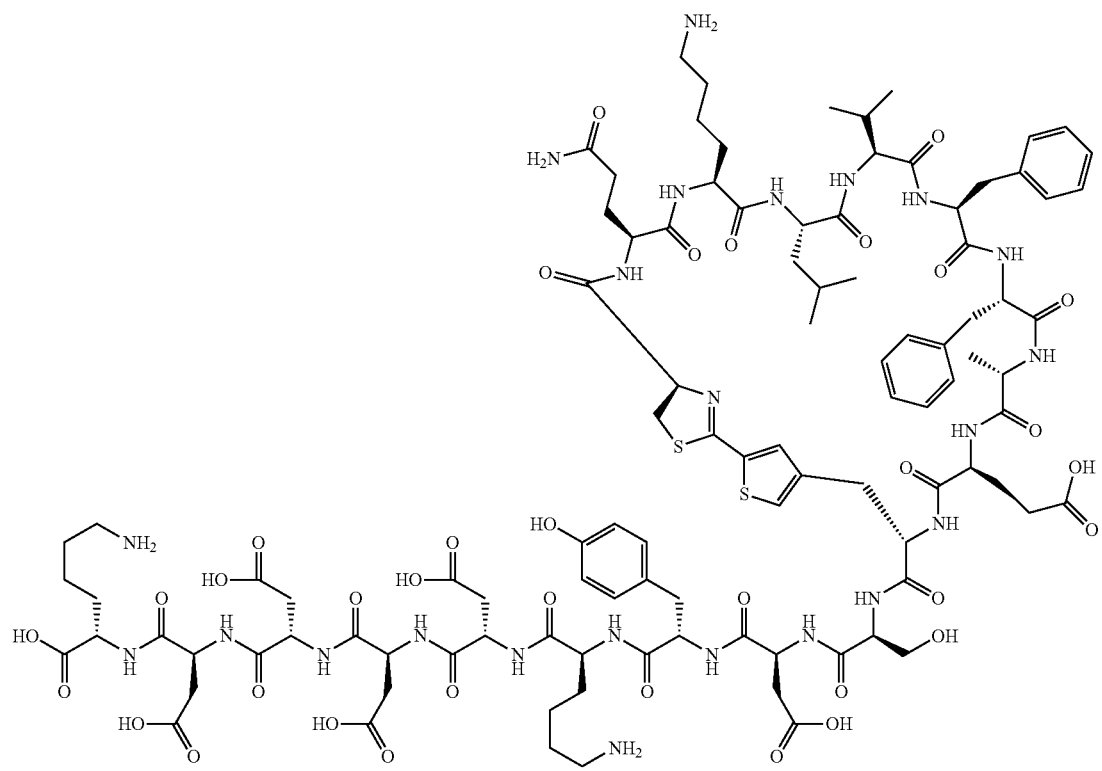 [SMILES: CC(C)C[C@@H]1NC(=O)[C@H](CCCCN)NC(=O)[C@H](CCC(N)=O)NC(=O)[C@@H]2CSC(=N2)c2cc(cs2)C[C@@H](C(=O)N[C@@H](CO)C(=O)N[C@@H](CC(=O)O)C(=O)N[C@@H](Cc2ccc(O)cc2)C(=O)N[C@@H](CCCCN)C(=O)N[C@@H](CC(=O)O)C(=O)N[C@@H](CC(=O)O)C(=O)N[C@@H](CC(=O)O)C(=O)N[C@@H](CC(=O)O)C(=O)N[C@@H](CCCCN)C(=O)O)NC(=O)[C@H](CCC(=O)O)NC(=O)[C@H](C)NC(=O)[C@H](Cc2ccccc2)NC(=O)[C@H](Cc2ccccc2)NC(=O)[C@H](C(C)C)NC1=O]

The synthesis of cyclic peptide 1-56 was carried out in the same manner as the synthesis of cyclic peptide 1-1, using a combination of mRNA-12 and aminoacyl-tRNA-10.

MS(MALDI-TOF, m/z): 2327.0 (M+H)

Synthesis of Cyclic Peptide 1-57 (SEQ ID NO: 36)

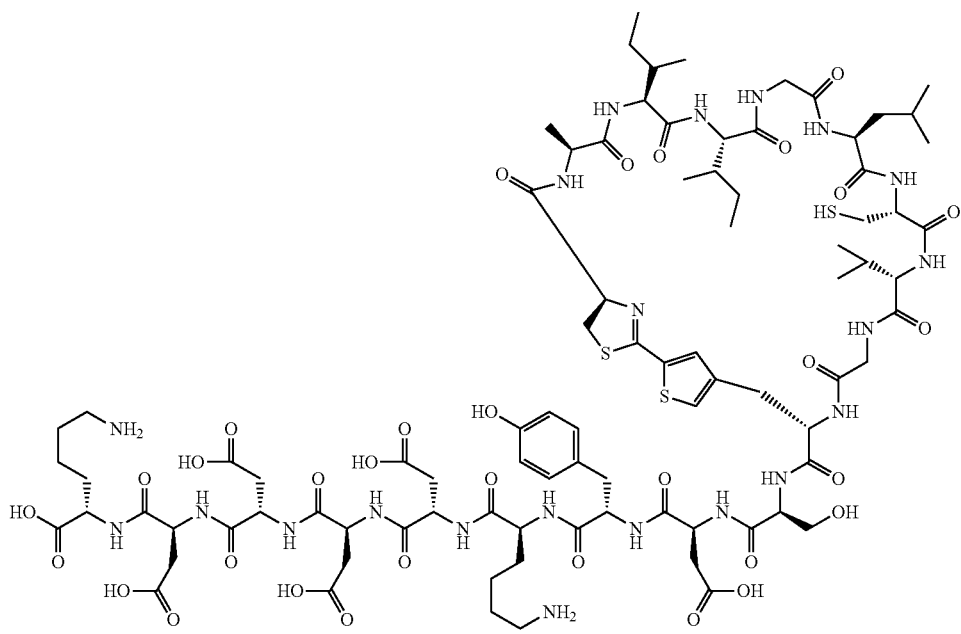 [SMILES: CCC(C)[C@@H]1NC(=O)[C@H](C)NC(=O)[C@@H]2CSC(=N2)c2cc(cs2)C[C@@H](C(=O)N[C@@H](CO)C(=O)N[C@@H](CC(=O)O)C(=O)N[C@@H](Cc2ccc(O)cc2)C(=O)N[C@@H](CCCCN)C(=O)N[C@@H](CC(=O)O)C(=O)N[C@@H](CC(=O)O)C(=O)N[C@@H](CC(=O)O)C(=O)N[C@@H](CC(=O)O)C(=O)N[C@@H](CCCCN)C(=O)O)NC(=O)CNC(=O)[C@H](C(C)C)NC(=O)[C@H](CS)NC(=O)[C@H](CC(C)C)NC(=O)CNC(=O)[C@H](C(C)CC)NC1=O]

The synthesis of cyclic peptide 1-57 was carried out in the same manner as the synthesis of cyclic peptide 1-1, using a combination of mRNA-13 and aminoacyl-tRNA-10.

MS(MALDI-TOF, m/z): 2090.9 (M+H)

General method for solid phase peptide synthesis by automated peptide synthesizer.

Solid phase peptide synthesis was carried out using an automated peptide synthesizer (SyroI, manufactured by Biotage AB). A Rink Amide-ChemMatrix (registered trademark, manufactured by Biotage AB), an N-methyl-2-pyrrolidone (NMP) solution of Fmoc amino acids (0.5 mol/L), an NMP solution of cyano-hydroxyimino-acetic acid ethyl ester (1.0 mol/L) and diisopropylethylamine (0.1 mol/L), an NMP solution of diisopropylcarbodiimide (1.0 mol/L), an NMP solution of piperidine (20% v/v), and an NMP solution of acetic anhydride (20% v/v) were set in the synthesizer, and synthesis was carried out according to the manual. The peptide chain was elongated by repeating a cycle of Fmoc deprotection (20 minutes), washing with NMP, condensation of Fmoc amino acids (1 hour), and washing with NMP in one cycle. The HPLC used in this section was a 1260 Infinity binary LC system (manufactured by Agilent Technologies, Inc.) or an LC system (manufactured by Waters Corporation).

Column: Waters X Select CSH130 C18 (10×250 mm) or Waters X Select CSH130 C18 (19×250 mm)

Column temperature: 40° C.

Flow rate: 4.0 mL/min (manufactured by Agilent Technologies, Inc.), 20 mL/min (manufactured by Waters Corporation)

Detection wavelength: 220 nm, 254 nm

Synthesis of Cyclic Peptide 2-1 (SEQ ID NO: 37)

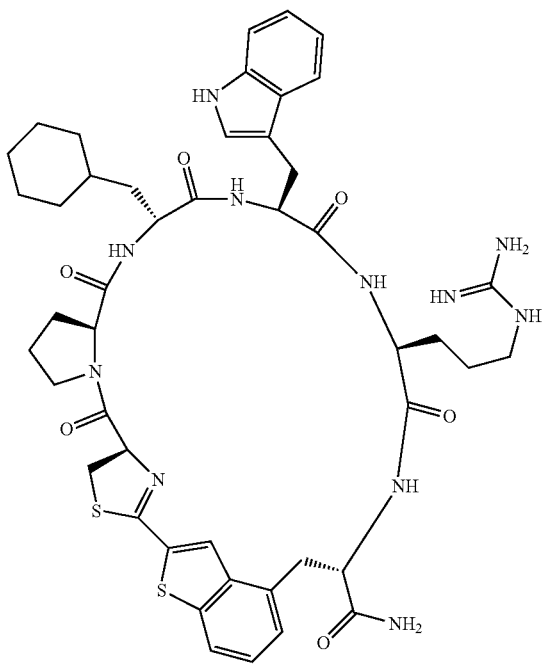 [SMILES: N=C(N)NCCC[C@@H]1NC(=O)[C@H](Cc2c[nH]c3ccccc23)NC(=O)[C@@H](CC2CCCCC2)NC(=O)[C@@H]2CCCN2C(=O)[C@@H]2CSC(=N2)c2cc3c(cccc3s2)C[C@@H](C(N)=O)NC1=O]

Solid phase peptide synthesis was carried out using 40 mg of Rink Amide-ChemMatrix (0.5 mmol/g) as a starting material. Condensation was carried out in the order of (S)-2-((((9H-fluoren-9-yl)methoxy)carbonyl)amino)-3-(2-cyanobenzo[b]thiophen-4-yl)propionic acid, N-α-(9-fluorenylmethoxycarbonyl)-N-(o-(2,2,4,6,7-pentamethyldihydrobenzofuran-5-sulfonyl)-L-arginine (Fmoc-Arg(Pbf)-OH), N-α-(9-fluorenylmethoxycarbonyl)-1-(t-butoxycarbonyl)-L-tryptophan (Fmoc-Trp(Boc)-OH), N-α-(9-fluorenylmethoxycarbonyl)-p-cyclohexyl-D-alanine (Fmoc-D-Cha-OH), N-(9-fluorenylmethoxycarbonyl)-L-proline (Fmoc-Pro-OH), and N-α-(t-butoxycarbonyl)-S-trityl-L-cysteine (Boc-Cys(Trt)-OH). After completion of the elongation, the resin was washed with dichloromethane and then the solvent was distilled off under reduced pressure. TFA:triisopropylsilane:water (=95:2.5:2.5, 2.0 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. HEPES buffer (pH 7.3, 2.5 mL) and methanol (0.5 mL) were added to the resulting solid, followed by reaction for 2 hours. The peptide was adsorbed to the carrier using Sep-pak C18 (available from Waters Corporation), followed by washing with water and elution with acetonitrile and methanol to remove salts. The solvent was distilled off under reduced pressure. The resulting residue was purified by HPLC (0.1% formic acid aqueous solution/ 0.1% formic acid acetonitrile solution) and then neutralized by adding a triethylammonium hydrogen carbonate solution (1.0 mol/L, pH 8.5). The solvent was distilled off under reduced pressure to give 0.91 mg of cyclic peptide 2-1 as a white solid.

MS(ESI m/z): 923.9 (M+H)
RT(min): 1.19

The compounds shown in Table 38 below were obtained in the same manner as the synthesis of cyclic peptide 2-1.

TABLE 38

(SEQ ID NO: 37)

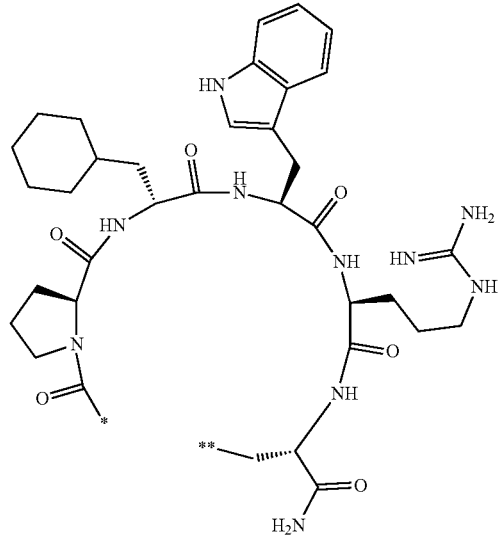

| Cyclic peptide No. | Structure | Observed MS | RT/min |
|---|---|---|---|
| 2-2 | (structure) | 924.2 | 1.18 |
| 2-3 | (structure) | 918.9 | 1.15 |
| 2-4 | (structure) | 919.2 | 1.12 |

TABLE 38-continued
(SEQ ID NO: 37)
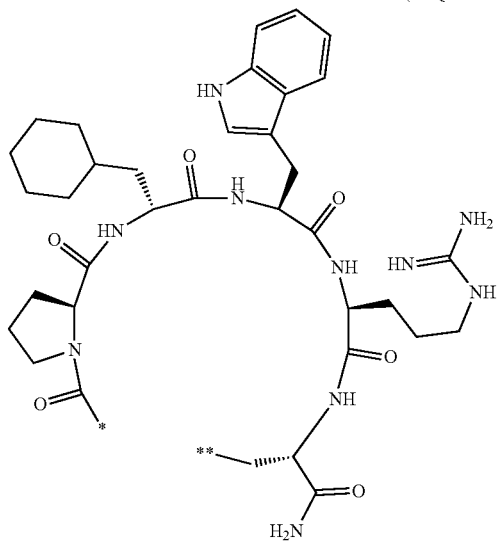
| Cyclic peptide No. | Structure | Observed MS | RT/min |
|---|---|---|---|
| 2-5 | 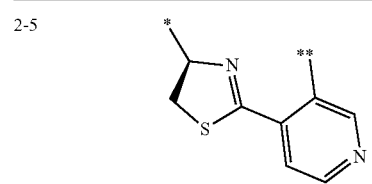 | 869.4 | 1.11 |
| 2-6 | 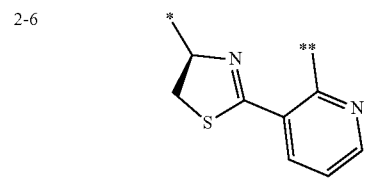 | 869.1 | 1.12 |
| 2-7 | 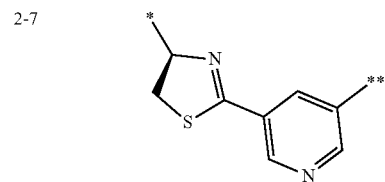 | 869.2 | 1.10 |
| 2-8 | 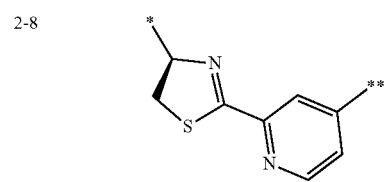 | 869.2 | 1.12 |
TABLE 38-continued
(SEQ ID NO: 37)
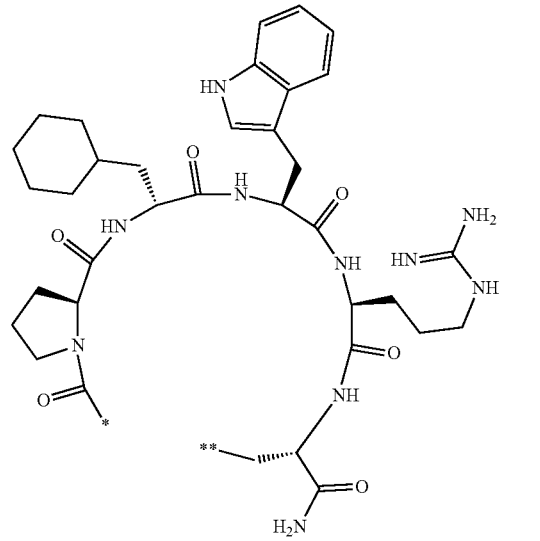
| Cyclic peptide No. | Structure | Observed MS | RT/min |
|---|---|---|---|
| 2-9 | 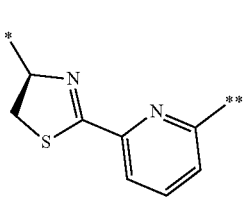 | 869.4 | 1.14 |
| 2-10 | 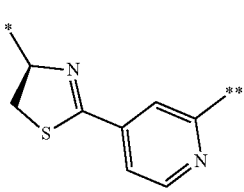 | 869.2 | 1.12 |
| 2-11 | 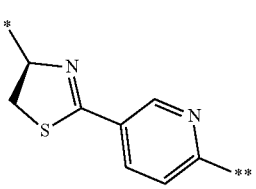 | 869.1 | 1.09 |
| 2-12 | 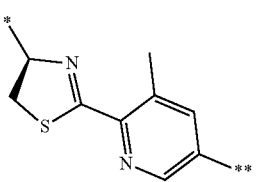 | 883.2 | 1.12 |

TABLE 38-continued
(SEQ ID NO: 37)
| Cyclic peptide No. | Structure | Observed MS | RT/min |
|---|---|---|---|
| 2-13 | 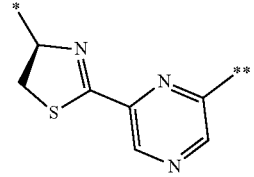 | 870.2 | 1.09 |
| 2-14 | 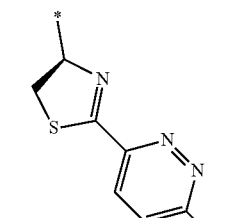 | 870.2 | 1.10 |
| 2-15 | 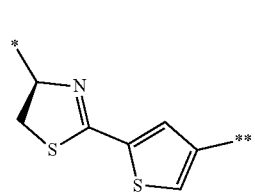 | 870.1 | 1.08 |
| 2-16 | 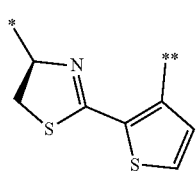 | 874.3 | 1.19 |
TABLE 38-continued
(SEQ ID NO: 37)
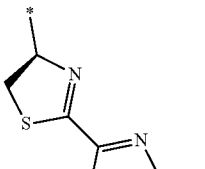
| Cyclic peptide No. | Structure | Observed MS | RT/min |
|---|---|---|---|
| 2-17 | 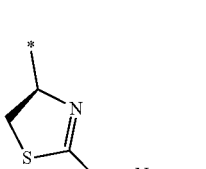 | 874.4 | 1.19 |
| 2-18 | 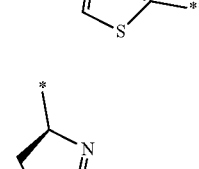 | 875.1 | 1.12 |
| 2-19 | 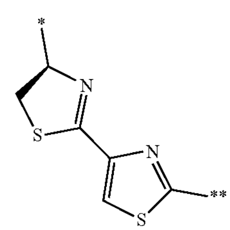 | 875.1 | 1.11 |
| 2-20 | 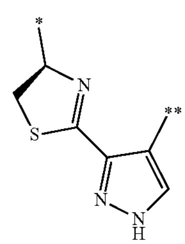 | 858.1 | 1.02 |

TABLE 38-continued (SEQ ID NO: 37)

| Cyclic peptide No. | Structure | Observed MS | RT/min |
|---|---|---|---|
| 2-21 | 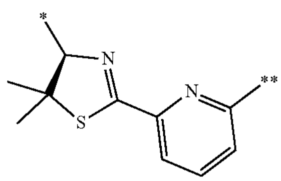 | 897.2 | 1.22 |
| 2-22 | 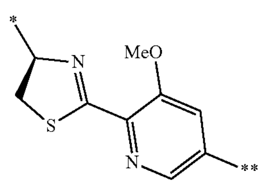 | 899.3 | 0.96 |
| 2-23 | 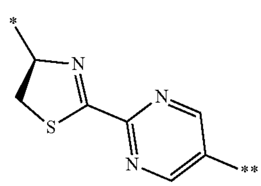 | 870.2 | 1.08 |
| 2-24 | 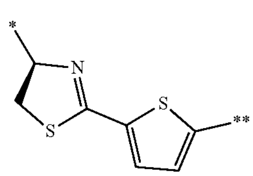 | 874.4 | 1.14 |

Synthesis of Cyclic Peptide 3-1 (SEQ ID NO: 37)

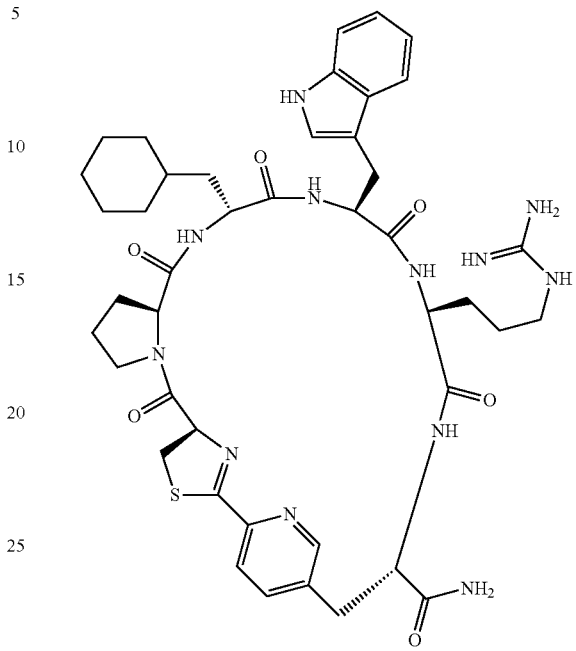

Solid phase peptide synthesis was carried out using 100 mg of Rink Amide-ChemMatrix (0.5 mmol/g) as a starting material. Condensation was carried out in the order of (S)-2-((((9H-fluoren-9-yl)methoxy)carbonyl)amino)-3-(6-cyanopyridin-3-yl)propionic acid, Fmoc-Arg(Pbf)-OH, Fmoc-Trp(Boc)-OH, Fmoc-D-Cha-OH, Fmoc-Pro-OH, and Boc-Cys(Trt)-OH. After completion of the elongation, the resin was washed with dichloromethane and then the solvent was distilled off under reduced pressure. TFA:triisopropylsilane:water (=95:2.5:2.5, 3.0 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. Phosphate buffer (pH 6.4, 5.0 mL) and acetonitrile (1.0 mL) were added to the resulting solid, followed by reaction for 2 hours. The peptide was adsorbed to the carrier using Sep-pak C18 (available from Waters Corporation), followed by washing with water and elution with acetonitrile and methanol to remove salts. The solvent was distilled off under reduced pressure. The resulting residue was purified by HPLC (0.1% formic acid aqueous solution/0.1% formic acid acetonitrile solution) and then neutralized by adding a triethylammonium hydrogen carbonate solution (1 mol/L, pH 8.5). The solvent was distilled off under reduced pressure to give 0.93 mg of cyclic peptide 3-1 as a colorless oil.

MS(ESI m/z): 869.2 (M+H)

RT(min): 1.09

The compounds shown in Table 39 below were obtained in the same manner as the synthesis of cyclic peptide 3-1.

TABLE 39

(SEQ ID NO: 37)

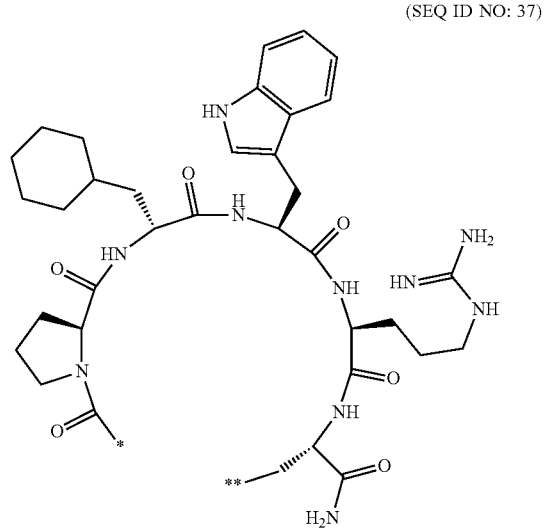

| Cyclic peptide No. | Structure | Observed MS | RT/min |
|---|---|---|---|
| 3-2 | 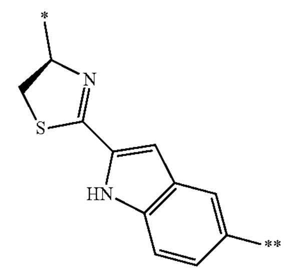 | 907.2 | 1.13 |
| 3-3 | 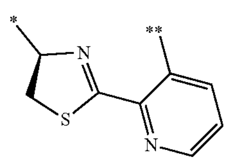 | 869.4 | 1.16 |
| 3-4 | 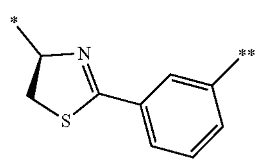 | 868.2 | 1.19 |
| 3-5 | 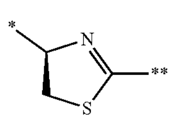 | 791.8 | 1.04 |

Synthesis of Cyclic Peptide 4-1 (SEQ ID NO: 38)

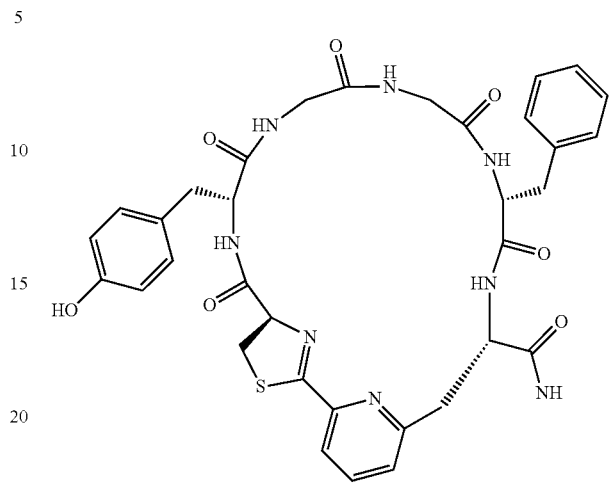

Solid phase peptide synthesis was carried out using 100 mg of Rink Amide-ChemMatrix (0.5 mmol/g) as a starting material. Condensation was carried out in the order of (S)-2-((((9H-fluoren-9-yl)methoxy)carbonyl)amino)-3-(6-cyanopyridin-2-yl)propionic acid, N-α-(9-fluorenylmethoxycarbonyl)-D-phenylalanine (Fmoc-D-Phe-OH), N-α-(9-fluorenylmethoxycarbonyl)glycine (Fmoc-Gly-OH), Fmoc-Gly-OH, N-α-(9-fluorenylmethoxycarbonyl)-O-(t-butyl)-D-tyrosine (Fmoc-D-Tyr (tBu)-OH), and Boc-Cys(Trt)-OH. After completion of the elongation, the resin was washed with dichloromethane and then the solvent was distilled off under reduced pressure. TFA:triisopropylsilane:water (=95:2.5:2.5, 3.0 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. HEPES buffer (pH 7.3, 5.0 mL), acetonitrile (1.0 mL), and an aqueous tris(2-carboxyethyl)phosphine (0.5 mol/L, 0.1 mL) solution were added to the resulting solid which was then stirred at room temperature for 2 hours and allowed to stand for 13 hours. The solution was concentrated under reduced pressure, and the resulting residue was purified by HPLC (0.1% formic acid aqueous solution/0.1% formic acid acetonitrile solution) and then neutralized by adding a triethylammonium hydrogen carbonate solution (1.0 M, pH 8.5). The solvent was distilled off under reduced pressure to give 2.61 mg of cyclic peptide 4-1 as a colorless oil.

MS(ESI m/z): 701.0 (M+H)

RT(min): 0.97

Cyclic peptides 4-2 to 7, and cyclic peptides 4-8 and 4-9 shown in Tables 40, 41, and 42 below were obtained in the same manner as the synthesis of cyclic peptide 4-1.

TABLE 40
(SEQ ID NO: 38)
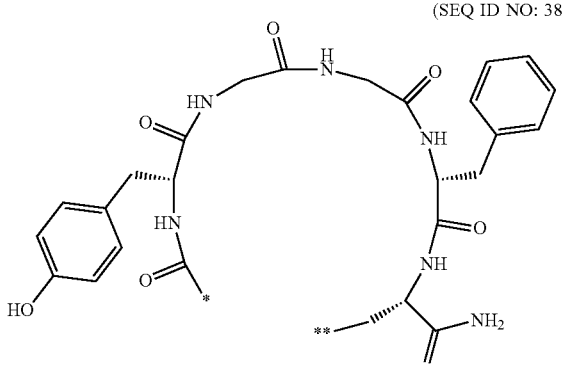
| Cyclic peptide No. | Structure | Observed MS | RT/min |
|---|---|---|---|
| 4-2 | 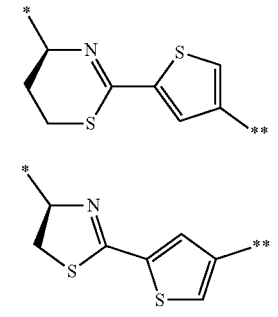 | 720.9 | 0.98 |
| 4-3 | 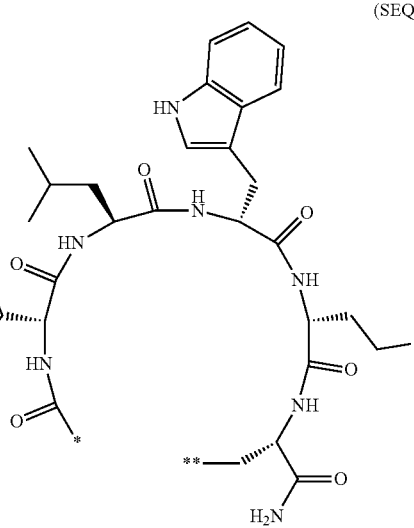 | 705.9 | 0.96 |
TABLE 41
(SEQ ID NO: 39)
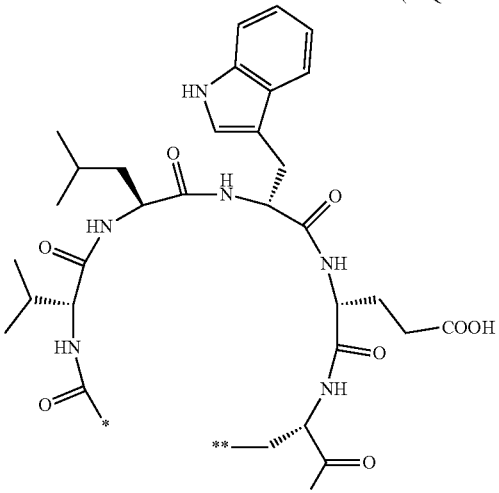
| Cyclic peptide No. | Structure | Observed MS | RT/min |
|---|---|---|---|
| 4-4 | 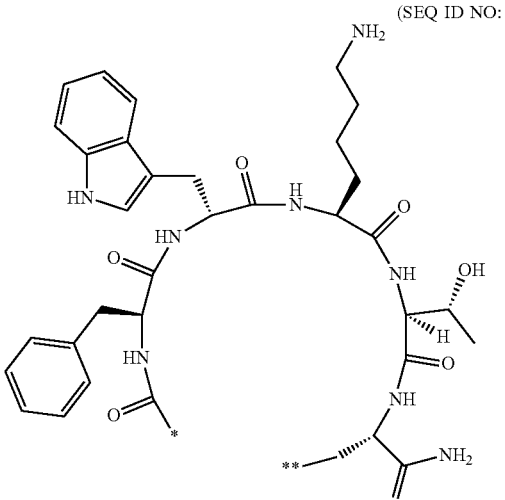 | 809.0 | 1.17 |
TABLE 41-continued
(SEQ ID NO: 39)
| Cyclic peptide No. | Structure | Observed MS | RT/min |
|---|---|---|---|
| 4-5 | 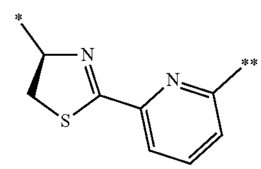 | 804.2 | 1.15 |
TABLE 42
(SEQ ID NO: 40)
| Cyclic peptide No. | Structure | Observed MS | RT/min |
|---|---|---|---|
| 4-6 | 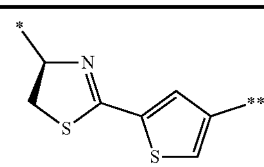 | 844.0 | 1.02 |

Cyclic peptide 4-9 (SEQ ID NO: 42)

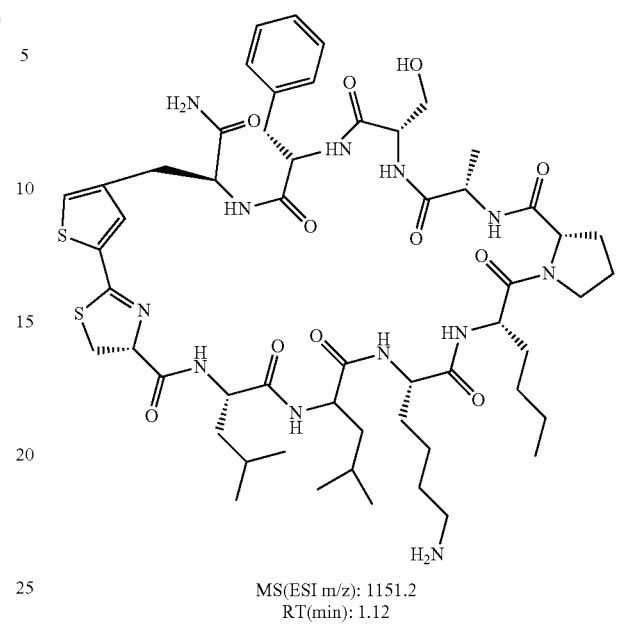

MS(ESI m/z): 1151.2
RT(min): 1.12

Synthesis of Cyclic Peptide 5-1 (SEQ ID NO: 43)

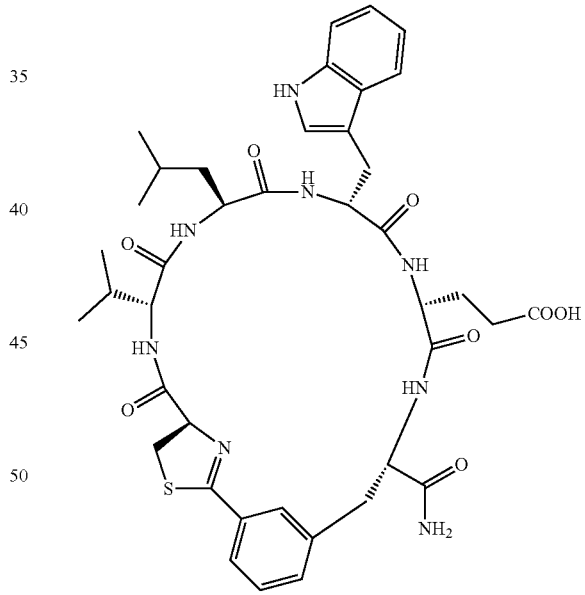

| Cyclic peptide No. | Structure | Observed MS | RT/min |
|---|---|---|---|
| 4-7 | 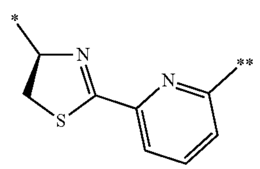 | 839.1 | 1.00 |

Cyclic peptide 4-8 (SEQ ID NO: 41)

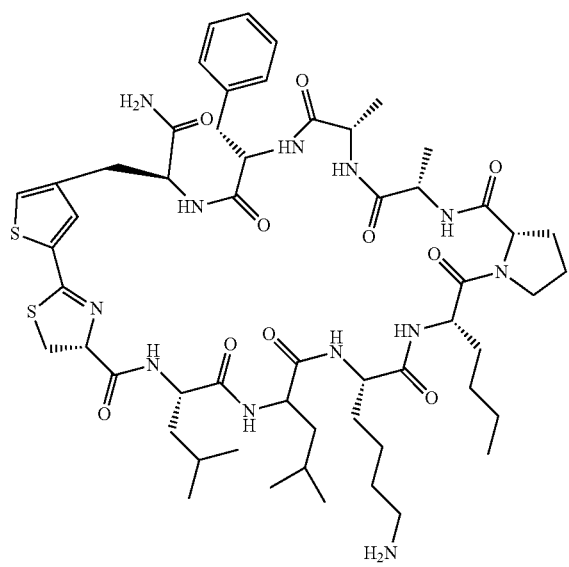

MS(ESI m/z): 1135.2
RT(min): 1.15

Solid phase peptide synthesis was carried out using 50 mg of Rink Amide-ChemMatrix (0.5 mmol/g) as a starting material. Condensation was carried out in the order of N-α-(9-fluorenylmethoxycarbonyl)-3-cyano-L-phenylalanine (Fmoc-Phe(3-CN)—OH), N-α-(9-fluorenylmethoxycarbonyl)-D-glutamic acid γ-t-butyl ester (Fmoc-D-Glu(OtBu)-OH), N-α-(9-fluorenylmethoxycarbonyl)-D-tryptophan (Fmoc-D-Trp-OH), N-α-(9-fluorenylmethoxycarbonyl)-L-leucine (Fmoc-Leu-OH), N-α-(9-fluorenylmethoxycarbonyl)-D-valine (Fmoc-D-Val-OH), and Boc-Cys(Trt)-OH. After completion of the elongation, the resin was washed with dichloromethane and then the solvent was distilled off under reduced pressure. TFA:

triisopropylsilane:water (=95:2.5:2.5, 3.0 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. Phosphate buffer (pH 6.4, 2.5 mL), methanol (1.0 mL), and an aqueous tris(2-carboxyethyl) phosphine (0.5 mol/L, 0.025 mL) solution were added to the resulting solid which was then stirred at room temperature for 42 hours. The peptide was adsorbed to the carrier using Sep-pak C18 (available from Waters Corporation), followed by washing with water and elution with acetonitrile and methanol to remove salts. The solvent was distilled off under reduced pressure, and the resulting residue was purified by HPLC (0.1% formic acid aqueous solution/0.1% formic acid acetonitrile solution) and then neutralized by adding a triethylammonium hydrogen carbonate solution (1.0 M, pH 8.5). The solvent was distilled off under reduced pressure to give 0.67 mg of cyclic peptide 5-1 as a colorless oil.

MS(ESI m/z): 802.9 (M+H)
RT(min): 1.21

Synthesis of Cyclic Peptide 6-1 (SEQ ID NO: 44)

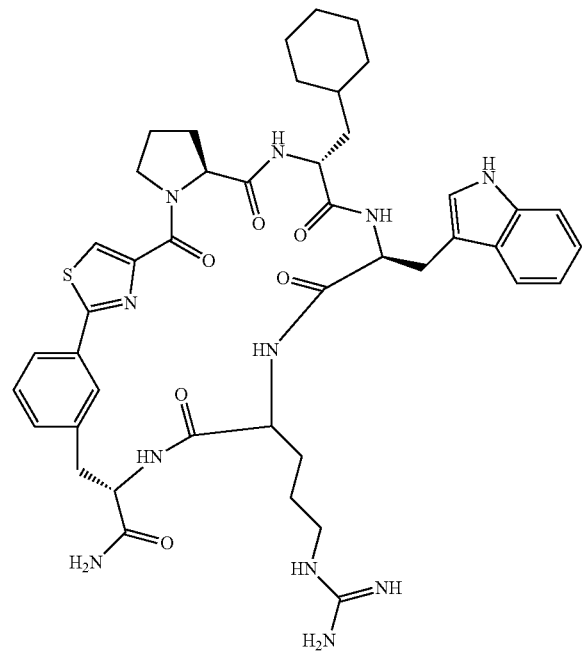 [SMILES: N=C(N)NCCCC1NC(=O)[C@H](Cc2c[nH]c3ccccc23)NC(=O)[C@@H](CC2CCCCC2)NC(=O)[C@@H]2CCCN2C(=O)c2csc(n2)-c2cccc(c2)C[C@@H](C(N)=O)NC1=O]

Solid phase peptide synthesis was carried out using 50 mg of Rink Amide-ChemMatrix (0.5 mmol/g) as a starting material. Condensation was carried out in the order of (S)-2-((((9H-fluoren-9-yl)methoxy)carbonyl)amino)-3-(6-(4-((allyloxy)carbonyl)thiazol-2-yl) pyridin-2-yl)propanoic acid, Fmoc-Arg(Pbf)-OH, Fmoc-Trp(Boc)-OH, Fmoc-D-Cha-OH, and Fmoc-Pro-OH. After peptide elongation, tetrakis(triphenylphosphine)palladium (0) (Pd(PPh$_3$)$_4$) (29 mg), and chloroform:acetic acid:N-methylmorpholine (=37:2:1, 1.5 mL) were added thereto, followed by reaction for 1 hour to remove the allyl group. An NMP solution of piperidine (20% v/v) was added thereto, followed by reaction for 20 minutes to remove an Fmoc group, and then O-(7-azabenzotriazol-1-yl)-N,N,N',N'-tetramethyluronium hexafluorophosphate (19 mg), diisopropylethylamine (17 μL), and 1-methyl-2-pyrrolidone (1.5 mL) were added thereto, followed by reaction for 2 hours to result in cyclization of the peptide. The resin was washed with dichloromethane and then the solvent was distilled off under reduced pressure. TFA:triisopropylsilane:water (=92.5:2.5:2.5, 2.0 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. The resulting residue was purified by HPLC (0.1% formic acid aqueous solution/0.1% formic acid acetonitrile solution) to give 0.91 mg of cyclic peptide 6-1 as a white solid.

MS(ESI m/z): 867.0 (M+H)
RT(min): 1.11

Synthesis of Cyclic Peptide a-1-1 (SEQ ID NO: 45)

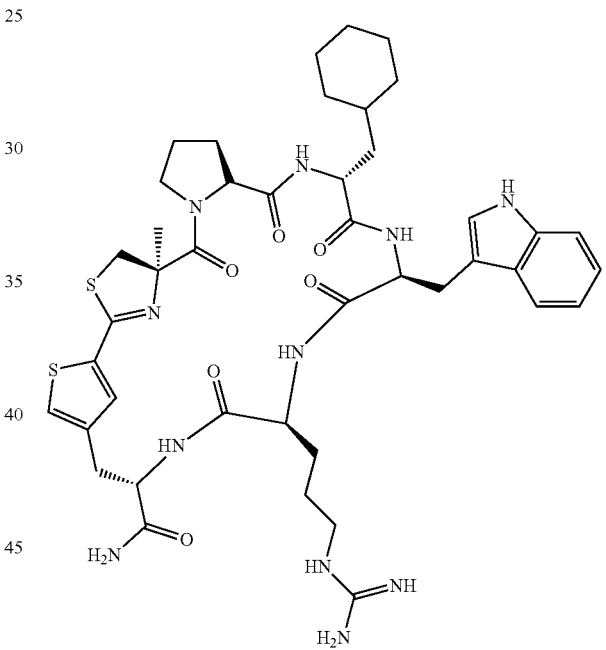

Solid phase peptide synthesis was carried out using 104 mg of Rink Amide-ChemMatrix (0.48 mmol/g) as a starting material. Condensation was carried out in the order of (S)-2-((((9H-fluoren-9-yl)methoxy)carbonyl)amino)-3-(5-cyanothiophen-3-yl)propanoic acid, Fmoc-Arg(Pbf)-OH, Fmoc-Trp(Boc)-OH, Fmoc-D-Cha-OH, Fmoc-Pro-OH, and N-(((9H-fluoren-9-yl)methoxy)carbonyl)-S-((4-methoxyphenyl)diphenyl methyl)-L-cysteine. After completion of the peptide elongation, an NMP solution of piperidine (20% v/v) was added thereto, followed by reaction for 20 minutes to remove the Fmoc group. The resin was washed with dichloromethane and then the solvent was distilled off under reduced pressure. TFA:3,6-dioxa-1,8-octanedithiol:triisopropylsilane:water (=92.5:2.5:2.5:2.5, 3.0 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. Phosphate buffer (pH 7.0, 5.0 mL), methanol (5.0 mL), and tris(2-carboxyethyl)phosphine (0.5 mol/L, 0.1 mL) were added to the resulting solid which was then stirred at room temperature for 1 hour. The solvent was distilled off under reduced pressure and the resulting residue was purified by HPLC (0.1% formic acid aqueous solution/ 0.1% formic acid acetonitrile solution) and then neutralized by adding a triethylammonium hydrogen carbonate solution (1 mol/L, pH 8.5). The solvent was distilled off under reduced pressure to give 2.63 mg of cyclic peptide a-1-1 as a white solid.

MS(ESI m/z): 888.2 (M+H)

RT(min): 1.12

Cyclic peptides a-1-2 to 18 shown in Table 43 below were obtained in the same manner as the synthesis of cyclic peptide a-1-1.

TABLE 43

(SEQ ID NO: 46)

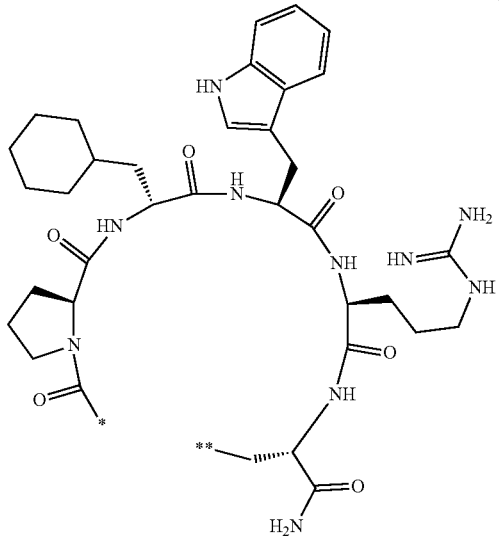

| Cyclic peptide No. | Structure | Observed MS | RT/min |
|---|---|---|---|
| a-1-2 | 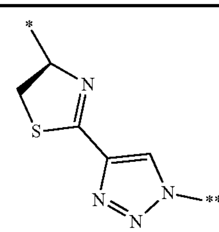 | 859.3 | 1.11 |
| a-1-3 | 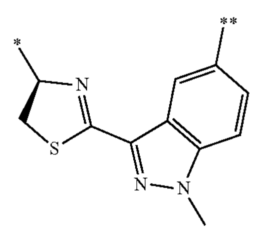 | 922 | 1.15 |
| a-1-4 | 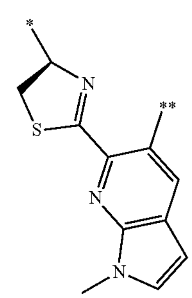 | 922 | 1.22 |

TABLE 43-continued
(SEQ ID NO: 46)
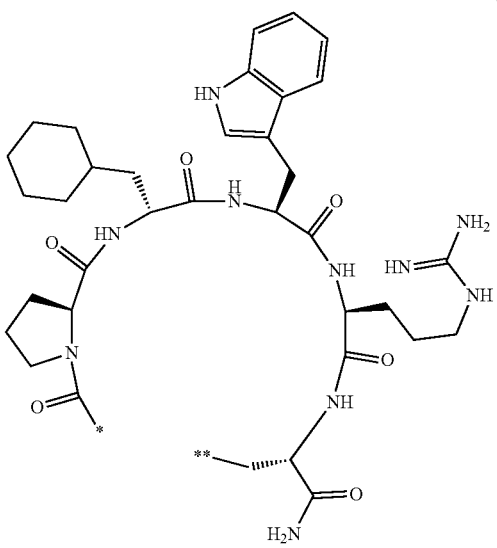
| Cyclic peptide No. | Structure | Observed MS | RT/ min |
|---|---|---|---|
| a-1-5 | 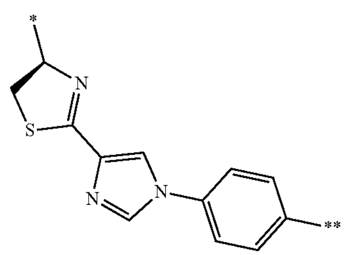 | 934.1 | 1.03 |
| a-1-6 | 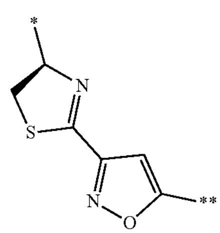 | 859.2 | 1.13 |
| a-1-7 | 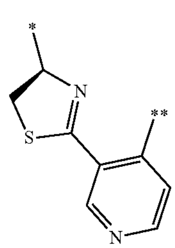 | 869.2 | 1.12 |

TABLE 43-continued
(SEQ ID NO: 46)
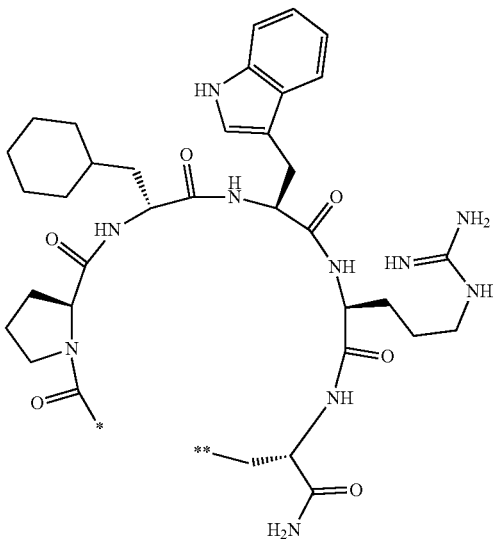
| Cyclic peptide No. | Structure | Observed MS | RT/ min |
|---|---|---|---|
| a-1-8 | 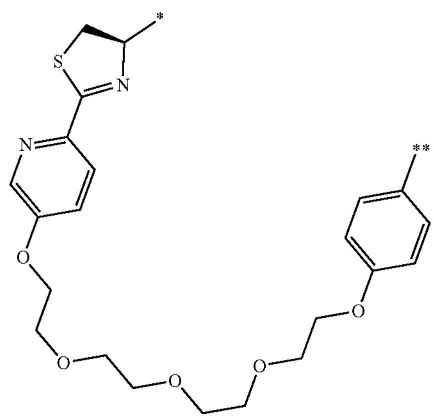 | 1137.3 | 1.30 |
| a-1-9 | 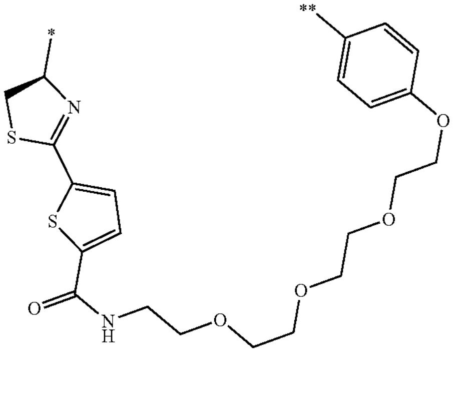 | 1169.2 | 1.27 |

TABLE 43-continued
(SEQ ID NO: 46)
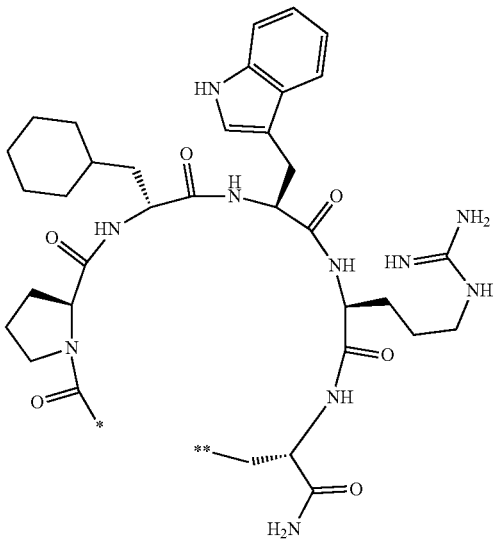
| Cyclic peptide No. | Structure | Observed MS | RT/min |
|---|---|---|---|
| a-1-10 | 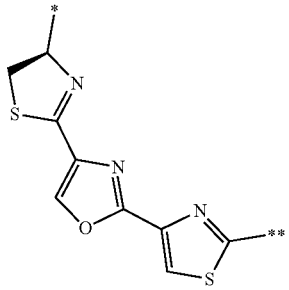 | 940.3 (M − H) | 1.15 |
| a-1-11 | 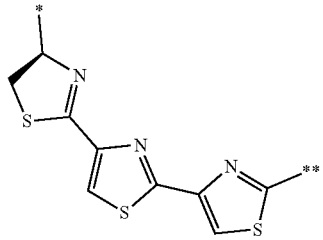 | 956.2 (M − H) | 1.15 |
| a-1-12 | 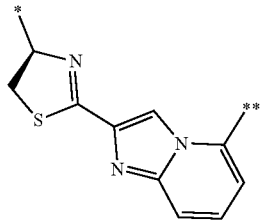 | 906.2 (M − H) | 1.11 |
| a-1-13 | 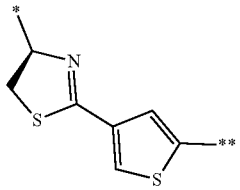 | 872.1 (M − H) | 1.15 |

TABLE 43-continued
(SEQ ID NO: 46)
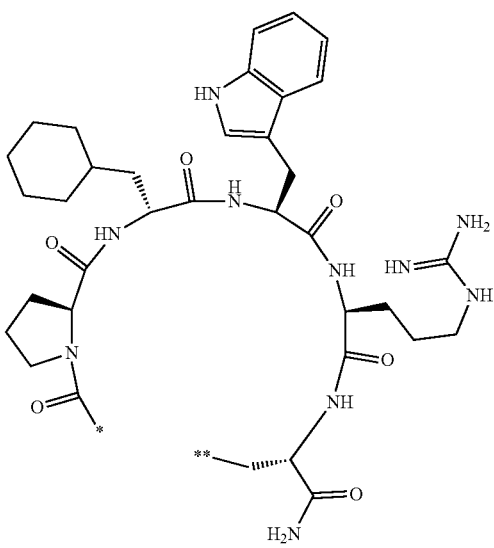
| Cyclic peptide No. | Structure | Observed MS | RT/ min |
|---|---|---|---|
| a-1-14 | 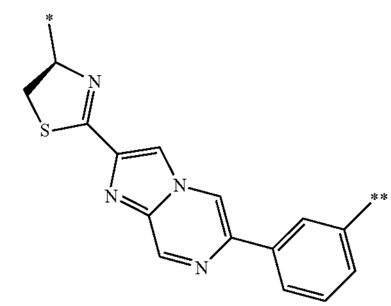 | 985.2 | 1.16 |
| a-1-15 | 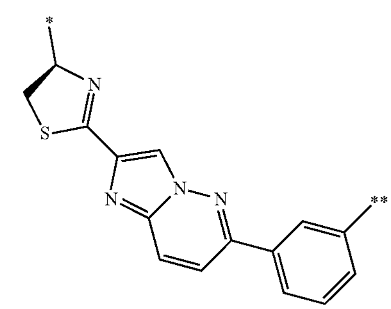 | 985.4 | 1.13 |
| a-1-16 | 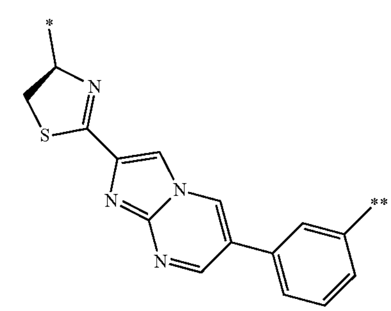 | 985.3 | 1.11 |

TABLE 43-continued
(SEQ ID NO: 46)
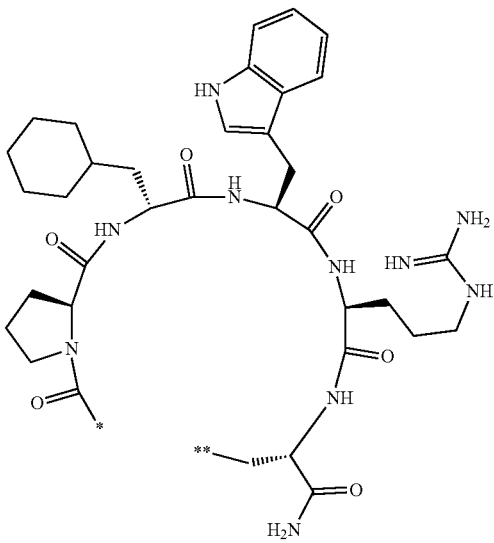
| Cyclic peptide No. | Structure | Observed MS | RT/min |
|---|---|---|---|
| a-1-17 | 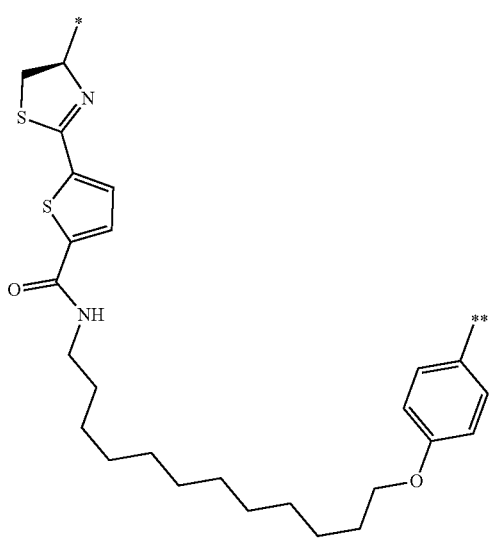 | 1177.3 | 1.69 |
| a-1-18 | 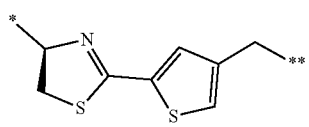 | 888.2 | 1.10 |

Cyclic Peptide a-1-19 (SEQ ID NO: 47)

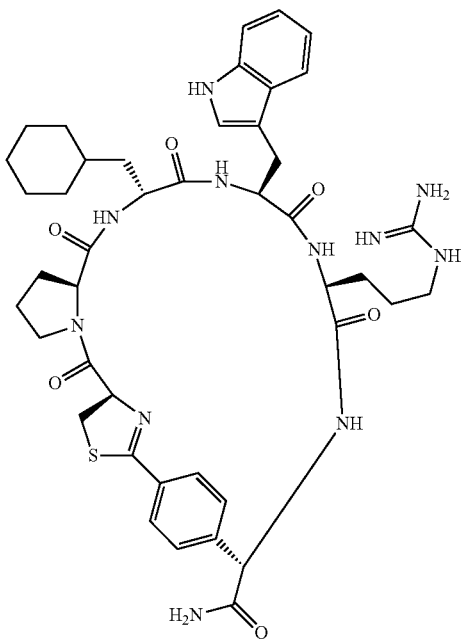 [SMILES: N=C(N)NCCC[C@@H]1NC(=O)[C@H](Cc2c[nH]c3ccccc23)NC(=O)[C@@H](CC2CCCCC2)NC(=O)[C@@H]2CCCN2C(=O)[C@@H]2CSC(=N2)c2ccc(cc2)[C@@H](C(N)=O)NC1=O]

The synthesis of cyclic peptide a-1-19 was carried out in the same manner as the synthesis of cyclic peptide a-1-1.
MS(ESI m/z): 854.1 (M+H)
RT(min): 1.14

Synthesis of Cyclic Peptide a-2-1 (SEQ ID NO: 48)

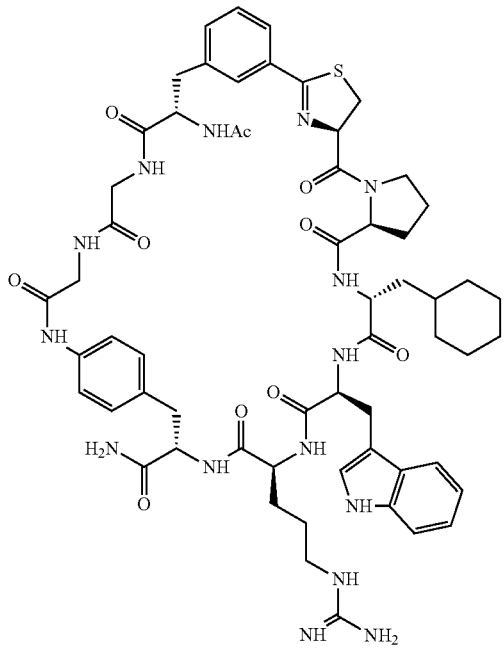 [SMILES: CC(=O)N[C@H]1Cc2cccc(c2)C2=N[C@@H](CS2)C(=O)N2CCC[C@H]2C(=O)N[C@H](CC2CCCCC2)C(=O)N[C@@H](Cc2c[nH]c3ccccc23)C(=O)N[C@@H](CCCNC(=N)N)C(=O)N[C@H](C(N)=O)Cc2ccc(cc2)NC(=O)CNC(=O)CNC1=O]

Solid phase peptide synthesis was carried out using 104 mg of Rink Amide-ChemMatrix (0.54 mmol/g) as a starting material. Condensation was carried out in the order of (S)-2-((((9H-fluoren-9-yl)methoxy)carbonyl)amino)-3-(4-((allyloxy)carbonyl)amino)phenyl)propanoic acid, Fmoc-Arg(Pbf)-OH, Fmoc-Trp(Boc)-OH, Fmoc-D-Cha-OH, Fmoc-Pro-OH, and Boc-Cys(Trt)-OH. After peptide elongation, Pd(PPh$_3$)$_4$ (58 mg), and chloroform:acetic acid:N-methylmorpholine (=37:2:1, 2.0 mL) were added thereto, followed by stirring for 1 hour to remove the Alloc group. Condensation was carried out in the order of Fmoc-Gly-OH, Fmoc-Gly-OH, and Fmoc-Phe(3-CN)—OH. An NMP solution of piperidine (20% v/v) was added thereto, followed by reaction for 20 minutes to deprotect the Fmoc group and an NMP solution of acetic anhydride (20% v/v) was added thereto, followed by reaction for 10 minutes to result in acetylation of the N-terminal amino group. The resin was washed with dichloromethane and then the solvent was distilled off under reduced pressure. TFA:triisopropylsilane:water (=95:2.5:2.5, 3.0 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. Phosphate buffer (pH 7.0, 5 mL), methanol (5 mL), and an aqueous tris(2-carboxyethyl)phosphine (0.5 mol/L, 0.1 mL) solution were added to the resulting solid, followed by reaction for 30 hours. The solvent was distilled off under reduced pressure. The resulting residue was purified by HPLC (0.1% formic acid aqueous solution/0.1% formic acid acetonitrile solution) and then neutralized by adding a triethylammonium hydrogen carbonate solution (1.0 mol/L, pH 8.5). The solvent was distilled off under reduced pressure to give 7.96 mg of cyclic peptide a-2-1 as a white solid.

MS(ESI m/z): 1184.2 (M−H)
RT(min): 1.11

Cyclic Peptide a-2-2

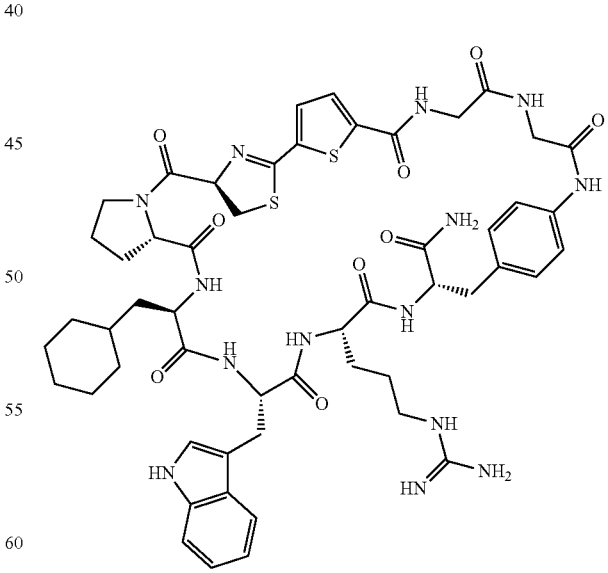

The synthesis of cyclic peptide a-2-2 was carried out in the same manner as the synthesis of cyclic peptide a-2-1.
MS(ESI m/z): 1107.3 (M+H)
RT(min): 1.17

Cyclic Peptide a-3-1 (SEQ ID NO: 49)

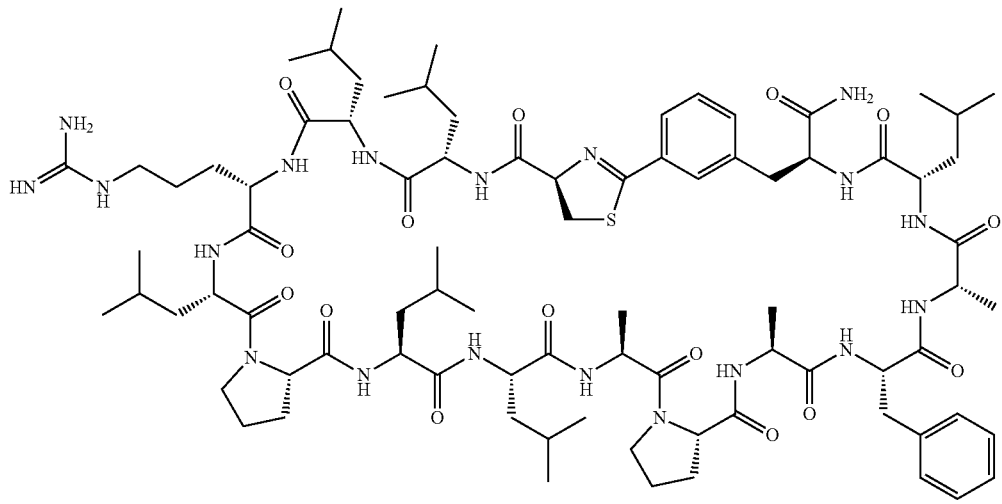 [SMILES: CC(C)C[C@@H]1NC(=O)[C@@H]2CSC(=N2)c2cccc(c2)C[C@@H](C(N)=O)NC(=O)[C@H](CC(C)C)NC(=O)[C@H](C)NC(=O)[C@H](Cc2ccccc2)NC(=O)[C@H](C)NC(=O)[C@@H]2CCCN2C(=O)[C@H](C)NC(=O)[C@H](CC(C)C)NC(=O)[C@H](CC(C)C)NC(=O)[C@@H]2CCCN2C(=O)[C@H](CC(C)C)NC(=O)[C@H](CCCNC(=N)N)NC(=O)[C@H](CC(C)C)NC1=O]

Solid phase peptide synthesis was carried out using 104 mg of Rink Amide-ChemMatrix (0.54 mmol/g) as a starting material. Condensation was carried out in the order of Fmoc-Phe(3-CN)—OH, N-(9-fluorenylmethoxycarbonyl)-L-leucine (Fmoc-Leu-OH), N-(9-fluorenylmethoxycarbonyl)-L-alanine (Fmoc-Ala-OH), N-(9-fluorenylmethoxycarbonyl)-L-phenylalanine (Fmoc-Phe-OH), Fmoc-Ala-OH, Fmoc-Pro-OH, Fmoc-Ala-OH, Fmoc-Leu-OH, Fmoc-Leu-OH, Fmoc-Pro-OH, Fmoc-Leu-OH, Fmoc-Arg(Pbf)-OH, Fmoc-Leu-OH, Fmoc-Leu-OH, and Boc-Cys(Trt)-OH. The resin was washed with dichloromethane and then the solvent was distilled off under reduced pressure. TFA:3,6-dioxa-1,8-octanedithiol:triisopropylsilane:water (=92.5:2.5:2.5:2.5, 3.0 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. Phosphate buffer (pH 7.0, 14 mL), methanol (15 mL), acetonitrile (4 mL), and an aqueous tris(2-carboxyethyl)phosphine (0.5 mol/L, 0.1 mL) solution were added to the resulting solid, followed by reaction for 38 hours. The solvent was distilled off under reduced pressure. The resulting residue was purified by HPLC (0.1% formic acid aqueous solution/0.1% formic acid acetonitrile solution) and then neutralized by adding a triethylammonium hydrogen carbonate solution (1.0 mol/L, pH 8.5). The solvent was distilled off under reduced pressure to give 8.05 mg of cyclic peptide a-3-1 as a white solid.

MS(ESI m/z): 1664.6 (M+H)
RT(min): 1.53

Cyclic Peptide a-3-2 (SEQ ID NO: 50)

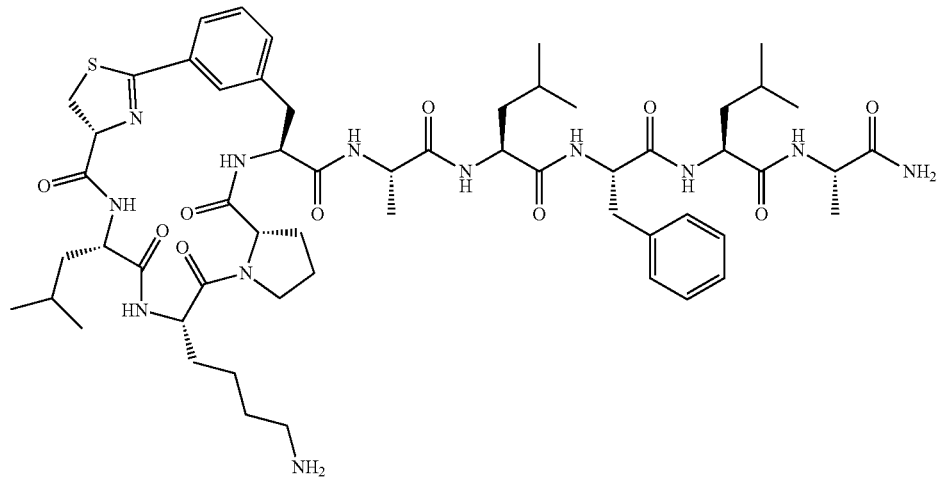 [SMILES: CC(C)C[C@@H]1NC(=O)[C@@H]2CSC(=N2)c2cccc(c2)C[C@@H](C(=O)N[C@@H](C)C(=O)N[C@@H](CC(C)C)C(=O)N[C@@H](Cc2ccccc2)C(=O)N[C@@H](CC(C)C)C(=O)N[C@@H](C)C(N)=O)NC(=O)[C@@H]2CCCN2C(=O)[C@H](CCCCN)NC1=O]

Cyclic peptide a-3-2 was obtained in the same manner as the synthesis of cyclic peptide a-3-1.

MS(ESI m/z): 1129.5 (M+H)

RT(min): 1.21

Cyclic Peptide a-4-1 (SEQ ID NO: 51)

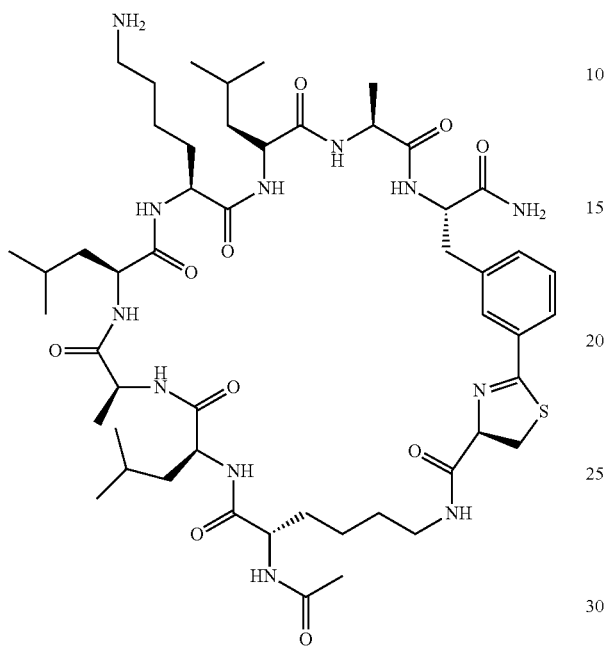

Solid phase peptide synthesis was carried out using 104 mg of Rink Amide-ChemMatrix (0.54 mmol/g) as a starting material. Condensation was carried out in the order of Fmoc-Phe(3-CN)—OH, Fmoc-Ala-OH, Fmoc-Leu-OH, Fmoc-Lys(Boc)-OH, Fmoc-Leu-OH, Fmoc-Ala-OH, Fmoc-Leu-OH, and N-α-(9-fluorenylmethoxycarbonyl)-N-ε-allyloxycarbonyl-L-lysine. An NMP solution of piperidine (20% v/v) was added thereto, followed by reaction for 20 minutes to deprotect the Fmoc group and an NMP solution of acetic anhydride (20% v/v) was added thereto, followed by reaction for 10 minutes to result in acetylation of the N-terminal amino group. Pd(PPh$_3$)$_4$ (58 mg) and chloroform:acetic acid:N-methylmorpholine (=37:2:1, 2.0 mL) were added thereto, followed by stirring for 1 hour to remove the Alloc group. After condensation of Boc-Cys(Trt)-OH, the resin was washed with dichloromethane and then the solvent was distilled off under reduced pressure. TFA:3,6-dioxa-1,8-octanedithiol:triisopropylsilane:water (=92.5:2.5:2.5:2.5, 3.0 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. Phosphate buffer (pH 7.0, 5 mL), methanol (5 mL), and an aqueous tris(2-carboxyethyl)phosphine (0.5 mol/L, 0.1 mL) solution were added to the resulting solid, followed by reaction for 30 hours. The solvent was distilled off under reduced pressure. The resulting residue was purified by HPLC (0.1% formic acid aqueous solution/0.1% formic acid acetonitrile solution) and then neutralized by adding a triethylammonium hydrogen carbonate solution (1.0 mol/L, pH 8.5). The solvent was distilled off under reduced pressure to give 0.24 mg of cyclic peptide a-4-1 as a white solid.

MS(ESI m/z): 1011.5 (M−H)

RT(min): 0.98

Cyclic Peptide 7-1

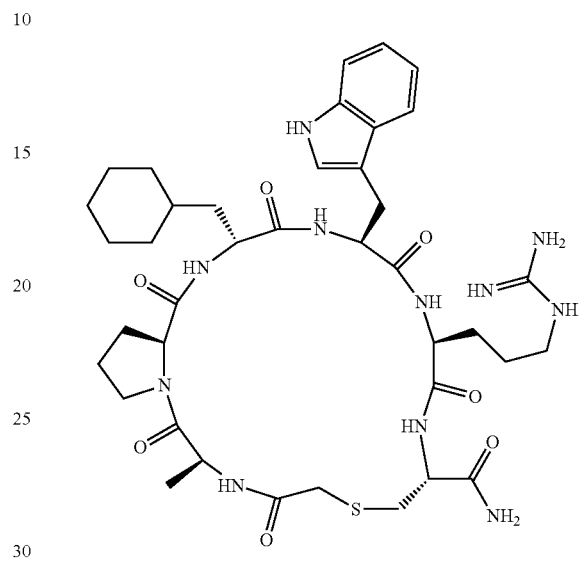

Solid phase peptide synthesis was carried out using 100 mg of Rink Amide-ChemMatrix (0.5 mmol/g) as a starting material. Condensation was carried out in the order of N-α-(9-fluorenylmethoxycarbonyl)-S-trityl-L-cysteine (Fmoc-Cys(Trt)-OH), Fmoc-Arg(Pbf)-OH, Fmoc-Trp(Boc)-OH, Fmoc-D-Cha-OH, Fmoc-Pro-OH, and Fmoc-Ala-OH. After peptide elongation, deprotection of the Fmoc group was carried out, and chloroacetic acid was condensed in the same manner as the condensation of amino acids. The resin was washed with dichloromethane and then the solvent was distilled off under reduced pressure. TFA:triisopropylsilane:water (=95:2.5:2.5, 3.0 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. HEPES buffer (pH 7.3, 5.0 mL) and acetonitrile (1.0 mL) were added to the resulting solid, followed by stirring at room temperature for 4 hours. The solvent was distilled off under reduced pressure. The resulting residue was purified by HPLC (0.1% TFA aqueous solution:0.1% TFA acetonitrile solution) to give 1.4 mg of cyclic peptide 7-1 as a white solid.

MS(ESI m/z): 824.4 (M+H)

RT(min): 1.09

The cyclic peptides shown in Table 44 below were obtained in the same manner as the synthesis of cyclic peptide 7-1.

TABLE 44

| Cyclic peptide No. | Structure | Observed MS | RT/min |
|---|---|---|---|
| 7-2 | 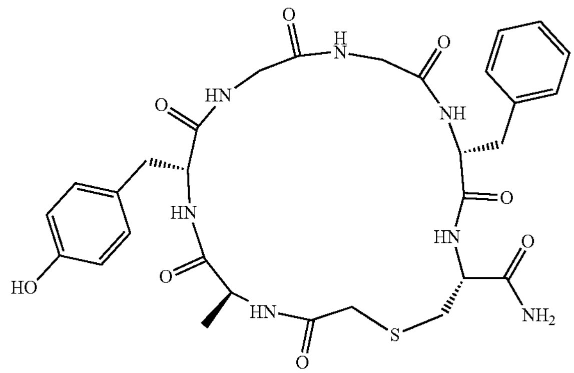 [SMILES: C[C@@H]1NC(=O)CSC[C@@H](C(N)=O)NC(=O)[C@@H](Cc2ccccc2)NC(=O)CNC(=O)CNC(=O)[C@@H](Cc2ccc(O)cc2)NC1=O] | 656.1 | 0.79 |
| 7-3 | 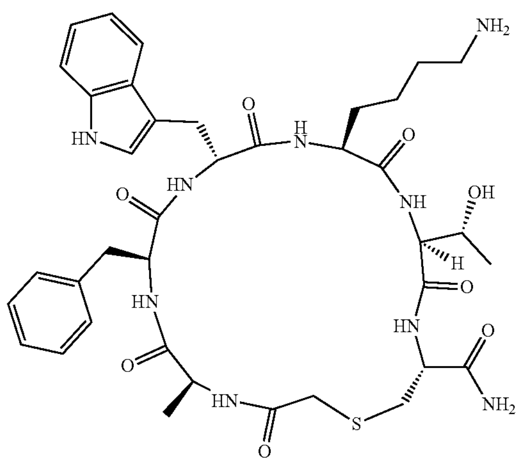 [SMILES: C[C@@H]1NC(=O)CSC[C@@H](C(N)=O)NC(=O)[C@H]([C@@H](C)O)NC(=O)[C@H](CCCCN)NC(=O)[C@@H](Cc2c[nH]c3ccccc23)NC(=O)[C@H](Cc2ccccc2)NC1=O] | 795.0 | 0.87 |
| 7-4 | 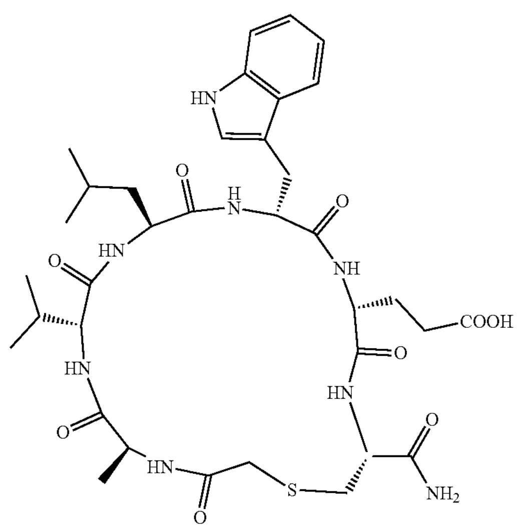 [SMILES: CC(C)C[C@@H]1NC(=O)[C@@H](C(C)C)NC(=O)[C@H](C)NC(=O)CSC[C@@H](C(N)=O)NC(=O)[C@@H](CCC(=O)O)NC(=O)[C@@H](Cc2c[nH]c3ccccc23)NC1=O] | 759.2 | 1.12 |

TABLE 44-continued
| Cyclic peptide No. | Structure | Observed MS | RT/min |
|---|---|---|---|
| 7-5 | 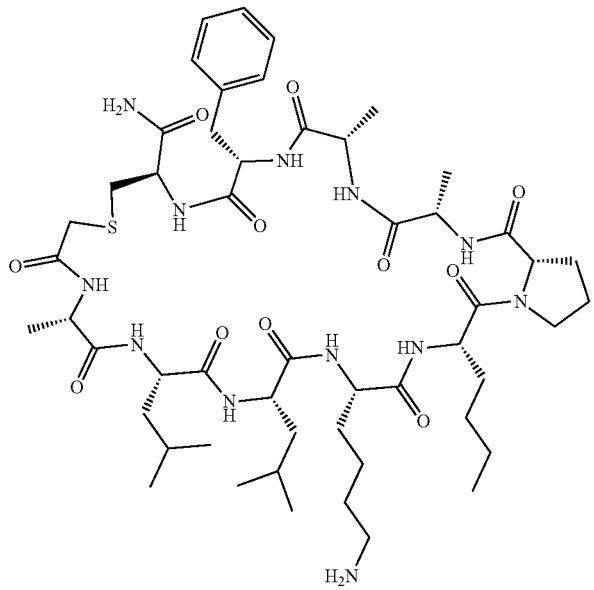 [SMILES: CCCC[C@@H]1NC(=O)[C@H](CCCCN)NC(=O)[C@H](CC(C)C)NC(=O)[C@H](CC(C)C)NC(=O)[C@H](C)NC(=O)CSC[C@@H](C(N)=O)NC(=O)[C@H](Cc2ccccc2)NC(=O)[C@H](C)NC(=O)[C@H](C)NC(=O)[C@@H]2CCCN2C1=O] (SEQ ID NO: 52) | 1085.2 | 1.10 |
| 7-6 | 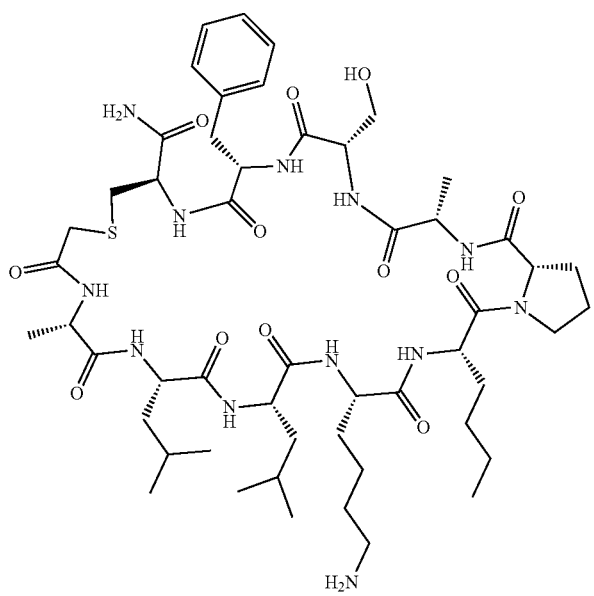 [SMILES: CCCC[C@@H]1NC(=O)[C@H](CCCCN)NC(=O)[C@H](CC(C)C)NC(=O)[C@H](CC(C)C)NC(=O)[C@H](C)NC(=O)CSC[C@@H](C(N)=O)NC(=O)[C@H](Cc2ccccc2)NC(=O)[C@H](CO)NC(=O)[C@H](C)NC(=O)[C@@H]2CCCN2C1=O] | 1101.5 | 1.08 |

Cyclic Peptide 8-1 (SEQ ID NO: 53)

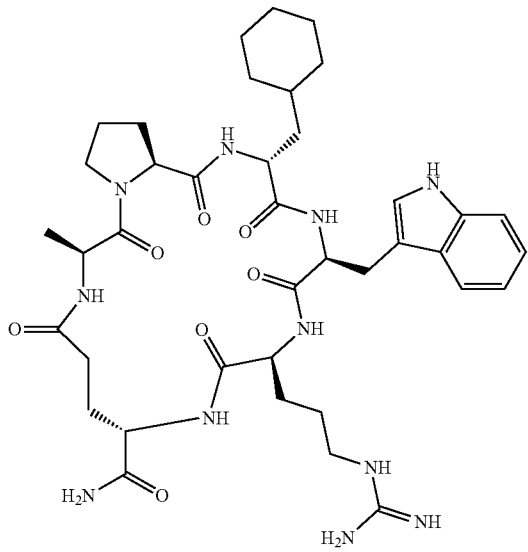 [SMILES: C[C@@H]1NC(=O)CC[C@@H](C(N)=O)NC(=O)[C@H](CCCNC(=N)N)NC(=O)[C@H](Cc2c[nH]c3ccccc23)NC(=O)[C@@H](CC2CCCCC2)NC(=O)[C@@H]2CCCN2C1=O]

Solid phase peptide synthesis was carried out using 100 mg of Rink Amide-ChemMatrix (0.5 mmol/g) as a starting material. Condensation was carried out in the order of N-α-(9-fluorenylmethoxycarbonyl)-L-glutamic acid γ-allyl ester (Fmoc-Glu(OAl)—OH), Fmoc-Arg(Pbf)-OH, Fmoc-Trp(Boc)-OH, Fmoc-D-Cha-OH, Fmoc-Pro-OH, and Fmoc-Ala-OH. After peptide elongation, (Pd(PPh$_3$)$_4$ (58 mg), and chloroform:acetic acid:N-methylmorpholine (=37:2:1, 2.0 mL) were added thereto, followed by stirring for 1 hour to remove the side chain allyl group. An NMP solution of piperidine (20% v/v) was added thereto, followed by reaction for 20 minutes to remove an Fmoc group. O-(7-azabenzotriazol-1-yl)-N,N,N',N'-tetramethyluronium hexafluorophosphate (57 mg), diisopropylethylamine (52 μL), and NMP (3.0 mL) were added thereto, followed by reaction at room temperature for 2 hours to result in cyclization of the peptide. The resin was washed with dichloromethane and then the solvent was distilled off under reduced pressure. TFA:triisopropylsilane:water (=95:2.5:2.5, 3.0 mL) was added at room temperature to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. The resulting residue was purified by HPLC (0.1% TFA aqueous solution/0.1% TFA acetonitrile solution) to give 7.1 mg of cyclic peptide 8-1 as a white solid.

MS(ESI m/z): 792.4 (M+H)
RT(min): 1.02

The cyclic peptides shown in Table 45 below were obtained in the same manner as the synthesis of cyclic peptide 8-1.

TABLE 45

| (SEQ ID NOS: 54 and 55) | | | |
|---|---|---|---|
| Cyclic peptide No. | Structure | Observed MS | RT/min |
| 8-2 | | 624.3 | 0.76 |

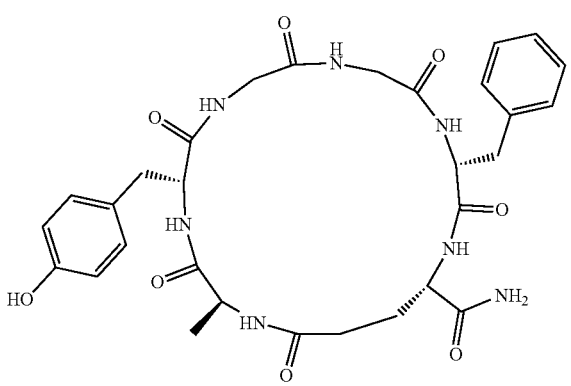 [SMILES: C[C@@H]1NC(=O)CC[C@@H](C(N)=O)NC(=O)[C@@H](Cc2ccccc2)NC(=O)CNC(=O)CNC(=O)[C@@H](Cc2ccc(O)cc2)NC1=O]

TABLE 45-continued (SEQ ID NOS: 54 and 55)

| Cyclic peptide No. | Structure | Observed MS | RT/min |
|---|---|---|---|
| 8-3 | 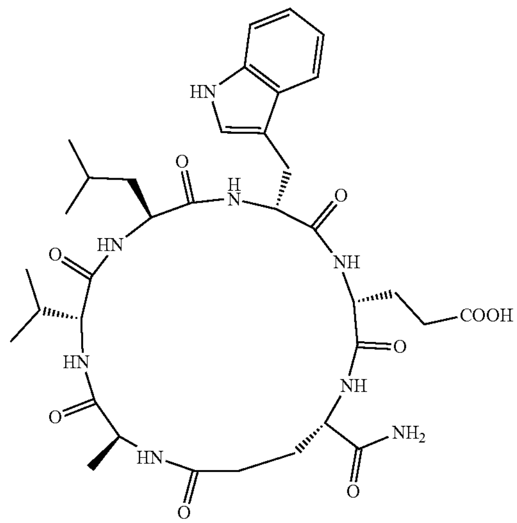 [SMILES: CC(C)C[C@@H]1NC(=O)[C@@H](C(C)C)NC(=O)[C@H](C)NC(=O)CC[C@@H](C(N)=O)NC(=O)[C@@H](CCC(=O)O)NC(=O)[C@@H](Cc2c[nH]c3ccccc23)NC1=O] | 727.1 | 1.11 |

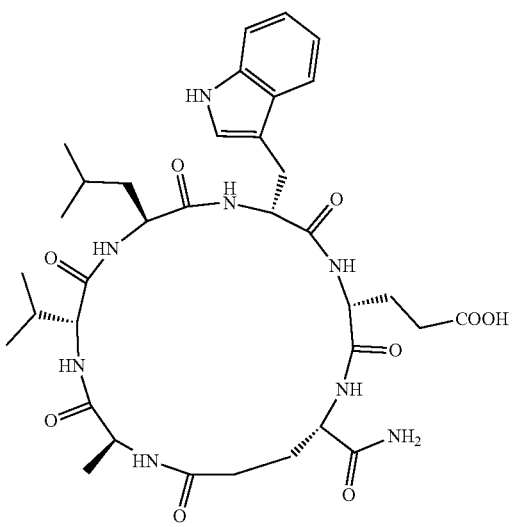

Cyclic Peptide 9-1 (SEQ ID NO: 56)

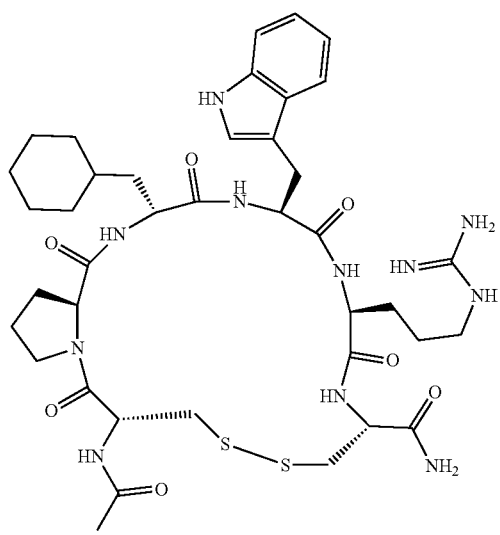 [SMILES: CC(=O)N[C@H]1CSSC[C@@H](C(N)=O)NC(=O)[C@H](CCCNC(=N)N)NC(=O)[C@H](Cc2c[nH]c3ccccc23)NC(=O)[C@@H](CC2CCCCC2)NC(=O)[C@@H]2CCCN2C1=O]

Solid phase peptide synthesis was carried out using 100 mg of Rink Amide-ChemMatrix (0.5 mmol/g) as a starting material. The peptide chain elongation was carried out in the order of Fmoc-Cys(Trt)-OH, Fmoc-Arg(Pbf)-OH, Fmoc-Trp(Boc)-OH, Fmoc-D-Cha-OH, Fmoc-Pro-OH, and Fmoc-Cys(Trt)-OH. Then, an NMP solution of piperidine (20% v/v) was added thereto, followed by reaction for 20 minutes to deprotect the Fmoc group and an NMP solution of acetic anhydride (20% v/v) was added thereto, followed by reaction for 10 minutes to result in acetylation of the N-terminal amino group. The resin was washed with dichloromethane and then the solvent was distilled off under reduced pressure. TFA:3,6-dioxa-1,8-octanedithiol:triisopropylsilane:water (=92.5:2.5:2.5:2.5, 3.0 mL) was added to the reaction solution to carry out cleavage and deprotection of the peptide. After 2 hours, the resin was filtered off, and methyl-t-butyl ether (12 mL) was added to the filtrate to give a solid. After centrifugation to precipitate the solid, the supernatant was removed. After washing the solid with methyl-t-butyl ether, the solvent was distilled off under reduced pressure. Following the addition of acetonitrile (20 mL) and water (20 mL), a triethylammonium hydrogen carbonate solution (1.0 mol/L, pH 8.5) was added little by little to adjust the pH of the reaction solution to 8.0. Subsequently, an acetonitrile solution of iodine (0.1 mol/L) was added at room temperature until the color of iodine disappeared, thus resulting in the formation of a disulfide bond. After 30 minutes, sodium ascorbate was added until the color of iodine disappeared, and the solvent was distilled off under reduced pressure. The residue was purified by HPLC (0.1% TFA aqueous solution/ 0.1% TFA acetonitrile solution) to give 7.0 mg of cyclic peptide 9-1 as a white solid.

MS(ESI m/z): 856.4 (M+H)

RT(min): 1.15

The cyclic peptides shown in Table 46 below were obtained in the same manner as the synthesis of cyclic peptide 9-1.

TABLE 46
(SEQ ID NOS: 57 to 59)
| Cyclic peptide No. | Structure | Observed MS | RT/min |
|---|---|---|---|
| 9-2 | 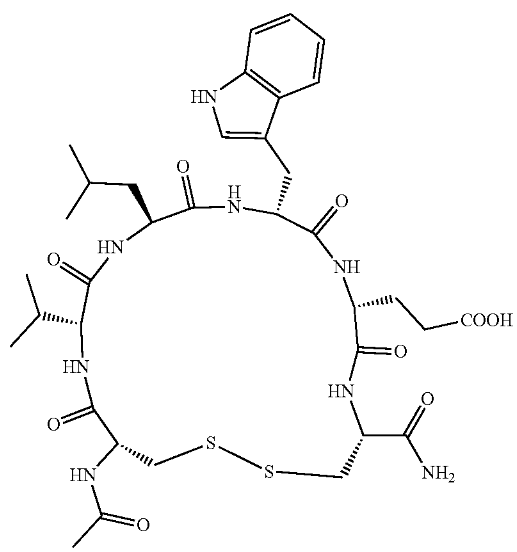 [SMILES: CC(=O)N[C@H]1CSSC[C@@H](C(N)=O)NC(=O)[C@@H](CCC(=O)O)NC(=O)[C@@H](Cc2c[nH]c3ccccc23)NC(=O)[C@H](CC(C)C)NC(=O)[C@@H](C(C)C)NC1=O] | 791.2 | 1.18 |
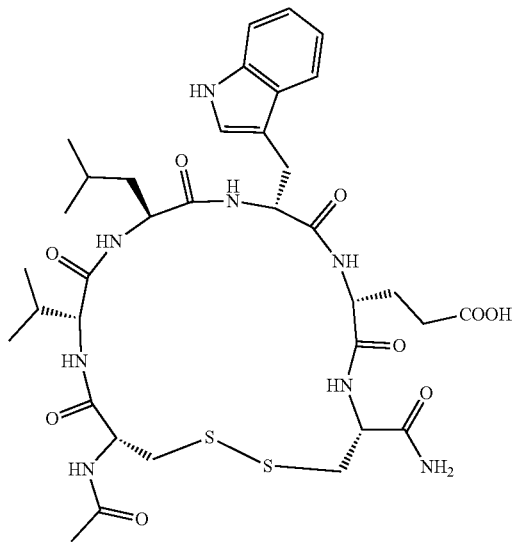
| | | | |
|---|---|---|---|
| 9-3 | | 825.9 | 0.91 |
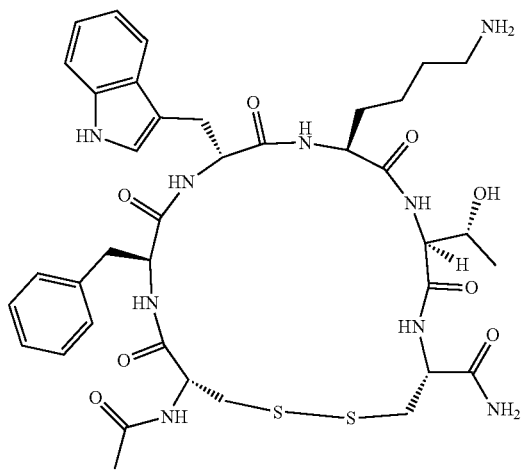 [SMILES: CC(=O)N[C@H]1CSSC[C@@H](C(N)=O)NC(=O)[C@H]([C@@H](C)O)NC(=O)[C@H](CCCCN)NC(=O)[C@@H](Cc2c[nH]c3ccccc23)NC(=O)[C@H](Cc2ccccc2)NC1=O]

TABLE 46-continued (SEQ ID NOS: 57 to 59)

| Cyclic peptide No. | Structure | Observed MS | RT/min |
|---|---|---|---|
| 9-4 | 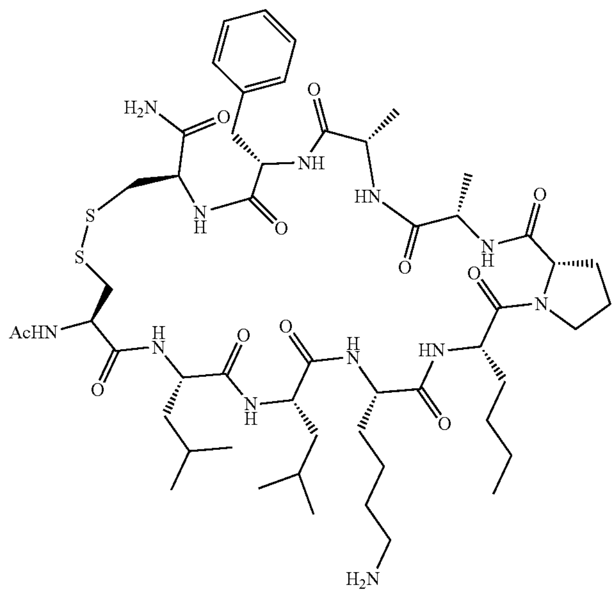 | 1117.2 | 1.08 |

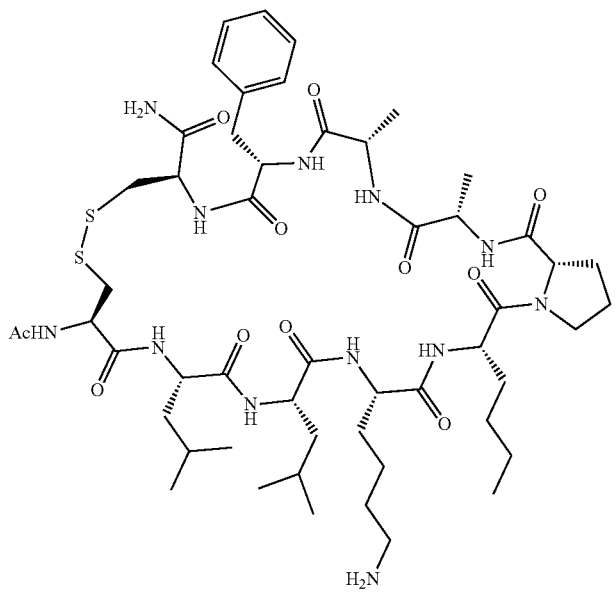 [SMILES: CCCC[C@@H]1NC(=O)[C@H](CCCCN)NC(=O)[C@H](CC(C)C)NC(=O)[C@H](CC(C)C)NC(=O)[C@@H](NC(C)=O)CSSC[C@@H](C(N)=O)NC(=O)[C@H](Cc2ccccc2)NC(=O)[C@H](C)NC(=O)[C@H](C)NC(=O)[C@@H]2CCCN2C1=O]

Cyclic Peptide 10-1 (SEQ ID NO: 60)

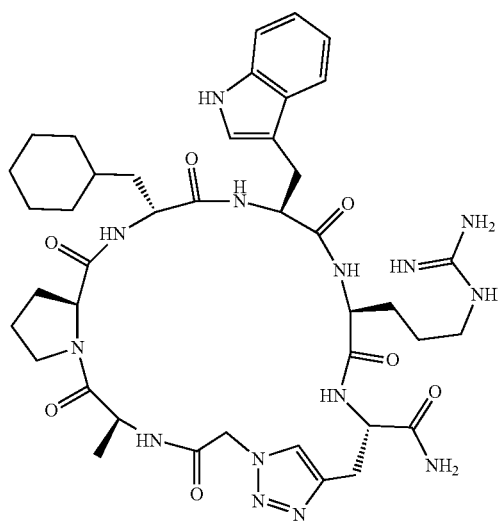 [SMILES: C[C@@H]1NC(=O)Cn2cc(nn2)C[C@@H](C(N)=O)NC(=O)[C@H](CCCNC(=N)N)NC(=O)[C@H](Cc2c[nH]c3ccccc23)NC(=O)[C@@H](CC2CCCCC2)NC(=O)[C@@H]2CCCN2C1=O]

Solid phase peptide synthesis was carried out using 80 mg of Rink Amide-ChemMatrix (0.5 mmol/g) as a starting material. The peptide elongation was carried out in the order of N-α-(9-fluorenylmethoxycarbonyl)-L-propargylglycine (Fmoc-Pra-OH), Fmoc-Arg(Pbf)-OH, Fmoc-Trp(Boc)-OH, Fmoc-D-Cha-OH, Fmoc-Pro-OH, and Fmoc-Ala-OH. Then, an NMP solution of piperidine (20% v/v) was added thereto, followed by reaction for 20 minutes to deprotect the N-terminal Fmoc group. Azidoacetic acid was condensed in the same manner as the condensation of amino acids. Copper iodide (7.6 mg), diisopropylethylamine (34.4 μL), tris[(1-benzyl-1H-1,2,3-triazol-4-yl)methyl]amine (6.4 mg), and NMP (2.0 mL) were added thereto, followed by stirring at room temperature for 1 hour to result in cyclization of the peptide. The resin was washed with dichloromethane and then the solvent was distilled off under reduced pressure. TFA:triisopropylsilane:water (=95:2.5:2.5, 2.4 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. The resulting residue was purified by HPLC (0.1% TFA aqueous solution/0.1% TFA acetonitrile solution) to give 1.26 mg of cyclic peptide 10-1 as a white solid.

MS(ESI m/z): 859.0 (M+H)

RT(min): 1.05

The cyclic peptides shown in Table 47 below were obtained in the same manner as the synthesis of cyclic peptide 10-1.

TABLE 47

(SEQ ID NOS: 61 to 63)

| Cyclic peptide No. | Structure | Observed MS | RT/min |
|---|---|---|---|
| 10-2 | 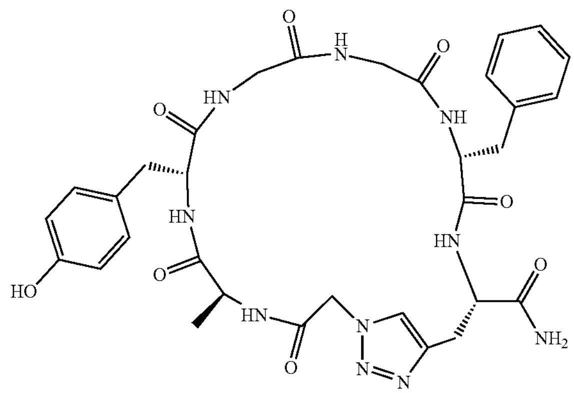 [SMILES: C[C@@H]1NC(=O)Cn2cc(nn2)C[C@@H](C(N)=O)NC(=O)[C@@H](Cc2ccccc2)NC(=O)CNC(=O)CNC(=O)[C@@H](Cc2ccc(O)cc2)NC1=O] | 691.0 | 0.78 |
| 10-3 | 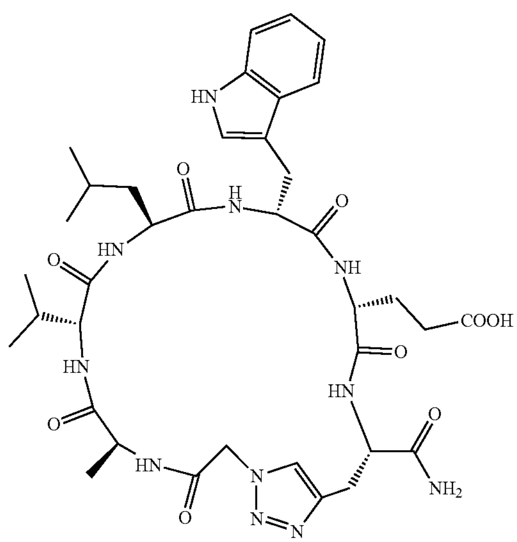 [SMILES: CC(C)C[C@@H]1NC(=O)[C@@H](C(C)C)NC(=O)[C@H](C)NC(=O)Cn2cc(nn2)C[C@@H](C(N)=O)NC(=O)[C@@H](CCC(=O)O)NC(=O)[C@@H](Cc2c[nH]c3ccccc23)NC1=O] | 794.0 | 1.10 |
| 10-4 | 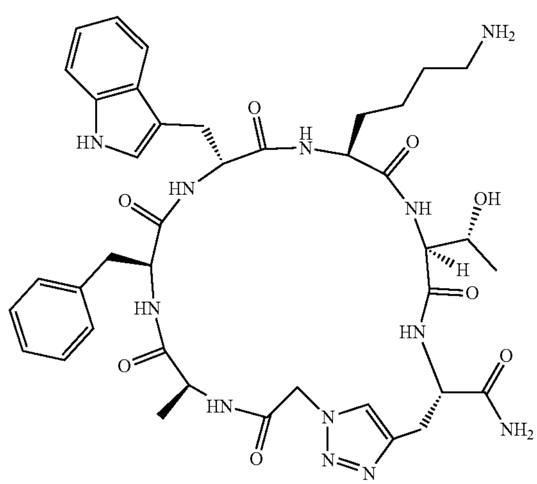 [SMILES: C[C@@H]1NC(=O)Cn2cc(nn2)C[C@@H](C(N)=O)NC(=O)[C@H]([C@@H](C)O)NC(=O)[C@H](CCCCN)NC(=O)[C@@H](Cc2c[nH]c3ccccc23)NC(=O)[C@H](Cc2ccccc2)NC1=O] | 829.1 | 0.88 |

Evaluation of membrane permeability of synthesized cyclic peptide by PAMPA method In order to compare and examine the membrane permeability of the synthesized cyclic peptide, parallel artificial membrane permeability assay (PAMPA) was carried out.

An artificial phospholipid membrane was produced by adding 5 μL of a phospholipid organic solvent solution consisting of L-α-phosphatidylcholine (Avanti Polar Lipids, Inc., Cat. 840051P, 1.67%), 1,2-dioleoyl-sn-glycero-3-phospho-L-serine (Avanti Polar Lipids, Inc., Cat. 840035P, 0.33%), and n-dodecane special grade (Wako Pure Chemical Industries, Ltd., 047-21612)/1-octanol reagent special grade (Kanto Chemical Co., Inc., Cat. 31013-08)=10:1 to Filter Plate (Merck Millipore Corporation, Cat. MAIPN4550).

Measurement Method—A

475 µL of 50 mmol/L potassium phosphate buffer (KPB, pH 7.4 or pH 6.5) was added to 25 µL of a DMSO solution containing the compound at a concentration of 20 µmol/L, so that the compound was diluted to a final concentration of 1 µmol/L. 300 µL of the compound solution was added to the lower side (donor side) of PAMPA 96-well plate (Filter Plate (Merck Millipore Corporation, Cat. MAIPN4550)) with an artificial phospholipid membrane being interposed therebetween. 200 µL of 5% DMSO KPB (pH 7.4) was added to the upper side (acceptor side) with the artificial phospholipid membrane being interposed therebetween. A permeation test through an artificial phospholipid membrane was carried out at 25° C. for 4 hours. The compound concentration in the solution in the donor plate and the acceptor plate was measured by LC/MS/MS, and the membrane permeation rate ($P_e$) of the compound was calculated from the following formula, assuming that $C_0$ is an initial compound concentration in donor solution, t is a test time, A is a membrane filter area=0.3 cm$^2$, $V_D$ is a donor solution amount=300 µL, $V_A$ is an acceptor solution amount=200 µL, and $C_D(t)$ is a compound concentration in donor solution at time t, $C_A(t)$ is a compound concentration in acceptor solution at time t, and $C_{equilibrium}=[C_D(t)*V_D+C_A(t)*V_A]/(V_D+V_A)$.

Measurement Method—B

475 µL of 50 mmol/L potassium phosphate buffer (KPB, pH 7.4 or pH 6.5) was added to 25 µL of a DMSO solution containing the compound at a concentration of 20 µmol/L, so that the compound was diluted to a final concentration of 10 µmol/L. The compound solution was added 300 µL each to the lower side (donor side) of an artificial phospholipid membrane of PAMPA 96-well plate (Filter Plate (Merck Millipore Corporation, Cat. MAIPN4550)). 200 µL of 5% DMSO KPB (pH 7.4) was added to the upper side (acceptor side) with the artificial phospholipid membrane being interposed therebetween. A permeation test through an artificial phospholipid membrane was carried out at 25° C. for 4 hours. The compound concentration in the solution in the donor plate and the acceptor plate was measured by LC/MS/MS, and the membrane permeation rate ($P_e$) of the compound was calculated from the following formula, assuming that Co is an initial compound concentration in donor solution, t is a test time, A is a membrane filter area=0.3 cm$^2$, $V_D$ is a donor solution amount=300 µL, $V_A$ is an acceptor solution amount=200 µL, and $C_D(t)$ is a compound concentration in donor solution at time t, $C_A(t)$ is a compound concentration in acceptor solution at time t, and $C_{equilibrium}=[C_D(t)*V_D+C_A(t)*V_A]/(V_D+V_A)$.

Permeability (in unit of cm/s):

$$P_e = \frac{-\ln[1 - C_A(t)/C_{equilibrium}]}{A*(1/V_D + 1/V_A)*t}$$

The membrane permeability (Pe($10^{-6}$ cm/s)) obtained by this method is described in the following table.

Evaluation standards are as follows.

+++ 0.5<$P_e$ ($10^{-6}$ cm/s)
++ 0.2<$P_e$ ($10^{-6}$ cm/s)≤0.5
+ 0.01<$P_e$ ($10^{-6}$ cm/s)≤0.2
− 0.01≤$P_e$ ($10^{-6}$ cm/s)

TABLE 48

| Example No. | Cyclic peptide No. | Pe($10^{-6}$ cm/sec) | Measurement method |
|---|---|---|---|
| 1-1 | 2-1 | +++ | A |
| 1-2 | 2-2 | +++ | A |
| 1-3 | 2-4 | +++ | A |
| 1-4 | 2-5 | ++ | A |
| 1-5 | 2-6 | ++ | A |
| 1-6 | 2-7 | +++ | A |
| 1-7 | 2-10 | +++ | A |
| 1-8 | 2-11 | +++ | A |
| 1-9 | 2-16 | +++ | A |
| 1-10 | 2-17 | +++ | A |
| 1-11 | 2-19 | +++ | A |
| 1-12 | 2-21 | +++ | A |
| 1-13 | 2-22 | ++ | A |
| 1-14 | 3-1 | +++ | A |
| 1-15 | 3-2 | +++ | A |
| 1-16 | 3-4 | +++ | A |
| 1-17 | 3-5 | ++ | A |
| 1-18 | 6-1 | +++ | A |
| Comparative Example No. | | | |
| 1-1 | 7-1 | + | A |
| 1-2 | 8-1 | + | A |
| 1-3 | 9-1 | + | A |
| 1-4 | 10-1 | + | A |
| Example No. | | | |
| 2-1 | 4-2 | +++ | A |
| 2-2 | 4-3 | +++ | A |
| Comparative Example No. | | | |
| 2-1 | 7-2 | + | A |
| 2-2 | 8-2 | + | A |
| 2-3 | 9-2 | + | A |
| Example No. | | | |
| 3-1 | 4-4 | ++ | A |
| 3-2 | 5-1 | +++ | A |
| Comparative Example No. | | | |
| 3-1 | 7-4 | + | A |
| 3-2 | 8-3 | − | A |
| 3-3 | 9-2 | + | A |
| 3-4 | 10-3 | − | A |
| Example No. | | | |
| 4-1 | 4-6 | + | A |
| Comparative Example No. | | | |
| 4-1 | 7-3 | − | A |
| 4-2 | 9-3 | Below the limit of quantitation | A |
| 4-3 | 10-4 | − | A |
| Example No. | | | |
| 5-1 | 4-9 | + | A |
| Comparative Example No. | | | |
| 5-1 | 7-6 | Below the limit of quantitation | A |
| Example No. | | | |
| 6-1 | 4-8 | ++ | A |
| Comparative Example No. | | | |
| 6-1 | 7-5 | Below the limit of quantitation | A |
| 6-2 | 9-4 | Below the limit of quantitation | A |
| Example No. | | | |
| 7-1 | a-1-1 | +++ | A |
| 7-2 | a-1-2 | ++ | A |
| 7-3 | a-1-3 | +++ | A |
| 7-4 | a-1-4 | +++ | A |
| 7-5 | a-1-5 | ++ | B |

TABLE 48-continued

| | Cyclic peptide No. | Pe(10$^{-6}$ cm/sec) | Measurement method |
|---|---|---|---|
| 7-6 | a-1-6 | +++ | A |
| 7-7 | a-1-8 | +++ | A |
| 7-8 | a-1-9 | +++ | A |
| 7-9 | a-1-10 | +++ | A |
| 7-10 | a-1-11 | +++ | A |
| 7-11 | a-1-12 | +++ | A |
| 7-12 | a-1-14 | +++ | B |
| 7-13 | a-1-15 | ++ | B |
| 7-14 | a-1-16 | ++ | B |
| 7-15 | a-1-19 | +++ | A |
| Example No. | | | |
| 8-1 | a-3-1 | +++ | B |
| 8-2 | a-3-2 | ++ | A |
| Example No. | | | |
| 9-1 | a-4-1 | + | B |

The amino acid sequences constituting cyclic peptides were identical except for the cyclization part, and the cyclic peptides were synthesized using the cyclic peptide production method of the present invention, thioether cyclization method, and triazole cyclization method, and disulfide cyclization method. Individual peptides were evaluated and compared for cell membrane permeability by a PAMPA method.

As a result, it was found that the cyclic peptide synthesized according to the present invention is superior in cell membrane permeability as compared to cyclic peptides synthesized by other production methods.

Test of metabolic stability of cyclic peptide in human liver microsome

An experiment using human liver microsomes (HLMs) was carried out in order to compare and examine the metabolic stability of the synthesized cyclic peptides.

The compound with a final concentration of 1 μmol/L was incubated in human liver microsomes (BD Cat #452117) prepared to a final concentration of 0.5 mg protein/mL using 100 mmol/L phosphate buffer (pH 7.4) at 37° C. for 20 minutes in the presence of reduced nicotinamide adenine dinucleotide phosphate (NADPH) and uridine 5'-diphosphate-α-D-glucuronic acid (UDPGA). Deproteinization treatment with acetonitrile was carried out, the amount of unaltered substance remaining was quantified using LC/MS/MS, and the residual rate (%) in 20 minutes was calculated. The HLM residual rate (%) obtained by this method is described in the following table.

Evaluation standards are as follows.
+++ 60%<HLM residual rate (%)
++ 40%<HLM residual rate (%)≤60%
+ HLM residual rate (%)≤40%

TABLE 49

| | Cyclic peptide No. | HLM residual rate |
|---|---|---|
| Example No. | | |
| 7-1 | 2-1 | +++ |
| 7-2 | 2-5 | ++ |
| 7-3 | 2-6 | +++ |
| 7-4 | 2-7 | +++ |
| 7-5 | 2-8 | +++ |
| 7-6 | 2-9 | +++ |
| 7-7 | 2-10 | +++ |
| 7-8 | 2-11 | +++ |
| 7-9 | 2-13 | +++ |
| 7-10 | 2-14 | +++ |
| 7-11 | 2-15 | ++ |
| 7-12 | 2-16 | ++ |
| 7-13 | 2-18 | ++ |
| 7-14 | 2-19 | +++ |
| 7-15 | 2-20 | ++ |
| 7-16 | 2-21 | +++ |
| 7-17 | 2-22 | +++ |
| 7-18 | 3-2 | +++ |
| 7-19 | 3-3 | +++ |
| 7-20 | 3-4 | +++ |
| 7-21 | 6-1 | +++ |
| Comparative Example No. | | |
| 7-1 | 7-1 | + |
| 7-2 | 9-1 | + |

The amino acid sequences constituting cyclic peptides were identical except for the cyclization part, and the cyclic peptides were synthesized using the cyclic peptide production method of the present invention and thioether cyclization method. Individual peptides were evaluated and compared for metabolic stability by a metabolic stability test in human liver microsomes.

As a result, it was found that the cyclic peptide synthesized according to the present invention is superior in metabolic stability as compared to cyclic peptides synthesized by other production methods.

<cDNA Display>
Preparation of DNA Library Used for Display Library

Using synthetic oligo DNA (SEQ ID NO: 15) and synthetic oligo DNA (SEQ ID NO: 16), the elongation reaction was carried out with KOD-plus—(manufactured by Toyobo Co., Ltd.). After denaturation at 94° C. for 3 minutes, a cycle of 1 minute at 55° C. and 2 minutes at 72° C. was repeated five times. Subsequently, PCR was carried out with KOD-plus—(manufactured by Toyobo Co., Ltd.) using this extension reaction product as a template, and synthetic oligo DNA (SEQ ID NO: 16) and synthetic oligo DNA (SEQ ID NO: 17). After denaturation at 94° C. for 2 minutes, a cycle of 1 minute at 94° C., 1 minute at 50° C., and 1 minute at 68° C. was repeated five times to construct a DNA library (SEQ ID NO: 18).

The point indicated by N in the sequence means that A, T, Q and C appear randomly, and the point indicated by K means that T and G appear randomly.

SEQ ID NO: 15
AAGAAGGAGATATACATATGTGCNNKNNKNNKNNKNNKNNKNNKNNKNN

KNNKNNKNNKNNKTAGGGCGGTTCTGGCGGTAGC

SEQ ID NO: 16
ATACTCAAGCTTATTTATTTACCCCCCGCCGCCCCCCGTCCTGCTACCG

CCAGAACCGCC

SEQ ID NO: 17
GAAATTAATACGACTCACTATAGGGAGACCACAACGGTTTCCCTCTAGA

AATAATTTTGTTTAACTTTAAGAAGGAGATATACATATG

SEQ ID NO: 18
GAAATTAATACGACTCACTATAGGGAGACCACAACGGTTTCCCTCTAGA

AATAATTTTGTTTAACTTTAAGAAGGAGATATACATATGTGCNNKNNKN

-continued

NKNNKNNKNNKNNKNNKNNKNNKNNKNNKNNKTAGGGCGGTTCTGGCGG

TAGCAGGACGGGGGCGGCGGGGGGTAAATAAATAAGCTTGAGTAT

Preparation of mRNA-Puromycin Linker Complex mRNA (SEQ ID NO: 19) was prepared using Thermo T7 RNA Polymerase (manufactured by Toyobo Co., Ltd.) with the DNA library (SEQ ID NO: 18) prepared by PCR as a template, and purified by ethanol precipitation. 5 μmol/L of the following puromycin linker A (manufactured by Tsukuba Oligo Service Co., Ltd.) and TBS (25 mmol/L Tris, 500 mmol/L NaCl, pH 7.5) were added to 2.8 μmol/L of mRNA, followed by reaction for 1 minute at 90° C., and the temperature of the reaction solution was decreased to 25° C. at a rate of 0.5° C./minute. Subsequently, UV irradiation at 365 nm for 30 minutes was followed by purification by ethanol precipitation to obtain an mRNA-puromycin linker complex.

The point indicated by N in the sequence means that A, U, G, and C appear randomly, and the point indicated by K means that U and G appear randomly.

SEQ ID NO: 19
GGGAGACCACAACGGUUUCCCUCUAGAAAUAAUUUUGUUUAACUUUAAG

AAGGAGAUAUACAUAUGUGCNNKNNKNNKNNKNNKNNKNNKNNKNNKNN

KNNKNNKNNKUAGGGCGGUUCUGGCGGUAGCAGGACGGGGGCGGCGGG

GGGUAAAUAAAUAAGCUUGAGUAU (SEQ ID NO: 82)

duced into plasmid pET28a, and a His6 tag, MBP, a HRV3C protease recognition sequence, and 3×FLAG tag were attached to the N terminal side thereof. This plasmid was transformed into *E. coli* strain BL21 (DE3) RIPL which was then cultured at 30° C. In a case where the O.D. reached 0.8, IPTG 0.5 μmol/L was added to induce large-scale expression, followed by culturing at 16° C. overnight. The recovered bacterial cells were suspended in Lysis Buffer B (25 mmol/L Tris (pH 7.5), 300 mmol/L NaCl), and then disrupted by sonication. This was followed by centrifugation at 15 krpm for 15 minutes. The supernatant after centrifugation was purified using a Ni-NTA resin (manufactured by QIAGEN GmbH). The sample adsorbed to the Ni-NTA resin was washed with Lysis Buffer B containing 20 mmol/L imidazole and then eluted with Lysis Buffer B containing 200 mmol/L imidazole. PreScission Protease (manufactured by GE lifesciences, Inc.) was added to the sample to cleave His6 tag and MBP portions, simultaneously followed by substitution with Dialysis Buffer (25 mmol/L Tris (pH 7.5), 150 mmol/L NaCl) overnight by dialysis. After confirming the cleavage of the tag, the sample was added to an amylose resin (available from New England BioLabs, Inc.) substituted with Dialysis Buffer, and the flow-through fraction was fractionated. The obtained sample was concentrated by Amicon Ultra (manufactured by Millipore Corporation) and then purified by HiLoad Superdex75 (manufactured by GE lifesciences, Inc.). The obtained sample was concentrated by Amicon Ultra and then stored at −80° C.

Preparation of Protein-Immobilized Beads

100 μL of ANTI-FLAG M2 Magnetic Beads (manufactured by Sigma-Aldrich LLC) was washed with TBS (20

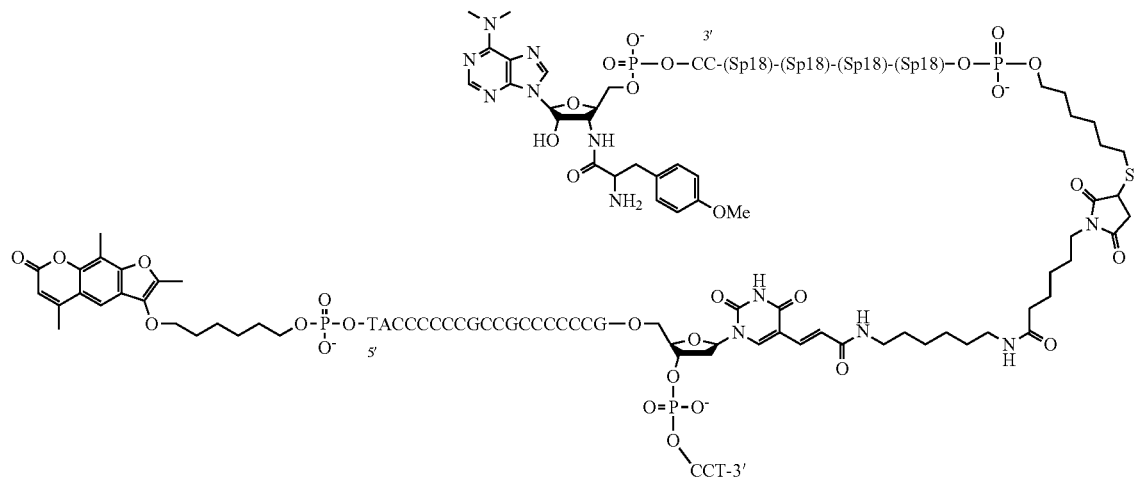

The above is puromycin linker A (manufactured by Tsukuba Oligo Service Co., Ltd.).

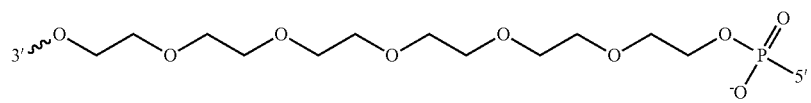

The above shows (Sp18)

Preparation of Target Protein

A plasmid construct was prepared in which a gene containing the amino acid 1-172 portion of MCL-1 was intrommol/L Tris, 150 mmol/L NaCl, pH 7.4). 33 μg of the target protein was added thereto, followed by rotational mixing for 10 minutes to bind the protein to the beads. The beads were recovered and washed with TBS to obtain target protein-immobilized beads.

Synthesis of Amber Suppressor tRNA (-CA)

The amber suppressor tRNA was synthesized in the same manner as described above.

Synthesis of aminoacyl-tRNA-15 (Table 31)

The aminoacyl-tRNA-15 was obtained in the same manner as described above.

Translation Solution Used for Panning

The following was added to 10 µL of the reaction solution using PUREfrex (registered trademark) custom ver 2 (manufactured by GeneFrontier Corporation, PFC-Z1802).

mRNA-puromycin linker complex: final concentration of 0.6 µmol/L

Aqueous solution of aminoacyl-tRNA-15 (0.2 OD/µL): 1 µL

Aqueous solution of amino acids (a mixture of 19 amino acids other than Met, each 0.3 mmol/L): 1.5 µL Translation for Carrying Out Round 1 Panning, Reverse Transcription, Panning, and PCR The above-mentioned translation solution was prepared and reacted at 37° C. for 30 minutes. 2 µL of a 60 mmol/L EDTA solution was added to 4 µL of this translation solution which was then left at room temperature for several minutes. Subsequently, ReverTra Ace (manufactured by Toyobo Co., Ltd.), 5×RT buffer (manufactured by Toyobo Co., Ltd.), and 1 mmol/L dNTPs were added to this solution which was then incubated at 30° C. for 10 minutes and 42° C. for 30 minutes to carry out reverse transcription to obtain 10 µL of a peptide-mRNA complex solution.

10 µL of the target protein-immobilized beads and TBS were added to the above solution, followed by rotational mixing for 45 minutes at room temperature. The supernatant was removed, followed by washing four times with TBS+ 0.05% tween-20, once with TBS, and once with pure water.

1 µL of the above beads was added to a PCR solution containing 1 µmol/L primer (SEQ ID NO: 20), 1 µmol/L primer (SEQ ID NO: 21), and KOD-plus—(manufactured by Toyobo Co., Ltd.), followed by PCR amplification of cDNA, and the DNA was purified by a QIAquick PCR purification kit (manufactured by QIAGEN GmbH). PCR was carried out again using the purified DNA as a template with 0.3 µmol/L primer (SEQ ID NO: 22), 0.3 µmol/L primer (SEQ ID NO: 23), and KOD-plus—(manufactured by Toyobo Co., Ltd.), and the DNA was purified by a QIAquick PCR purification kit (manufactured by QIAGEN GmbH).

```
                                   SEQ ID NO: 20
GAAATTAATACGACTCACTATAGGGAGACCACAACGGTTTCCCTC

SEQ ID NO: 21
ATACTCAAGCTTATTTATTTACCCCCCGCCGCCCCCCGTCC

SEQ ID NO: 22
GAAATTAATACGACTCACTA

SEQ ID NO: 23
ATACTCAAGCTTATTTATTT
```

Transcription for Round 2 Panning, mRNA-Puromycin Linker Complex Preparation, Translation, Reverse Transcription, Panning, and PCR mRNA was synthesized from the cDNA amplified in round 1, using Thermo T7 RNA Polymerase (manufactured by Toyobo Co., Ltd.) and purified by ethanol precipitation. Next, puromycin linker A (the structure has been shown above) was added to the mRNA, followed by reaction for 1 minute at 90° C., and the temperature of the reaction solution was decreased to 25° C. at a rate of 0.5° C./minute. Subsequently, UV irradiation at 365 nm for 30 minutes was followed by purification by ethanol precipitation to obtain an mRNA-puromycin linker complex. The aforementioned 4 µL translation solution containing 0.6 µmol/L mRNA-puromycin linker complex was prepared and incubated at 37° C. for 30 minutes, and 2 µL of a 60 mmol/L EDTA solution was added thereto, followed by being left for several minutes at room temperature. Subsequently, ReverTra Ace (manufactured by Toyobo Co., Ltd.), 5×RT buffer (manufactured by Toyobo Co., Ltd.), and 1 mmol/L dNTPs were added to this solution which was then incubated at 30° C. for 10 minutes and 42° C. for 30 minutes to carry out reverse transcription to obtain 10 µL of a peptide-mRNA complex solution.

10 µL of the target protein-immobilized beads and TBS were added to the above solution, followed by rotational mixing for 45 minutes at room temperature. The supernatant was removed, followed by washing four times with TBS+ 0.05% tween-20, once with TBS, and once with pure water.

1 µL of the above beads was added to a PCR solution containing 1 µmol/L primer (SEQ ID NO: 20), 1 µmol/L primer (SEQ ID NO: 21), and KOD-plus—(manufactured by Toyobo Co., Ltd.), followed by PCR amplification of cDNA, and the DNA was purified by a QIAquick PCR purification kit (manufactured by QIAGEN GmbH). PCR was carried out again using the purified DNA as a template with 0.3 µmol/L primer (SEQ ID NO: 22), 0.3 µmol/L primer (SEQ ID NO: 23), and KOD-plus—(manufactured by Toyobo Co., Ltd.), and the DNA was purified by a QIAquick PCR purification kit (manufactured by QIAGEN GmbH).

The same operation as in round 2 was repeated in round 3 to enrich for cDNA showing target protein specific binding. The sequence analysis of the enriched DNA pool was carried out to identify the enriched peptide sequence.

Synthesis of Chemically Synthesized Cyclic Peptide a-5-1 of Enriched Peptide Sequence (SEQ ID NO: 64)

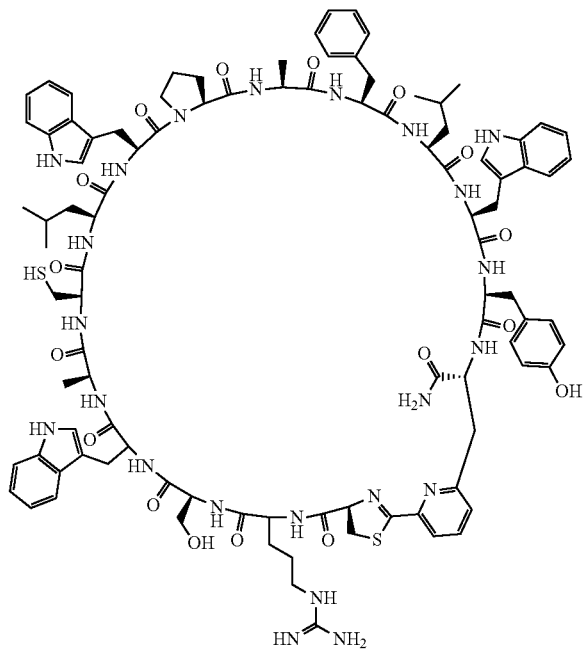 [SMILES: CC(C)C[C@@H]1NC(=O)[C@H](Cc2ccccc2)NC(=O)[C@H](C)NC(=O)[C@@H]2CCCN2C(=O)[C@H](Cc2c[nH]c3ccccc23)NC(=O)[C@H](CC(C)C)NC(=O)[C@@H](CS)NC(=O)[C@H](C)NC(=O)C(Cc2c[nH]c3ccccc23)NC(=O)[C@H](CO)NC(=O)C(CCCNC(=N)N)NC(=O)[C@@H]2CSC(=N2)c2cccc(n2)C[C@H](C(N)=O)NC(=O)[C@H](Cc2ccc(O)cc2)NC(=O)[C@H](Cc2c[nH]c3ccccc23)NC1=O]

Solid phase peptide synthesis was carried out using 100 mg of Rink Amide-ChemMatrix (0.5 mmol/g) as a starting material. Condensation was carried out in the order of (S)-2-((((9H-fluoren-9-yl)methoxy)carbonyl)amino)-3-(6-cyanopyridin-2-yl)propionic acid, N-α-(9-fluorenyl-methoxycarbonyl)-O-(t-butyl)-L-tyrosine (Fmoc-Tyr(tBu)-OH), Fmoc-Trp(Boc)-OH, Fmoc-L-Leu-OH, Fmoc-Phe-OH, Fmoc-Ala-OH, Fmoc-Pro-OH, Fmoc-Trp(Boc)-OH, Fmoc-Leu-OH, N-α-(9-fluorenylmethoxycarbonyl)-S-trityl-L-cysteine (Fmoc-Cys(Trt)-OH), Fmoc-Ala-OH, Fmoc-Trp(Boc)-OH, N-α-(9-fluorenylmethoxycarbonyl)-O-t-butyl-L-serine (Fmoc-Ser(OtBu)-OH), Fmoc-Arg(Pbf)-OH, and Fmoc-Cys(Trt)-OH. After completion of the peptide elongation, an NMP solution of piperidine (20% v/v) was added thereto, followed by reaction for 20 minutes to deprotect the Fmoc group. The resin was washed with dichloromethane and then the solvent was distilled off under reduced pressure. TFA:3,6-dioxa-1,8-octanedithiol:triisopropylsilane:water (=92.5:2.5:2.5:2.5, 3.0 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. Phosphate buffer (pH 7.0, 2.5 mL), methanol (2.5 mL), and an aqueous tris(2-carboxyethyl) phosphine solution (0.5 mol/L, 0.025 mL) were added to the resulting solid which was then stirred at 45° C. for 40 minutes. The solvent was distilled off under reduced pressure and the resulting residue was purified by HPLC (0.1% formic acid aqueous solution/0.1% formic acid acetonitrile solution) and then neutralized by adding a triethylammonium hydrogen carbonate solution (1.0 M, pH 8.5). The solvent was distilled off under reduced pressure to obtain 21.7 mg of cyclic peptide a-5-1 as a colorless oil.

MS(ESI m/z): 1957.6 (M+H)
RT(min): 1.40

Synthesis of Cyclic Peptide a-5-2 (SEQ ID NO: 65)

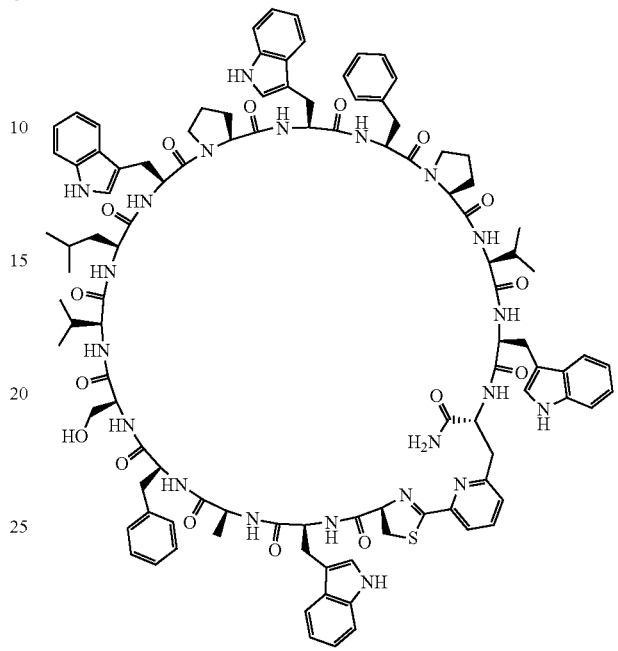

The procedure was carried out in the same manner as the synthesis of cyclic peptide a-5-1.

MS(ESI m/z): 1979.4 (M+H)
RT(min): 1.67

Synthesis of Cyclic Peptide a-5-3 (SEQ ID NO: 66)

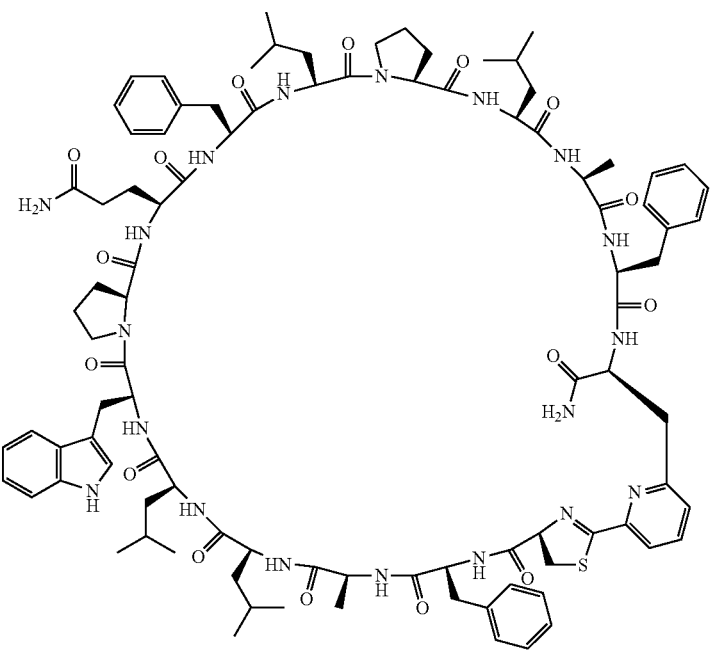 [SMILES: CC(C)C[C@@H]1NC(=O)[C@H](C)NC(=O)[C@@H](Cc2ccccc2)NC(=O)[C@@H]2CSC(=N2)c2cccc(n2)C[C@@H](C(N)=O)NC(=O)[C@H](Cc2ccccc2)NC(=O)[C@H](C)NC(=O)[C@H](CC(C)C)NC(=O)[C@@H]2CCCN2C(=O)[C@@H](CC(C)C)NC(=O)[C@@H](Cc2ccccc2)NC(=O)[C@H](CCC(N)=O)NC(=O)[C@@H]2CCCN2C(=O)[C@@H](Cc2c[nH]c3ccccc23)NC(=O)[C@H](CC(C)C)NC1=O]

Solid phase peptide synthesis was carried out using 100 mg of Rink Amide-ChemMatrix (0.5 mmol/g) as a starting material. Condensation was carried out in the order of (S)-2-((((9H-fluoren-9-yl)methoxy)carbonyl)amino)-3-(6-cyanopyridin-2-yl)propionic acid, Fmoc-Phe-OH, Fmoc-Ala-OH, Fmoc-Leu-OH, Fmoc-Pro-OH, Fmoc-Leu-OH, Fmoc-Phe-OH, N-α-(9-fluorenylmethoxycarbonyl)-N5-trityl-L-glutamine (Fmoc-L-Gln(Trt)-OH), Fmoc-Pro-OH, Fmoc-L-Trp(Boc)-OH, Fmoc-Leu-OH, Fmoc-Leu-OH, Fmoc-Ala-OH, Fmoc-Phe-OH, and Fmoc-Cys(Trt)-OH. After completion of the peptide elongation, the resin was washed with dichloromethane and then the solvent was distilled off under reduced pressure. TFA:3,6-dioxa-1,8-octanedithiol:triisopropylsilane:water (=92.5:2.5:2.5:2.5, 3.0 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. Phosphate buffer (pH 7.0, 2.5 mL), methanol (2.5 mL), and an aqueous tris(2-carboxyethyl)phosphine solution (0.5 mol/L, 0.025 mL) were added to the resulting solid which was then stirred at room temperature for 2 hours. The solvent was distilled off under reduced pressure and the resulting residue was purified by HPLC (0.1% formic acid aqueous solution/ 0.1% formic acid acetonitrile solution) and then neutralized by adding a triethylammonium hydrogen carbonate solution (1.0 M, pH 8.5). The solvent was distilled off under reduced pressure to obtain 13.4 mg of cyclic peptide a-5-3 as a colorless oil.

MS(ESI m/z): 1821.3 (M+H)
RT(min): 1.56

The compounds shown in Table 50 below were obtained in the same manner as the synthesis of cyclic peptide a-5-3.

TABLE 50

| Cyclic peptide No. | Structure | Observed MS | RT/min |
|---|---|---|---|
| | (SEQ ID NOS: 67 to 69) | | |
| a-5-4 | 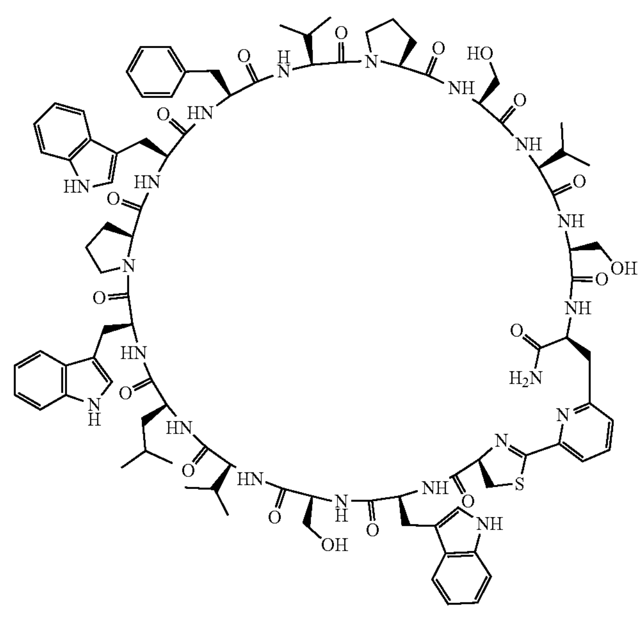 [SMILES: CC(C)C[C@@H]1NC(=O)[C@H](C(C)C)NC(=O)[C@H](CO)NC(=O)[C@H](Cc2c[nH]c3ccccc23)NC(=O)[C@@H]2CSC(=N2)c2cccc(n2)C[C@@H](C(N)=O)NC(=O)[C@H](CO)NC(=O)[C@H](C(C)C)NC(=O)[C@H](CO)NC(=O)[C@@H]2CCCN2C(=O)[C@H](C(C)C)NC(=O)[C@H](Cc2ccccc2)NC(=O)[C@H](Cc2c[nH]c3ccccc23)NC(=O)[C@@H]2CCCN2C(=O)[C@H](Cc2c[nH]c3ccccc23)NC1=O] | 1848.5 | 1.44 |

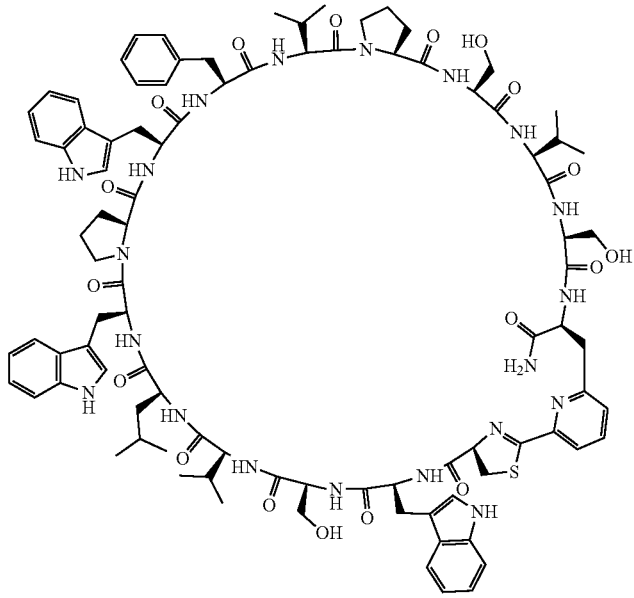

TABLE 50-continued

| Cyclic peptide No. | Structure | Observed MS | RT/min |
|---|---|---|---|
| a-5-5 | 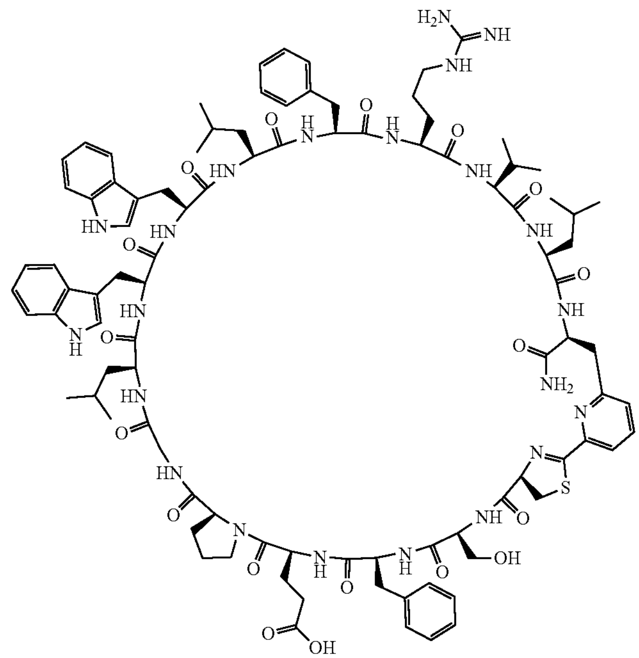 [SMILES: CC(C)C[C@@H]1NC(=O)CNC(=O)[C@@H]2CCCN2C(=O)[C@H](CCC(=O)O)NC(=O)[C@H](Cc2ccccc2)NC(=O)[C@H](CO)NC(=O)[C@@H]2CSC(=N2)c2cccc(n2)C[C@@H](C(N)=O)NC(=O)[C@H](CC(C)C)NC(=O)[C@H](C(C)C)NC(=O)[C@H](CCCNC(=N)N)NC(=O)[C@H](Cc2ccccc2)NC(=O)[C@H](CC(C)C)NC(=O)[C@H](Cc2c[nH]c3ccccc23)NC(=O)[C@H](Cc2c[nH]c3ccccc23)NC1=O] | 1906.4 (M − H) | 1.43 |
| a-5-6 | 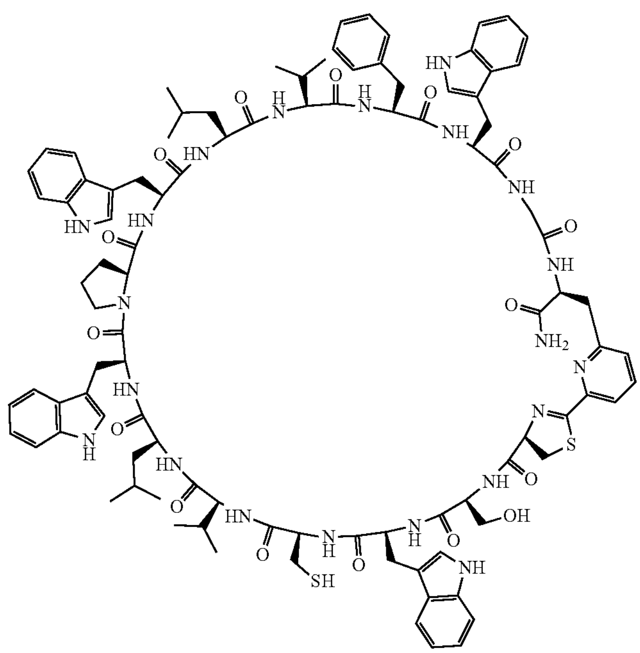 [SMILES: CC(C)C[C@@H]1NC(=O)[C@H](Cc2c[nH]c3ccccc23)NC(=O)[C@@H]2CCCN2C(=O)[C@H](Cc2c[nH]c3ccccc23)NC(=O)[C@H](CC(C)C)NC(=O)[C@H](C(C)C)NC(=O)[C@H](CS)NC(=O)[C@H](Cc2c[nH]c3ccccc23)NC(=O)[C@H](CO)NC(=O)[C@@H]2CSC(=N2)c2cccc(n2)C[C@@H](C(N)=O)NC(=O)CNC(=O)[C@H](Cc2c[nH]c3ccccc23)NC(=O)[C@H](Cc2ccccc2)NC(=O)[C@H](C(C)C)NC1=O] | 1936.3 | 1.65 |

TABLE 50-continued

| Cyclic peptide No. | Structure | Observed MS | RT/min |
|---|---|---|---|
| | (SEQ ID NOS: 70 to 71) | | |
| a-5-7 | [structure] | 1791.3 | 1.69 |
| a-5-8 | [structure] | 1822.2 | 1.57 |

Preparation of Target Protein

A plasmid construct was prepared in which a gene containing the amino acid 1-172 portion of MCL-1 was introduced into plasmid pET28a, and a His6 tag, MBP, and a TEV protease recognition sequence were attached to the N terminal side thereof. This plasmid was transformed into *E. coli* strain BL21 (DE3) RIPL which was then cultured at 30° C. In a case where the O.D. reached 0.8, IPTG 0.5 µmol/L was added to induce large-scale expression, followed by culturing at 16° C. overnight. The recovered bacterial cells were suspended in Lysis Buffer A (25 mmol/L Tris (pH 7.5), 150 mmol/L NaCl), and then disrupted by sonication. This was followed by centrifugation at 15 krpm for 15 minutes. The supernatant after centrifugation was purified using a Ni-NTA resin (manufactured by QIAGEN GmbH). The sample adsorbed to the Ni-NTA resin was washed with Lysis Buffer A containing 15 mmol/L imidazole and then eluted with Lysis Buffer A containing 200 mmol/L imidazole. The sample was stored at −80° C. after substitution with Lysis buffer by dialysis.

Evaluation of Binding of Synthetic Peptide to Target Protein Using Surface Plasmon Resonance (SPR)

An SPR experiment for analyzing the interaction of a synthetic peptide with Mcl-1 was carried out at 25° C. using Biacore T200 (manufactured by GE Healthcare Inc.). The synthetic peptide was added to the immobilized protein, and the interaction therebetween was evaluated.

A buffer obtained by adding dimethylformamide (DMF) or dimethylsulfoxide (DMSO) to a final concentration of 1 vol % to HBS-EP+ (manufactured by GE Healthcare Inc.) was used as a running buffer. Mcl-1 was immobilized on a Biacore Sensor Chip Series S Sensor Chip CM5 (manufactured by GE Healthcare Inc.) using an Amine Coupling Kit (manufactured by GE Healthcare Inc.). In order to measure the dissociation constant (KD), each synthetic peptide was added at multiple concentrations to obtain a sensorgram of binding to immobilized Mcl-1.

The analysis of the obtained sensorgram was carried out using T200 evaluation software (manufactured by GE Healthcare Inc.). Solvent correction to DMF or DMSO was carried out, and then the KD was determined by equilibrium value analysis using a sensorgram obtained by subtracting the sensorgram to a flow cell in which Mcl-1 is not immobilized. The results obtained by analysis as described above are shown in the following table.

One having a KD of less than 50 µmol/L is denoted as A, and one having a KD of 50 µmol/L or more is denoted as B.

TABLE 51

| Compound No. | Binding evaluation result |
| --- | --- |
| Cyclic peptide a-5-1 | B |
| Cyclic peptide a-5-2 | B |
| Cyclic peptide a-5-3 | B |
| Cyclic peptide a-5-4 | A |
| Cyclic peptide a-5-5 | A |
| Cyclic peptide a-5-6 | B |
| Cyclic peptide a-5-7 | B |
| Cyclic peptide a-5-8 | B | mRNA Display

Preparation of DNA Library Used for Display Library

A DNA library was prepared in the same manner as described above.

Preparation of mRNA-Puromycin Linker Complex mRNA (SEQ ID NO: 19) was prepared using Thermo T7 RNA Polymerase (manufactured by Toyobo Co., Ltd.) with the DNA library (SEQ ID NO: 18) prepared by PCR as a template, and purified by ethanol precipitation. 5 µmol/L of the following puromycin linker B (manufactured by Tsukuba Oligo Service Co., Ltd.) (the structure is shown below) and TBS (25 mmol/L Tris, 500 mmol/L NaCl, pH 7.5) were added to 2.8 µmol/L of mRNA, followed by reaction for 5 minutes at 90° C., and the temperature of the reaction solution was decreased to 25° C. Subsequently, UV irradiation at 365 nm for 2 minutes was followed by purification by ethanol precipitation to obtain an mRNA-puromycin linker complex.

(SEQ ID NO: 83)

The above is puromycin B (manufactured by Tsukuba Oligo Service Co., Ltd.) (Sp18): Spacer18

Preparation of Target Protein

The target protein was prepared in the same manner as described above.

Preparation of Protein-Immobilized Beads

Protein-immobilized beads were prepared in the same manner as described above.

Synthesis of Amber Suppressor tRNA (-CA)

An amber suppressor tRNA was synthesized in the same manner as described above.

Synthesis of aminoacyl-tRNA-10 (Table 31)

Aminoacyl-tRNA-10 was obtained in the same manner as described above.

Translation Solution Used for Panning

The following was added to 10 µL of the reaction solution using PUREfrex (registered trademark) custom ver 2 (manufactured by GeneFrontier Corporation, PFC-Z1802).

mRNA-puromycin linker complex: final concentration of 0.6 µmol/L

Aqueous solution of aminoacyl-tRNA-10 (0.2 OD/µL): 1 µL

Aqueous solution of amino acids (a mixture of 19 amino acids other than Met, each 0.3 mmol/L): 1.5 µL Translation for Carrying Out Round 1 Panning, Panning, Reverse Transcription, and PCR The above-mentioned translation solution was prepared and reacted at 37° C. for 30 minutes. 10 µL of target protein-immobilized beads and TBS (20 mmol/L Tris, 150 mmol/L NaCl, pH 7.4) were added to 4 μL of this translation solution, followed by rotational mixing at room temperature for 45 minutes. The supernatant was removed, followed by washing four times with TBS+0.05% tween-20, once with TBS, and once with pure water. Subsequently, ReverTra Ace (manufactured by Toyobo Co., Ltd.), 5×RT buffer (manufactured by Toyobo Co., Ltd.), and 1 mmol/L dNTPs were added to the bead solution which was then incubated at 30° C. for 10 minutes and 42° C. for 30 minutes to carry out reverse transcription to obtain 12 μL of a peptide-mRNA complex solution.

1 μL of the above beads was added to a PCR solution containing 1 μmol/L primer (SEQ ID NO: 20), 1 μmol/L primer (SEQ ID NO: 24), and KOD-Multi&Epi—(manufactured by Toyobo Co., Ltd.), followed by PCR amplification of cDNA, and the DNA was purified by a QIAquick PCR purification kit (manufactured by QIAGEN GmbH).

SEQ ID NO: 24
ATACTCAAGCTTATTTATTTACCCCCCGCCGCCCCCCGTCCTGCTACCG
CCAGAACCGCCCTA

Transcription for Round 2 Panning, mRNA-Puromycin Linker Complex Preparation, Translation, Panning, Reverse Transcription, and PCR mRNA was synthesized from the cDNA amplified in round 1, using Thermo T7 RNA Polymerase (manufactured by Toyobo Co., Ltd.) and purified by an RNeady MinElute Cleanup Kit (manufactured by QIAGEN GmbH). Next, puromycin linker B (the structure has been shown above) was added to the mRNA, followed by reaction for 5 minutes at 90° C., and the temperature of the reaction solution was decreased to 25° C. Subsequently, UV irradiation at 365 nm for 2 minutes was followed by purification by ethanol precipitation to obtain an mRNA-puromycin linker complex. The aforementioned 4 μL translation solution containing 0.6 μmol/L mRNA-puromycin linker complex was prepared and incubated at 37° C. for 30 minutes. 10 μL of ANTI-FLAG M2 Magnetic Beads (manufactured by Sigma-Aldrich LLC) and TBS were added to this solution which was then mixed by inverting for 10 minutes at room temperature, and the supernatant was repeatedly recovered three times. 10 μL of the target protein-immobilized beads and TBS were added to the supernatant, followed by rotational mixing at room temperature for 45 minutes. The supernatant was removed, followed by washing four times with TBS+ 0.05% tween-20, once with TBS, and once with pure water. Subsequently, ReverTra Ace (manufactured by Toyobo Co., Ltd.), 5×RT buffer (manufactured by Toyobo Co., Ltd.), and 1 mmol/L dNTPs were added to the bead solution which was then incubated at 30° C. for 10 minutes and 42° C. for 30 minutes to carry out reverse transcription to obtain 12 μL of a peptide-mRNA complex solution.

1 μL of the above beads was added to a PCR solution containing 1 μmol/L primer (SEQ ID NO: 20), 1 μmol/L primer (SEQ ID NO: 24), and KOD-Multi&Epi—(manufactured by Toyobo Co., Ltd.), followed by PCR amplification of cDNA, and the DNA was purified by a QIAquick PCR purification kit (manufactured by QIAGEN GmbH).

The same operation as in round 2 was repeated in round 3 and round 4 to enrich for cDNA showing target protein specific binding. The sequence analysis of the enriched DNA pool was carried out to identify the enriched peptide sequence.

Chemical Synthesis of Enriched Peptide Sequence

Synthesis of Cyclic Peptide a-6-1 (SEQ ID NO: 72)

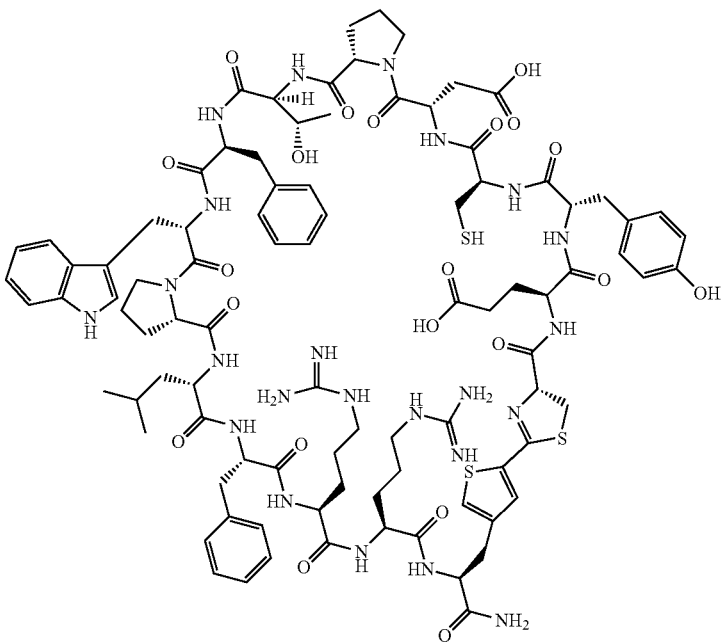 [SMILES: CC(C)C[C@@H]1NC(=O)[C@@H]2CCCN2C(=O)[C@H](Cc2c[nH]c3ccccc23)NC(=O)[C@H](Cc2ccccc2)NC(=O)[C@H]([C@H](C)O)NC(=O)[C@@H]2CCCN2C(=O)[C@H](CC(=O)O)NC(=O)[C@H](CS)NC(=O)[C@H](Cc2ccc(O)cc2)NC(=O)[C@H](CCC(=O)O)NC(=O)[C@@H]2CSC(=N2)c2cc(cs2)C[C@@H](C(N)=O)NC(=O)[C@H](CCCNC(=N)N)NC(=O)[C@H](CCCNC(=N)N)NC(=O)[C@H](Cc2ccccc2)NC1=O]

Solid phase peptide synthesis was carried out using 104 mg of Rink Amide-ChemMatrix (0.48 mmol/g) as a starting material. Condensation was carried out in the order of 2-((((9H-fluoren-9-yl)methoxy)carbonyl)amino)-3-(5-cyanothiophen-3-yl)propanoic acid, Fmoc-Arg(Pbf)-OH, Fmoc-Arg(Pbf)-OH, Fmoc-Phe-OH, Fmoc-Leu-OH, Fmoc-Pro-OH, Fmoc-Trp(Boc)-OH, Fmoc-Phe-OH, N-α-(9-fluorenylmethoxycarbonyl)-O-(t-butyl)-L-threonine (Fmoc-Thr(tBu)-OH), Fmoc-Pro-OH, N-α-(9-fluorenylmethoxycarbonyl)-L-aspartic acid-t-butyl ester (Fmoc-Asp(OtBu)-OH), Fmoc-Cys(Trt)-OH, Fmoc-Tyr(tBu)-OH, N-α-(9-fluorenylmethoxycarbonyl)-L-glutamic acid γ-t-butyl ester (Fmoc-Glu(tBu)-OH), and Boc-Cys(Trt)-OH. The resin was washed with dichloromethane and then the solvent was distilled off under reduced pressure. TFA:3,6-dioxa-1,8-octanedithiol:triisopropylsilane:water (=92.5:2.5:2.5:2.5, 3.0 mL) was added to the reaction solution to carry out cleavage and deprotection of the peptide. After 2 hours, the resin was filtered off, and n-hexane:methyl-t-butyl ether (=1:1, 12 mL) was added to the filtrate to give a solid. After centrifugation to precipitate the solid, the supernatant was removed. After washing the solid with methyl-t-butyl ether, the solvent was distilled off under reduced pressure. Phosphate buffer (pH 7.0, 5 mL), methanol (5 mL), and an aqueous tris(2-carboxyethyl)phosphine solution (0.5 mol/L, 0.1 mL) were added to the resulting solid, followed by reaction for 48 hours. The solvent was distilled off under reduced pressure, and the resulting residue was purified by HPLC (0.10% formic acid aqueous solution/0.1% formic acid acetonitrile solution) and then adjusted to neutral pH by adding a triethylammonium hydrogen carbonate solution (1.0 mol/L, pH 8.5). The solvent was distilled off under reduced pressure to obtain 7.6 mg of cyclic peptide a-6-1 as a white solid.

MS(ESI m/z): 1993.3 (M+H)
RT(min): 1.10

The cyclic peptides shown in Table 52 below were obtained in the same manner as the synthesis of cyclic peptide a-6-1.

TABLE 52

| Cyclic peptide No. | Structure | Observed MS | RT/min |
|---|---|---|---|
| | (SEQ ID NOS: 73 to 77) | | |
| a-6-2 | 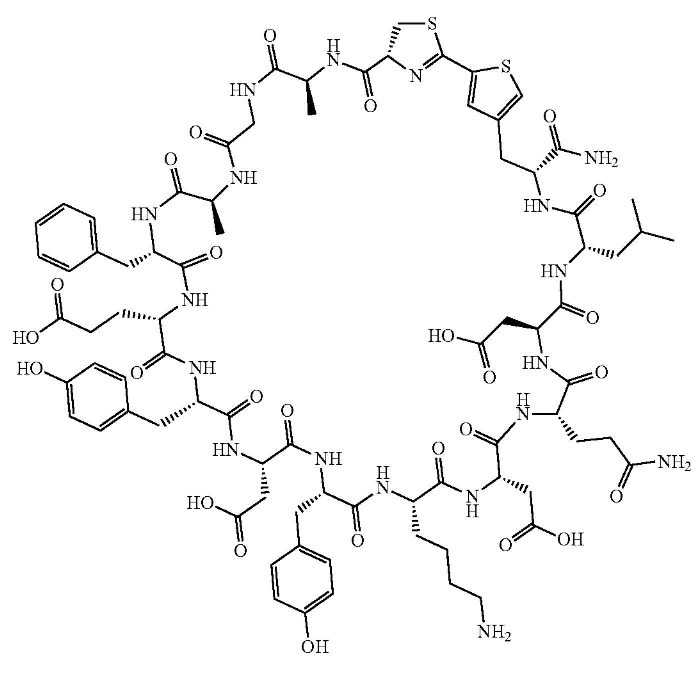 [SMILES: CC(C)C[C@@H]1NC(=O)[C@H](CC(=O)O)NC(=O)[C@H](CCC(N)=O)NC(=O)[C@H](CC(=O)O)NC(=O)[C@H](CCCCN)NC(=O)[C@H](Cc2ccc(O)cc2)NC(=O)[C@H](CC(=O)O)NC(=O)[C@H](Cc2ccc(O)cc2)NC(=O)[C@H](CCC(=O)O)NC(=O)[C@H](Cc2ccccc2)NC(=O)[C@H](C)NC(=O)CNC(=O)[C@H](C)NC(=O)[C@@H]2CSC(=N2)c2cc(cs2)C[C@H](C(N)=O)NC1=O] | 1795.3 (M − H) | 0.82 |

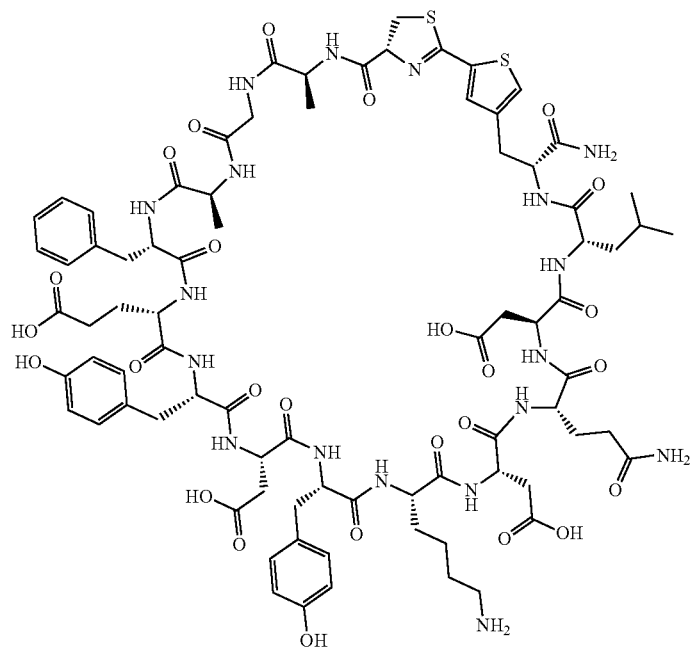

TABLE 52-continued
| Cyclic peptide No. | Structure | Observed MS | RT/min |
|---|---|---|---|
| a-6-3 | 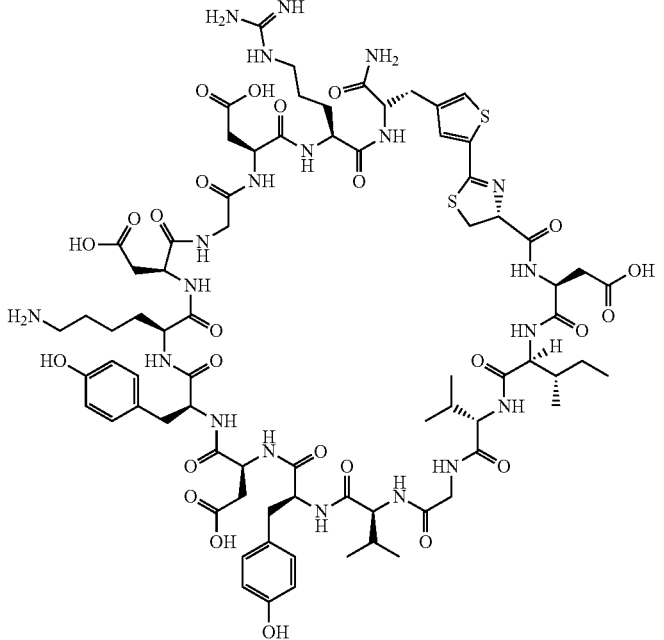 | 1778.4 | 0.88 |
| a-6-4 | 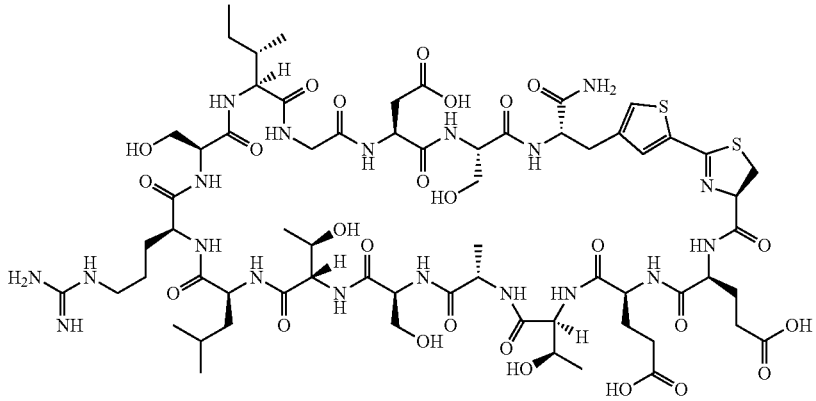 [SMILES: CC[C@H](C)[C@@H]1NC(=O)[C@H](CO)NC(=O)[C@H](CCCNC(=N)N)NC(=O)[C@H](CC(C)C)NC(=O)[C@H]([C@@H](C)O)NC(=O)[C@H](CO)NC(=O)[C@H](C)NC(=O)[C@H]([C@@H](C)O)NC(=O)[C@H](CCC(=O)O)NC(=O)[C@H](CCC(=O)O)NC(=O)[C@@H]2CSC(=N2)c2cc(cs2)C[C@@H](C(N)=O)NC(=O)[C@H](CO)NC(=O)[C@H](CC(=O)O)NC(=O)CNC1=O] | 1627.8 | 0.74 |
| a-6-5 | 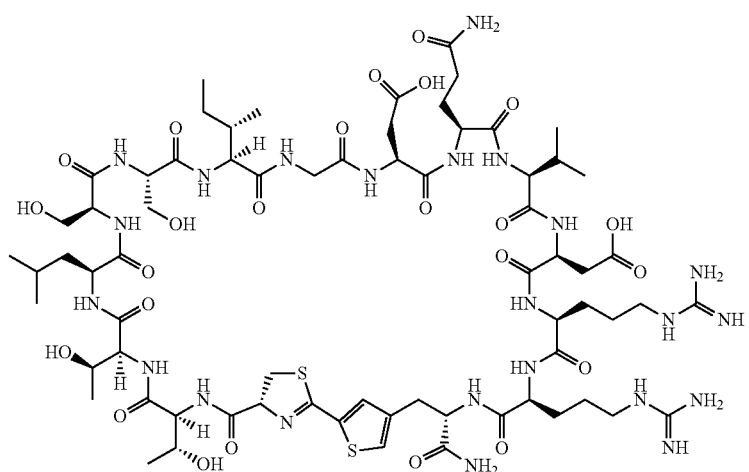 [SMILES: CC[C@H](C)[C@@H]1NC(=O)[C@H](CO)NC(=O)[C@H](CO)NC(=O)[C@H](CC(C)C)NC(=O)[C@H]([C@@H](C)O)NC(=O)[C@H]([C@@H](C)O)NC(=O)[C@@H]2CSC(=N2)c2cc(cs2)C[C@@H](C(N)=O)NC(=O)[C@H](CCCNC(=N)N)NC(=O)[C@H](CCCNC(=N)N)NC(=O)[C@H](CC(=O)O)NC(=O)[C@H](C(C)C)NC(=O)[C@H](CCC(N)=O)NC(=O)[C@H](CC(=O)O)NC(=O)CNC1=O] | 1711.4 | 0.79 |

TABLE 52-continued
| Cyclic peptide No. | Structure | Observed MS | RT/min |
|---|---|---|---|
| a-6-6 | 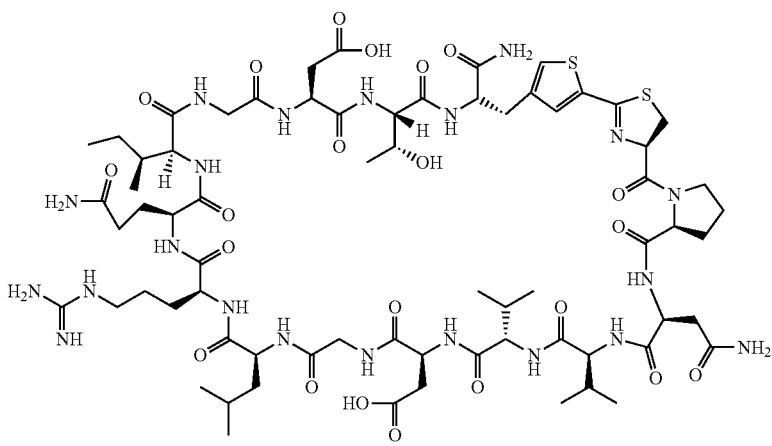 (SEQ ID NO: 78) | 1644.7 (M − H) | 0.89 |
| a-6-7 | 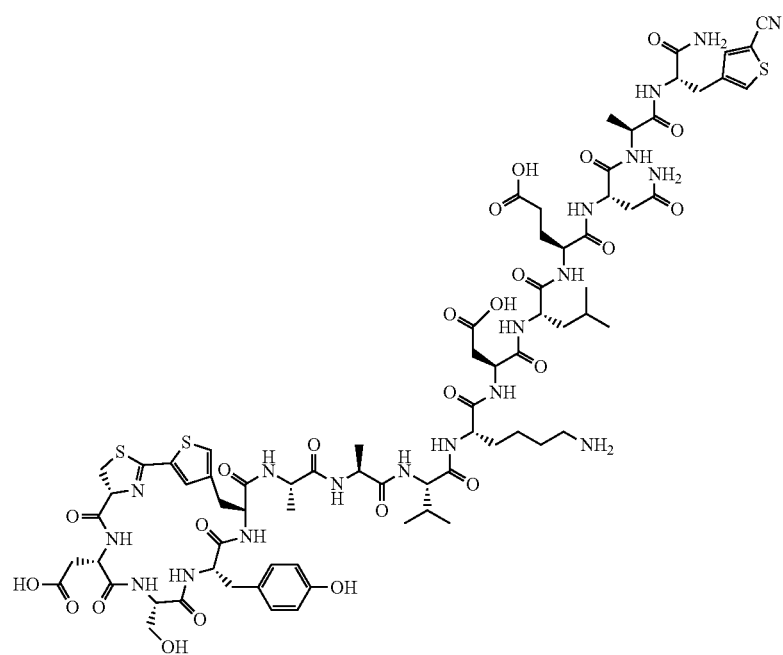 [SMILES: CC(C)C[C@H](NC(=O)[C@H](CC(=O)O)NC(=O)[C@H](CCCCN)NC(=O)[C@@H](NC(=O)[C@H](C)NC(=O)[C@H](C)NC(=O)[C@H]1Cc2csc(c2)C2=N[C@@H](CS2)C(=O)N[C@@H](CC(=O)O)C(=O)N[C@@H](CO)C(=O)N[C@@H](Cc2ccc(O)cc2)C(=O)N1)C(C)C)C(=O)N[C@@H](CCC(=O)O)C(=O)N[C@@H](CC(N)=O)C(=O)N[C@@H](C)C(=O)N[C@@H](Cc1csc(C#N)c1)C(N)=O] | 1736.3 (M − H) | 1.02 |

Identification of cyclization site of a-6-7 (SEQ ID NOS: 79 to 81)

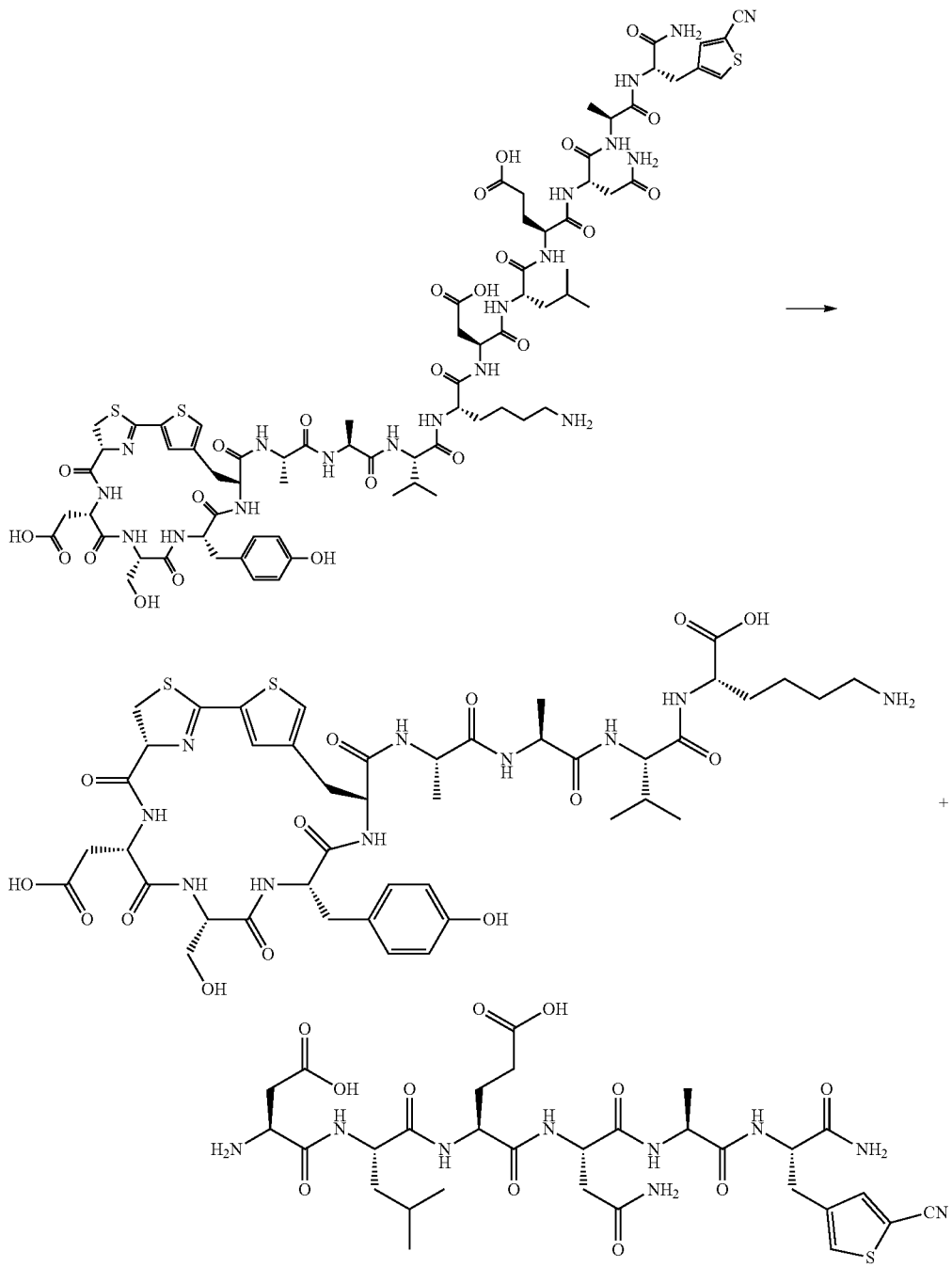

Since a-6-7 contains 2-((((9H-fluoren-9-yl)methoxy)carbonyl)amino)-3-(5-cyanothiophen-3-yl)propanoic acid, which is a cyclization site, at two points, trypsin digestion was carried out to determine the structure thereof. A triethylammonium hydrogen carbonate (50 mmol/L, pH 8.5, 95 μL) solution of trypsin (0.01 mg) (manufactured by Wako Pure Chemical Industries, Ltd.) was added to a DMSO solution (20 mM, 5 μL) of a-6-7, followed by being allowed to stand at 37° C. for 2 hours. The reaction solution was analyzed by LC/MS, and two types of MS of 1015.1 and 736.1 were observed, which confirmed that the cyclization site was the amino acid at the 5' residue from the N-terminus.

Preparation of Target Protein

The target protein was prepared in the same manner as described above.

Evaluation of Binding of Synthetic Peptide to Target Protein Using Surface Plasmon Resonance (SPR)

Binding of the synthetic peptide to the target protein was evaluated in the same manner as described above. The obtained KD is shown in the following table.

One having a KD of less than 50 μmol/L is denoted as A, and one having a KD of 50 μmol/L or more is denoted as B.

TABLE 53

| Compound No. | Binding evaluation result |
|---|---|
| a-6-1 | A |
| a-6-2 | B |
| a-6-3 | B |
| a-6-4 | A |
| a-6-5 | A |
| a-6-6 | A |
| a-6-7 | A |

The cyclic peptide obtained by the production method and selection method according to the embodiment of the present invention is used as an active ingredient of pharmaceuticals, agricultural chemicals, biochemical laboratory reagents, additives for cell culture, cosmetics, and functional foods, and can also be used as an adsorbent/separating agent used in filters and column chromatography. The cyclic peptide obtained by the production method and selection method according to the embodiment of the present invention can also be used as a catalyst for promoting a synthesis reaction, a dispersant for fine solids of pigments and nanoparticles, and a gelling agent for an aqueous solution.

SEQUENCE LISTING

International Application No. 17F02646 under Patent Cooperation Treaty—PEPTIDE COMPOUND AND METHOD FOR PRODUCING, JP18011143 20180320-03370483151800582611 Normal 2018032016-32162018030711014434430_P1AP101_17_326.app

What is claimed is:

1. A peptide compound represented by Formula (1) or a salt thereof:

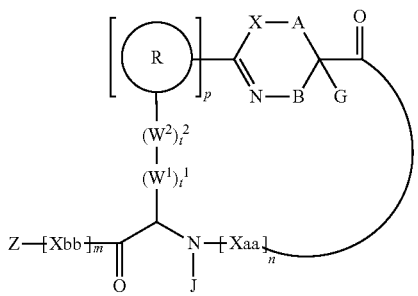

in the formula,

X represents S, NH, or O;

A represents a single bond, or a linear alkylene group having 1 or 2 carbon atoms which may have a substituent;

B represents a single bond or a linear alkylene group having 1 or 2 carbon atoms which may have a substituent, provided that A and B are not simultaneously a single bond;

Z represents a hydroxyl group or an amino group;

p pieces of R's may be the same as or different from one another and each represent a heteroarylene group which may have a substituent or an arylene group having 6 to 10 carbon atoms which may have a substituent;

G represents a hydrogen atom or an alkyl group having 1 to 6 carbon atoms which may have a substituent in a case where the carbon to which G is bonded together with A does not form a divalent group represented by *—CR$^O$=C(B)—;

$t^1$ pieces of W$^1$'s may be the same as or different from one another and each represent a single bond, —CH$_2$(C$_6$H$_5$NH)—, —CH$_2$(C$_6$H$_5$O)—, an amino acid residue which may have a substituent, a heteroarylene group which may have a substituent, an arylene group having 6 to 20 carbon atoms which may have a substituent, or an alkylene group having 1 to 6 carbon atoms which may have a substituent;

$t^2$ pieces of W$^2$'s may be the same as or different from one another and each represent a single bond, —CO—, —COO—, —NHCO—, —NHCONH—, —CONHCO—, —(CH$_2$CH$_2$O)—, —(CH$_2$CH$_2$CH$_2$O)—, an amino acid residue which may have a substituent, a heteroarylene group which may have a substituent, an arylene group having 6 to 20 carbon atoms which may have a substituent, or an alkylene group having 1 to 6 carbon atoms which may have a substituent;

J represents a hydrogen atom or an alkyl group having 1 to 6 carbon atoms which may have a substituent;

n pieces of Xaa's each independently represent any amino acid residue or any amino acid analog residue;

m pieces of Xbb's each independently represent any amino acid residue or any amino acid analog residue;

p represents an integer of 0 to 4;

$t^1$ represents an integer of 0 to 6;

$t^2$ represents an integer of 0 to 6;

m represents an integer of 0 to 20; and n represents an integer of 1 to 20.

2. The peptide compound or the salt thereof according to claim 1, wherein the R is at least one structure selected from a benzothiazolylene group which may have a substituent, a benzooxazolylene group which may have a substituent, a benzoimidazolylene group which may have a substituent, a benzothiophenylene group which may have a substituent, a benzofuranylene group which may have a substituent, an isobenzofuranylene group which may have a substituent, an indolylene group which may have a substituent, a quinolylene group which may have a substituent, an isoquinolylene group which may have a substituent, a quinazolylene group which may have a substituent, a cinnolylene group which may have a substituent, an indazolylene group which may have a substituent, a benzothiadiazolylene group which may have a substituent, a pyridinylene group which may have a substituent, a pyridazinylene group which may have a substituent, a pyrimidinylene group which may have a substituent, a pyrazinylene group which may have a substituent, a thiazolylene group which may have a substituent, an imidazolylene group which may have a substituent, an oxazolylene group which may have a substituent, an oxadiazolylene group which may have a substituent, a thiadiazolylene group which may have a substituent, a pyrazolylene group which may have a substituent, an isoxazolylene group which may have a substituent, a triazolylene group which may have a substituent, an imidazothiazolylene group which may have a substituent, an imidazopyridinylene group which may have a substituent, an imidazopyridazinylene group which may have a substituent, an imidazopyrimidinylene group which may have a substituent, an imidazopyrazinylene group which may have a substituent, a pyrazolopyrimidinylene group which may have a substituent, a pyrrolopyridinylene group which may have a substituent, a thiophenylene group which may have a substituent, a furanylene group which may have a substituent, a pyrrolene group which may have a substituent, a phenylene group which may have a substituent, and a naphthylene group which may have a substituent.

3. The peptide compound or the salt thereof according to claim 1, wherein R is at least one structure selected from a benzothiophenylene group which may have a substituent, an indolylene group which may have a substituent, a quinolylene group which may have a substituent, an indazolylene group which may have a substituent, a pyrrolopyridinylene group which may have a substituent, an imidazopyrazinylene group which may have a substituent, a pyridinylene group which may have a substituent, a pyridazinylene group which may have a substituent, a pyrazinylene group which may have a substituent, a thiazolylene group which may have a substituent, an oxazolylene group which may have a substituent, a triazolylene group which may have a substituent, a thiophenylene group which may have a substituent, and a phenylene group which may have a substituent.

4. The peptide compound or the salt thereof according to claim 1, wherein the total number of amino acid residues and amino acid analog residues constituting a cyclic portion of the peptide compound is 3 to 20.

5. The peptide compound or the salt thereof according to claim 1, wherein the total number of amino acid residues and amino acid analog residues constituting the peptide compound is 3 to 20.

6. The peptide compound or the salt thereof according to claim 1, wherein each of Xaa's is independently an α-amino acid residue.

7. The peptide compound or the salt thereof according to claim 1, wherein p is 1.

8. A composition for screening use, comprising:
the peptide compound or the salt thereof according to claim 1.

9. A method for selecting a peptide compound or a salt thereof that binds to a target substance, comprising:
bringing a target substance into contact with a peptide library containing the peptide compound or the salt thereof according to claim 1 to select a peptide compound or a salt thereof that binds to the target substance.

10. A peptide compound represented by Formula (1A) or a salt thereof:

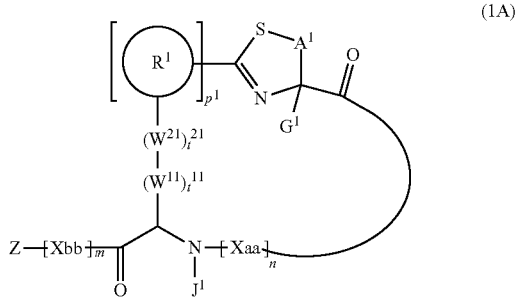

in the formula,
$A^1$ represents a linear alkylene group having 1 or 2 carbon atoms which may have a substituent;
$p^1$ pieces of $R^1$'s may be the same as or different from one another and each represent a heteroarylene group which may have a substituent or an arylene group having 6 to 10 carbon atoms which may have a substituent;
$t^{11}$ pieces of $W^{11}$'s may be the same as or different from one another and each represent a single bond, —CH$_2$(C$_6$H$_5$NH)—, —CH$_2$(C$_6$H$_5$O)—, an amino acid residue which may have a substituent, a heteroarylene group which may have a substituent, an arylene group having 6 to 20 carbon atoms which may have a substituent, or an alkylene group having 1 to 6 carbon atoms which may have a substituent;
$t^{21}$ pieces of $W^{21}$'s may be the same as or different from one another and each represent a single bond, —CO—, —COO—, —NHCO—, —NHCONH—, —CONHCO—, —(CH$_2$CH$_2$O)—, —(CH$_2$CH$_2$CH$_2$O)—, an amino acid residue which may have a substituent, a heteroarylene group which may have a substituent, an arylene group having 6 to 20 carbon atoms which may have a substituent, or an alkylene group having 1 to 6 carbon atoms which may have a substituent;
$G^1$ represents a hydrogen atom or an alkyl group having 1 to 6 carbon atoms which may have a substituent in a case where the carbon to which $G^1$ is bonded together with $A^1$ does not form a divalent group represented by *—CH=C(N)—;
$J^1$ represents a hydrogen atom or an alkyl group having 1 to 6 carbon atoms which may have a substituent;
$p^1$ represents an integer of 0 to 4;
$t^{11}$ represents an integer of 0 to 6;
$t^{21}$ represents an integer of 0 to 6; and
Z represents a hydroxyl group or an amino group;
n pieces of Xaa's each independently represent any amino acid residue or any amino acid analog residue;
m pieces of Xbb's each independently represent any amino acid residue or any amino acid analog residue;
m represents an integer of 0 to 20; and
n represents an integer of 1 to 20.

11. The peptide compound or the salt thereof according to claim 10, wherein the $R^1$ is at least one structure selected from a benzothiazolylene group which may have a substituent, a benzooxazolylene group which may have a substituent, a benzoimidazolylene group which may have a substituent, a benzothiophenylene group which may have a substituent, a benzofuranylene group which may have a substituent, an isobenzofuranylene group which may have a substituent, an indolylene group which may have a substituent, a quinolylene group which may have a substituent, an isoquinolylene group which may have a substituent, a quinazolylene group which may have a substituent, a cinnolylene group which may have a substituent, an indazolylene group which may have a substituent, a benzothiadiazolylene group which may have a substituent, a pyridinylene group which may have a substituent, a pyridazinylene group which may have a substituent, a pyrimidinylene group which may have a substituent, a pyrazinylene group which may have a substituent, a thiazolylene group which may have a substituent, an imidazolylene group which may have a substituent, an oxazolylene group which may have a substituent, an oxadiazolylene group which may have a substituent, a thiadiazolylene group which may have a substituent, a pyrazolylene group which may have a substituent, an isoxazolylene group which may have a substituent, a triazolylene group which may have a substituent, an imidazothiazolylene group which may have a substituent, an imidazopyridinylene group which may have a substituent, an imidazopyridazinylene group which may have a substituent, an imidazopyrimidinylene group which may have a substituent, an imidazopyrazinylene group which may have a substituent, a pyrazolopyrimidinylene group which may have a substituent, a pyrrolopyridinylene group which may have a substituent, a thiophenylene group which may have a substituent, a furanylene group which may have a substituent, a pyrrolene group which may have a substituent, a phenylene group which may have a substituent, and a naphthylene group which may have a substituent.

12. The peptide compound or the salt thereof according to claim 10, wherein $R^1$ is at least one structure selected from a benzothiophenylene group which may have a substituent, an indolylene group which may have a substituent, a quinolylene group which may have a substituent, an indazolylene group which may have a substituent, a pyrrolopyridinylene group which may have a substituent, an imidazopyrazinylene group which may have a substituent, a pyridinylene group which may have a substituent, a pyridazinylene group which may have a substituent, a pyrazinylene group which may have a substituent, a thiazolylene group which may have a substituent, an oxazolylene group which may have a substituent, a triazolylene group which may have a substituent, a thiophenylene group which may have a substituent, and a phenylene group which may have a substituent.

13. The peptide compound or the salt thereof according to claim 10, wherein $p^1$ is 1.

14. A peptide compound represented by Formula (IB) or a salt thereof:

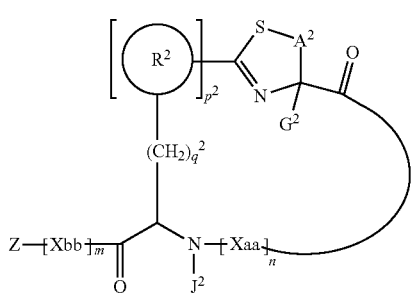

in the formula,
- A² represents a linear alkylene group having 1 or 2 carbon atoms which may have a substituent, or a divalent group represented by *—CH=C(N)— together with the carbon atom to which N is bonded, in which * represents a position that is bonded to S;
- G² represents a hydrogen atom or an alkyl group having 1 to 6 carbon atoms which may have a substituent in a case where the carbon to which G² is bonded together with A² does not form a divalent group represented by *—CH=C(N)—;
- J² represents a hydrogen atom or an alkyl group having 1 to 6 carbon atoms which may have a substituent;
- p² pieces of R²'s may be the same as or different from one another and each represent a heteroarylene group which may have a substituent or an arylene group having 6 to 10 carbon atoms which may have a substituent;
- p² represents an integer of 0 to 4;
- q² represents an integer of 0 to 6, provide that p² and q² are not simultaneously 0; and
- Z represents a hydroxyl group or an amino group;
- n pieces of Xaa's each independently represent any amino acid residue or any amino acid analog residue;
- m pieces of Xbb's each independently represent any amino acid residue or any amino acid analog residue;
- m represents an integer of 0 to 20; and
- n represents an integer of 1 to 20.

15. The peptide compound or the salt thereof according to claim 14, wherein the R² is at least one structure selected from a benzothiazolylene group which may have a substituent, a benzooxazolylene group which may have a substituent, a benzoimidazolylene group which may have a substituent, a benzothiophenylene group which may have a substituent, a benzofuranylene group which may have a substituent, an isobenzofuranylene group which may have a substituent, an indolylene group which may have a substituent, a quinolylene group which may have a substituent, an isoquinolylene group which may have a substituent, a quinazolylene group which may have a substituent, a cinnolylene group which may have a substituent, an indazolylene group which may have a substituent, a benzothiadiazolylene group which may have a substituent, a pyridinylene group which may have a substituent, a pyridazinylene group which may have a substituent, a pyrimidinylene group which may have a substituent, a pyrazinylene group which may have a substituent, a thiazolylene group which may have a substituent, an imidazolylene group which may have a substituent, an oxazolylene group which may have a substituent, an oxadiazolylene group which may have a substituent, a thiadiazolylene group which may have a substituent, a pyrazolylene group which may have a substituent, an isoxazolylene group which may have a substituent, a triazolylene group which may have a substituent, an imidazothiazolylene group which may have a substituent, an imidazopyridinylene group which may have a substituent, an imidazopyridazinylene group which may have a substituent, an imidazopyrimidinylene group which may have a substituent, an imidazopyrazinylene group which may have a substituent, a pyrazolopyrimidinylene group which may have a substituent, a pyrrolopyridinylene group which may have a substituent, a thiophenylene group which may have a substituent, a furanylene group which may have a substituent, a pyrrolene group which may have a substituent, a phenylene group which may have a substituent, and a naphthylene group which may have a substituent.

16. The peptide compound or the salt thereof according to claim 14, wherein R² is at least one structure selected from a benzothiophenylene group which may have a substituent, an indolylene group which may have a substituent, a quinolylene group which may have a substituent, an indazolylene group which may have a substituent, a pyrrolopyridinylene group which may have a substituent, an imidazopyrazinylene group which may have a substituent, a pyridinylene group which may have a substituent, a pyridazinylene group which may have a substituent, a pyrazinylene group which may have a substituent, a thiazolylene group which may have a substituent, an oxazolylene group which may have a substituent, a triazolylene group which may have a substituent, a thiophenylene group which may have a substituent, and a phenyl ene group which may have a substituent.

17. The peptide compound or the salt thereof according to claim 14, wherein p² is 1.

18. A composition for screening use, comprising a peptide compound having a cyclic portion or a salt thereof, wherein the cyclic portion has a structure represented by Formula (1):

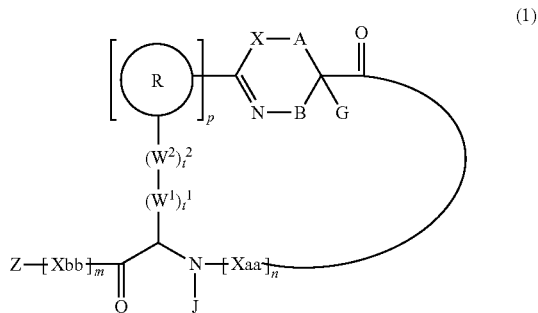

in the formula,
- X represents S, NH, or O;
- A represents a single bond, or a linear alkylene group having 1 or 2 carbon atoms which may have a substituent;
- B represents a single bond or a linear alkylene group having 1 or 2 carbon atoms which may have a substituent, provided that A and B are not simultaneously a single bond;
- Z represents a hydroxyl group or an amino group;
- p pieces of R's may be the same as or different from one another and each represent a heteroarylene group which may have a substituent or an arylene group having 6 to 10 carbon atoms which may have a substituent;

G represents a hydrogen atom or an alkyl group having 1 to 6 carbon atoms which may have a substituent in a case where the carbon to which G is bonded together with A does not form a divalent group represented by *—$CR^0$=C(B)—;

$t^1$ pieces of $W^1$'s may be the same as or different from one another and each represent a single bond, —$CH_2$($C_6H_5$NH)—, —$CH_2$($C_6H_5$O)—, an amino acid residue which may have a substituent, a heteroarylene group which may have a substituent, an arylene group having 6 to 20 carbon atoms which may have a substituent, or an alkylene group having 1 to 6 carbon atoms which may have a substituent;

$t^2$ pieces of $W^2$'s may be the same as or different from one another and each represent a single bond, —CO—, —COO—, —NHCO—, —NHCONH—, —CONHCO—, —($CH_7CH_7O$)—, —($CH_7CH_7CH_7O$)—, an amino acid residue which may have a substituent, a heteroarylene group which may have a substituent, an arylene group having 6 to 20 carbon atoms which may have a substituent, or an alkylene group having 1 to 6 carbon atoms which may have a substituent;

J represents a hydrogen atom or an alkyl group having 1 to 6 carbon atoms which may have a substituent;

n pieces of Xaa's each independently represent any amino acid residue or any amino acid analog residue;

m pieces of Xbb's each independently represent any amino acid residue or any amino acid analog residue;

p represents an integer of 0 to 4;
$t^1$ represents an integer of 0 to 6;
$t^2$ represents an integer of 0 to 6;
m represents an integer of 0 to 20; and
n represents an integer of 1 to 20.

\* \* \* \* \*

```
                        SEQUENCE LISTING

<160> NUMBER OF SEQ ID NOS: 83

<210> SEQ ID NO 1
<211> LENGTH: 169
<212> TYPE: DNA
<213> ORGANISM: Artificial Sequence
<220> FEATURE:
<223> OTHER INFORMATION: Synthetic sequence

<400> SEQUENCE: 1
cgaaattaat acgactcact atagggagac cacaacggtt ccctctaga aataattttg      60 tttaacttta agaaggagat atacatatgt gcaaacagaa accgcggagc aaaaactaga    120
gcgactacaa agacgatgac gacaaataag cttgagtatt ctatagtgt                169

<210> SEQ ID NO 2
<211> LENGTH: 169
<212> TYPE: DNA
<213> ORGANISM: Artificial Sequence
<220> FEATURE:
<223> OTHER INFORMATION: Synthetic sequence

<400> SEQUENCE: 2
cgaaattaat acgactcact atagggagac cacaacggtt ccctctaga aataattttg      60 tttaacttta agaaggagat atacatatgt gcaaatgcaa accgcggagc aaaaactaga    120
gcgactacaa agacgatgac gacaaataag cttgagtatt ctatagtgt                169

<210> SEQ ID NO 3
<211> LENGTH: 169
<212> TYPE: DNA
<213> ORGANISM: Artificial Sequence
<220> FEATURE:
<223> OTHER INFORMATION: Synthetic sequence

<400> SEQUENCE: 3
cgaaattaat acgactcact atagggagac cacaacggtt ccctctaga aataattttg      60 tttaacttta agaaggagat atacatatgt gcaaacagaa accgcggtgc aaaaactaga    120
gcgactacaa agacgatgac gacaaataag cttgagtatt ctatagtgt                169

<210> SEQ ID NO 4
<211> LENGTH: 169
<212> TYPE: DNA
<213> ORGANISM: Artificial Sequence
<220> FEATURE:
<223> OTHER INFORMATION: Synthetic sequence
```

<400> SEQUENCE: 4

```
cgaaattaat acgactcact atagggagac cacaacggtt tccctctaga aataattttg      60
tttaacttta agaaggagat atacatatgt gcgcgcaggc gccgcggagc gcgaactaga     120
gcgactacaa agacgatgac gacaaataag cttgagtatt ctatagtgt                169
```

<210> SEQ ID NO 5
<211> LENGTH: 166
<212> TYPE: DNA
<213> ORGANISM: Artificial Sequence
<220> FEATURE:
<223> OTHER INFORMATION: Synthetic sequence

<400> SEQUENCE: 5

```
cgaaattaat acgactcact atagggagac cacaacggtt tccctctaga aataattttg      60
tttaacttta agaaggagat atacatatgt gcaaacagaa accgcggagc aaatagagcg     120
actacaaaga cgatgacgac aaataagctt gagtattcta tagtgt                   166
```

<210> SEQ ID NO 6
<211> LENGTH: 163
<212> TYPE: DNA
<213> ORGANISM: Artificial Sequence
<220> FEATURE:
<223> OTHER INFORMATION: Synthetic sequence

<400> SEQUENCE: 6

```
cgaaattaat acgactcact atagggagac cacaacggtt tccctctaga aataattttg      60
tttaacttta agaaggagat atacatatgt gcaaacagaa accgcggagc tagagcgact     120
acaaagacga tgacgacaaa taagcttgag tattctatag tgt                      163
```

<210> SEQ ID NO 7
<211> LENGTH: 160
<212> TYPE: DNA
<213> ORGANISM: Artificial Sequence
<220> FEATURE:
<223> OTHER INFORMATION: Synthetic sequence

<400> SEQUENCE: 7

```
cgaaattaat acgactcact atagggagac cacaacggtt tccctctaga aataattttg      60
tttaacttta agaaggagat atacatatgt gcaaacagaa accgcggtag agcgactaca     120
aagacgatga cgacaaataa gcttgagtat tctatagtgt                          160
```

<210> SEQ ID NO 8
<211> LENGTH: 157
<212> TYPE: DNA
<213> ORGANISM: Artificial Sequence
<220> FEATURE:
<223> OTHER INFORMATION: Synthetic sequence

<400> SEQUENCE: 8

```
cgaaattaat acgactcact atagggagac cacaacggtt tccctctaga aataattttg      60
tttaacttta agaaggagat atacatatgt gcaaacagaa accgtagagc gactacaaag     120
acgatgacga caaataagct tgagtattct atagtgt                             157
```

<210> SEQ ID NO 9
<211> LENGTH: 154
<212> TYPE: DNA
<213> ORGANISM: Artificial Sequence
<220> FEATURE:

```
<223> OTHER INFORMATION: Synthetic sequence

<400> SEQUENCE: 9
cgaaattaat acgactcact atagggagac cacaacggtt tccctctaga aataattttg      60
tttaacttta agaaggagat atacatatgt gcaaacagaa atagagcgac tacaaagacg     120
atgacgacaa ataagcttga gtattctata gtgt                                 154

<210> SEQ ID NO 10
<211> LENGTH: 184
<212> TYPE: DNA
<213> ORGANISM: Artificial Sequence
<220> FEATURE:
<223> OTHER INFORMATION: Synthetic sequence

<400> SEQUENCE: 10
cgaaattaat acgactcact atagggagac cacaacggtt tccctctaga aataattttg      60
tttaacttta agaaggagat atacatatgt gcaaacagaa accgcggagc aaaaacccgt    120
tttggtgcca ttagagcgac tacaaagacg atgacgacaa ataagcttga gtattctata    180
gtgt                                                                  184

<210> SEQ ID NO 11
<211> LENGTH: 199
<212> TYPE: DNA
<213> ORGANISM: Artificial Sequence
<220> FEATURE:
<223> OTHER INFORMATION: Synthetic sequence

<400> SEQUENCE: 11
cgaaattaat acgactcact atagggagac cacaacggtt tccctctaga aataattttg      60
tttaacttta agaaggagat atacatatgt gcaaacagaa accgcggagc aaaaaccaga    120
aacggaacag cccgttttgg tgccattaga gcgactacaa agacgatgac gacaaataag    180
cttgagtatt ctatagtgt                                                  199

<210> SEQ ID NO 12
<211> LENGTH: 169
<212> TYPE: DNA
<213> ORGANISM: Artificial Sequence
<220> FEATURE:
<223> OTHER INFORMATION: Synthetic sequence

<400> SEQUENCE: 12
cgaaattaat acgactcact atagggagac cacaacggtt tccctctaga aataattttg      60
tttaacttta agaaggagat atacatatgt gccagaaact ggtgttcttt gcggaataga    120
gcgactacaa agacgatgac gacaaataag cttgagtatt ctatagtgt                169

<210> SEQ ID NO 13
<211> LENGTH: 169
<212> TYPE: DNA
<213> ORGANISM: Artificial Sequence
<220> FEATURE:
<223> OTHER INFORMATION: Synthetic sequence

<400> SEQUENCE: 13
cgaaattaat acgactcact atagggagac cacaacggtt tccctctaga aataattttg      60
tttaacttta agaaggagat atacatatgt gcgcgatcat tggcctgtgc gtgggctaga    120
gcgactacaa agacgatgac gacaaataag cttgagtatt ctatagtgt                169
```

<210> SEQ ID NO 14
<211> LENGTH: 75
<212> TYPE: RNA
<213> ORGANISM: Artificial Sequence
<220> FEATURE:
<223> OTHER INFORMATION: Synthetic sequence, tRNA gene

<400> SEQUENCE: 14
gggagaguag uucaauggua gaacgucggu cucuaaaacc gagcguugag gguucgauuc    60
cuuucucucc cacca                                                    75

<210> SEQ ID NO 15
<211> LENGTH: 83
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t

<400> SEQUENCE: 15
aagaaggaga tatacatatg tgcnnknnkn nknnknnkn knnknnknnk nnknnknnkn    60
nktagggcgg ttctggcggt agc                                          83

<210> SEQ ID NO 16
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 16
atactcaagc ttatttattt acccccccgcc gcccccccgtc ctgctaccgc cagaaccgcc    60

<210> SEQ ID NO 17
<211> LENGTH: 88
<212> TYPE: DNA
<213> ORGANISM: Artificial Sequence
<220> FEATURE:
<223> OTHER INFORMATION: Synthetic oligonucleotide

<400> SEQUENCE: 17
gaaattaata cgactcacta tagggagacc acaacggttt ccctctagaa ataattttgt    60 ttaacttaa gaaggagata tacatatg                                         88

<210> SEQ ID NO 18
<211> LENGTH: 193
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t

<400> SEQUENCE: 18
gaaattaata cgactcacta tagggagacc acaacggttt ccctctagaa ataattttgt    60
ttaactttaa gaaggagata tacatatgtg cnnknnknnk nnknnknnkn nknnknnknn   120
knnknnknnk tagggcggtt ctggcggtag caggacgggg ggcggcgggg ggtaaataaa   180
taagcttgag tat                                                     193

<210> SEQ ID NO 19
<211> LENGTH: 171
<212> TYPE: RNA
<213> ORGANISM: Artificial Sequence
<220> FEATURE:
<223> OTHER INFORMATION: Synthetic sequence, mRNA prepared by RNA
      polymerase
<220> FEATURE:
<221> NAME/KEY: misc_feature
<222> LOCATION: (70)..(71)
<223> OTHER INFORMATION: n is a, c, g, or u
<220> FEATURE:
<221> NAME/KEY: misc_feature
<222> LOCATION: (73)..(74)
<223> OTHER INFORMATION: n is a, c, g, or u
<220> FEATURE:
<221> NAME/KEY: misc_feature
<222> LOCATION: (76)..(77)
<223> OTHER INFORMATION: n is a, c, g, or u
<220> FEATURE:
<221> NAME/KEY: misc_feature
<222> LOCATION: (79)..(80)
<223> OTHER INFORMATION: n is a, c, g, or u
<220> FEATURE:
<221> NAME/KEY: misc_feature
<222> LOCATION: (82)..(83)
<223> OTHER INFORMATION: n is a, c, g, or u
<220> FEATURE:
<221> NAME/KEY: misc_feature
<222> LOCATION: (85)..(86)
<223> OTHER INFORMATION: n is a, c, g, or u
<220> FEATURE:
<221> NAME/KEY: misc_feature
<222> LOCATION: (88)..(89)
<223> OTHER INFORMATION: n is a, c, g, or u
<220> FEATURE:
<221> NAME/KEY: misc_feature
<222> LOCATION: (91)..(92)
<223> OTHER INFORMATION: n is a, c, g, or u
<220> FEATURE:
<221> NAME/KEY: misc_feature
<222> LOCATION: (94)..(95)
<223> OTHER INFORMATION: n is a, c, g, or u
<220> FEATURE:
<221> NAME/KEY: misc_feature
<222> LOCATION: (97)..(98)
<223> OTHER INFORMATION: n is a, c, g, or u
<220> FEATURE:
<221> NAME/KEY: misc_feature
<222> LOCATION: (100)..(101)
<223> OTHER INFORMATION: n is a, c, g, or u
<220> FEATURE:
<221> NAME/KEY: misc_feature
<222> LOCATION: (103)..(104)
<223> OTHER INFORMATION: n is a, c, g, or u
<220> FEATURE:
<221> NAME/KEY: misc_feature
<222> LOCATION: (106)..(107)
<223> OTHER INFORMATION: n is a, c, g, or u

<400> SEQUENCE: 19
gggagaccac aacgguuucc cucuagaaau aauuuuguuu aacuuuaaga aggagauaua    60
cauaugugcn nknnknnknn knnknnknnk nnknnknnkn nknnknnkua gggcgguucu   120
ggcgguagca ggacgggggg cggcgggggg uaaauaaaua agcuugagua u            171

<210> SEQ ID NO 20
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 20
gaaattaata cgactcacta tagggagacc acaacggttt ccctc                    45

<210> SEQ ID NO 21
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 21
atactcaagc ttatttattt accccccgcc gccccccgtc c                        41

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
gaaattaata cgactcacta                                                20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
atactcaagc ttatttattt                                                20

<210> SEQ ID NO 24
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 24
atactcaagc ttatttattt accccccgcc gccccccgtc ctgctaccgc cagaaccgcc    60
cta                                                                  63

<210> SEQ ID NO 25
<211> LENGTH: 18
<212> TYPE: PRT
<213> ORGANISM: Artificial Sequence
<220> FEATURE:
<223> OTHER INFORMATION: Synthetic peptide
<220> FEATURE:

```
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 25

Lys Gln Lys Xaa Arg Ser Lys Asn Xaa Ser Asp Tyr Lys Asp Asp
1               5                   10                  15

Asp Lys

<210> SEQ ID NO 26
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 26

Lys Gln Lys Xaa Arg Cys Lys Asn Xaa Ser Asp Tyr Lys Asp Asp
1               5                   10                  15

Asp Lys

<210> SEQ ID NO 27
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 27

Ala Gln Ala Xaa Arg Ser Ala Asn Xaa Ser Asp Tyr Lys Asp Asp
1               5                   10                  15

Asp Lys

<210> SEQ ID NO 28
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
```

<400> SEQUENCE: 28

Lys Gln Lys Xaa Arg Ser Lys Xaa Ser Asp Tyr Lys Asp Asp Asp Asp
1               5                   10                  15
Lys

<210> SEQ ID NO 29
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 29

Lys Gln Lys Xaa Arg Ser Xaa Ser Asp Tyr Lys Asp Asp Asp Asp Lys
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 30

Lys Gln Lys Xaa Arg Xaa Ser Asp Tyr Lys Asp Asp Asp Asp Lys
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(5)
<223> OTHER INFORMATION: Xaa can be any naturally occurring amino acid

<400> SEQUENCE: 31

Lys Gln Lys Xaa Xaa Ser Asp Tyr Lys Asp Asp Asp Asp Lys
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

```
<400> SEQUENCE: 32

Lys Gln Lys Xaa Ser Asp Tyr Lys Asp Asp Asp Lys
1               5                  10

<210> SEQ ID NO 33
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 33

Lys Gln Lys Xaa Arg Ser Lys Asn Xaa Phe Trp Cys His Xaa Ser Asp
1               5                  10                  15

Tyr Lys Asp Asp Asp Lys
            20

<210> SEQ ID NO 34
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 34

Lys Gln Lys Xaa Arg Ser Lys Asn Gln Lys Arg Asn Ser Xaa Phe Trp
1               5                  10                  15

Cys His Xaa Ser Asp Tyr Lys Asp Asp Asp Lys
            20                  25

<210> SEQ ID NO 35
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 35

Gln Lys Leu Val Phe Phe Ala Glu Xaa Ser Asp Tyr Lys Asp Asp
1               5                  10                  15

Asp Lys
```

```
<210> SEQ ID NO 36
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 36

Ala Ile Ile Gly Leu Cys Val Gly Xaa Ser Asp Tyr Lys Asp Asp
1               5                   10                  15

Asp Lys

<210> SEQ ID NO 37
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 37

Xaa Phe Trp Arg
1

<210> SEQ ID NO 38
<211> LENGTH: 4
<212> TYPE: PRT
<213> ORGANISM: Artificial Sequence
<220> FEATURE:
<223> OTHER INFORMATION: Synthetic peptide

<400> SEQUENCE: 38

Tyr Gly Gly Phe
1

<210> SEQ ID NO 39
<211> LENGTH: 4
<212> TYPE: PRT
<213> ORGANISM: Artificial Sequence
<220> FEATURE:
<223> OTHER INFORMATION: Synthetic peptide

<400> SEQUENCE: 39

Val Leu Trp Glu
1

<210> SEQ ID NO 40
<211> LENGTH: 4
<212> TYPE: PRT
<213> ORGANISM: Artificial Sequence
<220> FEATURE:
<223> OTHER INFORMATION: Synthetic peptide

<400> SEQUENCE: 40

Phe Trp Lys Thr
1

<210> SEQ ID NO 41
<211> LENGTH: 8
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(5)
<223> OTHER INFORMATION: Xaa can be any naturally occurring amino acid

<400> SEQUENCE: 41

Leu Leu Lys Xaa Xaa Ala Ala Phe
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(5)
<223> OTHER INFORMATION: Xaa can be any naturally occurring amino acid

<400> SEQUENCE: 42

Leu Leu Lys Xaa Xaa Ala Ser Phe
1               5

<210> SEQ ID NO 43
<211> LENGTH: 4
<212> TYPE: PRT
<213> ORGANISM: Artificial Sequence
<220> FEATURE:
<223> OTHER INFORMATION: Synthetic peptide

<400> SEQUENCE: 43

Val Leu Trp Glu
1

<210> SEQ ID NO 44
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 44

Xaa Phe Trp Arg
1

<210> SEQ ID NO 45
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 45

Xaa Phe Trp Arg
1
```

```
<210> SEQ ID NO 46
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 46

Xaa Phe Trp Arg
1

<210> SEQ ID NO 47
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 47

Xaa Phe Trp Arg
1

<210> SEQ ID NO 48
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 48

Xaa Phe Trp Arg
1

<210> SEQ ID NO 49
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 49

Leu Leu Ala Xaa Ala Phe Ala Leu
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid
<220> FEATURE:
```

```
<221> NAME/KEY: misc_feature
<222> LOCATION: (9)..(9)
<223> OTHER INFORMATION: Xaa can be any naturally occurring amino acid

<400> SEQUENCE: 50

Leu Lys Xaa Xaa Ala Leu Phe Leu Xaa
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide

<400> SEQUENCE: 51

Leu Ala Leu Lys Leu Ala
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(5)
<223> OTHER INFORMATION: Xaa can be any naturally occurring amino acid

<400> SEQUENCE: 52

Leu Leu Lys Xaa Xaa Ala Ser Phe
1               5

<210> SEQ ID NO 53
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 53

Xaa Phe Trp Arg
1

<210> SEQ ID NO 54
<211> LENGTH: 5
<212> TYPE: PRT
<213> ORGANISM: Artificial Sequence
<220> FEATURE:
<223> OTHER INFORMATION: Synthetic peptide

<400> SEQUENCE: 54

Ala Tyr Gly Gly Phe
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic peptide
```

```
<400> SEQUENCE: 55

Ala Val Leu Trp Glu
1               5

<210> SEQ ID NO 56
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 56

Xaa Xaa Trp Arg
1

<210> SEQ ID NO 57
<211> LENGTH: 4
<212> TYPE: PRT
<213> ORGANISM: Artificial Sequence
<220> FEATURE:
<223> OTHER INFORMATION: Synthetic peptide

<400> SEQUENCE: 57

Val Leu Trp Glu
1

<210> SEQ ID NO 58
<211> LENGTH: 4
<212> TYPE: PRT
<213> ORGANISM: Artificial Sequence
<220> FEATURE:
<223> OTHER INFORMATION: Synthetic peptide

<400> SEQUENCE: 58

Phe Trp Lys Thr
1

<210> SEQ ID NO 59
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(5)
<223> OTHER INFORMATION: Xaa can be any naturally occurring amino acid

<400> SEQUENCE: 59

Leu Leu Lys Xaa Xaa Ala Ala Phe
1               5

<210> SEQ ID NO 60
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Xaa can be any naturally occurring amino acid
```

<400> SEQUENCE: 60

Xaa Xaa Trp Arg
1

<210> SEQ ID NO 61
<211> LENGTH: 5
<212> TYPE: PRT
<213> ORGANISM: Artificial Sequence
<220> FEATURE:
<223> OTHER INFORMATION: Synthetic peptide

<400> SEQUENCE: 61

Ala Tyr Gly Gly Phe
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic peptide

<400> SEQUENCE: 62

Ala Val Leu Trp Glu
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic peptide

<400> SEQUENCE: 63

Ala Phe Trp Lys Thr
1               5

<210> SEQ ID NO 64
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 64

Arg Ser Trp Ala Cys Leu Trp Xaa Ala Phe Leu Trp Tyr
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

```
<400> SEQUENCE: 65

Trp Ala Phe Ser Val Leu Trp Xaa Trp Phe Xaa Val Trp
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 66

Phe Ala Leu Leu Trp Xaa Gln Phe Leu Xaa Leu Ala Phe
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 67

Trp Ser Val Leu Trp Xaa Trp Phe Val Xaa Ser Val Ser
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 68

Ser Phe Glu Xaa Gly Leu Trp Trp Leu Phe Arg Val Leu
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: Xaa can be any naturally occurring amino acid
```

<400> SEQUENCE: 69

Ser Trp Cys Val Leu Trp Xaa Trp Leu Val Phe Trp Gly
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 70

Xaa Trp Val Leu Leu Trp Xaa Ile Leu Val Xaa Ser Leu
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 71

Trp Ala Cys Leu Trp Xaa Ala Phe Ala Leu Ser Trp Leu
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 72

Xaa Arg Phe Leu Xaa Trp Phe Thr Xaa Asp Cys Tyr Glu
1               5                   10

<210> SEQ ID NO 73
<211> LENGTH: 13
<212> TYPE: PRT
<213> ORGANISM: Artificial Sequence
<220> FEATURE:

```
<223> OTHER INFORMATION: Synthetic peptide

<400> SEQUENCE: 73

Ala Gly Ala Phe Glu Tyr Glu Tyr Lys Asp Gln Asp Leu
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Synthetic peptide

<400> SEQUENCE: 74

Asp Ile Val Gly Val Tyr Asp Tyr Lys Asp Gly Asp Arg
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Synthetic peptide

<400> SEQUENCE: 75

Glu Glu Thr Ala Ser Thr Leu Arg Ser Ile Gly Asp Ala
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetic peptide

<400> SEQUENCE: 76

Thr Thr Leu Ser Ser Ile Gly Asp Gln Val Asp Arg Arg
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (13)..(13)
<223> OTHER INFORMATION: Xaa can be any naturally occurring amino acid

<400> SEQUENCE: 77

Asn Val Val Asp Gly Leu Arg Gln Ile Gly Asp Thr Xaa
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 78

Asp Ser Tyr Xaa Ala Ala Val Lys Asp Leu Glu Asn Ala
1               5                   10
```

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide

<400> SEQUENCE: 79

Ala Ala Val Lys Asp Leu Glu Asn Ala
1               5

<210> SEQ ID NO 80
<211> LENGTH: 4
<212> TYPE: PRT
<213> ORGANISM: Artificial Sequence
<220> FEATURE:
<223> OTHER INFORMATION: Synthetic peptide

<400> SEQUENCE: 80

Ala Ala Val Lys
1

<210> SEQ ID NO 81
<211> LENGTH: 5
<212> TYPE: PRT
<213> ORGANISM: Artificial Sequence
<220> FEATURE:
<223> OTHER INFORMATION: Synthetic peptide

<400> SEQUENCE: 81

Asp Leu Glu Asn Ala
1               5

<210> SEQ ID NO 82
<211> LENGTH: 19
<212> TYPE: DNA
<213> ORGANISM: Artificial Sequence
<220> FEATURE:
<223> OTHER INFORMATION: Synthetic sequence

<400> SEQUENCE: 82 tacccccgc cgccccccg                                                   19

<210> SEQ ID NO 83
<211> LENGTH: 23
<212> TYPE: DNA
<213> ORGANISM: Artificial Sequence
<220> FEATURE:
<223> OTHER INFORMATION: Synthetic sequence

<400> SEQUENCE: 83 tacccccgc cgccccccgt cct                                              23